(12) United States Patent
Huesca et al.

(10) Patent No.: US 8,148,392 B2
(45) Date of Patent: Apr. 3, 2012

(54) 2-INDOLYL IMIDAZO [4,5-D] PHENANTHROLINE DERIVATIVES AND THEIR USE IN THE TREATMENT OF CANCER

(75) Inventors: Mario Huesca, Toronto (CA); Aiping H. Young, Toronto (CA); Yoon Lee, Mississauga (CA); Aye Aye Khine, Concord (CA); Jim A. Wright, Oakville (CA); Lisa Lock, Toronto (CA); Raed Al-Qawasmeh, Amman (JO)

(73) Assignee: Lorus Therapeutics Inc., Ontario (CA)

( * ) Notice: Subject to any disclaimer, the term of this patent is extended or adjusted under 35 U.S.C. 154(b) by 632 days.

(21) Appl. No.: 11/915,257

(22) PCT Filed: May 25, 2006

(86) PCT No.: PCT/IB2006/051675
§ 371 (c)(1),
(2), (4) Date: Nov. 18, 2008

(87) PCT Pub. No.: WO2006/126177
PCT Pub. Date: Nov. 30, 2006

(65) Prior Publication Data
US 2010/0168417 A1 Jul. 1, 2010

Related U.S. Application Data

(60) Provisional application No. 60/684,162, filed on May 25, 2005, provisional application No. 60/710,551, filed on Aug. 22, 2005, provisional application No. 60/787,526, filed on Mar. 31, 2006.

(51) Int. Cl.
*A61K 31/4745* (2006.01)
*C07D 471/12* (2006.01)

(52) U.S. Cl. .......................................... 514/287; 546/64
(58) Field of Classification Search .................. 514/287; 546/64
See application file for complete search history.

(56) References Cited

U.S. PATENT DOCUMENTS

| | | | |
|---|---|---|---|
| 3,279,918 A | 10/1966 | Cassiers et al. |
| 3,297,710 A | 1/1967 | Silversmith |
| 3,714,181 A | 1/1973 | Lantos |
| 4,089,747 A | 5/1978 | Bruschi |
| 4,423,046 A | 12/1983 | Carlson |
| 4,466,976 A | 8/1984 | Klose et al. |
| 4,585,771 A | 4/1986 | Klose et al. |
| 4,705,855 A | 11/1987 | Desideri et al. |
| 4,721,670 A | 1/1988 | Osada et al. |
| 4,758,421 A | 7/1988 | Chang et al. |
| 4,902,705 A | 2/1990 | Hirota et al. |
| 4,970,226 A | 11/1990 | Sun et al. |
| 5,024,935 A | 6/1991 | McClune et al. |
| 5,047,318 A | 9/1991 | Snyder et al. |
| 5,161,389 A | 11/1992 | Rockenfeller et al. |
| 5,328,671 A | 7/1994 | Rockenfeller |
| 5,441,716 A | 8/1995 | Rockenfeller |
| 5,496,702 A | 3/1996 | Bishop et al. |
| 5,501,959 A | 3/1996 | Lancaster et al. |
| 5,514,550 A | 5/1996 | Findlay et al. |
| 5,656,644 A | 8/1997 | Adams et al. |
| 5,686,455 A | 11/1997 | Adams et al. |
| 5,693,589 A | 12/1997 | Goswami et al. |
| 5,700,826 A | 12/1997 | Mjalli et al. |
| 5,753,687 A | 5/1998 | Mjalli et al. |
| 5,809,775 A | 9/1998 | Tarabulski et al. |
| 5,916,891 A | 6/1999 | Adams et al. |
| 5,945,418 A | 8/1999 | Bemis et al. |
| 6,060,216 A | 5/2000 | Ichikawa et al. |
| 6,117,609 A | 9/2000 | Maeda |
| 6,194,441 B1 | 2/2001 | Roberts et al. |
| 6,266,955 B1 | 7/2001 | Liang et al. |
| 6,268,370 B1 | 7/2001 | Adams et al. |
| 6,521,655 B1 | 2/2003 | Beers et al. |
| 6,589,966 B1 | 7/2003 | Torti et al. |
| 6,852,727 B2 | 2/2005 | Goulet et al. |

(Continued)

FOREIGN PATENT DOCUMENTS

CA      2 351 694      7/1993

(Continued)

OTHER PUBLICATIONS

U.S. Appl. No. 10/525,690, filed Oct. 24, 2006, Raed Al-Qawasmeh.
U.S. Appl. No. 10/579,149, filed Jan. 19, 2007, Huesca et al.
Chaston, T.B. et al., Clin. Cancer Res., vol. 9(1) (2003) pp. 402-414.
Chen, C. et al., Oncogene, vol. 21 (2002) pp. 6567-6572.
Chen, J. et al., Nat. Rev. Cancer, vol. 5(2) (2005)pp. 102-112.
Chen, X., et al. J. Biol. Chem., vol. 276(32) (2001)pp. 30423-30428.
Dang, D.T. et al., FEBS Lett., vol. 476 (2000) pp. 203-207.
Dang, D.T. et al., Oncogene, vol. 22(22) (2003) pp. 3424-3430.
Downey, K.M. et al., Biochem. Biophys. Res. Commun., vol. 93(1) (1980) pp. 264-270.

(Continued)

*Primary Examiner* — Charanjit Aulakh
(74) *Attorney, Agent, or Firm* — Frost Brown Todd LLC

(57) ABSTRACT

2-indolyl imidazo[4,5-d]phenanthroline compounds of Formula (I) and methods of using same in the treatment of cancer, in particular, solid cancers and leukemia are provided. Pharmaceutical compositions comprising the compounds are also provided.

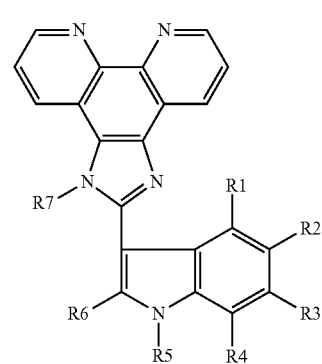

36 Claims, 58 Drawing Sheets

U.S. PATENT DOCUMENTS

| | | | |
|---|---|---|---|
| 7,115,645 | B2 | 10/2006 | Halfbrodt et al. |
| 7,291,404 | B2 | 11/2007 | Aziz et al. |
| 2002/0119955 | A1 | 8/2002 | Doyle et al. |
| 2004/0127527 | A1 | 7/2004 | Hongu et al. |
| 2004/0176601 | A1 | 9/2004 | Goulet et al. |
| 2004/0265628 | A1 | 12/2004 | Wang et al. |
| 2005/0282285 | A1 | 12/2005 | Radhamohan et al. |

FOREIGN PATENT DOCUMENTS

| | | |
|---|---|---|
| CN | 128 9774 | 4/2001 |
| CN | 128 9775 | 4/2001 |
| DE | 3422175 | 12/1985 |
| DE | 10323591 | 12/2004 |
| EP | 0 077 024 | 10/1982 |
| EP | 0 165 588 | 12/1985 |
| EP | 0 812 829 | 12/1997 |
| EP | 1 428 831 | 6/2004 |
| JP | 02258017 | 10/1990 |
| JP | 11199582 | 7/1999 |
| JP | 2000/273088 | 10/2000 |
| JP | 2001/506997 | 5/2001 |
| JP | 2002-275458 | 9/2002 |
| JP | 2002-364578 | 12/2002 |
| JP | 2004/528206 | 9/2004 |
| JP | 2006/503817 | 2/2006 |
| WO | WO 93/14081 | 7/1993 |
| WO | WO 94/11685 | 5/1994 |
| WO | WO 97/36587 | 10/1994 |
| WO | WO 95/03297 | 2/1995 |
| WO | WO 96/18626 | 6/1996 |
| WO | WO 97/36587 | 10/1997 |
| WO | WO 98/14081 | 4/1998 |
| WO | WO 98/27065 | 6/1998 |
| WO | WO 98/27108 | 6/1998 |
| WO | WO 99/01128 | 1/1999 |
| WO | WO 99/01205 | 1/1999 |
| WO | WO 99/02155 | 1/1999 |
| WO | WO 99/07701 | 2/1999 |
| WO | WO 00/33836 | 6/2000 |
| WO | WO 00/59541 | 10/2000 |
| WO | WO 2000/68206 | 11/2000 |
| WO | WO 00/78761 | 12/2000 |
| WO | WO 01/26467 | 4/2001 |
| WO | WO 02/024680 | 3/2002 |
| WO | WO 02/24680 | 3/2002 |
| WO | WO 02/46168 | 6/2002 |
| WO | WO 02/072576 | 9/2002 |
| WO | WO 03/004023 | 1/2003 |
| WO | WO 03/032984 | 4/2003 |
| WO | WO 03/066579 | 8/2003 |
| WO | WO 03/087026 | 10/2003 |
| WO | WO 2004/005264 | 1/2004 |
| WO | WO 2004/016086 | 2/2004 |
| WO | WO 2004/042207 | 5/2004 |
| WO | WO 2005/047266 | 5/2005 |
| WO | WO 2006/012903 | 2/2006 |
| WO | WO 2006/081824 | 8/2006 |
| WO | WO 2006/126177 | 11/2006 |
| WO | WO 2007/000170 | 1/2007 |

OTHER PUBLICATIONS

Foster, K.W. et al., Cancer Res. vol. 60(22) (2000) pp. 6488-6495.
Foster, K.W. et al., Cell Growth Differ., vol. 10(6) (1999)pp. 423-434.
Ghaleb, A.M. et al., Cell Res., vol. 15(2) (2001)pp. 92-96.
Kaczynski, J. et al., Genome Biol., vol. 4(2) (2003) p. 206.1-206.8.
Kindermann, B.F. et al., Biochem. Cell Biol., vol. 83(2) (2005) pp. 221-229.
Kindermann, B.F. et al., J. Nut., vol. 134(1) (2004) pp. 57-62.
Mann K.J. et al., Biochemistry, vol. 40(5) (2001) pp. 1205-1213.
McCabe M.J, Jr. et al., Lab. Invest., vol. 69(1) (1993)pp. 101-110.
Narla, G. et al., Science, vol. 294 (2001) pp. 2563-2566.
Ohnishi, S. et al., Biochem. Biophys. Res. Commun., vol. 308(2) (2003) pp. 251-256.
Pan, C.Q. et al. Mol. Microbiol., vol. 12(3) (1994) pp. 335-342.
Pandya, A.Y. et al. Clin. Cancer Res., vol. 10(8) (2004) pp.-2709-2719.
Richardson, D.R. Crit. Rev. Oncol. Hematol., vol. 42(3) (2002) p. 267-281.
Shulman, A. et al., Chem. Biol. Interact., vol. 16(1) (1977) pp. 89-99.
Sigman, D.S. et al., J. Biol. Chem., vol. 254(24) (1979) pp. 12269-12272.
Springman, E.B. et al., Biochemistry, vol. 34(48) (1995) pp. 15713-15720.
Subramaniam, M. et al., J. Cell Biochem., vol. 68 (1998)pp. 226-236.
Wang, N. et al., World J. Gastroenterol., vol. 8(6) (2002) 966-970.
Wei, D. et al., Cancer Res., vol. 65(7) (2005) pp. 2746-2754.
Yasunaga, J. et al., Cancer Res., vol. 64(17) (2004) pp. 6002-6009.
Zhao, R. et al., Biocham. Pharmacol., vol. 67(9) (2004) pp. 1677-1688.
Adams, J.L. et al., "Phyriidinylimidazole Inhibitors of p38: cyclic N-1 Imidazole Substituents Enhance p38 Kinase Inhibition and Oral Activity," Bioorg. Med. Chem. Lett., vol. 11 (2001) pp. 2867-2870.
Adbel-Meguid, et al., "An Orally Bioavailable HIV-1 Protease Inhibitor Containing an Imidazole-Derived Peptide Bond Replacement: Crystallographic and Pharmacokinetic Analysis," Biochemistry, vol. 33(39) (Oct. 4, 1994) pp. 11671-11677.
Antolini, M. et la., "Analogues of 4,5-bis(3,5-Dichlorophenyl)-2-Trifluoromethyl-1H-Imidazole as Potential Antibacterial Agents," Bioorg. Med. Chem. Lett, vol. 9(7) (Apr. 1999) pp. 1023-1028.
Armesto, D. et al., "A New Site Selective Synthesis of Benzoin Esters, Synthesis of Symmetrically and Unsymmetrically Substituted Benzils," Synthesis (Oct. 1988) pp. 799-801.
Bhaduri, A. P. et al., "Potential Antifertility Agents: Syntheses of 2,4,5-Substituted Imidazoles," Indian Journal of Chemistry, vol. 4(9) (Sep. 1966). pp. 419-420.
Botana et al., "p-(1 H-Phenanthro[9,10-d]imidazol-2-y1)-Substituted Calix[4]arene, a Deep Cavity for Guest Inclusion," Organic Letters, vol. 6(7) (2004) pp. 1091-1094.
Bu et al., "A Novel Approach to Synthesis of Tricyanovinylthiophene for Heterocyclic Imidazole Nonlinear Optical Chromophores," Tetrahedron Lett., vol. 37(41) (1996) pp. 7331-7334.
Chi, K. et al., "Palladium Catalyst in DMSO for the Oxidation of Tolans to Benzils," Synth. Comm., vol. 24(15) (1994) pp. 2119-2122.
Cuenda et al., "Activation of stress-activated protein kinase-3 (SAPK3) by cytokines and cellular stresses is mediated via SAPKK3 (MKK6); comparison of the specificities of SAPK3 and SA:K2 (RK/p38)," EMBO J., vol. 16(2) (1997) pp. 295-305.
Cuenda et al., "SB 203580 is a specific inhibitor of a MAP kinase homologue which is stimulated by cellular stresses and interleukin-1," Febs. Lett., vol. 364 (1995) pp. 229-233.
Demirayak, S. et al., "Synthesis of Certain Derivatives of Ethyl α-[(Phenanthro [9,10-d]—1Midazol-2-YL) Phenoxy] Alkanoate," Acta Pharmaceutica Turcica, vol. 31(1)(1989) pp. 19-25.
Fischer, A. et al., "Dissociation Constants of the Conjugate Acids of Substituted Benzyl Phenyl Ketones and of Alkyl-substituted Benzophenones," J. A. Chem. Soc., vol. 83 (Oct. 20, 1961) pp. 4208-4210.
Gales, A.C. et al., "Characterization of Pseudomonas aeruginosa Isolates: Occurrence. Rates, Antimicrobial Susceptibility Patterns, and Molecular Typing in the Global Sentry Antimicrobial Surveillance Program, 1997-1999," Clin. Infect. Dis., vol. 32 (2001) pp. S146-S155.
Guijarro, A. et al., "The Reaction of Active Zinc with Organic Bromides," J. Am. Chem. Soc., vol. 121 (1999) pp. 4155-4166.
Heerding D.A. et al., "1,4-Disubstituted Imidazoles are Potential Antibacterial Agents Functioning as Inhibitors of Enoyl Acyl Carrier Protein Reductase (FabI)," Bioorg. Med. Chem. Lett., vol. 11 (2001) pp. 2061-2065.
International Search Report dated Jan. 3, 2007 for Application No. PCT/IB2006/051675.
Isikdag, I. et al., "2,4,5-Trisübstitüe Imidazol Bilesiklerinin Tubifex Solucanlari Uzerindeki Inhibitör Etkilerinin Kantitatif Yapi-Etki Iliskileri," Acta Pharmaceutica Turcica, vol. 37(1)(1995) pp. 19-24.
Kimura, M. et al., "Preparation of 4-(4,5-Diphenyl-1H- imidazol-2-yl) benzadehyde and its Practical Synthetic Use in the Synthesis of Unsymmetrically Substituted Imidazoles," New Technologies & Medicine, vol. 3(1) (2002),pp. 30-34.

Krieg, B. et al., "Synthese und Halbleitereigenschaften arylsubstituierter Imidazole," Naturforsch, vol. 22b (1967) pp. 132-141.

Lee et al., "A protein kinase involved in the regulation of inflammatory cytokine biosynthesis," Nature, vol. 327 (Dec. 1994) pp. 739-746.

Lewis, J.R., "Muscarine, imidazole, oxazole, thiazole and peptide alkaloids, and other miscellaneous alkaloids," Nat. Prod. Rep., vol. 15 (1998) pp. 417-437.

Lewis, J.R., "Muscarine, imidazole, osazole, thiazole and peptide alkaloids, and other miscellaneous alkaloids," Nat. Prod. Rep., vol. 15 (1998) pp. 371-395.

Lewis, J.R., "Miscellaneous alkaloids: Amaryllidaceae, Sceletium, muscarine, imidazole, oxazole, peptide and other miscellaneous alkaloids," Nat. Prod. Rep, vol. 16 (1999) pp. 389-418.

Lock, L. et al., "Molecular Mechanisms of Growth Inhibition Induced by Novel Aryl-imidazole Compounds in Human Cancer Cells," Lorus Therapeutics, IBC's 9$^{th}$ Annual World Congress Drug Discovery Technology Meeting (Aug. 8-13, 2004) Boston.

Lograsso et al., "Kinetic Mechanism for p38 MAP kinase," Biochemistry, vol. 36 (1997)pp. 10422-10427.

McLay, I.M. et al, "The Discovery of RPR 200765A, a p38 MAP Kinase Inhibitor Displaying a Good Oral Anti-Arthritic Efficacy," Bioorg. Med. Chem. , vol. 9 (2001). pp. 537-554.

Moylan et al., "Synthesis and Nonlinear Optical Properties of Donor-Acceptor Substituted Triaryl Azole Derivitatives," Chemistry of Materials, vol. 5(10) (1993) pp. 1499-1508.

Office Action dated Jul. 20, 2009 for U.S. Appl. No. 10/525,690.
Office Action dated Dec. 31, 2007 for U.S. Appl. No. 10/579,149.
Office Action dated Jun. 17, 2008 for U.S. Appl. No. 10/579,149.
Office Action dated Dec. 8, 2008 for U.S. Appl. No. 10/579,149.
Office Action dated Jun. 8, 2009 for U.S. Appl. No. 10/579,149.

Press Release—May 12, 2004-13 "Lorus Announces Discovery of Noel Low Molecular Weight Compounds with Anticancer and Antibacterial Activity," BioFinance conference, Toronto, CA, http://www.lorusthera.com/news-events/press-release-lorus-announces-discovery-novel-low-302.php.

Press Release—Aug. 9, 2004—"Lorus Therapeutics, Inc. to Present Results of Novel Anticancer Small Molecule Studies," http://www.lorusthera.com/news-events/press-release-lorus-therapeutics-inc-present-results-323.php.

Press Release—Aug. 23, 2005—"Lorus Indentifies Novel Class of Lead Drug Candidates from Small Molecule Anticancer Program."

Sarshar et al., "2,4,5-Trisubstituted Imidazoles: Novel Nontoxic Modulators of P-glycoprotein Mediated Multidrug Resistance. Part 1," Bioorg. Med. Chem. Lett., vol. 10 (2000) pp. 2599-2601.

Sarshar et al., "Imidazole Libraries on Solid Support," Tetrahedron Lett., vol. 37 (1996) pp. 835-838.

Tanaseichuk, B. et al, Uch. Zap. Mord. Univ., No. 81 (1971) pp. 95-97.

Zeytinoğlu, H. et al., "Mutagenicity Assay in *Salmonella* for Thirteen 2-Substituted-1H-phenanthro (9,10-*d*) Imidazoles," Drug and Chemical Toxicology, vol. 26(4) (2003) pp. 245-257.

Zhang et al., "2,4,5-Trisubstituted Imidazoles: Novel Nontoxic Modulators of P-glycoprotein Mediated Multidrug Resistence. Part 2," Bioorg. Med. Chem. Lett., vol. 10 (2000) pp. 2603-2605.

Buss, J.L. et al., Curr.Top Med. Chem., vol. 4 (15) (2004) pp. 1623-1635.

Chen, C. et al., Oncogene, vol. 21 (2002)pp. 6567-6572.
Chen, J. et al., Nat Rev. Cancer, vol. 5(2) (2005) pp. 102-112.
Chen, X., et al. J. Biol. Chem. vol. 276(32) (2001) pp. 30423-30428.

Choa, H. et al., Synthesis, electrochemical and spectroscopic properties of ruthenium(II) complexes containing 1,3-bis([1,10]phenanthroline-[5,6-d]imidazol-2-yl]benzene, Polyhedron, vol. 19(2000) pp. 1975-1983.

Dang, D.T. et al., Oncogene, vol. 22(22) (2003).pp. 3424-3430.
Downey K.M. et al., Biochem. Biophys. Res. Commun., vol. 93(1) (1980) pp. 264-270.
Foster, K.W. et al., Cancer Res., vol. 60(22) (2000) pp. 6488-6495.
Foster, K.W. et al., Cell Growth Differ., vol. 10(6) (1999) pp. 423-434.
Ghaleb, A.M. et al., Cell Res., vol. 15(2) (2001) pp. 92-96.

Kindermann, B.F. et al., Biochem. Cell Biol., vol. 83(2) (2005)pp. 221-229.
Kindermann, B.F. et al., J. Nutr., vol. 134(1) (2004)pp. 57-62.
Liu, J.G., Enantiomeric ruthenium (II) complexes binding to DNA: binding modes and enantioselectively, JBIC, vol. 27 (2000) pp. 119-128.
Mann, K.J. et al., Biochemistry, vol. 40(5) (2001)pp. 1205-1213.
U.S. Appl. No. 10/525,690, filed Oct. 24, 2006 Raed Al-Qawasmeh.
McCabe, M.J, Jr. et al., Lab. Invest., vol. 69(1)(1993) pp. 101-110.
Ohnishi, S. et al., Biochem. Biophys. Res. Commun., vol. 308(2) (2003) pp. 251-256.
Pan, C.Q. et al., Mol. Microbiol., vol. 12(3) (1994)pp. 335-342.
Pandya, A.Y. et al., Clin. Cancer Res, vol. 10(8) (2004) pp. 2709-2719.
Richardson, D.R., Crit. Rev. Oncol. Hematol., vol. 42(3) (2002) p. 267-281.
Sigman, D.S. et al., J. Biol. Chem., vol. 254(24) (1979)pp. 12269-12272.
Subramaniam, M. et al., J. Cell Biochem., vol. 68 (1998) pp. 226-236.
Wang, N. et al., World J. Gastroenterol., vol. 8(6) (2002) pp. 966-970.
Wei, D. et al. Cancer Res., vol. 65(7) (2005)pp. 2746-2754.
Xu, H et al., Effects of the ancillary ligands of polypyridyl ruthenium(II) complexes on the DNA-binding behaviors, New J. Chem., vol. 27 (2003) pp. 1255-1263.
Zhao, R. et al , Biocham. Pharmacol., vol. 67(9) (2004) pp. 1677-1688.
CAS Registry No. 404904-57-0, entered Registry file on STN on Apr. 10, 2002.
CAS Registry No. 309285-51-6, entered Registry file on STN on Dec. 18, 2000.
CAS Registry No. 330449-52-0 entered Registry file on STN on Apr. 6, 2001.
CAS Registry No. 332148-67-1, entered Registry file on STN on Apr. 21, 2001.
Abstract for Nippon Kagaku Zasshi, vol. 92 (1971) pp. 365-370.
Zhang, Q.L., et al, "Design of New Polypyridyl Ligands and Their Effects on DNA-binding Mechanisms of Complexes," Chemical Journal of Chinese Universities, vol. 24(10) (2003) pp. 1753-1755 (Article and Abstract).
Dora, E.K. et al., "Synthesis of some fused 2-arylimidazoles and their derivatives," Journal of the Indian Chemical Society, vol. 56(6) (1979) pp. 620-624.
Isikdag et al., "Synthesis and analgesic activities of 2-substitutes-1H-phenantro [9,10-d]imidazoles," Boll. Chim. Farmaceutico, vol. 138 (1999) pp. 453-456.
Ito, Y. et al., "Photchemical Reaction of Imidazoles with Unstaturated Nitriles, Chemistry of Encounter Complex and Ion Pair," J. Org. Chem., vol. 44(1) (1979) pp. 41-49.
Lantos, I. et al., "Reaction of Phenanthrenequinone with Ammonium Acetate," J. Org. Chem., vol. 40 (1975) pp. 1641-1642.
Liu et al., "Synthesis, Characterization and Antitumor Activity of a Series of Polypyridyl Complexes" Metal Based drugs, vol. 7(6) (2000) pp. 343-350.
Nippon Kagaku Zasshi, vol. 92 (1971) pp. 365-370.
Pechkin, A.A. et al., "Synthesis and Properties of 2-(2-Furyl)-and2-(2-Thienyl)-1-methylphenanthro[9,10-d]imidazoles," Russian Journal of Organic Chemistry, vol. 38(5) (2002)pp, 726-730.
Pozharskii, F.T. et al., "Synthesis and Transformations of 2-(2-Furyl)- and 2-[β-(2-Furyl) Phenanthr[9,10] Imidazoles," Chem. Het. Comp., vol. 7 (1971) pp. 950-952.
Roshal, A.D. et al., "The Electronic Transitions and Spectra of Hetarylphenanthroimidazole Derivatives," Russian Journal of Physical Chemistry, vol. 77 (2003) pp. 1709-1714.
Sircar, A.C. et al., "Dyes Derived from Phenanthraquinone. Phenanthriminazoles.," J. Chem. Soc., vol. 123 (1923) pp. 1559-1565.
Steck, E.A. et al., "Reactions of Phenanthraquinone and Retenequinone with Aldehydes and Ammonium Acetate in Acetic Acid Solution," J. Am. Chem. Soc., vol.65 (1943) pp. 452-456.
Tanaseichuk et al., "Nitrogen-Containing Heterocyclic Free Radicals, VI. N-Methylindolyldiphenylimidazoles," Chemical Abstracts, vol. 78 (1973) p. 43368.

Wermuth, C.G. et al., the Practice of Medicinal Chemistry, Academic Press (1998) pp. 243-248.

Alakhov, V. et al., "Block copolymer-based formulation of doxorubicin. From cell screen to clinical trials," Colloids and Surfaces B: Biointerfaces, vol. 16 (1999) pp. 113-134.

Allen, C. et al., "Controlling the physical behavior and biological performance of liposome formulations through use of surface grafted poly(ethylene glycol)," Biosciences Reports, vol. 22(20 (2002) pp. 225-250.

Allen, T.M. et al., "Stealth liposomes: an improved sustained release system for 1-beta-D-arabinofuranosylcytosine," Cancer Res., vol. 52 (1992) pp. 2431-2439.

Al-Sarraj, A. et al., "Specificity of transcriptional regulation by the zinc finger transcription factors Sp1, Sp3, and Egr-1," J Cell Biochem., vol. 94(1) (2005) pp. 153-167.

Andrews, G.K., "Cellular zinc sensors: MTF-1 regulation of gene expression," Biometals, vol. 14 (2001) pp. 223-237.

Bertram et al., "FKBP12-Rapamycin-associated Protein or Mammalian Target of Rapamycin (FRAP/mTOR) Localization in the Endoplasmic Reticulum and the Golgi Apparatus," J. Biol. Chem., vol. 279(1)(Jan. 2, 2004) pp. 772-778.

Bhaduri, A.P. et al., "Potential Antifertility Agents: Syntheses of 2,4,5-Substituted Imidazoles," Indian J. Chem., vol. 4 (Sep. 1966) pp. 419-420.

Bian, Z. et al., "Syntheses, spectroscopic and crystal structual studies of novel imidazo[4,5-f]1,10-phenanthroline derivatives and their Eu(III) tenary complexes with dibenzoylmethane," Polyhedron, vol. 21 (2002) pp. 313-319.

Bian, et al., "The Convenient Synthesis of Amphiphilic Phenanthroline Derivatives," Synthetic Communications, vol. 33(20) (2003) pp. 3477-3482.

Bing et al., "Synthesis of efficient blue and red light emitting phenanthroline derivatives containing both hole and electron transporting properties," Tetrahedron Letters, vol. 45(33) (2004) pp. 6361-6363.

Boyd, M.R. et al., "Data Display and Analysis Strategies for the NCI Disease-Oriented In Vitro Antitumor Drug Screen," in Cytotoxic Anticancer Drugs: Models and Discovery and Development, Klimar Academic, Hingham, MA (1992) pp. 11-34.

Cairo, G. et al., "Induction of Ferritin Synthesis by Oxidative Stress," J. Biol. Chem., vol. 270(2) (1995) pp. 700-703.

Cammack et al, "EPR Spectroscopy of Iron," Methods Enzymol., vol. 227, Academic Press, Inc. (1993) pp. 353-384.

Cantley, L.C., "The phosphoinositide 3-kinase pathway," Science, vol. 296 (May 31, 2002) pp. 1655-1657.

Chao, H. et al., "Mono-,di- and tetra-nuclear ruthenium(II) complexes containing 2,2'-phenylenebis(imidazo[4,5-f]phenanthroline): synthesis, characterization and third-order non-linear optical properties," J. Chem. Soc., Dalton Trans., vol. 12 (2001) pp. 1920-1926.

Chen, J.L. et al., "Gut-enriched Kruppel-like factor represses cyclin D1 promoter activity through Sp1 motif," Nucleic Acids Research, vol. 28(15) (2000) pp. 2969-2976.

Chen, Z.Y. et al., "Gut-enriched Kruppel-like Factor Represses Ornithine Decarboxylase Gene Expression and Functions as Checkpoint Regulator in Colonic Cancer Cells," J. Biol. Chem., vol. 227(48) (Nov. 29, 2002) pp. 46831-46839.

Chen, X. et al., "Transcriptional Profiling of Kruppel-like Factor 4 Reveals a Function in Cell Cycle Regulation and Epithelial Differentiation," J. Mol. Biol., vol. 326(3) (2003) pp. 665-677.

Chen, S.F. et al., "Selective Inhibition of Dihydroorotate (DHO-DHase) by Brequinar Sodium," Proc. Am. Assoc. Cancer Res., vol. 31 (1990) p. A2644.

Chen et al., "Kruppel-like factor 4 is transactivated by butyrate in colon cancer cells," J. Nutr., vol. 134(4) (2004) pp. 792-798.

Cohen, S.R. et al, "The McGill Quality of Life Questionnaire: a measure of quality of life appropriate for people with advanced disease. A preliminary study of validity and acceptability," Palliative Medicine, vol. 9 (1995) pp. 207-219.

Coyle-Rink, J. et al., "Developmental Expression of Wnt Signaling Factors in Mouse Brain," Cancer Biology & Therapy, vol. 1(6) (2002) pp. 640-645.

Crosasso, P. et al., "Preparation, characeterization and properties of sterically stabilized paclitaxel-containing liposomes," J. Controlled Release, vol. 63 (2000) pp 19-30.

Dang, D.T. et al., "Expression of the gut-enriched Kruppel-like factor (Kruppel-like factor 4) gene in the human colon cancer cell line RKO is dependent on CDX2," Oncogene, vol. 20(35) (2001) pp. 4884-4890.

Dang, D.T. et al., "Opposing effects of Kruppel-like factor 4 (gut enriched Kruppel-like factor) and Kruppel-like factor 5 (intestinal-enriched Kruppel-like factor) on the promoter of the Kruppel-like factor 4 gene," Nucleic Acids Res., vol. 30(13) (2002) pp. 2736-2741.

Dos Santos, L.D. et al., "Improved retention of idarubicin after intravenous injection obtained for cholesterol-free liposomes," Biochim Biophys. Acta., vol. 1561 (2002) pp. 188-201.

Dos Santos, K.A. et al., "pH gradient loading of anthracyclines into cholesterol-free liposomes: enhancing drug loading rates through use of ethanol," Biochim. Biophys. Acta, vol. 1661 (2004) pp. 47-60.

Drummond, C. et al., "Optimizing liposomes for delivery of chemotherapeutic agents to solid tumors," Pharmacological Reviews, vol. 51(4) (1999) pp. 691-743.

Eisenstein, R.S. et al, "Iron Regulatory Proteins, Iron Responsive Elements nd Iron Homeostasisi[1,2]," J. Nutr., vol. 128(12) (1998) pp. 2295-2298.

Ekwall, B., "Screening of Toxic Compounds in Mammalian Cell Cultures," Annals N.Y. Acad. Sci, vol. 407 (1983) pp. 64-77.

Embree, L. et al., "Pharmacokinetic behavior of vincristine sulfate following administration of vincristine sulfate liposome injection," Cancer Chemothr. Pharmacol., vol. 41 (1998) pp. 347-352.

Fields, R.D. et al, "Dual-attribute continuous monitoring of cell proliferation/cytotoxicity," Am. Biotechnol. Lab., vol. 11 (1993) pp. 48-50.

File, T.M., Jr. et al., "Antimicrobial therapy of community-acquired pneumonia," Infect. Dis. Clin. North Am., vol. 18 (2004) pp. 993-1016.

Flatmark, T. et al., "Mitochondrial 'Non-Heme Non-FeS Iron' and It's Significance in the Cellular Metabolism of Iron," Proteins of Iron Metabolism, Brown, Aisen, Fielding and Crichton, eds., New York, Grun & Stratton (1976) pp. 349-358.

Fruman, D.A. et al., "Phosphoinositide binding domains: embracing 3-phosphate," Cell, vol. 97(7) (1999) pp. 817-820.

Fruman, D.A. et al., "Phosphoinositide kinases," Annu. Rev. Biochem., vol. 67 (1998) pp. 481-507.

Gabizon, A. et al., "Effect of liposome composition and other factors on the targeting of liposomes to experimental tumors: biodistribution and imaging studies," Cancer Res., vol. 50 (1990) pp. 6371-6378.

Gaidenko, T.A. et al., "The PrpC serine threonine phosphatase and PrkC kinase have opposing physiological roles in stationary-phase Bacillus subtilis cells," J. of Bacteriol., vol. 184(22) (2002) pp. 6109-6114.

Gaodeng et al., Chemical Journal of Chinese Universities, vol. 24(10) (2003) pp. 1753-1855 (translation needed).

Gower, J.D. et al, "Determination of Desferrioxamine-Available Iron in Biological Tissues by High-Pressure Liquid Chromatography," Analytical Biochemistry, vol. 180 (1989) pp. 126-130.

Grimmett, M.R., "Imidazoles and their Benzo Derivatives: (iii) Synthesis and Applications, 4.08.1 Ring Synthesis from Non-Heterocyclic Compounds," *Comprehensive Heterocyclic Chemistry: the Structure, Reaction, Synthesis and Uses of Hetrocyclic Compounds*, Katrizky and Rees, eds., vol. 5, Pergamon Press, Oxford (1984)pp. 457-498.

Gross, C. et al, "Identification of the Copper Regulon in Saccharomyces cerevisiae by DNA Microarrays," J. Biol. Chem., vol. 275(41) (Oct. 13, 2000) pp. 32310-32316.

Hanai, T. et al., "Prediction of retention factors of phenolic and nitrogen-containing compounds in reversed-phase liquid chromatography based on logP and pKa obtained by computational chemical calculation," Journal of Liquid Chromatography & Related Technologies, vol. 23(3) (2000) pp. 363-385.

Haroon, Z.A. et al., "Loss of metal transcription factor-1 suppresses tumor growth through enhanced matrix deposition," Faseb J., vol. 18(11) (2004) pp. 1176-1184.

Hiort, C. et al., "DNA Binding of $\Delta$- and $\lambda$-[Ru(phen)$_2$DPPZ]$^{2+}$," J. Am. Chem. Soc., vol. 115 (1993)pp. 3448-3454.

Hollingshead, M. et al., "In Vivo Cultivation of Tumor Cells in Hollow Fibers," Life Sciences, vol. 57)2) (1995) pp. 131-141.
Hong, X. et al., "Synthesis and spectroscopic RNA binding studies of [Ru(phen)$_2$MHPIP]$^{2+}$," Inorg. Chem. Commun., vol. 6(2003) pp. 766-768.
Hong, X. et al., "Effects of ligand planitary on the interaction of polypyridyl Ru(II) complexes with DNA," J. Royal Society of Chemistry., Dalton Trans., vol. 11 (2003) pp. 2260-2268.
Janoff, A.S., "Liposomal delivery of drugs, genes and vaccines," Liposomes: Rational Design, Biotechnology Advances, vol. 17 (1999) pp. 511-513.
Kihara, A. et al., "Beclin-phosphatidylinositol 3-kinase complex functions at the trans-Golgi network," EMBO Rep., vol. 2(4) (2001) pp. 330-335.
King, F.G. et al., "Physiological pharmacokinetic parameters for cisdichlorodiammineplatinum(II) (DDP) in the mouse," J. Pharmacokinet. Biophar., vol. 20 (1) (1992) pp. 95-99.
Kitano, Y. et al., "Suppression of proliferation of human epidermal keratinocytes by 1,25-dihydroxyvitamin D$_3$," Euro J. Clin. Investg., vol. 21 (1991) pp. 53-58.
Kozlov, A.V. et al., "Intracellular Free Iron in Liver Tissue and Liver Homogenate: Studies with Electron Paramagnetic Resonance on the Formation of Paramagnetic Complexes with Desferal and Nitric Oxide," Free Radic. Biol. Med., vol. 13 (1992) pp. 9-16.
Langmade, S.J. et al., "The Transcription Factor MTF-1 Mediates Metal Regulation of the Mouse ZnT1 gene," J. Biol. Chem., vol. 275(44) (Nov. 3, 2000) pp. 34803-34809.
Lichtlen, P. et al., "Putting its fingers on stressful situations: the heavy metal- regulatory transcription factor MTF-1," Bioessays, vol. 23(11) (2001) pp. 1010-1017.
Liggins, R.T.. et al., "Solid-state characterization of paclitaxel," J. Pharm. Sci., vol. 86)12) (Dec. 12, 1997) pp. 1458-1563.
Linden P.K., "Treatment options for vancomycin-resistant enterococcal infections," Drugs, vol. 62 (2002) pp. 425-441.
Liu, J. et al., "Influence of serum protein on polycarbonate-based copolymer micelles as a delivery system for a hydrophobic anti-cancer agent," J. Controlled Release, vol. 103 (2005) pp. 481-497.
Liu, J. et al., "Polymer-drug compatibility: a guide to the development of delivery systems for the anticancer agent, ellipticine," J. Pharm. Sci., vol. 93(1) (2004) pp. 132-143.
Lockshin, R.A. et al., "Apoptosis, autophagy and more," Int. J. Biochem. Cell Biol., vol. 36(12) (2004) pp. 2405-2419.
Lowry, F.D., Staphylococcus aures infections, N. Engl. J. Med, Vol. 339(8) (1998) pp. 520-532.
Lukyanov, A.N. et al., "Polyethylene glycol-diacyllipid micelles demonstrate increased accumulation in subcutaneous tumors, in mice," Phar. Res., vol. 19(10) (2002) pp. 1424-1429.
Martini, L.A. et al., "Iron Treatment Downregulates DMT1 and IREG1 mRNA.Expression in Caco-2 cells," J. Nutr., vol. 132(4) (2002) pp. 693-696.
McCorkle, R. et al., "Development of a system distress scale" Cancer Nursing, vol. 1 (1978) pp. 373-378.
Meijer, A.J. et al., "Regulation and role of autophagy in mammalian cells," Int. J.Biochem. Cell Biol., vol. 36(12) (2004) pp. 2445-2462.
Moghimi, S.M. et al., "Real-time evidence of surface modification at polystyrene lattices by poloxamine 908 in the presence of serum: in vivo conversion of macrophage-prone nanoparticles to stealth entities by poloxamine 908," FEBS. Lett., vol. 547 (2003) pp. 177-182.
Monks, A. et al., "Feasibility of a High-flux Anticancer Drug Screen Using a Diverse.Panel of Cultured Human Tumor Cell Lines," J. Natl. Cancer Inst., vol. 83(11) (Jun. 5, 1991)pp. 757-766.
Moribe, K. et al., "Encapsulation characteristics of nystatin in liposomes: effects of cholesterol and polyethylene glycol derivatives," International Journal of Pharmaceutics, vol. 188 (1999) pp. 193-202.
Mizumura, Y. et al., "Cisplatin-incorporated polymeric micelles eliminate.nephrotoxicity, while maintaining antitumor activity," Japanese Journal of Cancer Research, vol. 92 (2001) pp. 328-336.
Nielson, P. et al., "Non-Transferrin-Bound-Iron in Serum and Low-Molecular-Weight-Iron in the Liver of Sietary Iron-Loaded Rats," in. J. Biochem., vol. 25(2) (1993) pp. 223-232.

O'Brien, J. et al., "Investigation of the Alamar Blue (resazurin) fluorescent dye for the assessment of mammalian cell cytotoxicity," Eur. J. Biochem., vol. 267 (2000) pp. 5421-5426.
Office Action dated Nov. 18, 2009 for U.S. Appl. No. 10/525,690.
Office Action dated Dec. 14, 2009 for U.S. Appl. No. 10/525,690.
Office Action dated Jun. 4, 2010 for U.S. Appl. No. 10/525,690.
Notice of Allowance dated Aug. 26, 2010 for U.S. Appl. No. 10/525,690.
Office Action dated Jan. 28, 2008 for U.S. Appl. No. 10/579,149.
Office Action dated Jan. 8, 2010 for U.S. Appl. No. 10/579,149.
Office Action dated Oct. 29, 2010 for U.S. Appl. No. 10/579,149.
Öllinger, K. et al., "Nutrient Deprivation of Cultured Rat Hepatocytes Increases the Desferrioxamine-available Iron Pool and Augments the Sensitivity to Hydrogen Peroxide," J. Biol. Chem. vol. 272(38) (1997) pp. 23707-23711.
Patel, R., "Clinical impact of vancomycin-resistant enterococci," J. Antimicrob. Chemother., vol. 51(Suppl. S3) (2003) pp. 13-21.
Patel, H.M. et al., "Serum-mediated recognition of liposomes by phagocytic cells of the reticuloedothelial system—The concept of tissue specificity," Adv. Drug Deliv. Rev., vol. 32 (1998) pp. 45-60.
Petrat, F. et al., "The Chelatable Iron Pool in Living Cells: A Methodically Defined Quantity," Biol.Chem., vol. 383(3-4) (2002) pp. 489-502.
Rameh, L.E. et al., "The role of phosphoinositide 3-kinase lipid products in cell function," J. Biol. Chem., vol. 274(13) (1999) pp. 8347-8350.
Rubinstein, L.V. et al., "Comparison of in Vitro Anticancer-Drug-Screening Data Generated with a Tetrazolium Assay Versus a Protein Assay Against a Diverse Panel of Human Tumor Cell Lines," J. Natl. Cancer Inst., vol. 82 (1990) pp. 1113-1118.
Sakurai, Y. et al., "Development of the polymer micelle carrier system for doxorubicin," J. Controlled Release, vol. 74 (2001) pp. 295-302.
Scialli, R. et al., "Protective effects of liposome encapsulation on paclitaxel development toxicity in the rat," Teratology, vol. 56 (1997) pp. 305-310.
Sharma, E. et al., "Activity of paclitaxel liposome formulations against human ovarian tumor xenografts," Int. J. Cancer, vol. 71 (1997) pp. 103-107.
Sherr, C.J. et al., "Inhibitors of marrmalian G1 cyclin-dependent kinases," Genes and Development, vol. 9(10) (1995) pp. 1149-1163.
Shie, J.L. et al., "Gut-enriched Kruppel-like factor represses cyclin D1 promoter activity through Sp1 motif," Nucleic Acids Res., vol. 28(15) (2000) pp. 2969-2976.
Shie, J.L. et al., "Role of gut-enriched Kruppel-like factor in colonic cell growth and differentiation," A. J. Physiol. Gastrointest. Liver Physiol., vol. 279(4) (2000) pp. G806-G814.
Shields, J.M. et al., "Identification and Characterization of a Gene Encoding a Gut-enriched Kruppel-like Factor Expressed during Growth Arrest," The Journal of Biological Chemistry, vol. 271(33) (1996) pp. 20009-20017.
Siegel, T. et al., "Doxorubicin encapsulated in sterically stabilized liposomes for the treatment of a brain tumor model: biodistribution and therapeutic efficacy," J. Neurosurg., vol. 83 (1995) pp. 1029-1037.
Simor, A. et al., "Characterization and proposed nomenclature of epidemic strains of methicilin-resistant Staphylococcus aureus in Canada," Can. Commun. Dis. Rep., vol. 25(12) (1999) pp. 105-108.
Skehan, P. et al., "New Colorimetric Cytotoxicity Assay for Screening," J. Natl. Cancer Inst., vol. 82 (1990) pp. 1107-1112.
Tardi, P.G. et al., "Iposomal doxorubicin," J. Drug Targeting, vol. 4(3) (1996) pp. 129-140.
Torchilin, V.P. et al., "Immunomicelles: Targeted pharmaceutical carriers for poorly soluble drugs," Proc. Natl. Acad. Sci., USA, vol. 100 (2003) pp. 6039-6044.
Vanhaesebroeck, B. et al., "Signaling by distinct classes of phosphoinositide 3- kinases," Exp. Cell Res., vol. 253(1) (1999) pp. 239-254.
Vassilev, L.T. et al., "Cell-based screening approach for antitumor drug leads which.exploits sensitivity differences between normal and cancer cells: identification of two novel cell-cycle inhibitors," Anti-Cancer Drug Design, vol. 16 (2001) pp. 7-17.

Weissig, V. et al., "Accumulation of protein-loaded long-circulating micelles and liposomes in subcutaneous Lewis lung carcinoma in mice," Phar. Res., vol. 15(10) (1998) pp. 1552-1556.

West, M.R. et al, "Simple Assays of Retinoid Activity as Potential Screens for Compounds That May Be Useful in Treatment of Psoriasis," J. Investigative Derm., vol. 99 (1992) pp. 95-100.

Yamada, M. et al., "Synthesis of 2,9-Dichloro-1,10-phenanthroline from N,N'-Annelated Phenanthrolinediones," Bull. Soc. Chem. Jpn., vol. 63(9) (1990) pp. 2710-2712.

Yamamoto, Y. et al., "Long-circulating poly(ethylene glycol)-poly(D,L-lactide) block copolymer micelles with modulated surface charge," J. Controlled Release, vol. 77 (2001) pp. 27-38.

Yegorov, D.Y. et al., "Simultaneous Determination of Fe(III) and Fe(II) in Water Solutions and Tissue Homogenates Using Desferal and 1,10-Phenanthrolin," Free Radic. Biol. Med., vol. 15 (1993) pp. 565-574.

Yokoyama, M. et al., "Characterization of physical entrapment and chemical conjugation of adriamycin in polymeric micelles and their design for in vivo delivery to a solid tumor," J. of Controlled Release, vol. 50 (1998) pp. 79-92.

Zalewski, P.D. et al., "Correlation of apoptosis with change in intracellular labile Zn(II) using Zinquin [(2-methyl-8-p-toluenesulphonamido-6-quinolyloxy)acetic acid], a new specific fluorescent probe for Zn(II)," Biochem. J., vol. 296(Pt. 2) (1993) pp. 403-408.

Zhang, C., "Bacterial signaling involving eukaryotic-type protein kinases," Mol Microb., vol. 20(1) (1996) pp. 9-15.

Zhang, J.A. et al., "Development and characterization of a novel Cremophor® EL free liposome-based paclitaxel (LEP-ETU) formulation," Eur. J. Pharm. Biophar., vol. 59 (2005) pp. 177-187.

Zhang, W. et al., "The gut-enriched Kruppel-like factor (Kruppel-like factor 4) mediates the transactivating effect of p53 on the p21WAF1/Cip1 promoter," J. Biol. Chem., vol. 275 (24) (2000) pp. 18391-18398.

Zhao, W. et al., "Identification of Kruppel-like factor 4 as a potential tumor suppressor gene in colorectal cancer," Oncogene, vol. 23(2) (2004) pp. 395-402.

Zhuang, H. et al., Synthesis and character of two new N1-phenanthroline flue-rescence probe for nucleic acid determination, College of Environment Science and Engineering, Huaxue Shiji, vol. 25(6) (2003) pp. 325-328 (Abstract).

-322           KLF4 gene promoter region           -291

5' AACCTGCGCCCGGTTCCTCGCGCCCGCGCTG 3'

TGCGCCC

MTF-1

GCGCCCC

Sp1/KLF4

GCGCCCG

Sp1/KLF4

B

Sp1

DMSO      Cmpd 3

Excess unlabeled competitor    −    +    −    +

C

KLF4

DMSO      Cmpd 3

Excess unlabeled competitor    −    +    −    +

A

-135            Cyclin D1 gene promoter region           -100

5' GCCCCCTCCCCCTGCGCCCGCCCCCGCCCCCCTCCCG 3'
```
                        GCGCCCG     CCGCCCC
                         KLF4       Sp1/KLF4
                        CCGCCCC
                        Sp1/KLF4
```

B

| | DMSO | + | + | + | |
|---|---|---|---|---|---|
| | Cmpd 3 | | + | + | + |

Input DNA    Anti-KLF4 Pull-down    Anti-Sp1 Pull-down

A

B

A.

B.

A.

B.

A.

B.

A.

B.

A.

B.

A.

B.

A.

B.

A.

B.

A.

B.

A.

B.

A.

B.

C.

A.

B.

A.

B.

A.

B.

C.

D.

A.

B.

C.

2-INDOLYL IMIDAZO [4,5-D] PHENANTHROLINE DERIVATIVES AND THEIR USE IN THE TREATMENT OF CANCER

FIELD OF THE INVENTION

The present invention relates to the field of cancer therapies and in particular to the use of 2-indolyl imidazo[4,5-d] phenanthroline derivatives in the treatment of cancer.

BACKGROUND OF THE INVENTION

Metal chelators have been developed for the treatment of diseases resulting from metal overload. More recently, however, compounds capable of chelating iron are being studied as potential anticancer therapies, as iron has an important role in active sites of a wide range of proteins involved in energy metabolism, respiration, and DNA synthesis. One such protein, ribonucleotide reductase (RR) is an iron-containing protein that is essential for the conversion of ribonucleotides into deoxyribonucleotides for DNA synthesis and thus, a target for anti-cancer therapies. Many iron chelators are powerful inhibitors of RR due to their ability to bind iron (Richardson, D. R. (2002) Crit Rev Oncol Hematol 42(3): 267-81.). For example, the iron chelator desferrioxamine (DFO), which has been clinically approved for the treatment of iron overload diseases including β-thalassemia (Buss, J. L., B. T. Greene, J. Turner, F. M. Torti and S. V. Torti (2004) Curr Top Med Chem 4(15): 1623-35), has also been shown to be an inhibitor of RR. Moreover, some aggressive tumours have been shown to be sensitive to iron chelation by DFO. The use of DFO, however, is costly, requires long subcutaneous administration and the compound exhibits a short half-life. In addition to DFO, other iron chelators with anti-proliferative activity are in development, including Triapine (currently in phase II), 311, tachpyridine, and O-Trensox (Richardson, supra). Triapine may, however, have limited usefulness as an anticancer therapy as it exhibits low solubility in water.

U.S. Pat. No. 6,589,966 describes a novel family of metal chelators characterized as hexadentate chemical compounds that bind iron and that have antiproliferative activity against tumour cells. In addition, U.S. Patent Application No. 2002/0119955 describes additional compounds based on 3-AP (structurally related to Triapine) that may exhibit adequate therapeutic utility in the treatment of neoplasia, including cancer.

The chelation of zinc may also be an important but relatively unexplored determinant of the biological effects of iron chelators. For example, the iron chelator tachpyridine, which is under preclinical investigation as a potential anti-cancer agent, chelates zinc in addition to iron, and this may play a role in its cytotoxicity (Zhao, R., et al. (2004) Biochem Pharmacol 67(9): 1677-88.). Zinc has catalytic and structural roles in hundreds of zinc-dependent enzymes and zinc-finger motifs of proteins involved in DNA-protein or protein-protein interaction. Consequently, deficiency as well as overload of zinc causes a wide variety of alterations in mammalian metabolism. Depletion of zinc in vitro has been shown to cause apoptosis (McCabe, M. J., Jr., S. A. Jiang and S. Orrenius (1993) Lab Invest 69(1): 101-10), to significantly decrease cell proliferation of colon carcinoma HT-29 cells (Kindermann, B., F. Doring, M. Pfaffl and H. Daniel (2004) J Nutr 134(1): 57-62), and to alter cell cycle progression (Chen, X., et al. (2001) J Biol Chem 276(32): 30423-8.).

Alternatively, other metal chelators may exert anti-neoplastic effects through the formation of cytotoxic chelate complexes. This occurs predominantly with the redox-active metals, iron and copper. For example, bleomycins are a family of glycopeptide antibiotics with anti-tumour activity. They are used clinically in combination chemotherapy against lymphomas, squamous cell carcinomas and germ cell tumours. They contain a DNA binding domain and a metal binding domain, which binds Fe(II) or Cu(I). The presence of oxygen and a reductant leads to DNA cleavage through the formation of radical intermediates (Chen, J. and J. Stubbe (2005) Nat Rev Cancer 5(2): 102-12). The iron chelator Triapine, which inhibits RR by chelating iron, may also damage RR and other vital molecules by the generation of free radicals upon formation of the iron complex (Chaston, T. B., et al. (2003) Clin Cancer Res 9(1): 402-14). The use of bleomycin conjugates for targeting a compound to a body tumour are described in U.S. Pat. No. 4,758,421.

The cytotoxicity of the metal chelator 1,10-phenanthroline (OP) has been attributed to its ability to function as both chelator and chelate type. As a chelator, it has been shown to combine with zinc or iron and thus inhibit enzymes that require zinc or iron for activity. Alternatively, chelate complexes of 1,10-phenanthroline with divalent metal ions are reported to be cytotoxic (Shulman, A. and G. A. Laycock (1977) Chem Biol Interact 16(1): 89-99.) and the copper-chelate promotes the degradation of DNA (Downey, K. M., B. G. Que and A. G. So (1980). Biochem Biophys Res Commun 93(1): 264-70). Complexes of copper-OP can bind non-covalently to the DNA minor groove, and catalyze the single strand cleavage of nucleic acids in the presence of hydrogen peroxide and a reductant (Sigman, D. S., et al. (1979) J Biol Chem 254(24): 12269-72).

Copper-OP complexes are frequently used as chemical nucleases, and high-specificity DNA cleavage agents have been generated by attachment to sequence specific DNA binding proteins (Pan, C. Q., R. Landgraf and D. S. Sigman (1994) Mol Microbiol 12(3): 335-42.). OP is also used widely as an inhibitor of matrix metalloproteases (Springman, E. B., et al. (1995) Biochemistry 34(48): 15713-20) and has been shown to inhibit the synthesis of glycophosphatidylinositol (GPI) anchors (Mann, K. J. and D. Sevlever (2001) Biochemistry 40(5): 1205-13) through chelation of zinc.

Deregulation of tumour suppressor genes has been implicated in the development of cancer but the precise role of these tumour suppressor genes in the development of cancer is still not clear. The Krüppel-like factor (KLF) family of genes is a family of evolutionarily conserved zinc-finger containing transcription factors with diverse regulatory roles in cell growth, proliferation, differentiation and embryogenesis (Ghaleb, A. M., et al. (2005) Cell Res 15(2): 92-6). KLFs can function as either transcriptional activators or repressors or both, depending on their interaction with co-activators or co-repressors via specific amino-terminal domains, the promoters they bind, and the cellular context of their function (Kaczynski, J., T. Cook and R. Urrutia (2003) Genome Biol 4(2): 206). Several members of the KLF family are thought to be tumour suppressors and are involved in carcinogenesis. For example, down-regulation of KLF4 is found in colon cancer (Dang D T, et al. (2000) FEBS Lett, 476: 203-7) and down-regulation of KLF5 and KLF10 occurs in breast cancer (Chen C, et al. (2002) Oncogene, 21: 6567-72; Subramaniam M, et al. (1998) J Cell Biochem, 68: 226-36). KLF6 has also been suggested to be a candidate tumour suppressor gene at chromosomal location 10p15, with frequent mutations observed in prostate adenocarcinoma. Moreover, KLF6 was also shown to transactivate WAF1, which encodes a cyclin-dependent kinase inhibitor of the cell cycle via a p53-independent pathway (Narla G, et al. (2001) *Science,* 294: 2563-6).

Deregulation of KLF4 has been linked to cancers other than colon cancer both in vitro and in vivo, suggesting that KLF4 may have a tumour suppressor effect. In colorectal cancers, the level of KLF4 mRNA is reduced compared to normal matched tissues (Dang et al. (2000), supra), and re-expression of KLF4 in a colorectal cancer cell line results in diminished tumourigenicity (Dang, D. T., et al. (2003) *Oncogene* 22(22): 3424-30). A similar down-regulation and growth suppressive effect of KLF4 has also been described in bladder cancer (Ohnishi, S., et al. (2003) *Biochem Biophys Res Commun* 308(2): 251-6.), gastric cancer (Wei, D., et al. (2005) *Cancer Res* 65(7): 2746-54.), esophageal cancer (Wang, N., et al. (2002). *World J Gastroenterol* 8(6): 966-70), and adult T-cell leukemia (Yasunaga, J., et al. (2004). *Cancer Res* 64(17): 6002-9). In contrast to the tumour suppressor effect of KLF4, increased expression of KLF4 has been reported during progression of breast cancer (Foster, K. W., et al. (2000). *Cancer Res* 60(22): 6488-95.) and squamous cell carcinoma of the oral cavity (Foster, K. W., et al. (1999). *Cell Growth Differ* 10(6): 423-34.). In addition, KLF4 has been considered as a marker of an aggressive phenotype in early-stage infiltrating ductal breast carcinoma (Pandya, A. Y., et al. (2004). *Clin Cancer Res* 10(8): 2709-19.). Thus, while KLF4 likely plays a tumour suppressor role in gastrointestinal cancers and leukemia, the role of KLF4 in the development of other types of cancers is still not clear.

The expression of KLF4 is negatively regulated by zinc. Studies on the effect of zinc depletion on gene expression in colon carcinoma HT-29 cells using human oligonucleotide arrays showed that KLF4 gene expression was one of the most significantly up-regulated among ~10,000 target genes tested. It has been hypothesized, therefore, that KLF4 may be a direct link between cellular zinc status and growth inhibition (Kindermann, B., F. Doring, M. Pfaffl and H. Daniel (2004). *J Nutr* 134(1): 57-62.). In a subsequent study, expression of KLF4 was found to be increased in cells over-expressing metal transcription factor-1 (MTF-1) (Kindermann, B., F. Doring, J. Budczies and H. Daniel (2005). *Biochem Cell Biol* 83(2): 221-9.). MTF-1 is a zinc-sensory transcriptional activator with six zinc-fingers, which binds to metal-responsive elements (MREs) of target genes, and the promoter of KLF4 also has 3 MREs. MTF-1 is usually up-regulated in zinc deficient cells and increased expression of MTF-1 has been observed in zinc-deficient HT-29 cells (Kindermann et al. 2004, supra). Therefore, zinc responsiveness of KLF4 in HT-29 is mediated at least in part by MTF-1 (Kindermann et al. 2005, supra). The expression of KLF4 is primarily associated with a terminally differentiated state of epithelial cells in organs such as gut, skin and thymus (Kaczynski et al. 2003, supra).

As described above, 1,10-phenanthroline (OP) is a well known metal chelator. Recent studies have investigated derivatives of 1,10-phenanthroline and their ability to chelate various metals. For example, Chao et al., have synthesized 1,3-bis([1,10]) phenanthroline-[5,6-d]imidazol-2-yl)benzene (mbpibH2) and its (bpy)2Ru$^{2+}$ complexes and studied their electrochemical and spectroscopic properties (*Polyhedron,* 2000, 1975-1983). Liu et al., prepared ruthenium complexes with 2-(2-hydroxyphenyl)imidazo[4,5-f][1,10] phenanthroline (HPIP) and studied the binding behaviour of these complexes towards calf thymus DNA (*JBIC,* 2000, 5, 119-128). Similarly, Xu et al., have described the synthesis of 2-(4-methylphenyl)imidazol[4,5-f]1,10-phenanthroline and its Ru(II) complexes and binding of the prepared complexes to calf thymus DNA (New J. Chem., 2003, 27, 1255-1263).

International Patent Application No. PCT/IB04/052433 (WO 2005/047266) describes a broad class of 2,4,5-trisubstituted imidazole compounds, including some 1,10-phenanthroline substituted compounds, and their use in the treatment of cancer.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide 2-indolyl imidazo[4,5-d]phenanthroline derivatives and uses thereof in the treatment of cancer. In accordance with one aspect of the present invention, there is provided a use of a compound having structural formula (I), or a salt thereof, in inhibiting the proliferation of cancer cells:

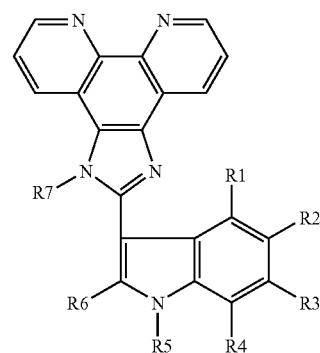

wherein:

R1, R2, R3, R4, R6 and R7 are independently selected from hydrogen, halogen, hydroxyl, thiol, lower alkyl, substituted lower alkyl, lower alkenyl, substituted lower alkenyl, lower alkynyl, substituted lower alkynyl, alkoxy, alkylthio, acyl, aryloxy, amino, amido, carboxyl, aryl, substituted aryl, heterocycle, substituted heterocycle, heteroalkyl, substituted heteroalkyl, heteroaryl, substituted heteroaryl, cycloalkyl, substituted cycloalkyl, nitro, or cyano or —S(O)$_{1-2}$R wherein R is alkyl, substituted alkyl, aryl, substituted aryl, heterocycle, heteroaryl, substituted heterocycle, or substituted heteroaryl;

R5 is H, alkyl, substituted alkyl, alkenyl, substituted alkenyl, alkynyl, substituted alkynyl, aryl, substituted aryl, heteroaryl, substituted heteroaryl, acyl, —CH$_2$-aryl, —CH$_2$—heteroaryl.

In accordance with another aspect of the present invention, there is provided a use of a compound having structural formula (I), or a salt thereof, in inducing apoptosis in a cancer cell.

In accordance with another aspect of the present invention, there is provided a use of a compound having structural formula (I), or a salt thereof, in chelating transition metal ions in a cell.

In accordance with another aspect of the present invention, there is provided a use of a compound having structural formula (I), or a salt thereof, in increasing expression of Krüppel-like factor 4 (KLF4) in a cancer cell nad/or a tumour.

In accordance with another aspect of the present invention, there is provided a use of a compound having structural formula (I), or a salt thereof, in the preparation of a medicament in the treatment of cancer.

In accordance with another aspect of the present invention, there is provided a compound having structural formula (I), or a salt thereof, wherein:
R1, R2, R3, R4 are independently hydrogen; halogen; $C_1$-$C_4$ alkyl; $C_1$-$C_4$ alkoxy; or $C_6$-$C_{14}$ aryl;
R5 is hydrogen; $C_1$-$C_4$ alkyl; $C_1$-$C_4$ alkyl substituted with $C_6$-$C_{14}$ aryl; or $C_4$-$C_6$ cycloalkyl;
R6 is hydrogen; halogen; $C_1$-$C_4$ alkyl; $C_1$-$C_4$ alkyl substituted with $C_5$-$C_6$ heterocycloalkyl wherein the heteroatom is N; $C_6$-$C_{14}$ aryl; $C_6$-$C_{14}$ aryl substituted with $C_1$-$C_4$ alkyl or halo; $C_5$-$C_6$ cycloalkyl; $C_5$-$C_6$ heterocycloalkyl; or polycycloalkyl.

In accordance with another aspect of the present invention, there is provided a compound having structural formula (I), or a salt thereof, wherein:
R1, R2, R3, R4 are independently hydrogen; halogen; $C_1$-$C_4$ alkyl; $C_1$-$C_4$ alkoxy; or phenyl;
R5 is hydrogen; $C_1$-$C_4$ alkyl; $C_1$-$C_4$ alkyl substituted with phenyl; or cyclopentyl;
R6 is hydrogen; halogen; $C_1$-$C_4$ alkyl; $C_1$-$C_4$ alkyl substituted with $C_5$-$C_6$ heterocycloalkyl wherein the heteroatom is N; phenyl; phenyl substituted with $C_1$-$C_4$ alkyl or halo; $C_5$-$C_6$ cycloalkyl; $C_5$-$C_6$ heterocycloalkyl; or adamantane; and
R7 is H.

BRIEF DESCRIPTION OF THE DRAWINGS

These and other features of the invention will become more apparent in the following detailed description in which reference is made to the appended drawings wherein.

FIG. 32 depicts transcription factor binding sites on KLF4 gene promoter (A) and DNA binding activities of Sp1 (B) and KLF4 (C) in HT-29 cells treated with compound 3.

Figure 33:

FIG. 33 depicts transcription factor binding sites on Cyclin D1 gene promoter (A) and in vivo KLF4 and Sp1 binding to Cyclin D1 promoter after compound 3 treatment in HT-29 cells by chromatin immuno-precipitation assay (B).

Figure 34:
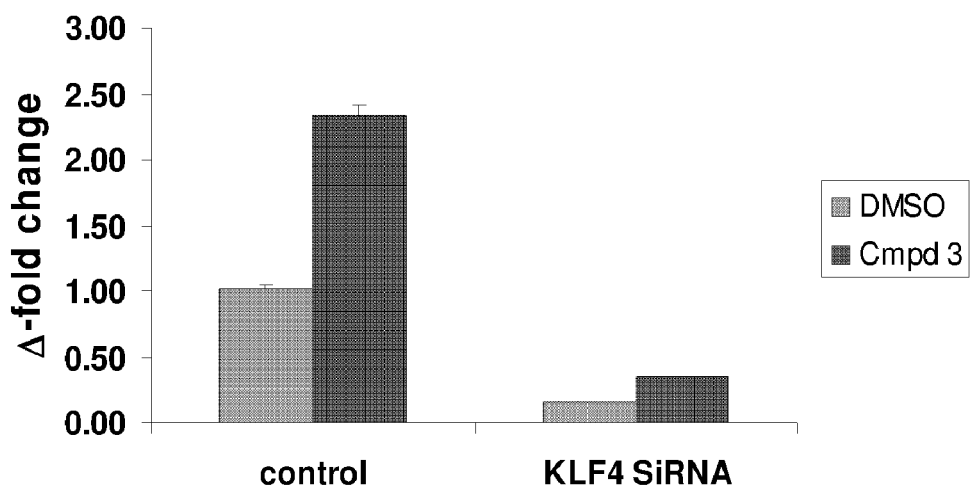
Figure 34:
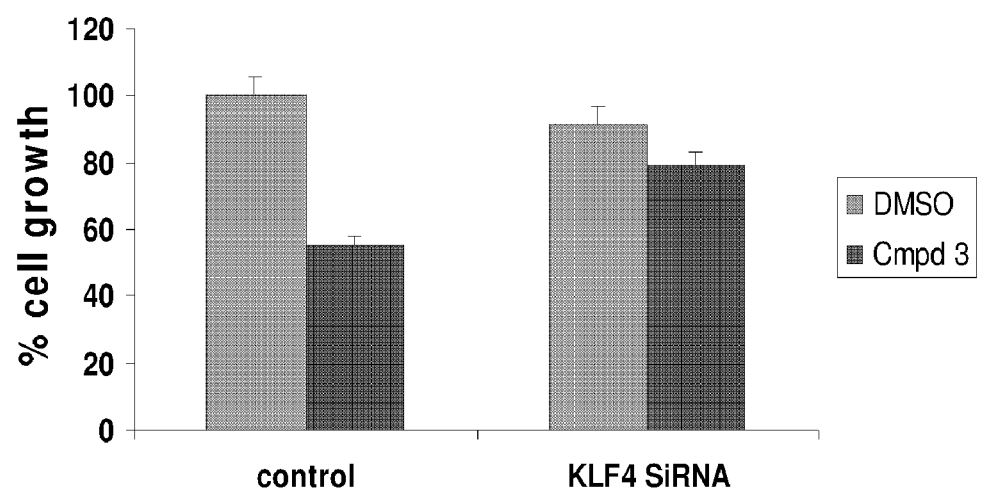

FIG. 34 depicts the effect of compound 3 and knock-down of KLF4 gene by siRNA in HT-29 cells on KLF4 gene expression measured by RT-PCR (A) and on cell proliferation (B).

Figure 35:
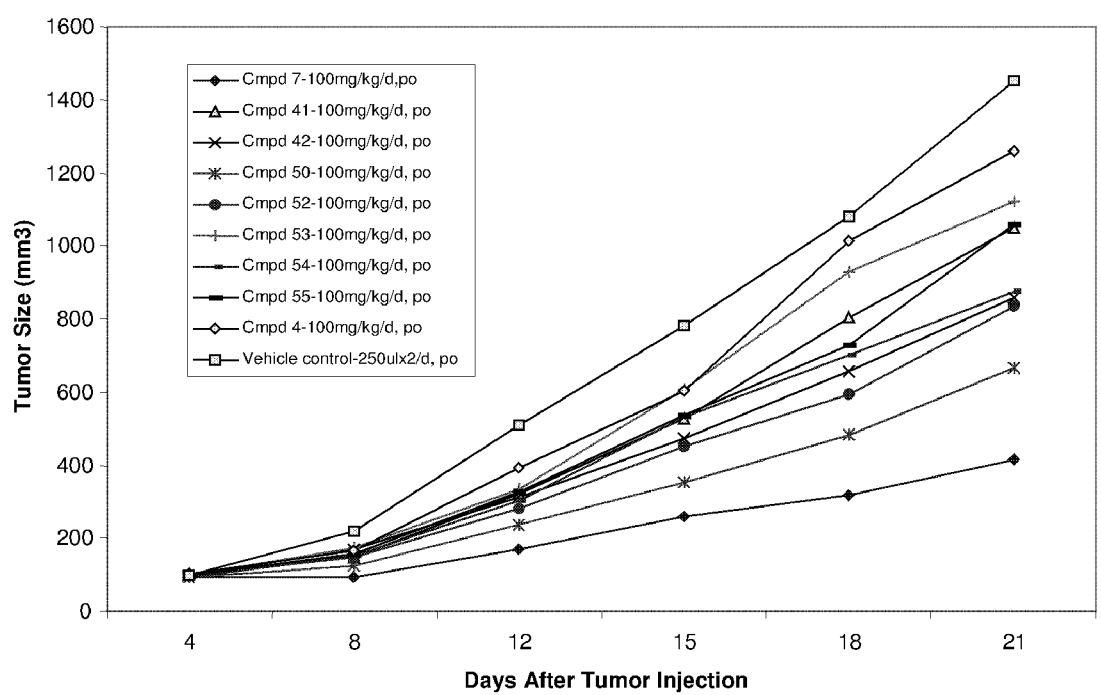

FIG. 35 depicts the ability of compounds 7, 41, 42, 50, 52, 53, 54, 55 and 4 to inhibit tumour cell growth in a large cell lung carcinoma xenograft model.

Figure 36:
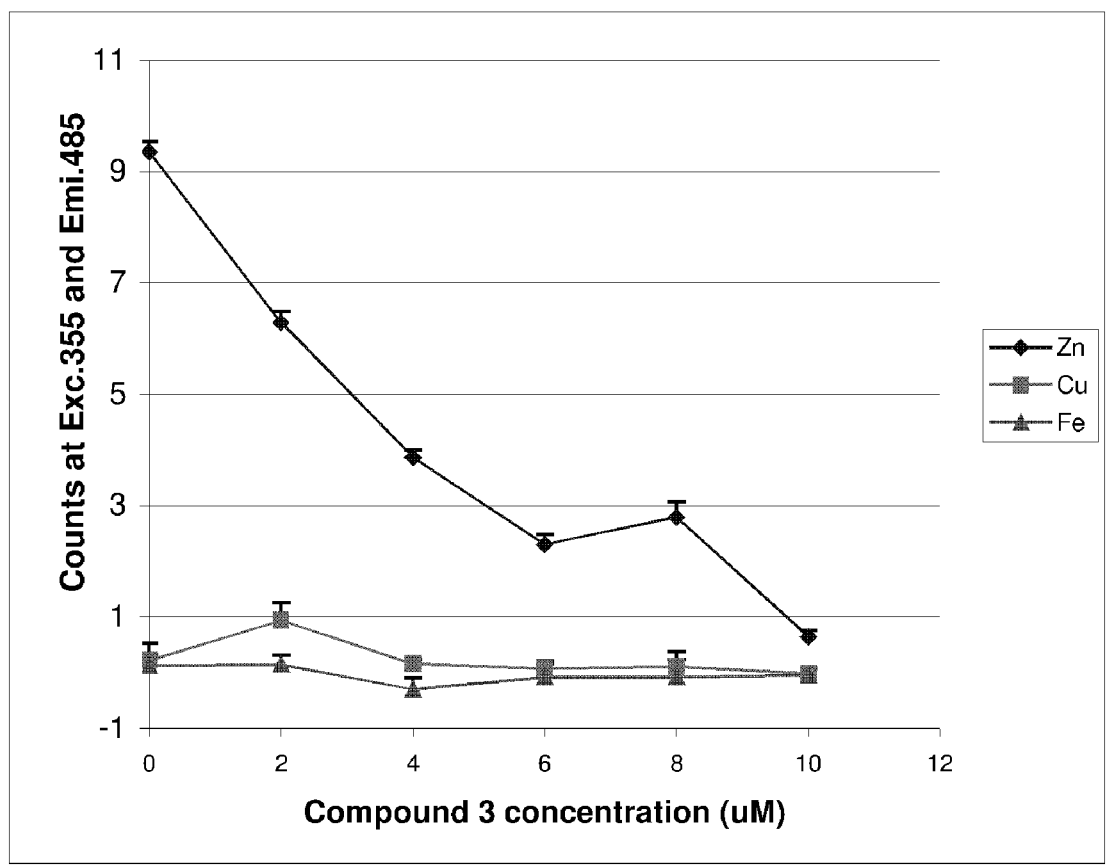

FIG. 36 depicts the ability of compound 3 to chelate zinc ions in vitro, using zinc-sensitive dye Zinquin.

Figure 37:
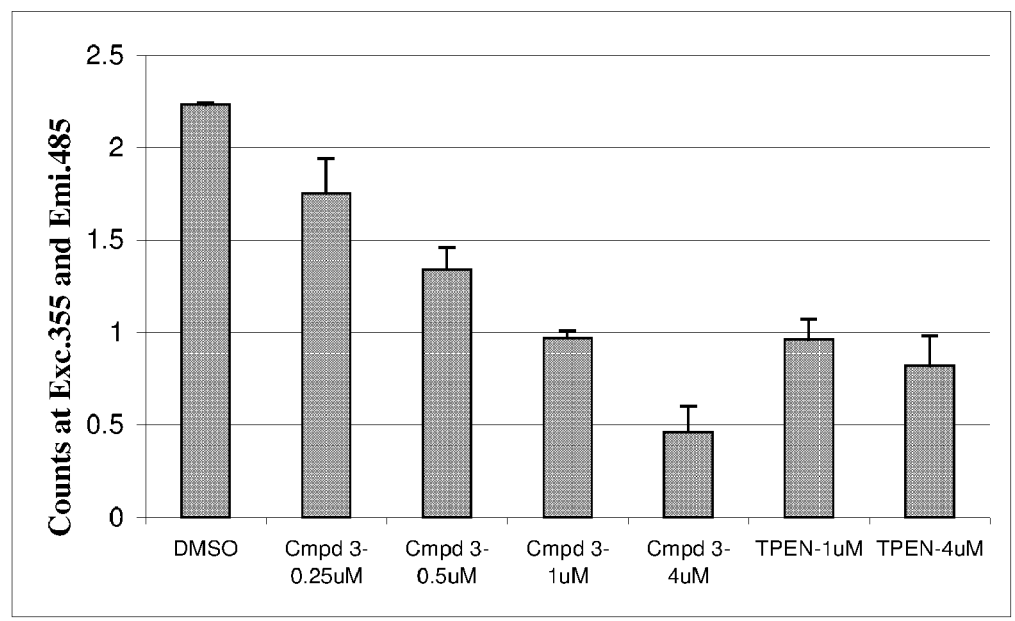
Figure 37:
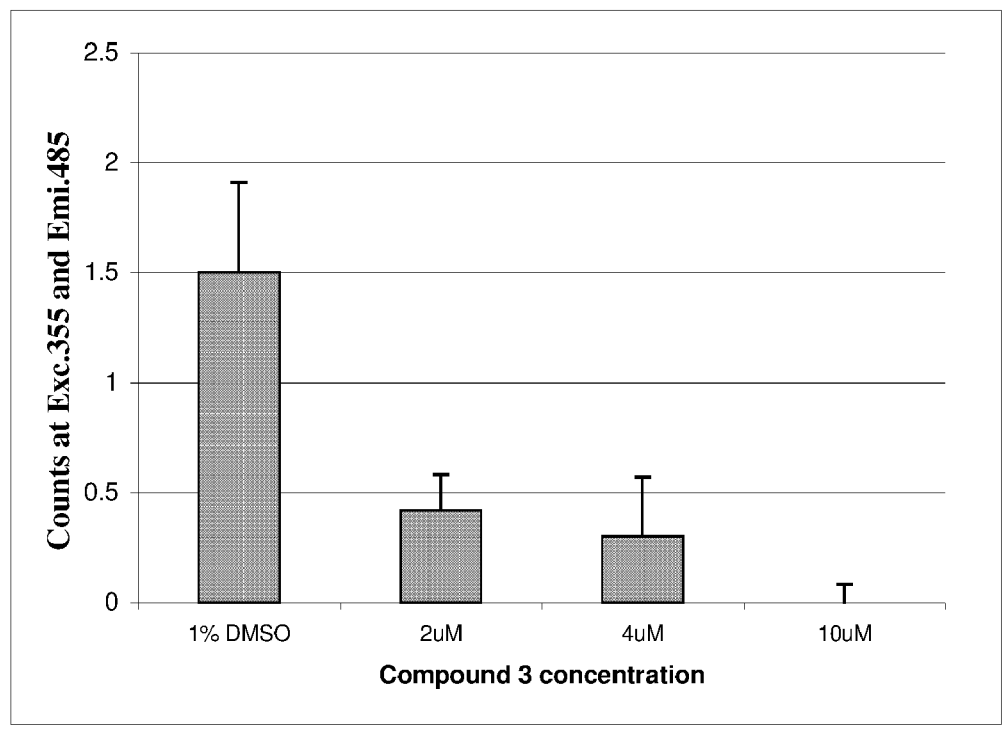

FIG. 37 depicts ability of compound 3 to chelate zinc ions in vitro in HT-29 cells preloaded with $ZnCl_2$ (A) or without preloaded $ZnCl_2$ (B) (endogenous zinc ions).

Figure 38:
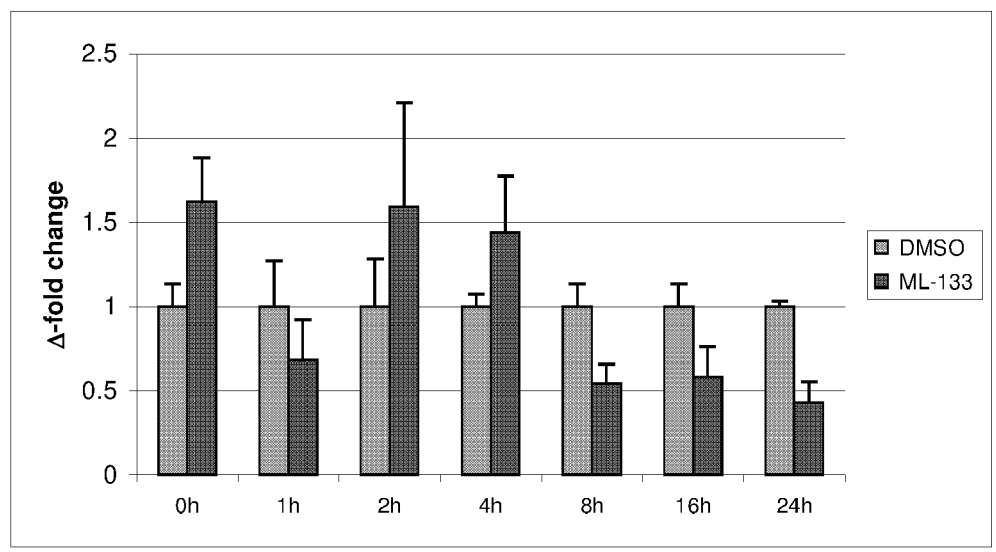
Figure 38:
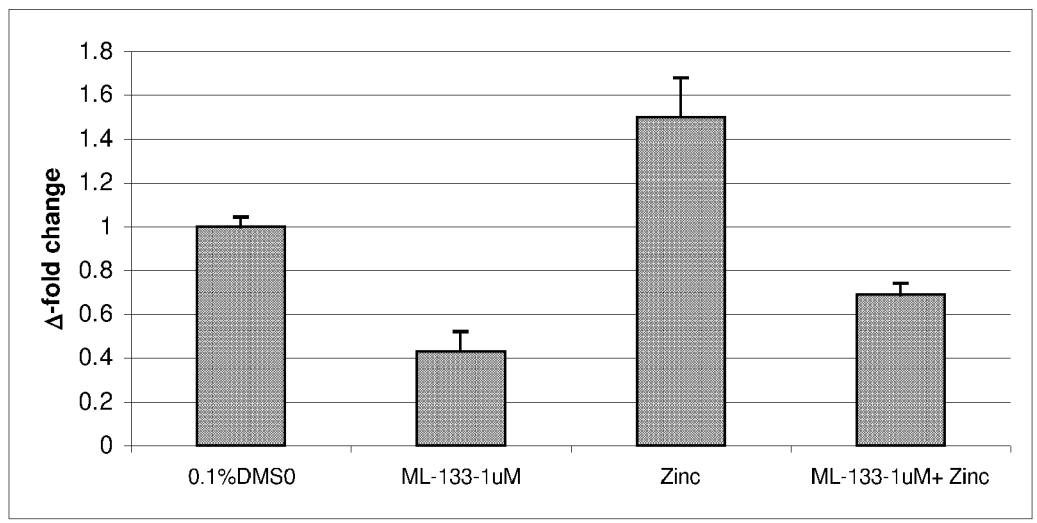

FIG. 38 depicts the effect of compound 3 on expression of metal-sensitive gene zinc-sensitive gene metallothionein 1A in HT-29 cells in vitro over time (A) and following treatment with zinc supplement (B).

Figure 39:
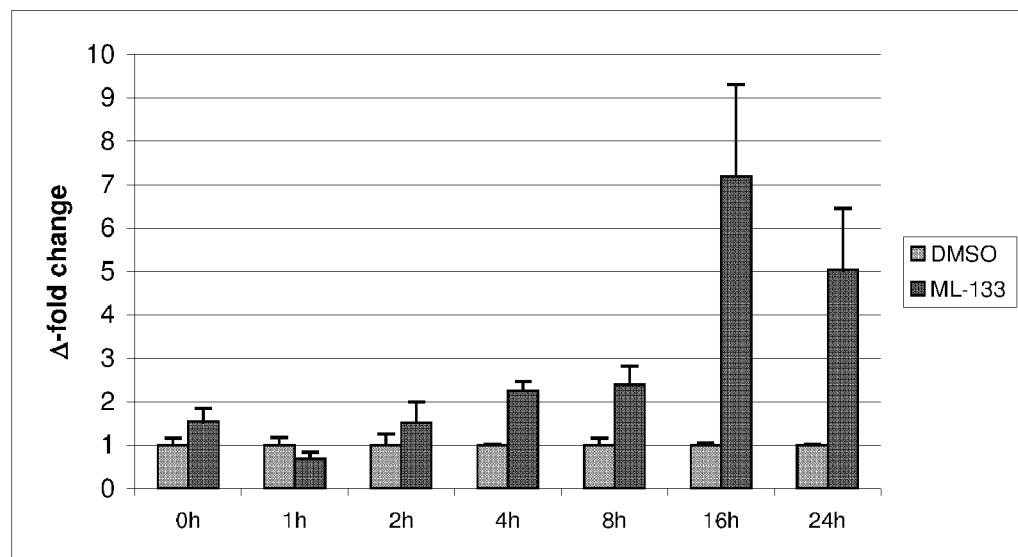
Figure 39:
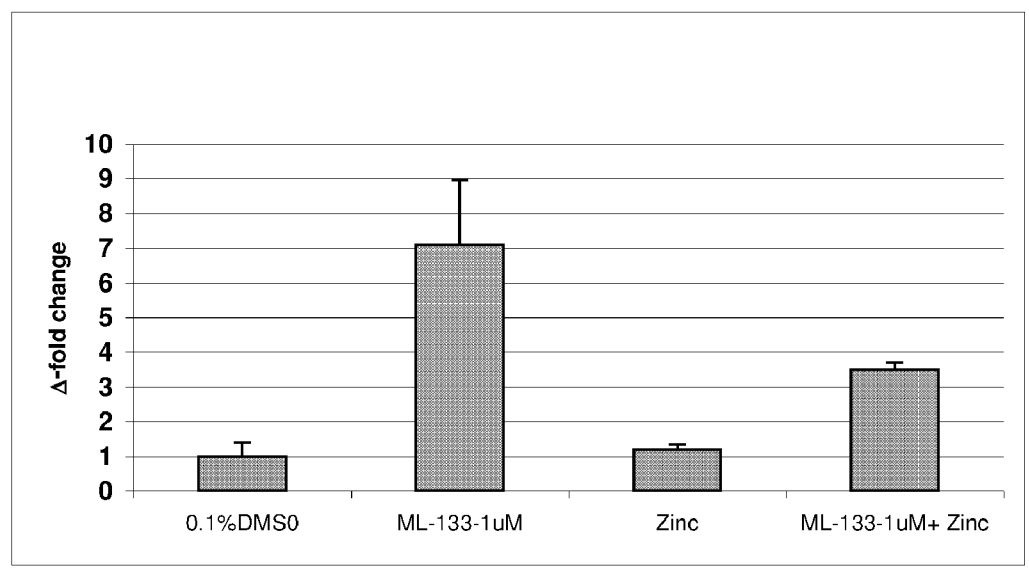

FIG. 39 depicts the effect of compound 3 on expression of metal-sensitive tumour suppressor KLF4 in HT-29 cells in vitro over time (A) and following treatment with zinc supplement (B).

Figure 40:
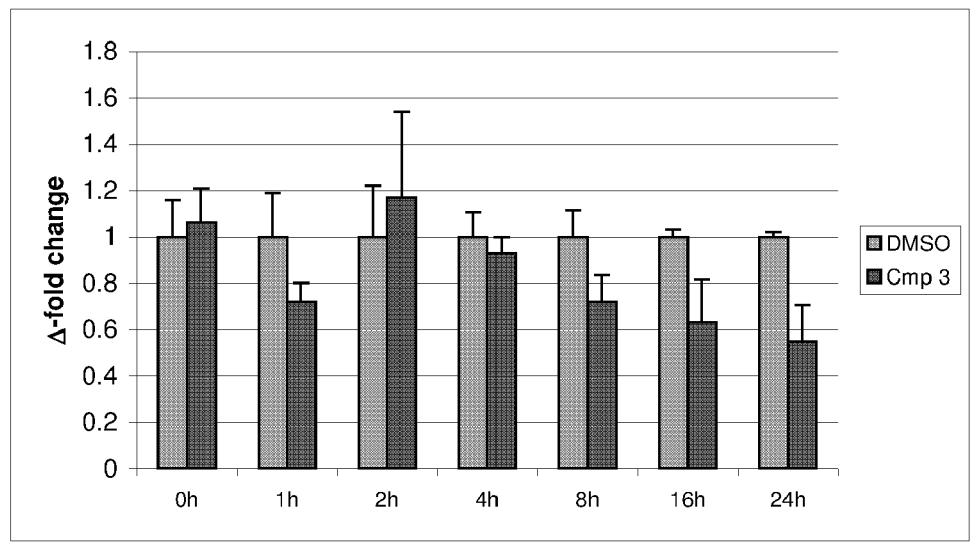
Figure 40:
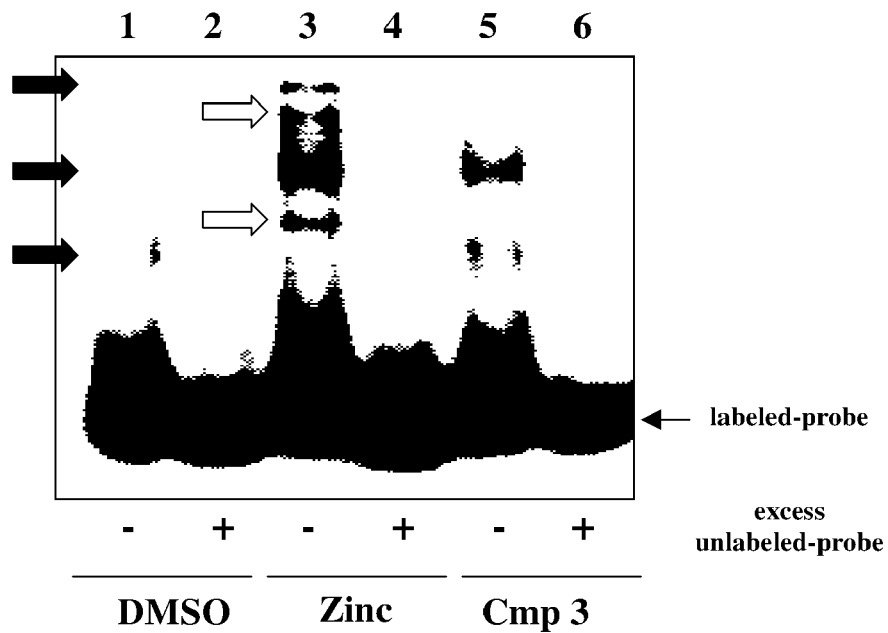

FIG. 40 depicts the effect of compound 3 on expression of zinc-sensitive metal-responsive element (MRE)-binding transcription factor 1 (MTF-1) in HT-29 cells in vitro over time.

Figure 41:
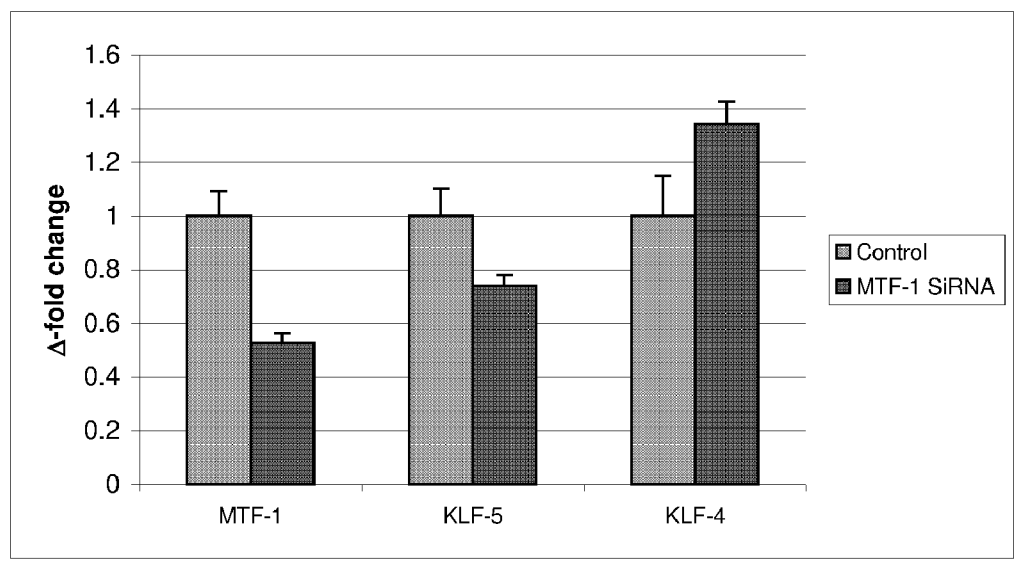
Figure 41:
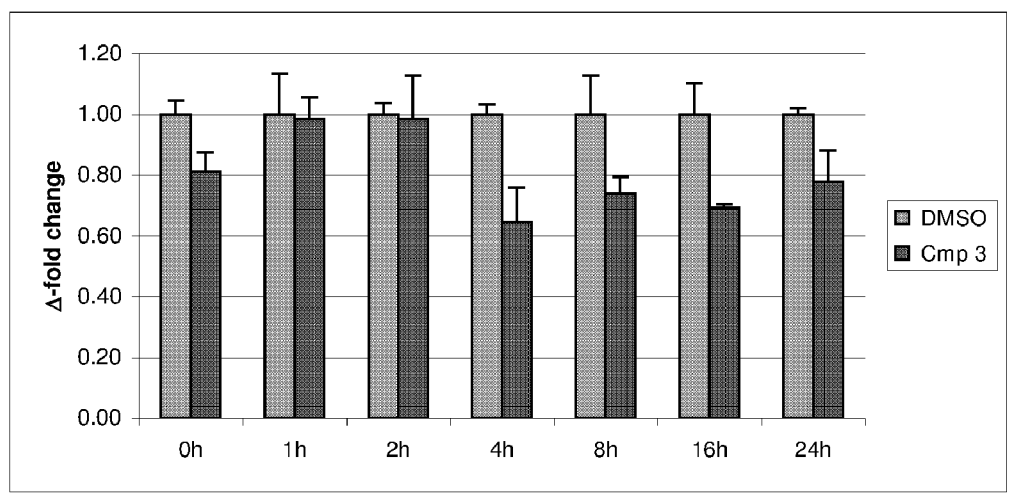

FIG. 41 the effect of MTF-1 gene knock-down by siRNA treatment in HT-29 cells in vitro on expression of MTF-1, KLF5 and KLF4 (A) and the effect of compound 3 treatment on expression of KLF5 in HT-29 cells in vitro over time (B).

Figure 42:
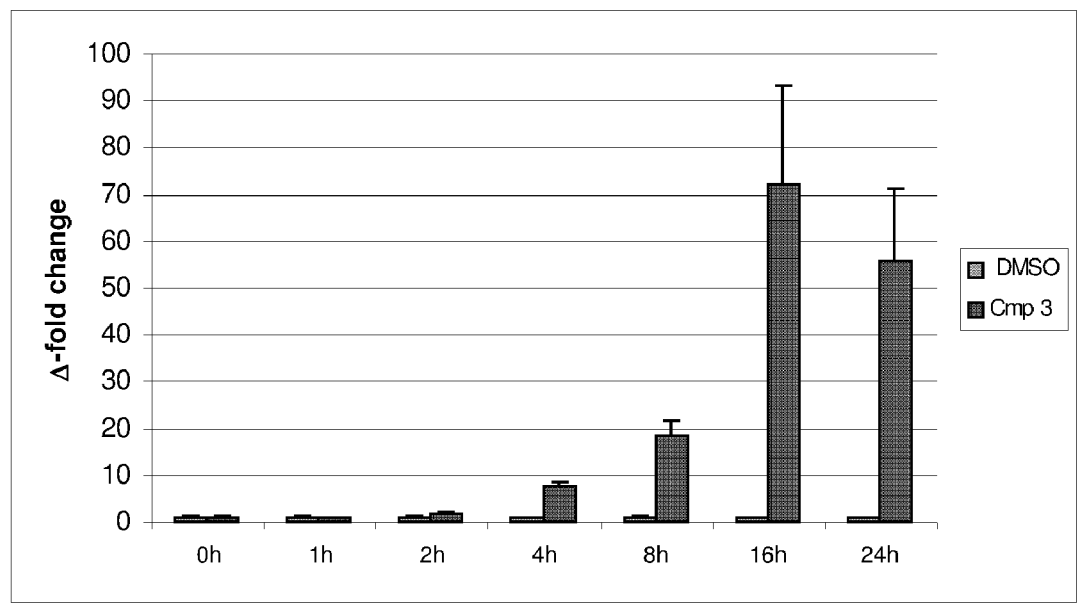
Figure 42:
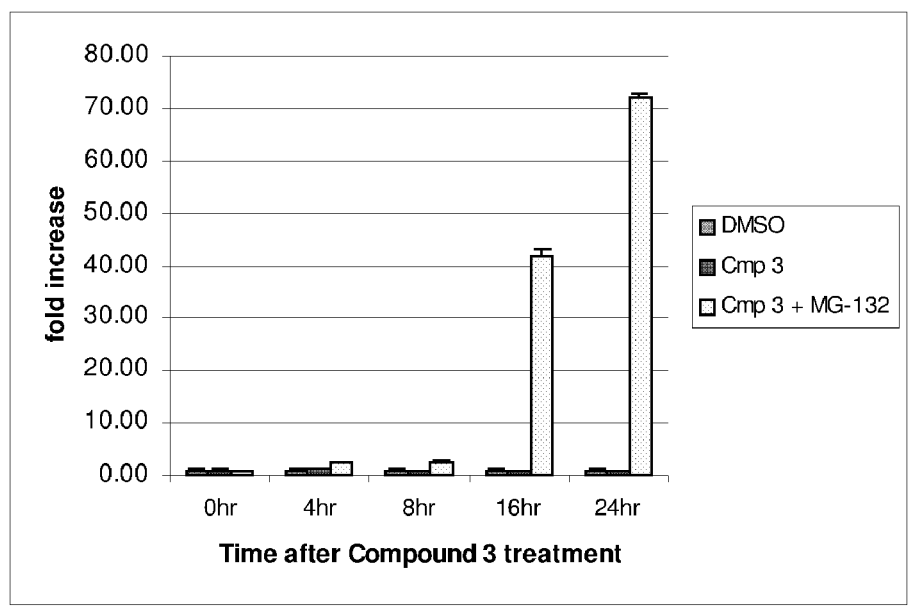

FIG. 42 depicts the effect of compound 3 on expression of cell-cycle regulatory protein p21 in HT-29 cells in vitro over time, mRNA levels (A) and protein levels (B).

Figure 43:
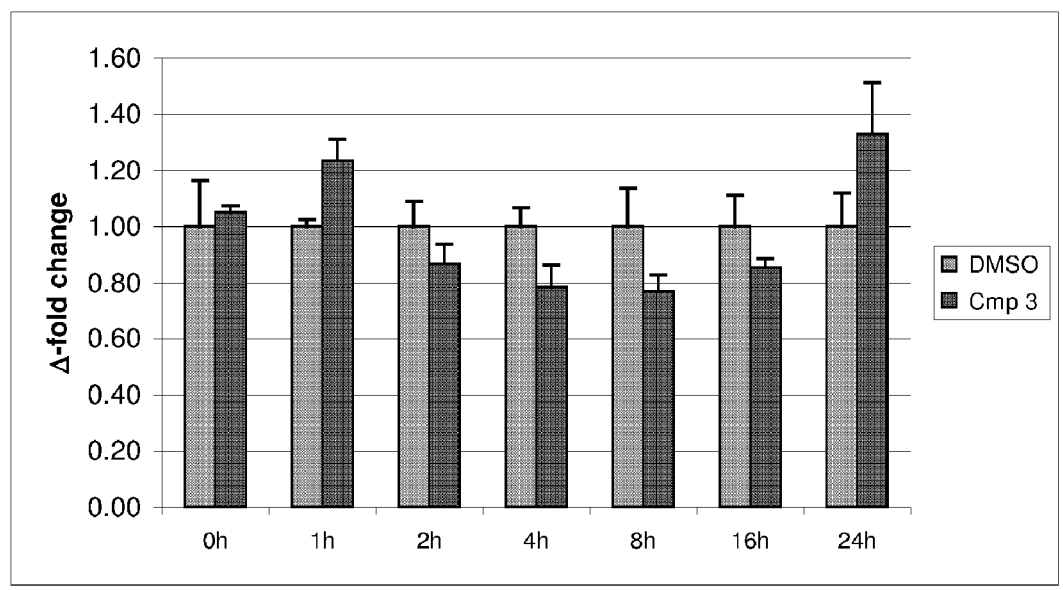
Figure 43:
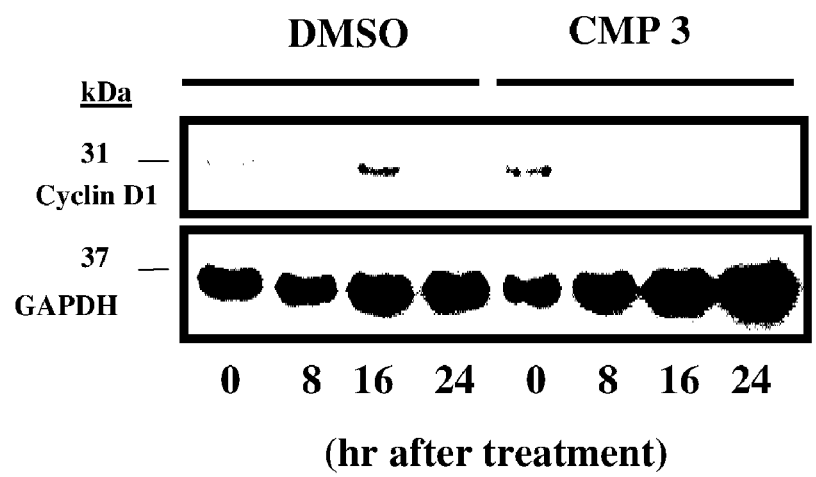

FIG. 43 depicts the effect of compound 3 on expression of Cyclin D1 in HT-29 cells in vitro over time mRNA levels (A) and protein levels (B).

Figure 44:
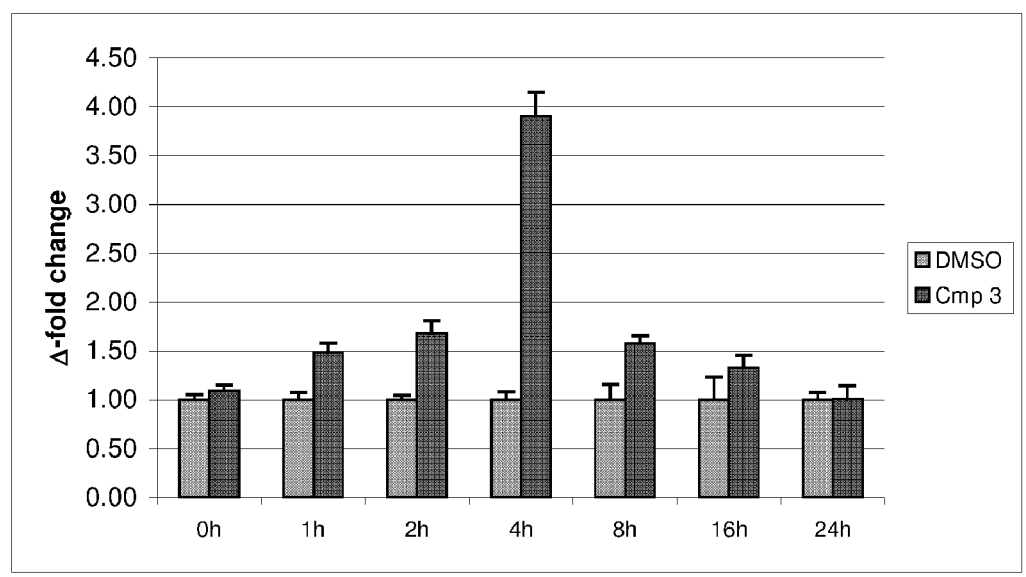
Figure 44:
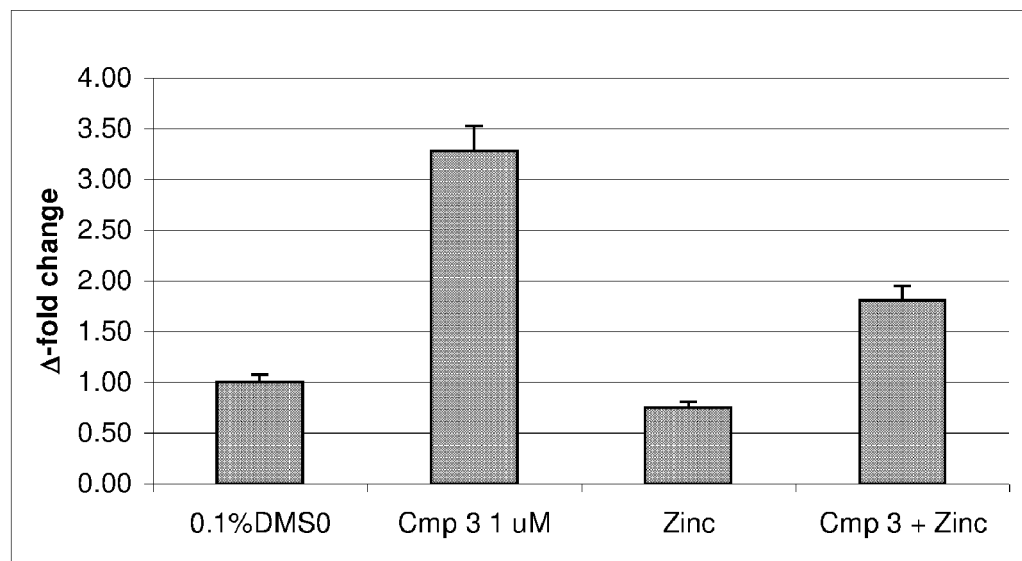

FIG. 44 depicts the effect of compound 3 on expression of a tumour suppressor gene, early growh response protein (EGR-1) in HT-29 cells in vitro over time (A) and following treatment with zinc supplement (B).

Figure 45:
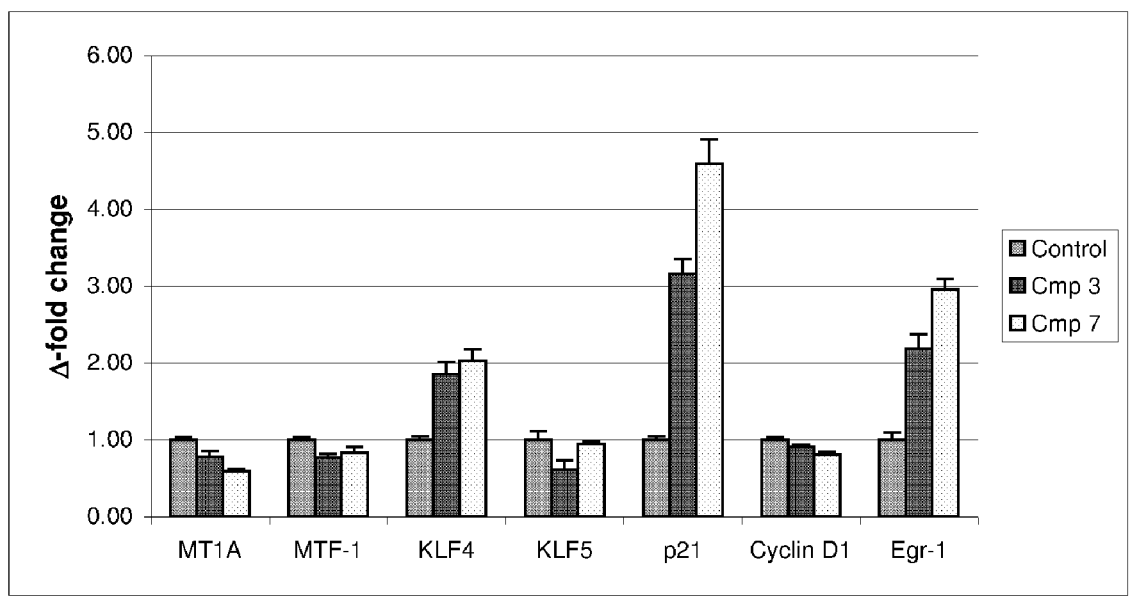

FIG. 45 depicts the effect of compound 3 and compound 7 on gene expression levels of MT1A, MTF-1, KLF4, KLF5, p21, Cyclin D1 and Erg-1 in HT-29 cells in vitro.

Figure 46:
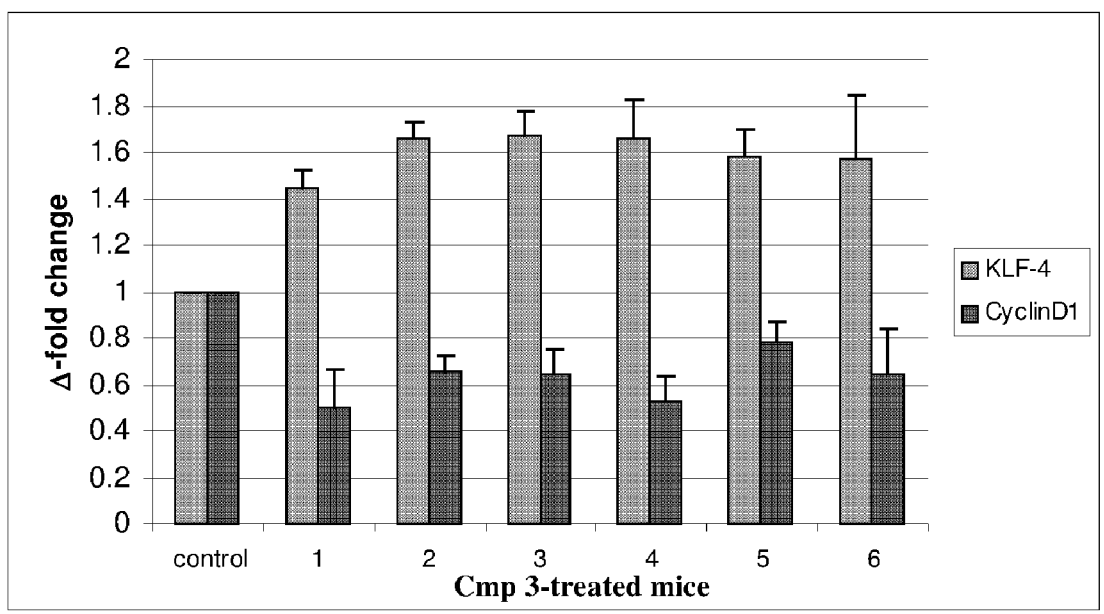

FIG. 46 depicts the in vivo effect of compound 3 on gene expression levels of KLF4 and Cyclin D1 in HT-29 colon cancer xenograft tissue from mice.

Figure 47:
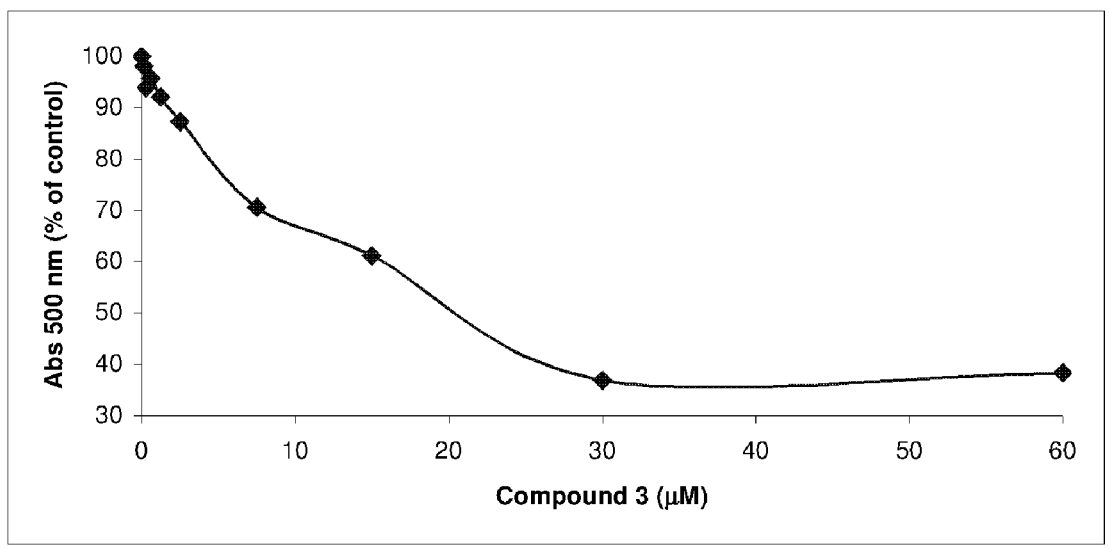

FIG. 47 depicts the ability of compound 3 to chelate zinc from the zinc-storage protein metallothionein 1 (MT-1) in vitro.

Figure 48:
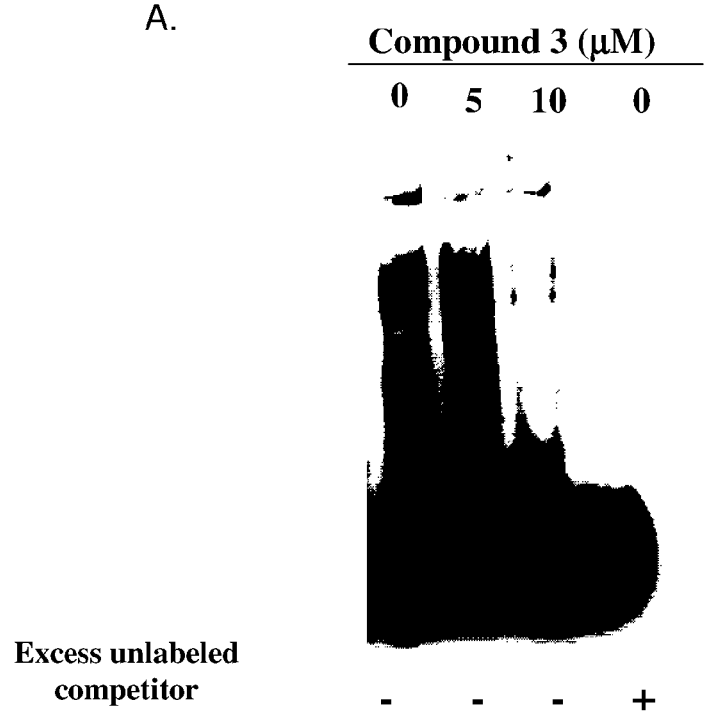
Figure 48:
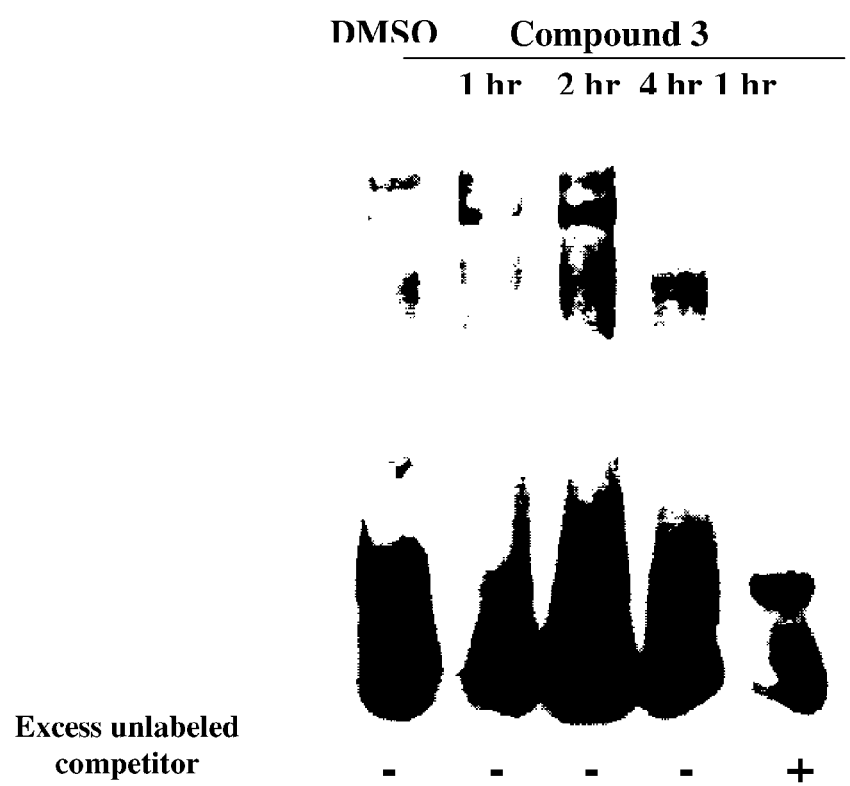

FIG. 48 depicts inactivation of DNA-binding activity of zinc-activated MTF-1 after treatment with compound 3 in vitro (A) and inactivation of DNA-binding activity of MTF-1 by compound 3 in HT-29 cells in vitro (B).

Figure 49:

FIG. 49 depicts the ability of compound 3 to decrease the DNA-binding activity of MTF-1 in HT-29 cells to Cyclin D1 promoter region by chromatin immuno-precipitation assay (ChIP).

Figure 50:
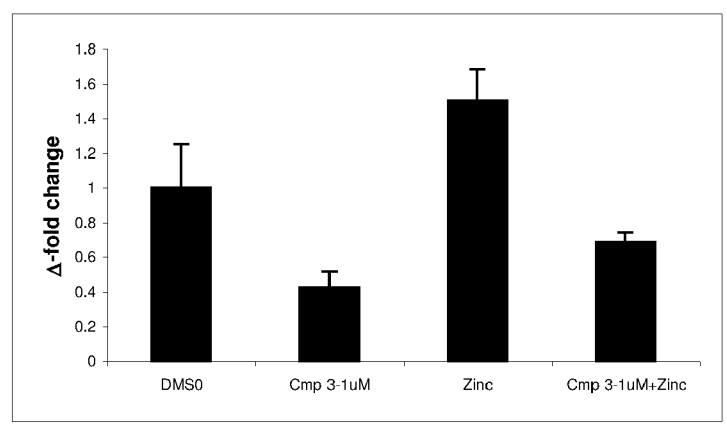
Figure 50:
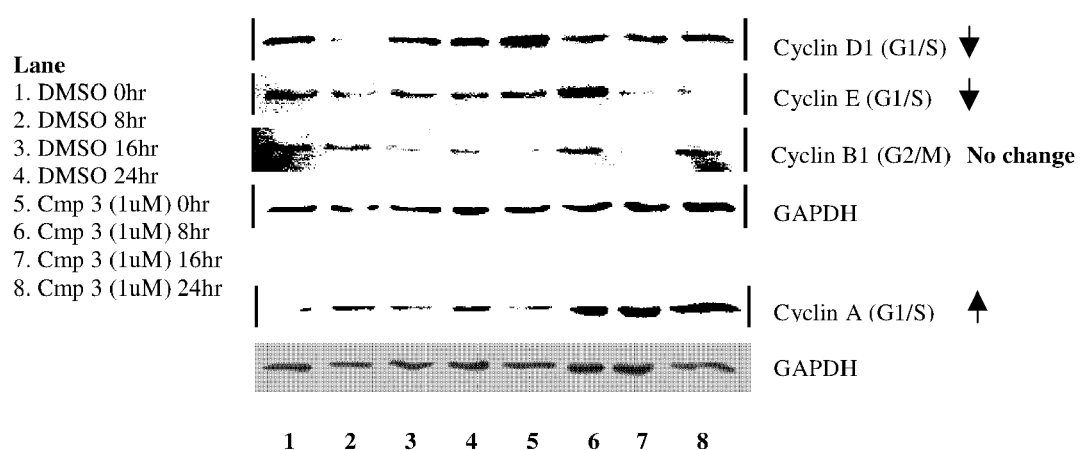

FIG. 50 depicts the effect of compound 3 and zinc supplement on gene expression of Cyclin D1 in HT-29 cells in vitro (A) and the effect of compound 3 on protein levels of Cyclin D1 and other Cyclins (B).

Figure 51:
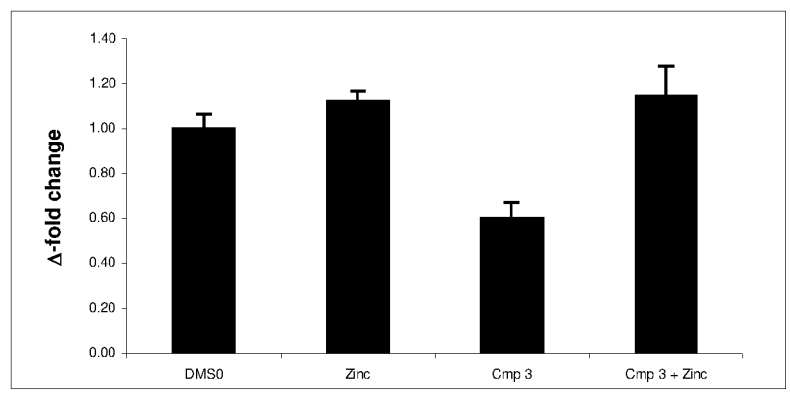
Figure 51:
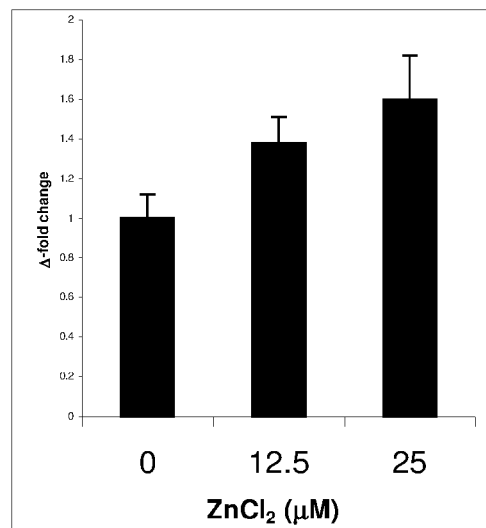
Figure 51:
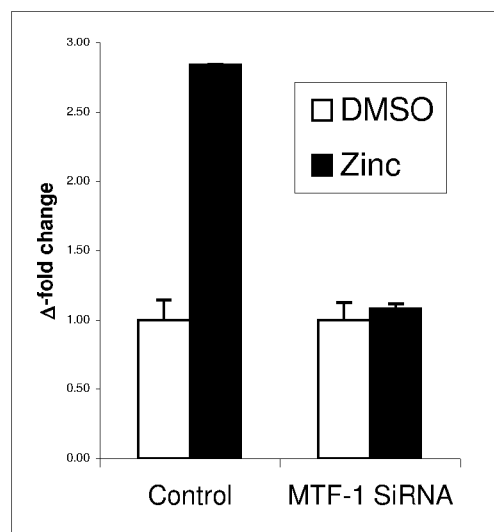

FIG. 51 depicts the effect of compound 3 and zinc supplement on expression of MTF-1 (A), effect of zinc supplement on expression of Cyclin D1 (B) and effect of zinc supplement and MTF-1 gene knock-down by siRNA on expression of Cyclin D1 (C) in HT-29 cells in vitro.

Figure 52:
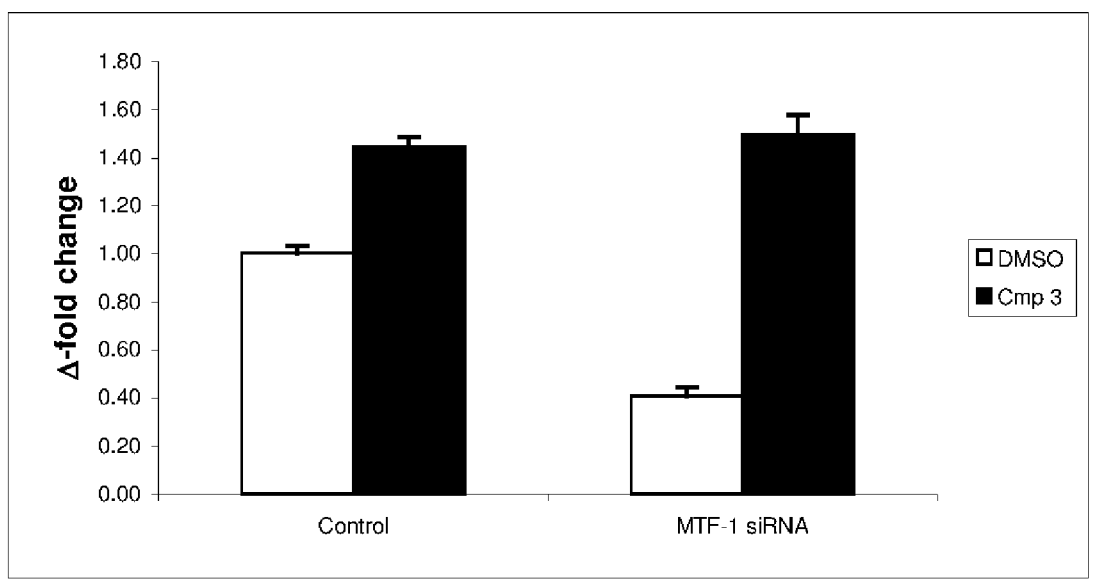

FIG. 52 depicts the effect of compound 3 and MTF-1 gene knock-down by siRNA on expression of KLF4 in HT-29 cells in vitro.

Figure 53:
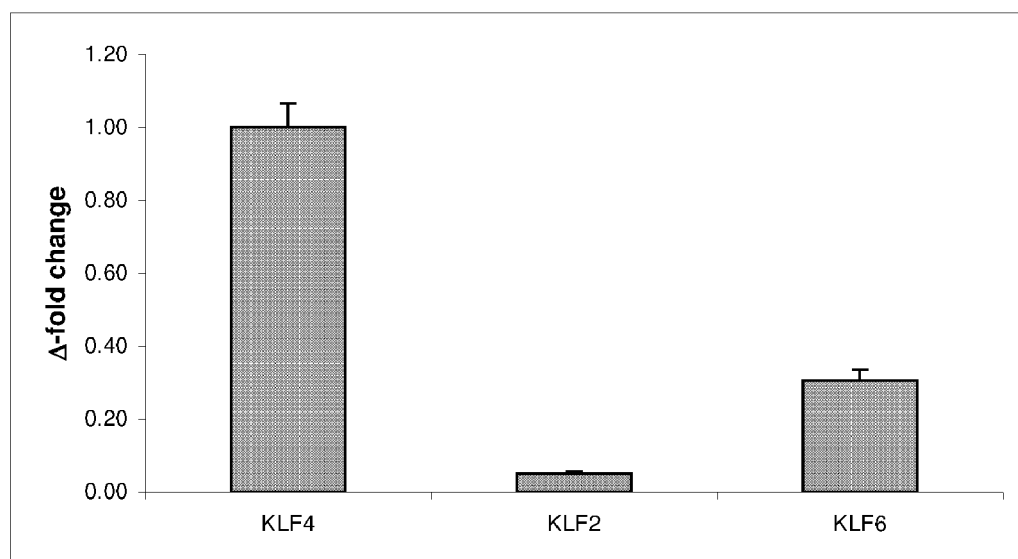
Figure 53:
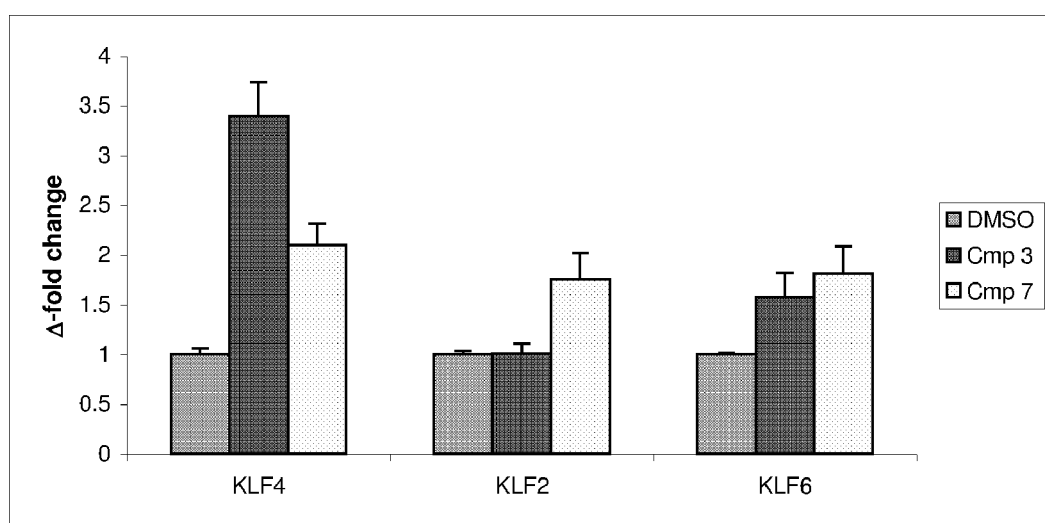

FIG. 53 depicts comparison of gene expression levels of KLF4, KLF2 and KLF6 in H-460 cancer cells in vitro (A) and the effect of compound 3 and compound 7 on expression of KLF4, KLF2 and KLF6 in H-460 cancer cells in vitro (B).

Figure 54:
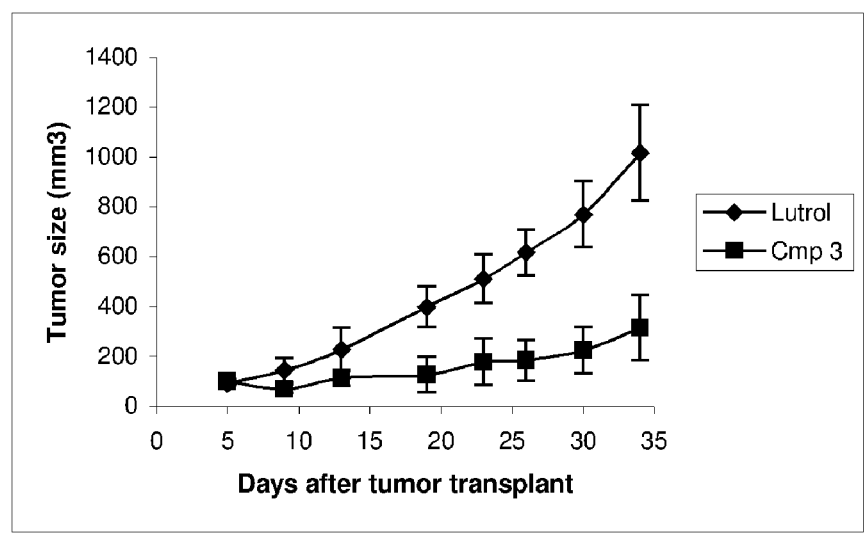
Figure 54:
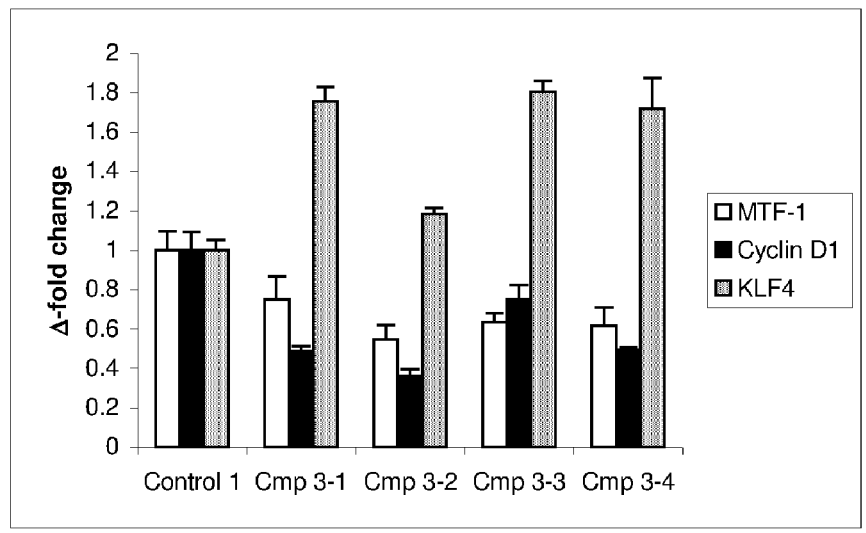

FIG. 54 depicts the ability of compound 3 to decrease tumour size (A) in a colon adenocarcinoma xenograft model and the effect on MTF-1, Cyclin D1 and KLF4 mRNA levels in vivo in tumours from a colon adenocarcinoma xenograft model (B).

Figure 55:
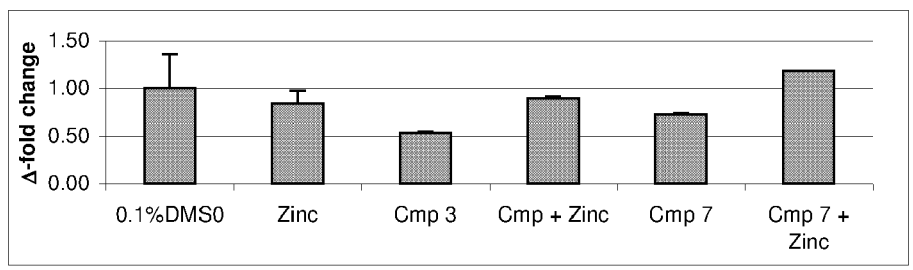
Figure 55:
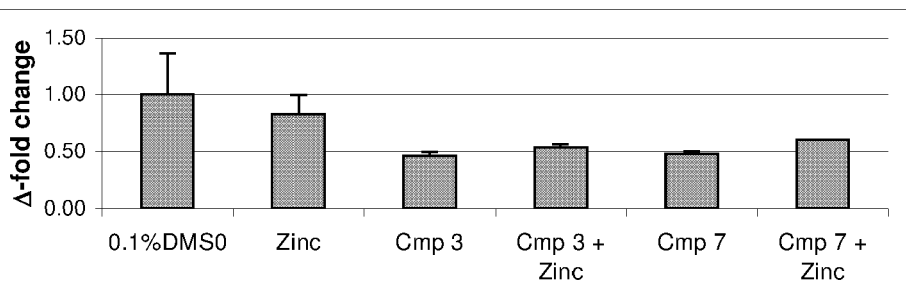
Figure 55:
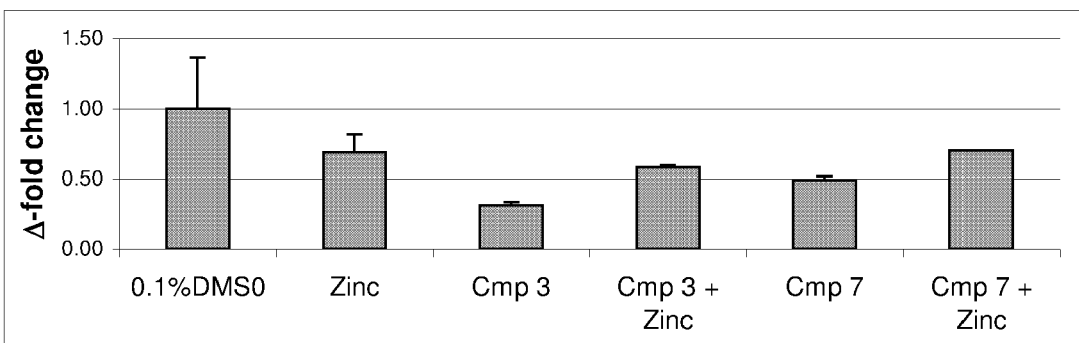
Figure 55:
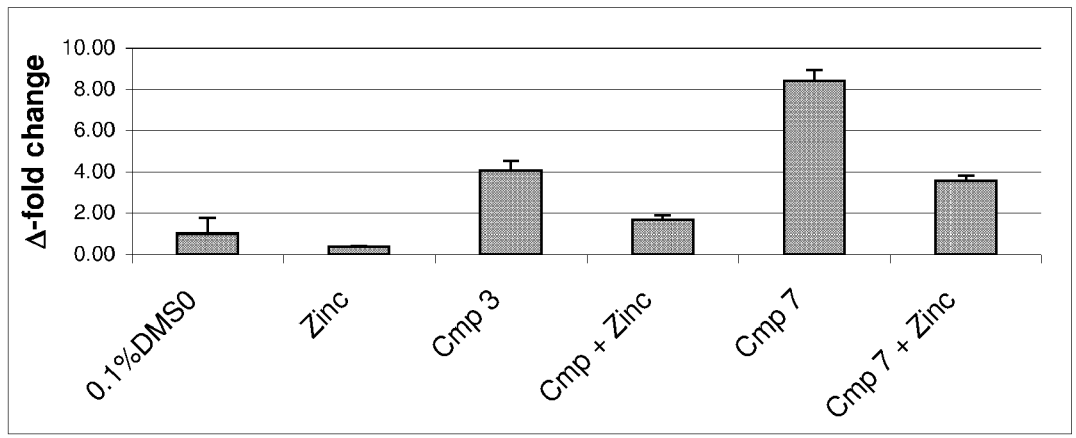

FIG. 55 depicts the effect of compound 3, compound 7 and zinc supplement on mRNA levels in HT-29 cells in vitro for MT1A (A), MTF-1 (B), Cyclin D1 (C) and KLF4 (D).

Figure 56:
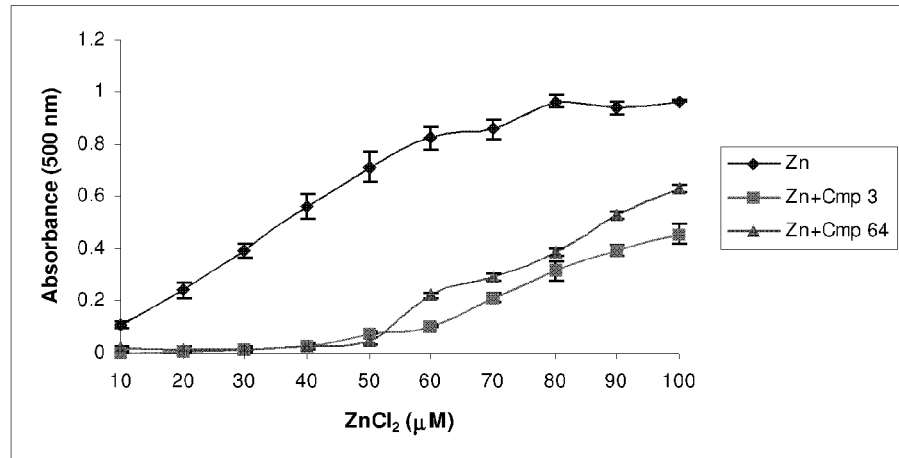
Figure 56:
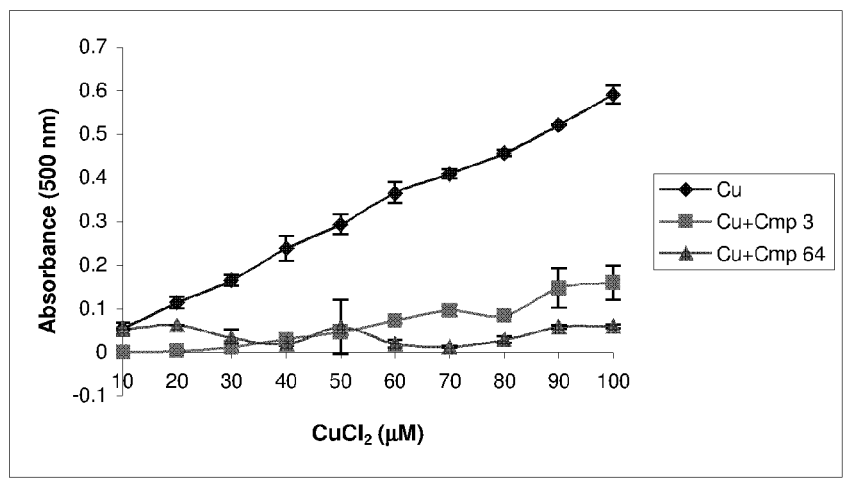
Figure 56:
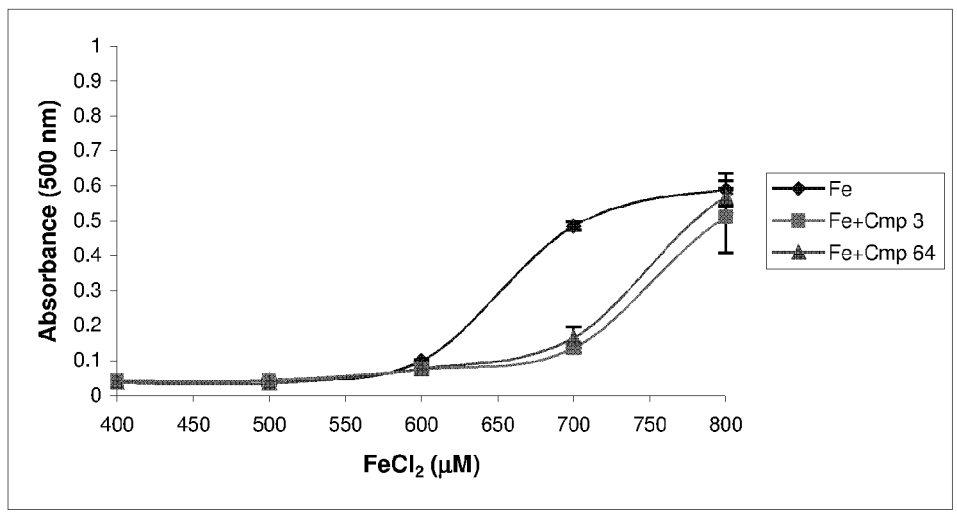

FIG. 56 depicts the metal chelation property of compound 3 and compound 64 in vitro in the presence of $ZnCl_2$ (A), $CuCl_2$ (B) and $FeCl_2$ (C).

Figure 57:
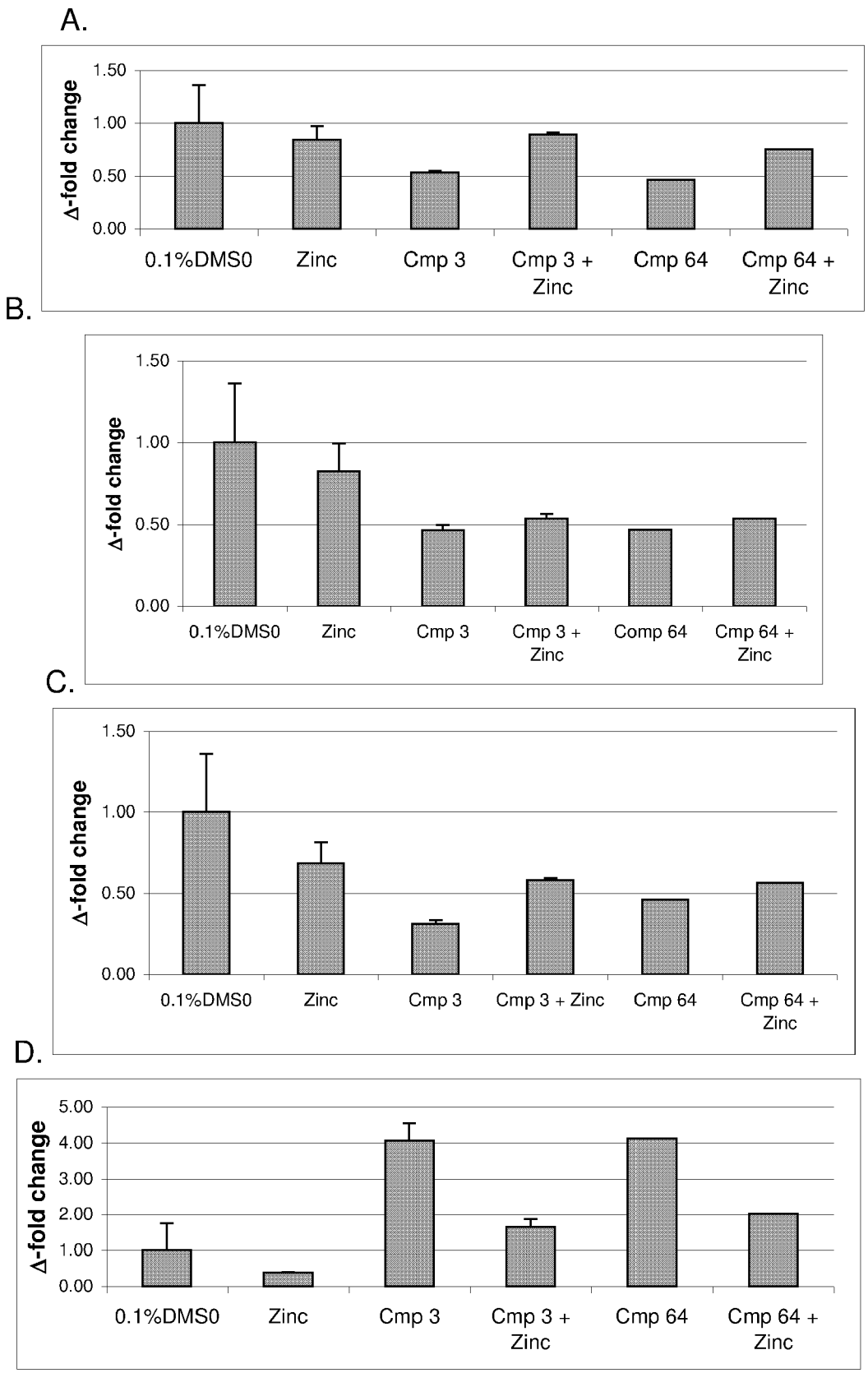

FIG. 57 depicts the effect of compound 3, compound 64 and zinc supplement on mRNA levels in HT-29 cells in vitro for MT1A (A), MTF-1 (B), Cyclin D1 (C) and KLF4 (D).

DETAILED DESCRIPTION OF THE INVENTION

The present invention relates to 2-indolyl imidazo[4,5-d] phenanthroline compounds of Formula I. The compounds of Formula I, as demonstrated herein, are capable of intracellular chelation of transition metals and of exerting antiproliferative effects in one or more cancer cells, that are cytostatic and/or cytotoxic. Accordingly, one embodiment of the present invention provides for the use of compounds of Formula I for inhibiting proliferation of cancer cells. The present invention further provides for methods and uses of compounds of Formula I in the treatment of cancer.

Induction of programmed cell death (apoptosis) is a useful approach for the treatment of cancer. As demonstrated herein, in one embodiment of the present invention, the compounds of Formula I are capable of inducing apoptosis in cancer cells and thus can exert a cytotoxic effect. Accordingly, the present invention further provides for methods and uses of the compounds of Formula I for the induction of apoptosis in cancer cells. In another embodiment, the use of compounds of Formula I for the induction of apoptosis for the treatment of various leukemias is provided.

In another embodiment of the present invention, compounds of Formula I are capable of selectively inhibiting the proliferation of one or more of prostate cancer cells, colon cancer cells, non-small cell lung cancer cells and leukemia cells. In this embodiment, therefore, the present invention provides for the use of compounds of Formula I for selectively inhibiting the proliferation of one or more of prostate cancer cells, colon cancer cells, non-small cell lung cancer cells and leukemia cells. The capability of the compounds of Formula I to selectively inhibit the proliferation of one or more of prostate cancer cells, colon cancer cells, non-small cell lung cancer cells and leukemia cells, further provides for methods and uses of the compounds of Formula I to treat a cancer selected from the group of prostate cancer, colon cancer, non-small cell lung cancer and leukemia.

As noted above, the compounds of Formula I are capable of chelating transition metal ions in a cellular environment. Accordingly, the present invention further provides for methods and uses of the compounds of Formula I for chelating transition metal ions in vivo or in vitro. In one embodiment of the present invention, the compounds of Formula I are capable of altering expression of genes that are regulated by transition metals in cancer cells through chelation of transition metals. For example, in one embodiment, the compounds of Formula I are capable of increasing the expression of a transition metal-regulated tumour suppressor gene in cancer cells. The function of tumour suppressor genes is often associated with the regulation of cell proliferation and thus, by increasing the expression of a transition metal-regulated tumour suppressor gene, which functions to regulate cell proliferation, the compounds of Formula I are capable of inhibiting the proliferation of cancer cells. In a specific embodiment, the compounds of Formula I are capable of increasing the expression of the zinc-regulated tumour suppressor, KLF4 and thus are useful in inhibiting the proliferation of cancer cells in which KLF4 acts as a tumour suppressor, including, but not limited to, bladder cancer, cancers of the gastrointestinal tract and various leukemias.

The present invention further provides for metal chelate complexes of compounds of Formula I, for example copper complexes of compounds of Formula I and the use of these complexes in the treatment of cancer.

The present invention also contemplates application of the compounds of Formula I therapeutically in the treatment of diseases or disorders in which there is a need to chelate transition metals, as well as in various non-therapeutic situations in which chelation of transition metals is required.

DEFINITIONS

Unless defined otherwise, all technical and scientific terms used herein have the same meaning as commonly understood by one of ordinary skill in the art to which this invention belongs.

The terms are defined as follows:

"Selective inhibition" as used herein with reference to the anti-cancer activity of the compounds of Formula I, in one embodiment of the invention, can be determined using a panel of cancer cell lines comprising at least 50 of the 60 cancer cells lines used in the NCI/NIH Developmental Therapeutics Program in vitro screen (shown in Table 1 below), wherein the panel comprises both of the listed prostate cancer cell lines and at least 4 cell lines from each of the other listed cancers. A compound is said to show selective inhibition of a selected cancer (i.e. prostate cancer, colon cancer, non-small cell lung cancer and/or leukemia) when the compound inhibits the proliferation of the cell lines from the selected cancer with an average $GI_{50}$ at least 10% lower than the average $GI_{50}$ for inhibition of cell lines from each of breast cancer, CNS cancer, melanoma, ovarian cancer and renal cancer.

TABLE 1

Cancer cell lines used in the NCI/NIH Developmental Therapeutics Program in vitro Screen

| Cancer Type | Cell Line | |
|---|---|---|
| Breast | MCF7 | MDA-MB-435 |
| | NCI/ADR-RES | MDA-N |
| | MDA-MB-231/ATCC | BT-549 |
| | HS 578T | T-47D |
| CNS | SF-268 | SNB-19 |
| | SF-295 | SNB-75 |
| | SF-539 | U251 |
| Colon | COLO 205 | HT29 |
| | HCC-2998 | KM12 |
| | HCT-116 | SW-620 |
| | HCT-15 | |
| Leukemia | CCRF-CEM | MOLT-4 |
| | HL-60(TB) | RPMI-8226 |
| | K-562 | SR |
| Melanoma | LOX IMVI | SK-MEL-28 |
| | MALME-3M | SK-MEL-5 |
| | M14 | UACC-257 |
| | SK-MEL-2 | UACC-62 |
| Non-Small Cell Lung | A549/ATCC | NCI-H23 |
| | EKVX | NCI-H322M |
| | HOP-62 | NCI-H460 |
| | HOP-92 | NCI-H522 |
| | NCI-H226 | |
| Ovarian | IGR-OV1 | OVCAR-5 |
| | OVCAR-3 | OVCAR-8 |
| | OVCAR-4 | SK-OV-3 |
| Prostate | PC-3 | |
| | DU-145 | |
| Renal | 786-0 | RXF 393 |
| | A498 | SN12C |
| | ACHN | TK-10 |
| | CAKI-1 | UO-31 |

The term "down-regulated" as used herein with respect to expression of a transition-metal tumour suppressor gene in cancer cells, means that the gene is not over-expressed in the cancer cells, i.e., that the cells exhibit a reduced level or substantially the same level of expression of the gene compared to normal cells. By way of example, colon cancer cells exhibit reduced expression of the KLF4 gene compared to normal colon cells, whereas prostate cancer cells exhibit the same level of KLF4 expression when compared to normal prostate cancer cells, but the level of expression is lower than in breast cancer cells, which over-express KLF4.

The term "halogen" refers to fluorine, bromine, chlorine, and iodine atoms.

The term "hydroxyl" refers to the group —OH.

The term "thiol" or "mercapto" refers to the group —SH, and —$S(O)_{0-2}$.

The term "lower alkyl" refers to a straight chain or branched, or cyclic, alkyl group of one to eight carbon atoms.

The term "substituted lower alkyl" refers to lower alkyl as just described including one or more groups such as hydroxyl, thiol, alkylthiol, halogen, alkoxy, amino, amido, carboxyl, cycloalkyl, substituted cycloalkyl, heterocycle, substituted heterocycle, cycloheteroalkyl, substituted cycloheteroalkyl, acyl, aryl, substituted aryl, aryloxy, hetaryl, substituted hetaryl, aralkyl, heteroaralkyl, alkyl alkenyl, alkyl alkynyl, alkyl cycloalkyl, alkyl cycloheteroalkyl, nitro, cyano. These groups may be attached to any carbon atom of the lower alkyl moiety.

The term "lower alkenyl" refers to a straight chain or branched hydrocarbon of two to eight carbon atoms having at least one carbon to carbon double bond.

The term "substituted lower alkenyl" refers to lower alkenyl as just described including one or more groups such as hydroxyl, thiol, alkylthiol, halogen, alkoxy, amino, amido, carboxyl, cycloalkyl, substituted cycloalkyl, heterocycle, substituted heterocycle, cycloheteroalkyl, substituted cycloheteroalkyl, acyl, aryl, substituted aryl, aryloxy, hetaryl, substituted hetaryl, aralkyl, heteroaralkyl, alkyl, alkenyl, alkynyl, alkyl alkenyl, alkyl alkynyl, alkyl cycloalkyl, alkyl cycloheteroalkyl, nitro, cyano. These groups may be attached to any carbon atom to produce a stable compound.

The term "lower alkynyl" refers to a straight chain or branched hydrocarbon of two to eight carbon atoms having at least one carbon to carbon triple bond.

The term "substituted lower alkynyl" refers to lower alkynyl as just described including one or more groups such as hydroxyl, thiol, alkylthiol, halogen, alkoxy, amino, amido, carboxyl, cycloalkyl, substituted cycloalkyl, heterocycle, substituted heterocycle, cycloheteroalkyl, substituted cycloheteroalkyl, acyl, aryl, substituted aryl, aryloxy, hetaryl, substituted hetaryl, aralkyl, heteroaralkyl, alkyl, alkenyl, alkynyl, alkyl alkenyl, alkyl alkynyl, alkyl cycloalkyl, alkyl cycloheteroalkyl, nitro, cyano. These groups may be attached to any carbon atom to produce a stable compound.

The term "alkoxy" refers to the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined below.

The term "alkylthio" denotes the group —SR, —S(O)$_{n=1-2}$—R, where R is lower alkyl, substituted lower alkyl, aryl, substituted aryl, aralkyl or substituted aralkyl as defined below.

The term "acyl" refers to groups —C(O)R, where R is hydrogen, lower alkyl, substituted lower alkyl, aryl, substituted aryl.

The term "aryloxy" refers to groups —OAr, where Ar is an aryl, substituted aryl, heteroaryl, or substituted heteroaryl group as defined below.

The term "amino" refers to the group NRR', where R and R' may independently be hydrogen, lower alkyl, substituted lower alkyl, aryl, substituted aryl, hetaryl, cycloalkyl, substituted cycloalkyl, or substituted hetaryl as defined below or acyl.

The term "amido" refers to the group —C(O)NRR', where R and R' may independently be hydrogen, lower alkyl, substituted lower alkyl, cycloalkyl, substituted cycloalkyl, aryl, substituted aryl, hetaryl, substituted hetaryl as defined below.

The term "carboxyl" refers to the group —C(O)OR, where R may independently be hydrogen, lower alkyl, substituted lower alkyl, aryl, substituted aryl, hetaryl, substituted hetaryl and the like as defined.

The terms "aryl" or "Ar" refer to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl, 9-fluorenyl etc.).

The term "substituted aryl" refers to aryl optionally substituted with one or more functional groups, e.g., halogen, hydroxyl, thiol, lower alkyl, substituted lower alkyl, trifluoromethyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, substituted heterocycle, heteroaryl, substituted heteroaryl, heteroalkyl, substituted heteroalkyl, cycloalkyl, substituted cycloalkyl, alkylcycloalkyl, alkylcycloheteroalkyl, nitro, sulfamido, cyano or —N=CRR', wherein R and R' are independemtly selected from H, alkyl, substituted alkyl, aryl, substituted aryl, heterocycle, substituted heterocycle, heteroaryl or substituted heteroaryl.

The term "heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl, indanyl or benzo[b]thienyl) and having at least one hetero atom, such as N, O or S, within the ring.

The term "substituted heterocycle" refers to heterocycle optionally substituted with, halogen, hydroxyl, thiol, lower alkyl, substituted lower alkyl, trifluoromethyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, substituted heterocycle, heteroaryl, substituted heteroaryl, heteroalkyl, substituted heteroalkyl, cycloalkyl, substituted cycloalkyl, alkylcycloalkyl, alkylcycloheteroalkyl, nitro, sulfamido or cyano and the like.

The terms "heteroaryl" or "hetaryl" refer to a heterocycle in which at least one heterocyclic ring is aromatic.

The term "substituted heteroaryl" refers to a heterocycle optionally mono or poly substituted with one or more functional groups, e.g., halogen, hydroxyl, thiol, lower alkyl, substituted lower alkyl, trifluoromethyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, substituted heterocycle, heteroaryl, substituted heteroaryl, heteroalkyl, substituted heteroalkyl, cycloalkyl, substituted cycloalkyl, alkylcycloalkyl, alkylcycloheteroalkyl, nitro, sulfamido or cyano and the like.

The term "cycloalkyl" refers to a cyclic or polycyclic alkyl group containing 3 to 15 carbon. For polycyclic groups, these may be multiple condensed rings in which one of the distal rings may be aromatic (e.g. tetrahydronaphthalene, etc.).

The term "substituted cycloalkyl" refers to a cycloalkyl group comprising one or more substituents with, e.g halogen, hydroxyl, thiol, lower alkyl, substituted lower alkyl, trifluoromethyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, sulfamido or cyano and the like.

The terms "therapy" and "treatment," as used interchangeably herein, refer to an intervention performed with the intention of alleviating the symptoms associated with, preventing the development of, or altering the pathology of a disease, disorder or condition. Thus, the terms therapy and treatment are used in the broadest sense, and include the prevention (prophylaxis), moderation, management, reduction, or curing of a disease, disorder or condition at various stages. Prevention or reduction of the progression of a disease, disorder or condition are encompassed by these terms. Also encompassed by these terms is an intervention resulting in an alteration of physiology and/or biochemistry of a living subject. Those in need of therapy/treatment include those already having the disease, disorder or condition as well as those prone to, or at risk of developing, the disease, disorder or condition and those in whom the disease, disorder or condition is to be prevented. The therapeutic application of compounds of the invention, therefore, refers to a therapy or treatment, as defined herein.

The terms "subject" or "patient," as used herein, refer to an animal in need of treatment, including humans and other mammals.

Administration of the compounds of the invention "in combination with" one or more further therapeutic agents, is intended to include simultaneous (concurrent) administration and consecutive administration. Consecutive administration is intended to encompass various orders of administration of the therapeutic agent(s) and the compound(s) of the invention to the subject.

The term "adjuvant therapy," as used herein, refers to a treatment that is added to increase the effectiveness of a primary treatment. In cancer, adjuvant therapy usually refers to chemotherapy, hormonal therapy or radiation therapy after surgery (primary therapy) to increase the likelihood of killing all cancer cells.

The term "neoadjuvant therapy," as used herein, refers to a treatment given before the primary treatment. Examples of neoadjuvant therapy include chemotherapy, radiation therapy, and hormone therapy.

As used herein, the term "about" refers to a ±10% variation from the nominal value. It is to be understood that such a variation is always included in any given value provided herein, whether or not it is specifically referred to.

I. 2-Indolyl imidazo[4,5-d]phenanthroline Compounds

The present invention provides compounds of the general formula (I):

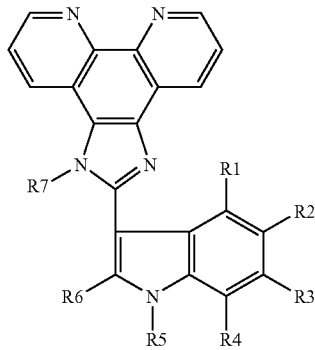

I or salts thereof, wherein:

R1, R2, R3, R4, R6 and R7 are independently selected from hydrogen, halogen, hydroxyl, thiol, lower alkyl, substituted lower alkyl, lower alkenyl, substituted lower alkenyl, lower alkynyl, substituted lower alkynyl, alkoxy, alkylthio, acyl, aryloxy, amino, amido, carboxyl, aryl, substituted aryl, heterocycle, substituted heterocycle, heteroalkyl, substituted heteroalkyl, heteroaryl, substituted heteroaryl, cycloalkyl, substituted cycloalkyl, nitro, or cyano or —S(O)$_{1-2}$R wherein R is alkyl, substituted alkyl, aryl, substituted aryl, heterocycle, heteroaryl, substituted heterocycle, or substituted heteroaryl;

R5 is H, alkyl, substituted alkyl, alkenyl, substituted alkenyl, alkynyl, substituted alkynyl, aryl, substituted aryl, heteroaryl, substituted heteroaryl, acyl, —CH$_2$-aryl, —CH$_2$—heteroaryl.

In another embodiment of the present invention, in the compound of Formula I, R1, R3, R4, R5 and R7 are H, and R2 and R6 are as defined above.

In another embodiment of the present invention, the compounds of Formula I are those, wherein:

R1, R2, R3, R4 are independently hydrogen; halogen; $C_1$-$C_4$ alkyl; $C_1$-$C_4$ alkoxy; or $C_6$-$C_{14}$ aryl;

R5 is hydrogen; $C_1$-$C_4$ alkyl; $C_1$-$C_4$ alkyl substituted with $C_6$-$C_{14}$ aryl; or $C_4$-$C_6$ cycloalkyl;

R6 is hydrogen; halogen; $C_1$-$C_4$ alkyl; $C_1$-$C_4$ alkyl substituted with $C_5$-$C_6$ heterocycloalkyl wherein the heteroatom is N; $C_6$-$C_{14}$ aryl; $C_6$-$C_{14}$ aryl substituted with $C_1$-$C_4$ alkyl or halo; $C_5$-$C_6$ cycloalkyl; $C_5$-$C_6$ heterocycloalkyl; or polycycloalkyl.

In another embodiment of the present invention, the compounds of Formula I are those, wherein:

R1, R2, R3, R4 are independently hydrogen; halogen; $C_1$-$C_4$ alkyl; $C_1$-$C_4$ alkoxy; or phenyl;

R5 is hydrogen; $C_1$-$C_4$ alkyl; $C_1$-$C_4$ alkyl substituted with phenyl; or cyclopentyl;

R6 is hydrogen; halogen; $C_1$-$C_4$ alkyl; $C_1$-$C_4$ alkyl substituted with $C_5$-$C_6$ heterocycloalkyl wherein the heteroatom is N; phenyl; phenyl substituted with $C_1$-$C_4$ alkyl or halo; $C_5$-$C_6$ cycloalkyl; $C_5$-$C_6$ heterocycloalkyl; or adamantane; and R7 is H.

In another embodiment of the present invention, the compounds of Formula I are those, wherein:

R1, R2, R3, R4 are independently hydrogen; halogen; or $C_1$-$C_4$ alkyl;

R5 is hydrogen; $C_1$-$C_4$ alkyl; $C_1$-$C_4$ alkyl substituted with phenyl; or $C_4$-$C_6$ cycloalkyl;

R6 is $C_1$-$C_4$ alkyl; $C_1$-$C_4$ alkyl substituted with $C_5$-$C_6$ heterocycloalkyl wherein the heteroatom is N; $C_5$-$C_6$ cycloalkyl; adamantane; phenyl; or phenyl substituted with $C_1$-$C_4$ alkyl or halo; and R7 is H.

In another embodiment of the present invention, the compounds of Formula I are those wherein:

R1, R2, R3, R4 are independently hydrogen; halogen; or $C_1$-$C_4$ alkyl;

R5 is hydrogen; $C_1$-$C_4$ alkyl; or $C_4$-$C_6$ cycloalkyl;

R6 is $C_1$-$C_4$ alkyl; adamantane; phenyl; or phenyl substituted with $C_1$-$C_4$ alkyl or halo; and R7 is H.

In another embodiment of the present invention, the compounds of Formula I are those wherein:

R1, R2, R3, R4 are independently hydrogen; halogen; or $C_1$-$C_4$ alkyl;

R5 is hydrogen;

R6 is $C_1$-$C_4$ alkyl or adamantane; and

R7 is H.

In another embodiment of the present invention, the compounds of Formula I are those wherein:

R1, R2, R3, R4 are independently hydrogen; halogen; or $C_1$-$C_4$ alkyl;

R5 is hydrogen;

R6 is $C_1$-$C_4$ alkyl; and

R7 is H.

In another embodiment of the present invention, the compounds of Formula I are those wherein:

R1, R2, R3, R4 are independently hydrogen; $C_1$-$C_4$ alkyl; or $C_1$-$C_4$ alkoxy;

R5 is $C_1$-$C_4$ alkyl, or $C_4$-$C_6$ cycloalkyl;

R6 is hydrogen; $C_1$-$C_4$ alkyl; adamantane; phenyl; or phenyl substituted with $C_1$-$C_4$ alkyl or halo; and R7 is H.

In another embodiment of the present invention, the compounds of Formula I are those wherein:

R1, R2, R3, R4 are independently hydrogen; $C_1$-$C_4$ alkyl; or $C_1$-$C_4$ alkoxy;

R5 is $C_1$-$C_4$ alkyl; $C_1$-$C_4$ alkyl substituted with phenyl; or $C_4$-$C_6$ cycloalkyl;

R6 is hydrogen; $C_1$-$C_4$ alkyl; or $C_5$-$C_6$ heterocycloalkyl; and

R7 is H.

Compounds of the present invention include, but are not limited to the following exemplary compounds:
1
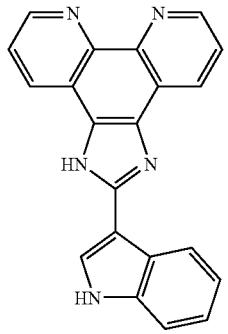
2
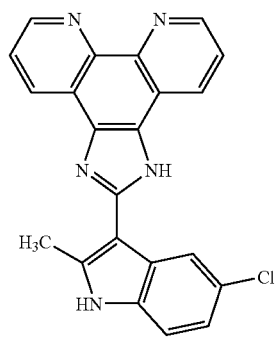
3
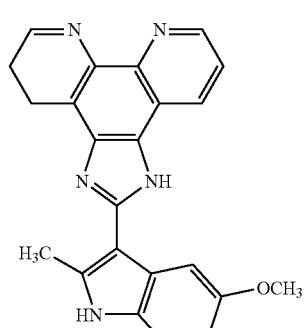
4
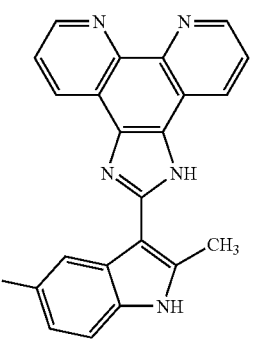
5
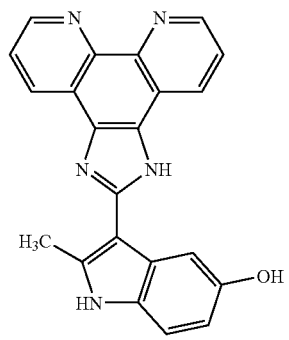
6
7
8

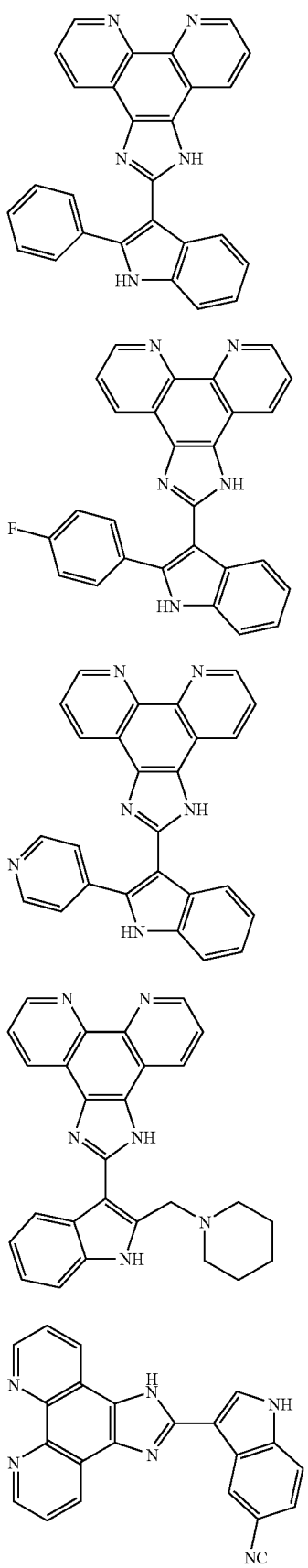
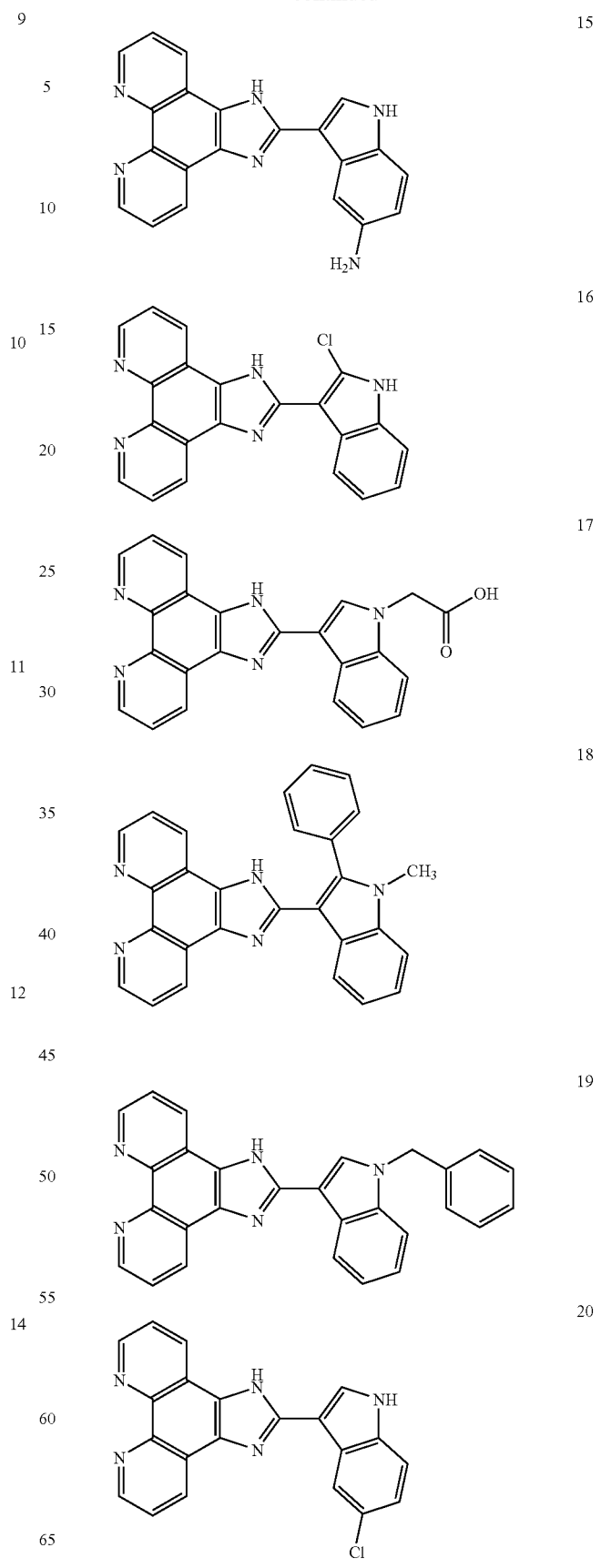

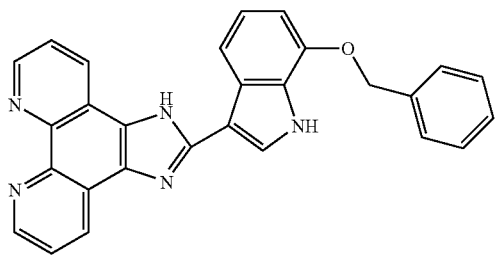
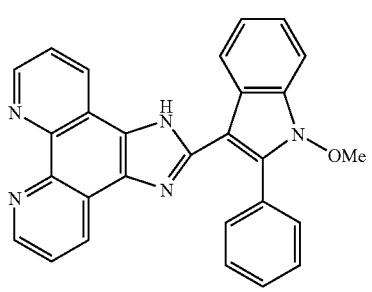
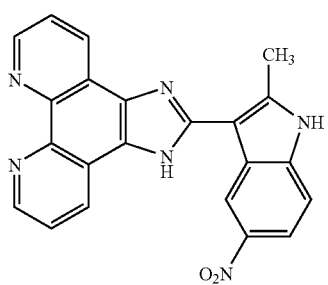
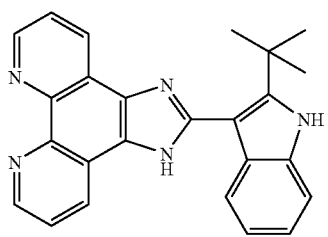
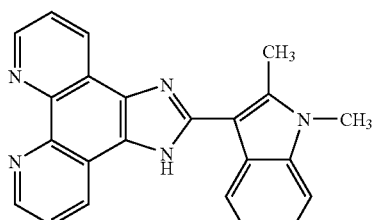
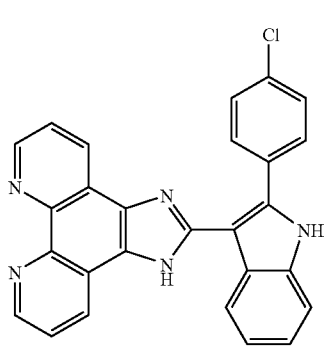
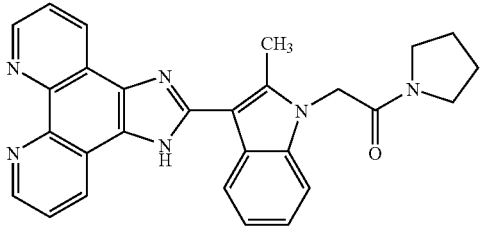
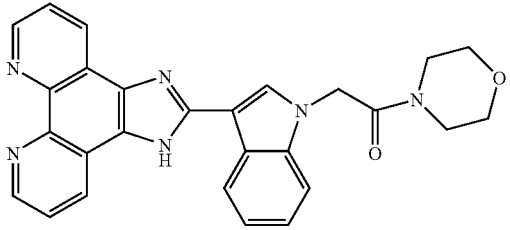
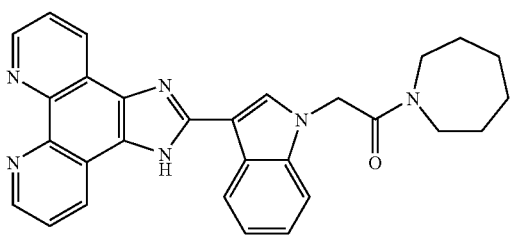
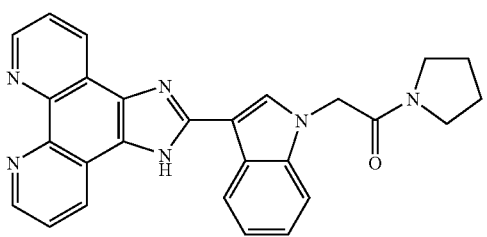
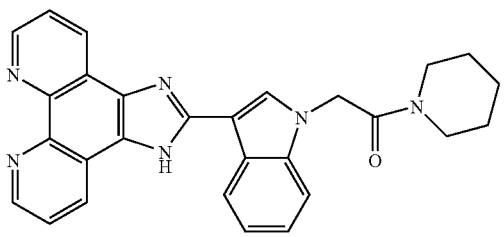
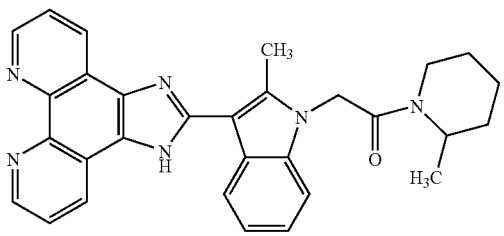

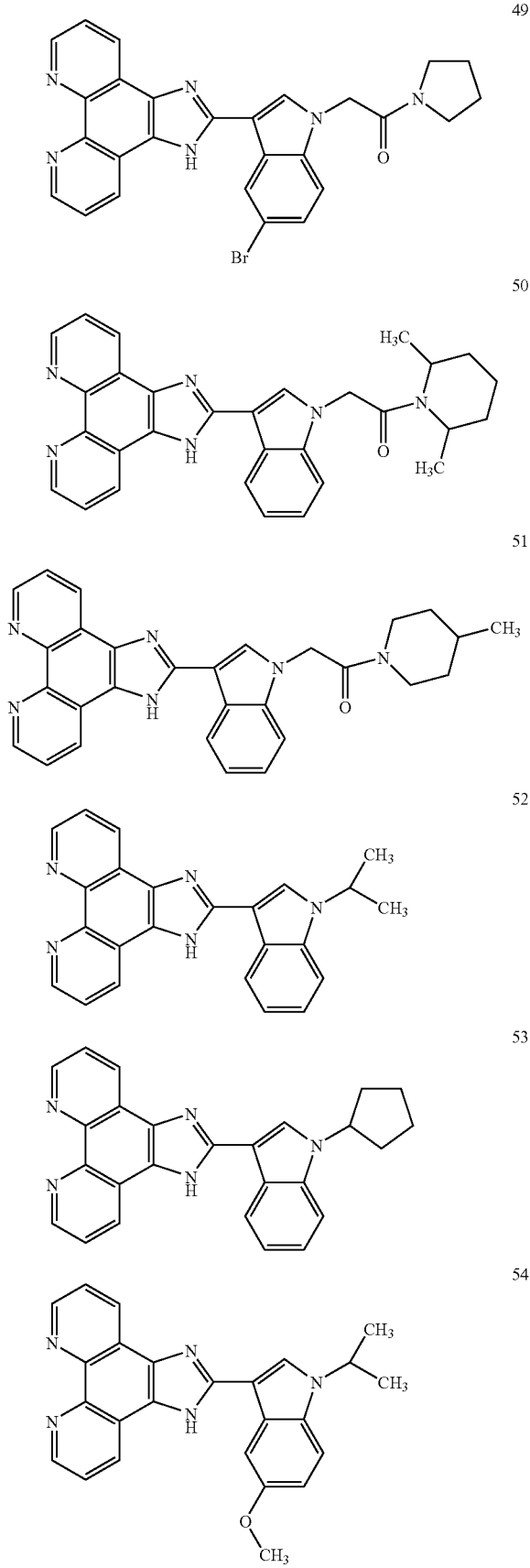
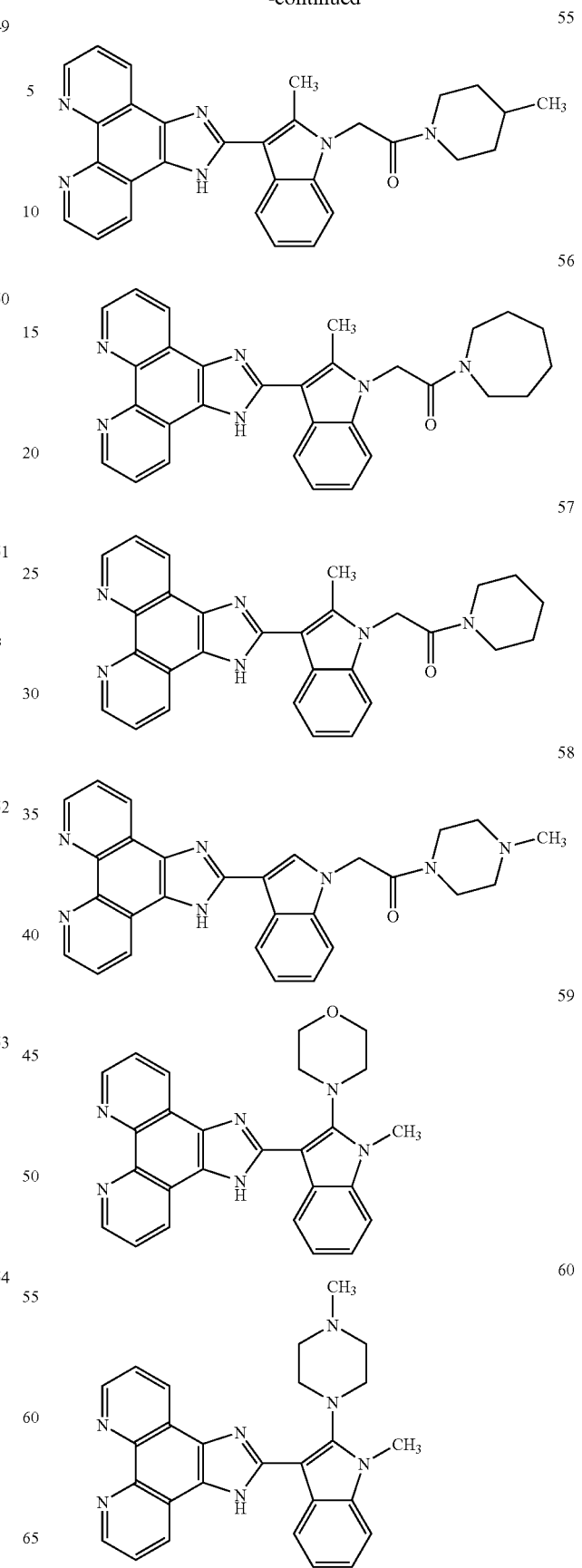

61 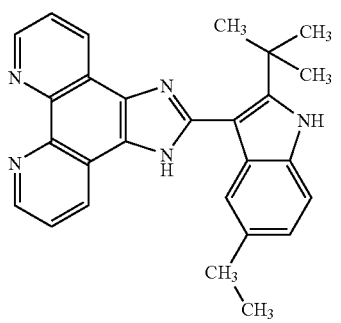
62 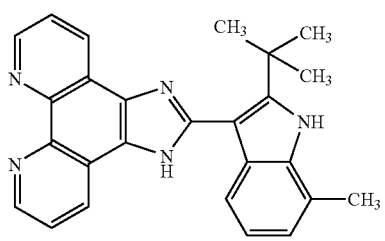
63 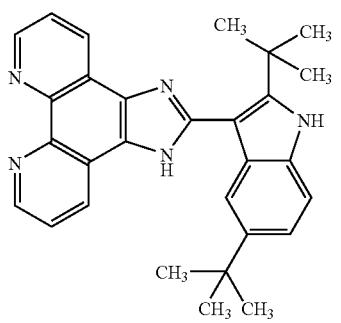
64 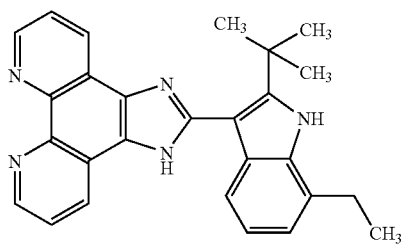
65 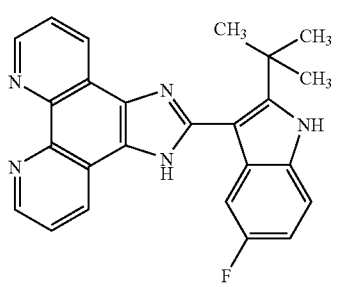
66 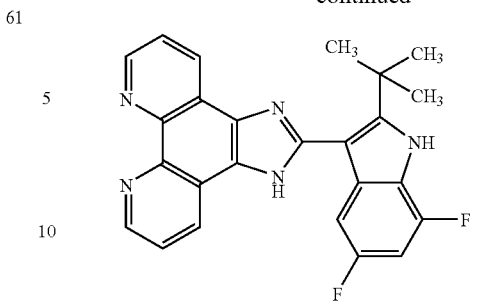
67 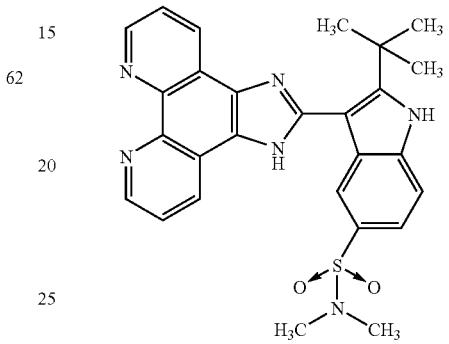
68 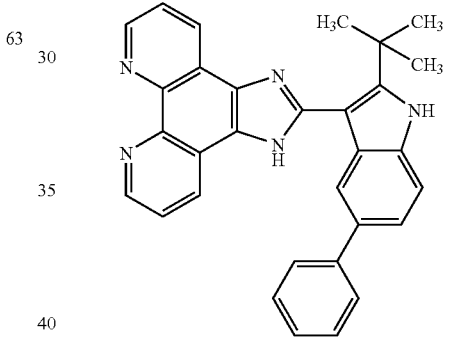
69 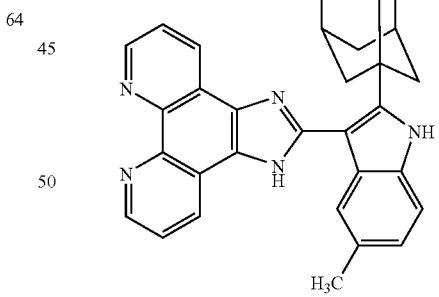
70 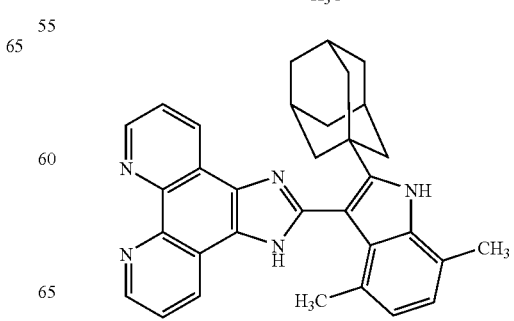

71 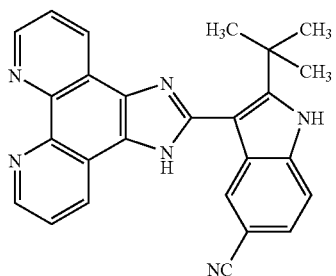
72 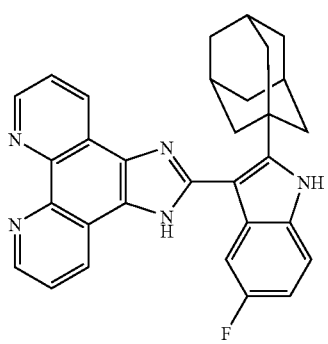
73 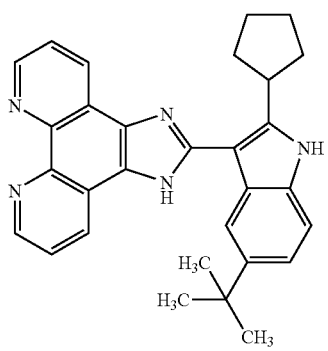
74 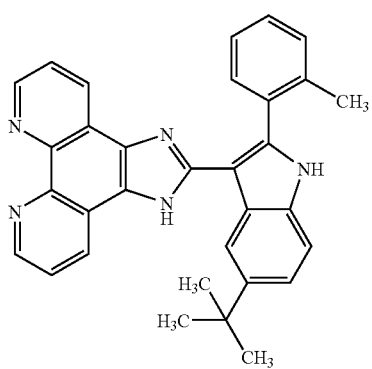
75 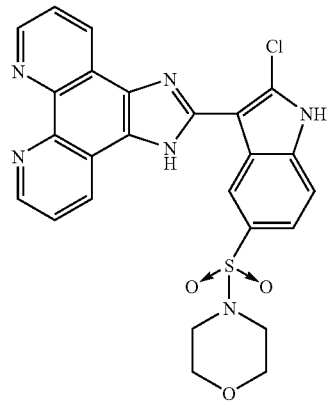
76 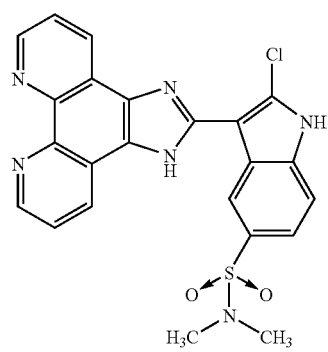
77 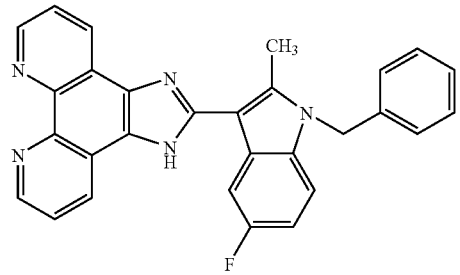
78 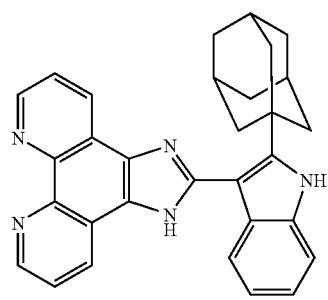
79 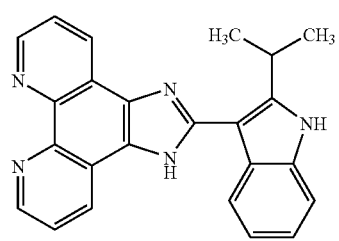

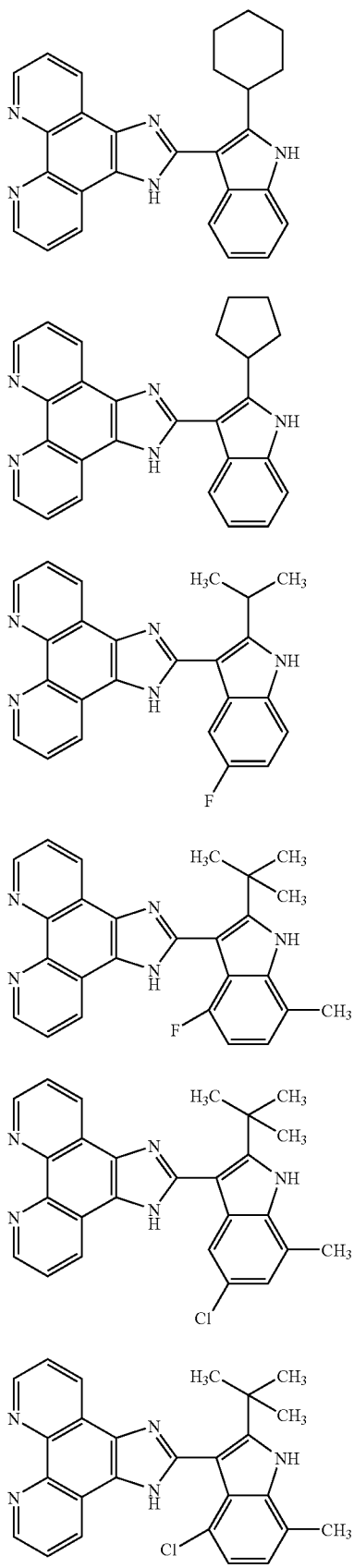

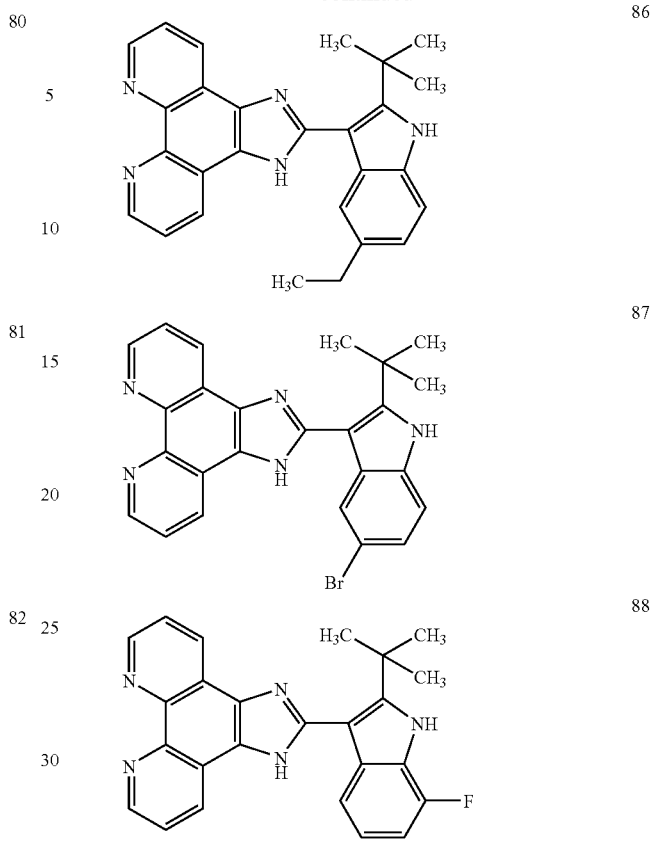

The present invention includes various salts of the compounds defined by Formula I, including pharmaceutically acceptable salts. Compounds according to the present invention can possess a sufficiently acidic, a sufficiently basic, or both functional groups, and accordingly react with a number of organic and inorganic bases, and organic and inorganic acids, to form pharmaceutically acceptable salts.

The term "pharmaceutically acceptable salt" as used herein, refers to a salt of a compound of Formula I, which is substantially non-toxic to living organisms. Typical pharmaceutically acceptable salts include those salts prepared by reaction of the compound of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulphuric acid, phosphoric acid, and the like, and organic acids such as p-toluenesulphonic acid, methanesulphonic acid, oxalic acid, p-bromophenylsulphonic acid, carbonic acid, succinic acid, citric acid, benzoic acid, acetic acid, and the like. Examples of such pharmaceutically acceptable salts are the sulphate, pyrosulphate, bisulphate, sulphite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulphonate, phenylacetate, phenylpropionate, phenylbutyrate, citrate, lactate, gamma-hydroxybutyrate, glycolate, tartrate, methanesulphonate, propanesulphonate, naphthalene-1-sulfonate, napthhalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulphonic acid.

Salts of amine groups may also comprise quarternary ammonium salts in which the amino nitrogen carries a suitable organic group such as an alkyl, lower alkenyl, substituted lower alkenyl, lower alkynyl, substituted lower alkynyl, or aralkyl moiety.

Base addition salts include those derived from inorganic bases, such as ammonium or alkali or alkaline earth metal hydroxides, carbonates, bicarbonates, and the like. Bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like.

One skilled in the art will understand that the particular counter ion forming a part of a salt of this invention is usually not of a critical nature, so long as the salt as a whole is pharmacologically acceptable and as long as the counter ion does not contribute undesired qualities to the salt as a whole. The present invention further encompasses the pharmaceutically acceptable solvates of a compound of Formula I. Many of the compounds of Formula I can combine with solvents such as water, methanol, ethanol and acetonitrile to form pharmaceutically acceptable solvates such as the corresponding hydrate, methanolate, ethanolate and acetonitrilate.

The compounds of the present invention may have multiple asymmetric (chiral) centres. As a consequence of these chiral centres, the compounds of the present invention occur as racemates, mixtures of enantiomers and as individual enantiomers, as well as diastereomers and mixtures of diastereomers. All asymmetric forms, individual isomers and combinations thereof, are within the scope of the present invention.

It will be readily understood by one skilled in the art that if the stereochemistry of a compound of Formula I is critical to its activity, then the relative stereochemistry of the compound is established early during synthesis to avoid subsequent stereoisomer separation problems. Further manipulation of the molecule will then employ stereospecific procedures so as to maintain the desired chirality.

II. Preparation of Compounds of Formula I

As is known in the art, compounds of the present invention can be prepared by a number of standard techniques. Compounds of Formula I, therefore, can be prepared by several general synthetic methods, for example, as described by Grimmett, (Grimmett, M. R., *Comprehensive Heterocyclic Chemistry: The Structure, Reaction, Synthesis and Uses of Heterocyclic Compounds*, A. R. Katrizky and C. W. Rees, eds., Vol. 5, Pergamon Press. Oxford, 1984, pp. 457-498; Grimmett, M. R., *Imidazole and Benzimidazole Synthesis, Academic Press*, San Diego Calif., 1997).

In one embodiment of the present invention, compounds of Formula I are prepared via solution or solid phase synthesis, by reacting a dione of Formula II with the aldehyde (III) in the presence of ammonium acetate in acetic acid (see, for example, Krieg et al., *Naturforsch.* 1967, 22b, 132; Sarshar et al., *Tetrahedron Lett.* 1996, 37, 835-838; Bian et al., *Synthetic communications* 2003, 33, 3477-3482; Hong Xu et al., *J. Chem. Soc., Dalton Trans.*, 2003, 11, 2260-2268; Hong Xu et al., *Inorg. Chem. Commun.*, 2003, 6, 766-768; Bian et al., *Polyhedron* 2002, 21, 313-319; Chao et al., *J. Chem. Soc., Dalton Trans.*, 2001, 12, 1920-1926.

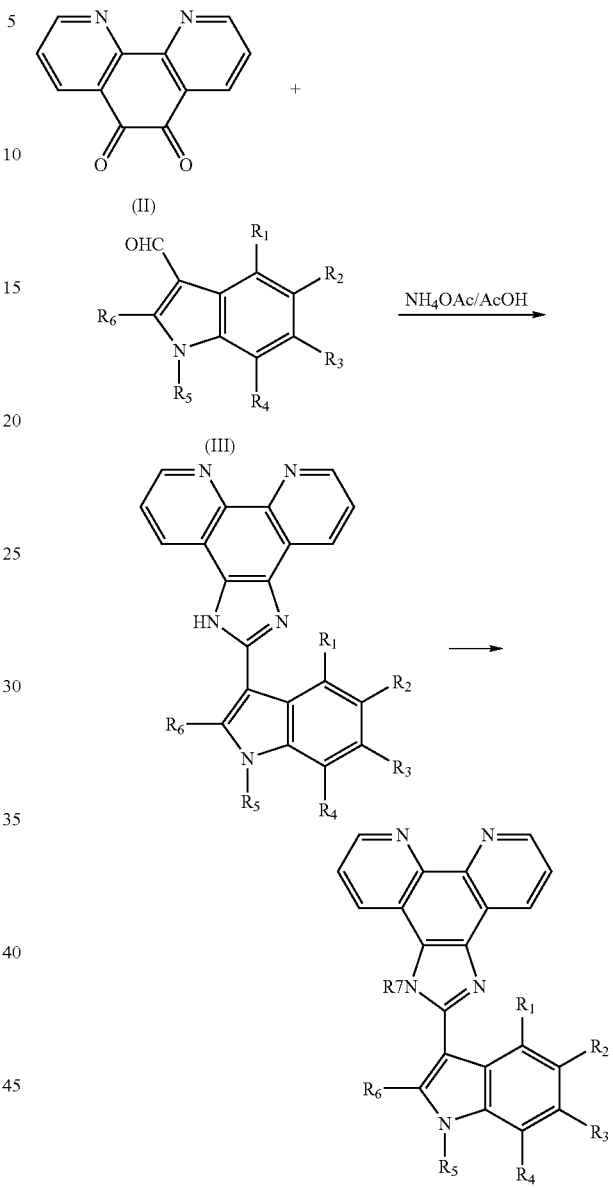

The compounds of Formula (II) and (III) are either commercially available or may be prepared using standard procedures known to a person skilled in the relevant art. Compounds of Formula (II), can be prepared by several general synthetic methods, for example, as described by: Fischer et. al (*J. Am. Chem. Soc.* 1961, 83, 4208-4210); Guijarro et al. (*J. Am. Chem. Soc.* 1999, 121, 4155-4157); Chi et. al. (*Synth. Comm.* 1994, 24(15), 2119-2122) and Armesto et. al. (*Synthesis*, 1988, 799-801); Yamada et. al. (*Bull. Soc Chem. Jpn.*, 1990, 63, (9), 2710-2712); Hiort et. al. (*J. Am. Chem Soc.* 1993, 115, 3448-3454; and Tetrahedron Letters 2004, 45(33), 6361-6363). Compounds of Formula (III) can be prepared by general synthetic methods described by Vilsmeier et. al. (Chem. Ber. 1958, 91, 850-861 and Synthesis 1985, 8, 641-645). For example, compounds of formula (III) can be prepared by reacting a compound of formula (IV) with $POCl_3$ in dimethylformamide (DMF) as shown below:

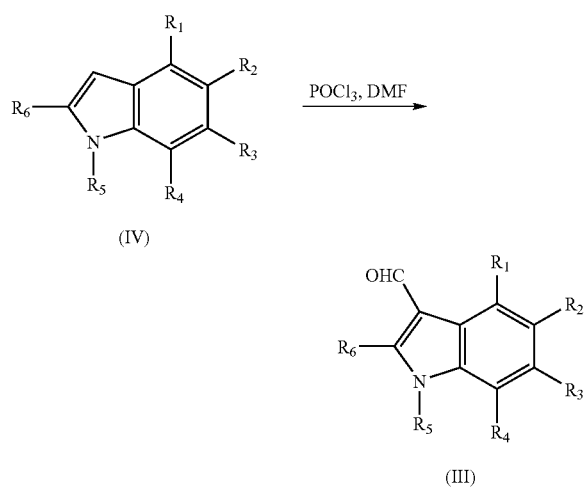

The separation and purification of the products (1) is generally based on their property to form water-soluble salts. After the reaction media is diluted with water, the impurities are extracted from the obtained solution with a nonpolar solvent, the aqueous layer is basified and the separated imidazo[4,5-d]phenanthroline (1) is filtered and recrystallized from a suitable solvent.

Testing Compounds of Formula I

As described above, compounds of Formula I contemplated for use in the methods of the present invention are capable of chelating transition metals and of inhibiting the proliferation of cancer cells. In addition, in one embodiment of the present invention, the compounds of Formula I are capable of increasing the expression of a transition metal-regulated tumour suppressor gene, such as KLF4, in cancer cells. In a further embodiment of the present invention, the compounds of Formula I induce apoptosis in cancer cells and exert a cytotoxic effect on cancer cells.

The ability of a candidate compound of Formula I to chelate transition metals and inhibit neoplastic cell proliferation in vitro and in vivo can be tested using standard techniques known in the art. Similarly, the ability of the compounds to increase the expression of a tumour suppressor gene and/or induce apoptosis in cancer cells can be tested using standard techniques. Exemplary methods of testing candidate compounds of Formula I are provided below and in the Examples included herein. One skilled in the art will understand that other methods of testing the compounds are known in the art and are also suitable for testing candidate compounds.

Compounds of Formula I that demonstrate inhibitory activity may be further tested in vitro and/or in vivo in combination with various known chemotherapeutics to evaluate their potential use in combination therapies.

Metal chelate complexes of compounds of Formula I are also contemplated by the present invention. Such chelate complexes can also be tested using the methods described below.

A. Metal Chelation Ability

In accordance with the present invention, the compounds of Formula I are capable of chelating transition metal ions in a cellular environment. In one embodiment, compounds of Formula I are capable of chelating iron, zinc, copper, ruthenium and cobalt ions. In a further embodiment, compounds of Formula I are capable of chelating first-row transition metal ions. In a further embodiment, compounds of Formula I are capable of chelating iron, zinc and copper ions. In another embodiment of the present invention, compounds of Formula I are capable of chelating zinc ions. In another embodiment, compounds of Formula I are capable of chelating copper ions.

The metal chelating properties of the compounds of Formula I can be determined using various techniques known in the art, including but not limited to X-ray crystallography, NMR spectroscopy, fluorescence spectroscopy, atomic absorption spectroscopy (AAS), electron paramagnetic resonance spectroscopy, high-performance liquid chromatography (HPLC), combined liquid chromatography/mass spectrometry, and potentiometric titrations.

For example, peracetic acid (PAA) is decomposed rapidly in the presence of metal ions such as manganese, iron or copper. The efficiency of a chelating compound to stabilize PAA solutions in the presence of metal ions can be assessed to determine the metal chelating ability of the compound. Briefly, a water solution containing metal ions can be prepared and the appropriate amount of a candidate compound of Formula I added to the solution, followed by pH and temperature adjustment. The stability of PAA solutions containing the compounds of Formula I can then be followed by iodometric titration. Other tests to determine metal chelation ability can include, for example, measurement of non-chelated metal ions in a solution containing metal ions and a chelating compound, with a metal ion selective electrode. Briefly, a solution containing a metal is titrated with a solution containing a chelating compound followed by measurement with a metal selective electrode to determine the amount of non-chelated metal ions, thereby providing an indication of the metal chelating ability of the compounds of Formula I.

The metal-chelation property of the compounds of Formula I can also be assessed spectrophotometrically utilizing the in vitro 4-(2-pyridylazo) resorcinol (PAR) metal binding assay. PAR is a commercially available dye that behaves as a terdentate or a bidentate ligand to form soluble or insoluble coloured complexes with cations of Mg, Al, Ca, Sr, Ba, Sc, Ti, V, Cr, Mn, Fe, Co, Ni, Cu, Zn, Ga, Y, Zr, Nb, Ru, Rh, Pd, Ag, Cd, In, Sn, Hf, Ta, Os, Ir, Pt, Au, Hg, Tl, Pb, Bi, Th, U, Np and the lanthanides at specific pH values, with a maximal absorbance around 500 nm. To determine the metal-chelation property of the compounds of Formula I, the resulting PAR-metal ion complexes that form in the presence of metal ions, can be measured spectrophotometrically at about 500 nm and a comparison can be made between PAR-metal ion complexes that form in samples containing compounds of Formula I and control samples, for example in samples containing a known chelator and/or samples not containing the compounds of Formula I but containing a control vehicle.

The ability of the compounds of Formula I to chelate transition metals in a cellular environment can be assessed utilizing methods well known in the art, for example, by measuring the chelatable pools of intracellular zinc, iron or copper in the presence and absence of a candidate compound using specific fluorescent indicators, such as zinquin or Phen Green SK (see, for example, Zalewski et al., *Biochem J.* 1993, 296 (Pt 2), 403-8; and Petrat et al., *Biol Chem.* 2002, 383(3-4), 489-502). Additionally, the metal chelating ability of the compounds of Formula I in a cellular environment can be assessed in various biological samples such as cellular extracts, isolated cells, tissues, or body fluids, by measuring the chelatable pools of intracellular metal ions utilizing methods such as high-performance liquid chromatography (HPLC), spectrophotometrical detection, electron spin resonance (ESR) or atomic absorption spectroscopy, as described, for example, by Gower et al., *Anal. Biochem.* 1989, 180, 126-130; Öllinger and Roberg, *J. Biol. Chem.* 1997, 272, 23707-23711; Flatmark and Tangeras, *Proteins of Iron Metabolism*, Brown, Aisen, Fielding, and Crichton, eds. (New York, USA: Grune & Stratton), 1976, pp. 349-358; Kozlov et al., *Free Radic. Biol. Med.* 1992, 13, 9-16; Cammack and Cooper, *Methods Enzymol.* 1993, 227, 353-384. Yegorov et al., *Free Radic. Biol. Med.* 1993, 15, 565-574; Cairo et al., *J. Biol. Chem.* 1995, 270, 700-703; and Nielsen et al., *Int. J. Biochem.* 1993, 25, 223-232.

The metal chelating ability of the compounds of Formula I in a cellular environment can also be assessed indirectly by assessing cell growth, changes in expression of genes associated with metal regulation, cytoxicity, enzyme assays, or other measurable endpoints that are known in the art, in the presence of the candidate compound and varying concentrations of metal ions. For example, the metal chelation ability of the compounds of Formula I can be assessed in cultured cells or in whole animals by manipulating cellular metal pools and measuring changes in cell growth in the presence and absence of the candidate compound.

Alternatively, or in addition to measuring changes in cell growth, changes in gene expression of known metal-regulated genes or metal regulatory proteins such as metallothionein, or metal transcription factor-1, can determined using standard protocols known in the art. As is known in the art, expression of metallothionein (MT) proteins is tightly regulated by intracellular zinc concentrations. The binding of zinc to the metal transcription factor (MTF-1) allows MTF-1 to bind to metal response elements (MREs) in the promoter of MT, which in turn inititates MT-gene transcription. Accordingly the ability of compounds of Formula I to modulate expression of MT or MTF-1 can be determined as an indication of the metal-chelating ability of the compounds. Other metal-regulated genes known in the art include, for example, the genes encoding iron regulatory proteins (IRP), ferritin, or transferrin receptor, which are regulated by iron levels (see, for example, Eisenstein and Blemings, *J. Nutr.* 1998, 128(12): 2295-2295; and Martini et al., *J. Nutr.* 2002, 132(4):693-696); and the gene encoding zinc transporter protein-1, which is regulated by zinc levels (see, for example, Kindermann et al., *J. Nutr.* 2004, 134(1):57-62; and Langmade et al., *J. Biol. Chem.* 2000, 275(44):34803-24809).

B. In vitro Testing
i) Inhibition of Cancer Cell Proliferation

Candidate compounds of Formula I can be assayed initially in vitro for their ability to inhibit proliferation of cancer cells using standard techniques.

In general, the ability of a candidate compound of Formula I to inhibit proliferation of cancer cells can be tested as follows. Cells of a specific test cancer cell line are grown to a suitable density (e.g. approximately $1\times10^4$) and various concentrations of the candidate compound are added. After an appropriate incubation time (typically between about 48 to 74 hours), cell survival is assessed, for example, by assaying for tetrazolium salt (or modified tetrazolium salt) cleavage, or by using the resazurin reduction test (see Fields & Lancaster (1993) *Am. Biotechnol. Lab.* 11:48-50; O'Brien et al., (2000) *Eur J. Biochem.* 267:5421-5426 and U.S. Pat. No. 5,501, 959), the sulforhodamine assay (Rubinstein et al., (1990) *J. Natl. Cancer Inst.* 82:113-118), the neutral red dye test (Kitano et al., (1991) *Euro. J. Clin. Investg.* 21:53-58; West et al., (1992) *J. Investigative Derm.* 99:95-100) or the XTT assay. Inhibition of cell proliferation is determined by comparison of cell survival in the treated culture with cell survival in one or more control cultures, for example, cultures not pre-treated with the candidate compound, those pre-treated with a control vehicle and/or those pre-treated with a control compound (typically a known therapeutic).

Other assays known in the art that measure metabolic activity (such as tetrazolium-based assays) can also be used to assess the effect of candidate compounds on cell proliferation, given that proliferating cells tend to be metabolically more active than resting cells.

Candidate compounds can also be tested in vitro for their ability to inhibit anchorage-independent growth of tumour cells. Anchorage-independent growth is known in the art to be a good indicator of tumourigenicity. In general, anchorage-independent growth is assessed by plating cells from an appropriate cancer cell-line onto soft agar and determining the number of colonies formed after an appropriate incubation period. Growth of cells treated with the candidate compound can then be compared with that of cells treated with an appropriate control (as described above).

A wide variety of cancer cell lines suitable for testing the compounds of Formula I are available commercially, for example the American Type Culture Collection (ATCC; Manassas, Va.) currently supplies over 700 different human cancer cell lines and the DCTD Tumor Depository (NCI at Frederick, Frederick, Md.) supplies a variety of mammalian cell lines, including the human cancer cell lines used in the NCI/NIH screen.

Examples of suitable human cancer cell-lines against which the compounds of Formula I can be tested include, but are not limited to, bladder cancer cell lines HT-1376, HT-1197, and Hs 195.T; colon and colorectal adenocarcinoma and carcinoma cell lines such as CaCo, COLO320, HCT-116, LoVo, NCI-H498, NCI-H548 and SNU-C2B; duodenal cancer cell line HuTu 80; gastric adenocarcinoma and carcinoma cell lines Hs 740.T, AGS, Hs 746T, NCI-N87, NCI-SNU-1 and RF-48; large cell lung cancer cell lines NCI-H661 and NCI-H1581; prostate adenocarcinoma and carcinoma cell lines MDA PCa 2b, LNCaP-FGC and 22Rv1; Burkitts lymphoma (Non-Hodgkin's) cell lines raji, Namalwa and HS Sultan; histiocytic lymphoma cell line U-937; acute lymphoblastic leukemia (T-ALL) cell line Jurkat, T-cell lymphoma cell line Karpas 299; plasma cell leukemia cell line L-363; and rectal adenocarcinoma and carcinoma cell lines NCI-H630 and SW837. Drug-resistant cancer cell lines can also be used to determine the ability of the compounds of the present invention to inhibit growth and/or proliferation of drug- or multi-drug resistant neoplastic cells.

The differential neoplastic selectivity of the candidate compounds of Formula I can also be tested, i.e. the ability of the compound to demonstrate some level of selective action toward neoplastic (or cancer) cells in comparison to normal proliferating cells. An exemplary method of assessing the differential sensitivity between normal and cancer cells for a compound has been described by Vassilev et al. (*Anti-Cancer Drug Design* (2001) 16:7). This method involves the comparison of $IC_{90}$ values, i.e. the molar concentration of a test compound required to cause 90% growth inhibition of exponentially growing cells. Thus, the $IC_{90}$ values for candidate compounds can be evaluated in various cancer cell lines (such as those outlined above) and normal cells (such as HUVEC and/or WI38 cells) and compared. $IC_{90}$ values can be measured using a variety of standard techniques as known in the art. Cancer cell selectivity is calculated as a ratio between the average $IC_{90}$ for all normal cell lines and the average $IC_{90}$ for all cancer cell lines. Compounds with an $IC_{90}$ ratio (normal/cancer) of >4 are considered to be selective for cancer cells (L. T. Vassilev et al., Anti-cancer Drug Design, 2001, 16: 7-17).

In one embodiment of the present invention, compounds of Formula I selectively inhibit the proliferation of one or more of leukemia cells, prostate cancer cells, non-small cell lung cancer cells and colon cancer cells. Selectivity of the candidate compounds is assessed using human cancer cell-lines used in the NCI/NIH Therapeutic Drug Program in vitro screen. The cancer cell lines used in this screen are listed in Table 1 supra.

In accordance with this embodiment of the present invention, a compound shows selective inhibition of the selected cancer (i.e. prostate cancer, colon cancer, non-small lung cancer and/or leukemia) when the compound inhibits the proliferation of the cell lines from the selected cancer with an average $GI_{50}$ at least 10% lower than the average $GI_{50}$ for inhibition of cell lines from each of breast cancer, CNS cancer, melanoma, ovarian cancer and renal cancer. In one embodiment, the average $GI_{50}$ for prostate cancer cells, colon cancer cells, non-small lung cancer cells and/or leukemia cells is at least 15% lower than the average $GI_{50}$ for inhibition of cell lines from each of breast cancer, CNS cancer, melanoma, ovarian cancer and renal cancer. In another embodiment, the average $GI_{50}$ for prostate cancer cells, colon cancer cells, non-small cell lung cancer cells and/or leukemia cells is at least 20% lower than the average $GI_{50}$ for inhibition of cell lines from each of breast cancer, CNS cancer, melanoma, ovarian cancer and renal cancer.

Methods of calculating the $GI_{50}$ are known in the art (see, for example, Boyd, M. R., et al. In *Cytotoxic Anticancer Drugs: Models and Concepts for Drug Discovery and Development*; Vleriote, F. A.; Corbett, T. H.; Baker, L. H., Eds.; Kluwer Academic: Hingham, Mass., 1992 and Monks, A.; et al., (1991) *JNCI, J. Natl. Cancer Inst.* 83, 757-766; pp 11-34). As described in the art, the $GI_{50}$ is a renaming of the $IC_{50}$ value (the concentration that causes 50% growth inhibition) that emphasizes the correction in the calculation of the $GI_{50}$ for the cell count at time zero. The $GI_{50}$ is thus the concentration of a candidate compound where:

$$100 \times (T-T0)/(C-T0) = 50.$$

And wherein, the optical density of the test well after a 48-h period of exposure to test drug is T, the optical density at time zero is TO, and the control optical density is C.

For example, the following methodology, which is currently employed by the NCI, can be used to assess the $GI_{50}$ of a candidate compound of Formula I in the selected cancer cell lines. Briefly, cell suspensions are diluted (5000-40,000 cells per well) and 100 μL of the diluted cell suspension is added into 96-well microtiter plates. Inoculates are allowed a pre-incubation period of 24 h at 37° C. for stabilization. Dilutions at twice the intended test concentration of the candidate compound are added at time zero in 100 μL aliquots to the microtiter plate wells. Test compounds are generally evaluated at five 10-fold dilutions. In routine testing, the highest well concentration is usually 10E-4 M, but this may be adjusted depending on the compound being tested. The cells are incubated with the test compound for 48 h in 5% $CO_2$ atmosphere and 100% humidity. The cells are then assayed by using the sulforhodamine B assay (see, for example, Skehan, P., et al. (1990) *JNCI, J. Natl. Cancer Inst.* 82, 1107-1112; and Chen, S. F., et al. (1990) *Proc. Am. Assoc. Cancer Res.* 31, A2644) employing a plate reader which can be used to read the optical densities.

ii) Ability to Increase Expression of Transition Metal Regulated Tumour Suppressor Genes In accordance with one embodiment of the present invention, compounds of Formula I increase the expression of a transition metal regulated tumour suppressor gene in cancer cells. In another embodiment, the compounds of Formula I increase expression of the tumour suppressor gene in cancer cells in which the expression of the tumour suppressor gene is down-regulated. Increased or up-regulated expression of a transition metal regulated tumour suppressor gene in cancer cells can be determined as a percentage increase in expression of the gene in treated cells versus untreated cells. In one embodiment, the compounds of Formula I increase the expression of a transition metal regulated tumour suppressor gene by about 10%. In another embodiment, the compounds of Formula I increase the expression of a transition metal regulated tumour suppressor gene by about 20%. In other embodiments, the compounds of Formula I can increase the expression of a transition metal regulated tumour suppressor gene by about 25%, 50%, 75% or 100%.

The increase or up-regulation of expression of a transition metal regulated tumour suppressor gene in cancer cells can also be determined as a "fold" increase or up-regulation of expression of the gene in cancer cells, in which gene expression in untreated cancer cells is presented as "1" and respective "fold" increase in gene expression in treated cancer cells is presented relative to respective gene expression in untreated cancer cells. In one embodiment of the present invention, the compounds of Formula I are capable of increasing or up-regulating expression of a transition metal regulated tumour suppressor gene by about 1.5-fold. In another embodiment, compounds of Formula I are capable of increasing the expression of a transition metal regulated tumour suppressor gene by about 2.0-fold.

In another embodiment of the invention, the transition metal regulated tumour suppressor gene is KLF4. The ability of candidate compounds to modulate the expression of tumour suppressor genes, such as KLF-4, can be assessed by measuring changes in the levels of the KLF4 mRNA or protein. Methods of performing these assays are known in the art.

For example, the candidate compound can be introduced into a selected cancer cell line and the amount of mRNA transcribed from the tumour suppressor gene of interest can be measured by standard techniques such as Northern blot analysis, RT-PCR, and the like. Alternatively, the amount of tumour suppressor protein produced by the cell can be measured by standard techniques such as Western blot analysis. The amount of mRNA or protein produced in a cell treated with the candidate compound can then be compared with the amount produced in control cells and will provide an indication of how successfully the compound has inhibited expression of the tumour suppressor gene. Suitable control cells include, for example, untreated cells and/or cells treated with a control compound.

Alternatively, the candidate compounds can be screened for their ability to increase gene expression in a selected cancer cell line using standard methods for screening expression of multiple genes ("expression profiling"). Such methods are well known in the art and include, for example, microarray analysis, such as high density microarray assays containing 10-fold more (for example, 19,000) human genes to identify suitable functional clusters of genes whose expression is affected by the compound.

Typically, expression profiling makes use of pre-fabricated microarrays of short DNA sequences or oligonucleotides. Methods of constructing microarrays are well known in the art [see, for example, Ausubel, et al., *Current Protocols in Molecular Biology*, John Wiley & Sons, Inc, NY. (1989 and updates)]. As an alternative, microarrays can be custom made, for example, to include sequences corresponding to known tumour suppressor genes. Pre-made microarrays are also commercially available for many organisms including, for example, GeneChip® (Affimetrix, Santa Clara, Calif.), AtlaS™ (BD Biosciences-CLONTECH, Palo Alto, Calif.), GEM Microarrays, GeneJet™ array and LifeSeq® (Incyte Genomics, Palo Alto, Calif.), MICROMAX™ Human cDNA Microarray Systems (PerkinElmer Life Sciences, Boston, Mass.) and ResGen™ GeneFilters® (Invitrogen, Huntsville, Ala.). For expression analysis, RNA is isolated from cells treated with the candidate compound and from control cells. If necessary, the RNA can be amplified by conventional techniques to ensure a sufficient quantity for analysis. The RNA is then hybridised to the microarray under suitable conditions and a routine analysis of the microarray by commercially available scanners and software is conducted to identify genes whose expression is altered in the treated cells relative to the control cells. Suitable hybridization conditions can readily be determined by one skilled in the art using standard techniques. Following the identification of such other genes, mRNA quantitation and respective protein levels can also be evaluated to determine the extent of the effect of the compound on the genes under investigation.

iii) Induction of Apoptosis

In accordance with another embodiment of the present invention, compounds of Formula I are capable of inducing apoptosis in cancer cells. Methods of assessing the ability of candidate compounds to induce apoptosis are known in the art (see, for example, Current Protocols in Cell Biology, 2000 and updates, K. Morgan, ed., J. Wiley & Sons, New York, N.Y.) and include, for example, DNA fragmentation analysis, flow cytometry in conjunction with annexin V-FITC and propidium iodide staining, fluorochrome labelling of DNA strand breaks by terminal deoxynucleotidyl transferase (TdT-assay) and analysis by flow cytometry, detection by flow cytometry or detection in situ with immunocytochemistry utilizing the terminal deoxynucleotidyl transferase (TdT) mediated dUTP nick end labeling (TUNEL) assay, immuno-histochemical or flow cytometric detection of proteolytic cleavage or proteolysis of poly(ADP-ribose)polymerase (PARP), and/or detection of activation of cysteinyl-aspartic acid proteases (caspases).

For example, the effect of compounds of Formula I on apoptosis can be assessed by incubating cells with the candidate compound for a period of time, followed by cytometric analysis using the annexinV-FITC-propidium iodide method. Entry into apoptosis leads to the translocation of phosphatidylserine from the inner leaflet to the extracellular side of the plasma membrane. Annexin V, a protein that binds with high affinity to phosphatidylserine, can be used to detect this apoptosis-induced membrane alteration. The DNA binding dye, propidium iodide (PI) readily enters and stains non-viable cells, but cannot cross the membrane of viable cells. Therefore, cells that are stained with Annexin V only are considered to be in early apoptosis, whereas cells stained with both Annexin V and PI are considered to be in late apoptosis. Cells stained with PI only are considered non-viable, whereas no staining indicates viable cells.

Assays to investigate potential mechanisms of action of the compounds may be conducted if desired in order to provide information useful in determining what aspects of tumour growth the compounds affect. This type of information may help to determine cancer types that will benefit from treatment with the compounds. Examples of such assays include, but are not limited to, cell-cycle analysis (for example, employing flow cytometry techniques), anti-angiogenesis assays (for example, various Matrigel assays, including cord formation and Matrigel plug assays) and immunohistochemical analysis.

C. In Vivo Testing

The ability of the candidate compounds to inhibit tumour growth, proliferation and/or metastasis in vivo can be determined in an appropriate animal model using standard techniques known in the art (see, for example, Enna, et al., Current Protocols in Pharmacology, J. Wiley & Sons, Inc., New York, N.Y.). Exemplary protocols are provided below and in the Examples.

For example, the in vivo activity of candidate compounds can also be tested using the Hollow Fiber Assay (Hollingshead, M., et al., (1995) Life Sciences 57:131-141; and Decker et al., Eur. J. of Cancer 40: 821-826 (2004)). In this assay, cells growing in hollow fibers (polyvinylidine fluoride, PVDF) are implanted in various body compartments of mice. A standard panel of 12 tumour cell lines can be used for the hollow fiber screening of candidate compounds which have shown activity in vitro. These cell lines may include NCI-H23, NCI-H522, MDA-MB-231, MDA-MB-435, SW-620, COLO 205, LOX-IMVI, UACC-62, OVCAR-3, OVCAR-5, U251 and SF-295. In addition, alternate lines such as those described in the above in vitro section can be used for specialized testing of compounds. The cell lines are cultivated according to standard protocols, and fibers are prepared by flushing cells into the PVDF fibers and sealing them at 2 cm intervals. The samples generated from these seals are placed into tissue culture medium and incubated at 37° C. in 5% $CO_2$ for 24 to 48 hours prior to implantation. A total of 3 different tumour lines are prepared for each experiment so that each mouse receives 3 intraperitoneal implants (1 of each tumour line) and 3 subcutaneous implants (1 of each tumour line). On the day of implantation, samples of each tumour cell line preparation are quantitated for viable cell mass by, for example, a stable endpoint MTT assay, so that the time zero cell mass is known. Mice are treated with experimental agents starting on day 3 or 4 following fiber implantation and continuing daily for 4 days. Each agent is administered by intraperitoneal injection at 2 dose levels. The fibers are collected from the mice on the day following the fourth compound treatment and subjected to the stable endpoint MTT assay. The optical density of each sample is determined spectrophotometrically at 540 nm and the mean of each treatment group is calculated. The percent net growth for each cell line in each treatment group is calculated and compared to the percent net growth in the vehicle treated controls. A 50% or greater reduction in percent net growth in the treated samples compared to the vehicle control samples is considered a positive result. Each positive result is given a score of 2 and all of the scores are totaled for a given compound. The maximum possible score for an agent is 96 (12 cell lines×2 sites×2 dose levels×2 [score]).

A candidate compound that is screened initially in the hollow fiber assay may subsequently be tested in a xenograft model if it has a combined ip+sc score of 20 or greater, a sc score of 8 or greater, or produces cell kill of any cell line at either dose level evaluated. This scoring system has been validated by DCTDC statisticians in CTEP to represent a level of detection expected to score current "standard" agents as active.

Alternatively, compounds of Formula I can be tested directly in xenograft models. Xenograft models, in which a human tumour has been implanted into an animal, are a standard model in which to assess the anti-cancer activity of a candidate compound. Examples of xenograft models of human cancer include, but are not limited to, human solid tumour xenografts, implanted by sub-cutaneous injection or implantation and used in tumour growth assays; human solid tumour isografts, implanted by fat pad injection and used in tumour growth assays; human solid tumour orthotopic xenografts, implanted directly into the relevant tissue and used in tumour growth assays; disseminated disease models for solid tumours or for leukemias, via intravenous injection, used in survival assays; experimental models of lymphoma and leukaemia in mice, used in survival assays, and experimental models of lung metastasis in mice. In addition to the implanted human tumour cells, the xenograft models can further comprise transplanted human peripheral blood leukocytes, which allow for evaluation of the anti-cancer immune response. In various xenograft models, the implanted or transplanted human tumour cells can be primary tumour cells or tumour cells derived from a cell line.

Several host animal options exist for xenograft models, which includes but is not limited to the use of severe combined immunodeficient (SCID) mice, athymic nude mice, and athymic rats. Non-obese diabetic/severe combined immunodeficient mice (NOD/SCID) represent another host animal that can be used in various xenograft transplantation models, for example, for the engraftment of hematological cancer cells, such as leukemia and/or lymphoma cells.

Alternatively, murine cancer models can be used for screening anti-tumour compounds. Examples of appropriate murine cancer models are known in the art and include, but are not limited to, implantation models in which murine cancer cells are implanted by intravenous, subcutaneous, fat pad or orthotopic injection; murine metastasis models; transgenic mouse models; and knockout mouse models. The effect of the candidate compound can also be assessed on spontaneous tumours in normal mice.

For example, the candidate compounds can be tested in vivo on solid tumours using mice that are subcutaneously grafted or injected with 30 to 60 mg of a tumour fragment, or an appropriate number of tumour cells (e.g. about $10^6$ to $10^7$) on day 0. The animals bearing tumours are mixed before being subjected to the various treatments and controls. In the case of treatment of advanced tumours, tumours are allowed to develop to the desired size, animals having insufficiently developed tumours being eliminated. The selected animals are distributed at random to undergo the treatments and controls. Animals not bearing tumours may also be subjected to the same treatments as the tumour-bearing animals in order to be able to dissociate the toxic effect from the specific effect on the tumour. Chemotherapy generally begins from 3 to 22 days after grafting, depending on the type of tumour, and the animals are observed every day. Candidate compounds can be administered to the animals, for example, by bolus infusion. The different animal groups are weighed about 3 or 4 times a week until the maximum weight loss is attained, after which the groups are weighed at least once a week until the end of the trial.

The tumours are measured about 2 or 3 times a week until the tumour reaches a pre-determined size and/or weight, or until a pre-determined time period has passed, or until the animal dies (if this occurs before the tumour reaches the pre-determined size/weight). The animals are then sacrificed and the tissue histology, size and/or proliferation of the tumour assessed.

The effect of the candidate compounds on drug-resistant tumours can be assessed in vivo by utilising a drug- or multidrug-resistant cancer cell in the xenograft experiments.

For the study of the effect of the candidate compounds on haematologic tumours, such as lymphomas or leukaemias, the animals are grafted or injected with a particular number of cells, and the anti-tumour activity is determined by the increase in the survival time of the treated mice relative to the controls. Assessing disease burden in leukemia xenograft models can also be performed by measuring various indicators of leukemia, such as cell surface markers or expression of leukemia specific genes, using flow cytometry or polymerase chain reaction (PCR) from serial blood samples.

To study the effect of the candidate compounds on tumour metastasis, tumour cells are typically treated with the compound ex vivo and then injected into a suitable test animal. The spread of the tumour cells from the site of injection is then monitored over a suitable period of time.

The ability of the candidate compounds to act in combination with, or to sensitise a tumour to the effects of, another chemotherapeutic agent can also be tested in the above models. In this case, the test animals would be treated with both the chemotherapeutic agent and the candidate compound of Formula I. Control animals could include animals treated with the chemotherapeutic alone, animals treated with the candidate compound alone and/or untreated animals.

In vivo toxic effects of the compounds of Formula I can be evaluated by standard techniques, for example, by measuring their effect on animal body weight during treatment and by performing haematological profiles and liver enzyme analysis after the animal has been sacrificed (survival assays).

TABLE 2

Examples of in vivo models of human cancer

| CANCER MODEL | CELL TYPE |
| --- | --- |
| Tumour Growth Assay Human solid tumour xenografts in mice (sub-cutaneous injection) | Prostate (PC-3, DU145) Breast (MDA-MB-231, MVB-9) Colon (HT-29) Lung (NCI-H460, NCI-H209) Pancreatic (ASPC-1, SU86.86) Pancreatic: drug resistant (BxPC-3) Skin (A2058, C8161) Cervical (SIHA, HeLa-S3) Cervical: drug resistant (HeLa S3-HU-resistance) Liver (HepG2) Brain (U87-MG) Renal (Caki-1, A498) Ovary (SK-OV-3) Bladder (T24) |
| Tumour Growth Assay Human solid tumour isografts in mice (fat pad injection) | Breast: drug resistant (MDA-CDDP-S4, MDA-MB435-To.1) |
| Survival Assay Experimental model of lymphoma and leukaemia in mice | Human: Burkitts lymphoma (Non-Hodgkin's) (raji, Namalwa, HS Sultan), histiocytic lymphoma (U-937), chronic myelogenous leukemia (K-562), acute lymphoblastic leukemia (T-ALL) (Jurkat, CEM, MOLT-4), T-cell lymphoma (Karpas 299), plasma cell leukemia (L-363) Murine: erythroleukemia (CB7 Friend retrovirus-induced), lymphocytic leukemia (L1210), lymphoma (P388) |
| Experimental model of lung metastasis in mice | Human: melanoma (C8161) Murine: fibrosarcoma (R3) |

In addition, if desired the effect of the compound of Formula I on the expression level of a transition metal regulated tumour suppressor gene can be assessed in the tumour from the test animals by measuring, for example, changes in the tumour suppressor mRNA or protein levels. Methods of carrying out these assays are known in the art as described above.

If desired, one or more standard immunohistochemical tests may also be conducted on tissues isolated from the test animals in order to determine the effects of the compound on tumour growth, differentiation, apoptosis and/or angiogenesis. Examples of such tests include, but are not limited to, the use of specific antibodies (for example, antibodies against Ki-67 to assess proliferation, CD31 to assess angiogenesis, NK1.1 as an indication of the presence of NK cells, F4/80 as an indication of the presence of macrophages) and TUNEL assays to determine apoptosis.

D. Toxicity Testing

The compounds of Formula I can also be submitted to toxicity testing if desired. Toxicity tests for potential drugs are well-known in the art (see, for example, Hayes, A. W., ed., (1994), *Principles and Methods of Toxicology*, 3$^{rd}$ ed., Raven Press, NY; Maines, M., ed., *Current Protocols in Toxicology*, John Wiley & Sons, Inc., NY).

In vitro acute toxicity testing of a compound of Formula I can be performed using mammalian cell lines (see, for example, Ekwall, B., *Ann. N.Y. Acad. Sci.*, (1983) 407:64-77). Selection of an appropriate cell line is dependent on the potential application of the candidate compound and can be readily determined by one skilled in the art. For example, these tests include the treatment of human primary fibroblasts in vitro with the compounds of Formula I in the presence of a commercial carrier. Cells are then tested at different time points following treatment for their viability using a standard viability assay, such as the trypan-blue exclusion assay, XTT or MTT assays. Cells can also be assayed for their ability to synthesize DNA, for example, using a thymidine incorporation assay, and for changes in cell cycle dynamics, for example, using a standard cell sorting assay in conjunction with a fluorocytometer cell sorter (FACS).

In vivo toxicity testing can be performed by standard methodology, for example, by injecting varying concentrations of the candidate compound into an appropriate animal model. The compound can be injected once, or administration can be repeated over several days. The toxic effects of the compound can be evaluated over an appropriate time period by monitoring the mortality, changes in behavior, appearance, and body weight of the animals. After the completion of the period of assessment, the animals can be sacrificed and the appearance and weight of the relevant organs determined. If necessary, additional assessments of, for example, hematological profiles, histology, and liver enzyme analysis may be performed. An indication of the toxicity of a compound can also be obtained during the in vivo anti-cancer testing of the compound.

The genotoxicity of compounds of Formula I can be assessed in vitro if necessary using standard techniques such as the Ames Assay to screen for mutagenic activity, the mouse lymphoma assay to determine the ability of a test article to induce gene mutation in a mammalian cell line, in vitro chromosomal aberration assays using, for example, Chinese hamster ovary cells (CHO) to determine any DNA rearrangements or damage induced by the test article. Other assays include the sister chromatid assay, which determines any exchange between the arms of a chromosome induced by the test article and in vitro mouse micronucleus assays to determine any damage to chromosomes or to the mitotic spindle. The genotoxicity of compounds of Formula I can also be assessed in vivo if necessary using the in vivo sister chromatid exchange assay, in vivo micronucleus assay, or the in vivo chromosomal abberation assay. Protocols for these and other standard assays are known in the art, for example, see *OECD Guidelines for the Testing of Chemicals* and protocols developed by the ISO.

IV. Uses of Compounds of Formula I

Compounds of Formula I can be used to treat, stabilize or prevent cancer in a subject. In this context, the compounds may exert either a cytotoxic or cytostatic effect resulting in a reduction in the size of a tumour, the slowing or prevention of an increase in the size of a tumour, an increase in the disease-free survival time between the disappearance or removal of a tumour and its reappearance, prevention of an initial or subsequent occurrence of a tumour (e.g. metastasis), an increase in the time to progression, reduction of one or more adverse symptom associated with a tumour, or an increase in the overall survival time of a subject having cancer. In accordance with one embodiment of the present invention, the compounds of Formula I exert a cytotoxic effect on cancer cells through induction of apoptosis in the cancer cells.

Exemplary tumours include, but are not limited to, haematologic neoplasms, including leukaemias, myelomas and lymphomas; carcinomas, including adenocarcinomas and squamous cell carcinomas; melanomas and sarcomas. Carcinomas and sarcomas are also frequently referred to as "solid tumours." Examples of commonly occurring solid tumours include, but are not limited to, cancer of the brain, breast, cervix, colon, head and neck, kidney, lung, ovary, pancreas, prostate, stomach and uterus, non-small cell lung cancer and colorectal cancer. Various forms of lymphoma also may result in the formation of a solid tumour and, therefore, are also often considered to be solid tumours.

One embodiment of the present invention provides for the use of the compounds of Formula I in the treatment of one or more of prostate cancer, non-small cell lung cancer, colon cancer and leukemia. In addition, in accordance with one embodiment of the present invention, the compounds of Formula I can be used in the treatment of a cancer for increasing expression of a transition metal-regulated tumour suppressor gene in cancer cells. In a specific embodiment, the compounds of Formula I can be used to treat, stabilize or prevent a cancer in which the metal-regulated tumour suppressor gene KLF4 functions as a tumour suppressor, including cancers of the gastrointestinal (GI) tract, bladder cancer and leukemia. Cancers of the GI tract include gastric (stomach) cancers, oesophageal cancers, small intestine cancers, duodenal cancers, colon cancers, colorectal cancers, rectal cancers and anal cancers.

In one embodiment, the present invention also provides for the use of a compound of Formula I to increase expression of a transition metal-regulated tumour suppressor gene in cancer cells. In another embodiment, the invention provides for the use of a compound of Formula I to increase expression of the KLF4 tumour suppressor gene in cancer cells.

The cancers which can be treated in accordance with one embodiment of the present invention thus include, but are not limited to, leukaemias; adenocarcinomas and carcinomas, including squamous cell carcinomas. Carcinomas are also frequently referred to as "solid tumours," as described above, and examples of commonly occurring solid tumours that can be treated in accordance with the present invention include, but are not limited to, anal cancer, bladder cancer, colon cancer, colorectal cancer, duodenal cancer, gastric (stomach) cancer, lung (non-small cell) cancer, oesophageal cancer, prostate cancer, rectal cancer and small intestine cancer. Accordingly, one embodiment of the present invention provides for the use of a compound of Formula I in the treatment of a cancer selected from the group of leukemia, bladder cancer, lung (non-small cell) cancer, prostate cancer and a cancer of the GI tract, wherein cancers of the GI tract include, but are not limited to, anal cancer, colon cancer, colorectal cancer, duodenal cancer, gastric (stomach) cancer, oesophageal cancer, rectal cancer and small intestine cancer.

The term "leukaemia" refers broadly to progressive, malignant diseases of the blood-forming organs. Leukaemia is typically characterized by a distorted proliferation and development of leukocytes and their precursors in the blood and bone marrow but can also refer to malignant diseases of other blood cells such as erythroleukaemia, which affects immature red blood cells. Leukaemia is generally clinically classified on the basis of (1) the duration and character of the disease—acute or chronic; (2) the type of cell involved—myeloid (myelogenous), lymphoid (lymphogenous) or monocytic, and (3) the increase or non-increase in the number of abnormal cells in the blood—leukaemic or aleukaemic (subleukaemic). Leukaemia includes, for example, acute nonlymphocytic leukaemia, chronic lymphocytic leukaemia, acute granulocytic leukaemia, chronic granulocytic leukaemia, acute promyelocytic leukaemia, adult T-cell leukaemia, aleukaemic leukaemia, aleukocythemic leukaemia, basophylic leukaemia, blast cell leukaemia, bovine leukaemia, chronic myelocytic leukaemia, leukaemia cutis, embryonal leukaemia, eosinophilic leukaemia, Gross' leukaemia, hairy-cell leukaemia, hemoblastic leukaemia, hemocytoblastic leukaemia, histiocytic leukaemia, stem cell leukaemia, acute monocytic leukaemia, leukopenic leukaemia, lymphatic leukaemia, lymphoblastic leukaemia, lymphocytic leukaemia, lymphogenous leukaemia, lymphoid leukaemia, lymphosarcoma cell leukaemia, mast cell leukaemia, megakaryocytic leukaemia, micromyeloblastic leukaemia, monocytic leukaemia, myeloblastic leukaemia, myelocytic leukaemia, myeloid granulocytic leukaemia, myelomonocytic leukaemia, Naegeli leukaemia, plasma cell leukaemia, plasmacytic leukaemia, promyelocytic leukaemia, Rieder cell leukaemia, Schilling's leukaemia, stem cell leukaemia, subleukaemic leukaemia, and undifferentiated cell leukaemia.

The term "carcinoma" refers to a malignant new growth made up of epithelial cells tending to infiltrate the surrounding tissues and give rise to metastases. The term "carcinoma" also encompasses adenocarcinomas. Adenocarcinomas are carcinomas that originate in cells that make organs which have glandular (secretory) properties or that originate in cells that line hollow viscera, such as the gastrointestinal tract or bronchial epithelia, and include adenocarcinomas of the lung and prostate.

In accordance with the present invention, the compounds according to Formula I can be used to treat various stages and grades of cancer cell, tumour and/or cancer development and progression. The present invention, therefore, contemplates the use of the combinations in the treatment of early stage cancers including early neoplasias that may be small, slow growing, localized and/or nonaggressive, for example, with the intent of curing the disease or causing regression of the cancer, as well as in the treatment of intermediate stage and in the treatment of late stage cancers including advanced and/or metastatic and/or aggressive neoplasias, for example, to slow the progression of the disease, to reduce metastasis or to increase the survival of the patient. Similarly, the combinations may be used in the treatment of low grade cancers, intermediate grade cancers and or high grade cancers.

The present invention also contemplates that the compounds can be used in the treatment of indolent cancers, recurrent cancers including locally recurrent, distantly recurrent and/or refractory cancers (i.e. cancers that have not responded to treatment), metastatic cancers, locally advanced cancers and aggressive cancers. Thus, an "advanced" cancer includes locally advanced cancer and metastatic cancer and refers to overt disease in a patient, wherein such overt disease is not amenable to cure by local modalities of treatment, such as surgery or radiotherapy. The term "metastatic cancer" refers to cancer that has spread from one part of the body to another. Advanced cancers may also be unresectable, that is, they have spread to surrounding tissue and cannot be surgically removed.

One skilled in the art will appreciate that many of these categories may overlap, for example, aggressive cancers are typically also metastatic. "Aggressive cancer," as used herein, refers to a rapidly growing cancer. One skilled in the art will appreciate that for some cancers, such as breast cancer or prostate cancer the term "aggressive cancer" will refer to an advanced cancer that has relapsed within approximately the earlier two-thirds of the spectrum of relapse times for a given cancer, whereas for other types of cancer, such as small cell lung carcinoma (SCLC) nearly all cases present rapidly growing cancers which are considered to be aggressive. The term can thus cover a subsection of a certain cancer type or it may encompass all of other cancer types.

The compounds may also be used to treat drug resistant cancers, including multidrug resistant tumours. As is known in the art, the resistance of cancer cells to chemotherapy is one of the central problems in the management of cancer.

Certain cancers, such as prostate, can be treated by hormone therapy, i.e. with hormones or anti-hormone drugs that slow or stop the growth of certain cancers by blocking the body's natural hormones. Such cancers may develop resistance, or be intrinsically resistant, to hormone therapy. The present invention further contemplates the use of the compounds in the treatment of such "hormone-resistant" or "hormone-refractory" cancers.

The present invention also contemplates the use of the compounds as "sensitizing agents," which selectively inhibit the growth of cancer cells. In this case, the compound alone does not have a cytotoxic effect on the cancer cell, but provides a means of weakening the cancer cells, and better facilitate the benefit obtained from the application of conventional anti-cancer therapeutics, or to otherwise potentiate said therapeutics.

Thus, the present invention contemplates the administration to a subject of a therapeutically effective amount of one or more compounds together with one or more anti-cancer therapeutics. The compound(s) can be administered before, during or after treatment with the anti-cancer therapeutic. An "anti-cancer therapeutic" is a compound, composition or treatment that prevents or delays the growth and/or metastasis of cancer cells. Such anti-cancer therapeutics include, but are not limited to, chemotherapeutic drug treatment, radiation, gene therapy, hormonal manipulation, immunotherapy and antisense oligonucleotide therapy. Examples of useful chemotherapeutic drugs include, but are not limited to, hydroxyurea, busulphan, cisplatin, carboplatin, chlorambucil, melphalan, cyclophosphamide, Ifosphamide, danorubicin, doxorubicin, epirubicin, mitoxantrone, vincristine, vinblastine, Navelbine® (vinorelbine), etoposide, teniposide, paclitaxel, docetaxel, gemcitabine, cytosine, arabinoside, bleomycin, neocarcinostatin, suramin, taxol, mitomycin C and the like. The compounds of the invention are also suitable for use with standard combination therapies employing two or more chemotherapeutic agents. It is to be understood that anti-cancer therapeutics for use in the present invention also include novel compounds or treatments developed in the future.

The compounds of Formula I are also suitable for use in a variety of applications in which chelation of a transition metal is desired, for example, in therapeutic applications. Metal chelation is relevant to the treatment of metal poisoning, metal toxicity, excess metals in the body such as iron overload associated with genetic disorders and/or transfusion-dependent anemias, microorganism infection, immune-mediated diseases or disorders, skin diseases or disorders, neurological diseases or disorders, cardiovascular diseases or disorders, aging related diseases or disorders, or genetic diseases or disorders. In one embodiment of the present invention, the compounds of Formula I can be used in therapeutic applications, for example, for chelating metal ions in vivo, for the treatment of diseases or disorders other than cancer.

The compounds of Formula I can also be used in products or processes in which chelation of a transition metal is desired, for example, for preventing or controlling scaling, chemical degradation, discoloration, precipitation, microbial growth, emulsion instability, rancidity and/or other problems associated with unwanted metal ions such as off-odors, off-flavors, clouding, loss of clarity, deterioration of texture, crystal formation, viscosity shifts, oxidation. The use of chelators in these situations can help to improve product quality, consumer appeal, shelf-life, or value, improve processing efficiency, decrease equipment downtime, or reduce processing costs. Thus, the present invention contemplates use of the compounds of Formula I for chelating metal ions in various applications including but not limited to food and beverage products, cleaning products, personal care products, pharmaceuticals, diagnostic applications, pulp and paper applications, water treatment applications, metalworking applications, textile applications, agriculture products and applications, rubber processing applications, photography applications, printing ink, oilfield applications, mining applications, gas sweetening, building applications, electronic applications, or scale removal and prevention.

V. Pharmaceutical Compositions

The compounds of the present invention are typically formulated prior to administration. The present invention thus provides pharmaceutical compositions comprising one or more compounds of Formula I and a pharmaceutically acceptable carrier, diluent, or excipient. The pharmaceutical compositions are prepared by known procedures using well-known and readily available ingredients. Pharmaceutical compositions comprising one or more compounds of Formula I in combination with one or more known cancer chemotherapeutics are also contemplated by the present invention.

Compounds of the general Formula I or pharmaceutical compositions comprising the compounds may be administered orally, topically, parenterally, by inhalation or spray, or rectally in dosage unit formulations containing conventional non-toxic pharmaceutically acceptable carriers, adjuvants and vehicles. In the usual course of therapy, the active compound is incorporated into an acceptable vehicle to form a composition for topical administration to the affected area, such as hydrophobic or hydrophilic creams or lotions, or into a form suitable for oral, rectal or parenteral administration, such as syrups, elixirs, tablets, troches, lozenges, hard or soft capsules, pills, suppositories, oily or aqueous suspensions, dispersible powders or granules, emulsions, injectables, or solutions. The term parenteral as used herein includes subcutaneous injections, intradermal, intra-articular, intravenous, intramuscular, intravascular, intrastemal, intrathecal injection or infusion techniques.

The present invention also provides for pharmaceutical compositions comprising one or more of the compounds of Formula I and a vehicle, such as an artificial membrane vesicle (including a liposome, lipid micelle and the like), microparticle or microcapsule.

Compositions intended for oral use may be prepared in either solid or fluid unit dosage forms. Fluid unit dosage form can be prepared according to procedures known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Solid formulations such as tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate: granulating and disintegrating agents for example, corn starch, or alginic acid: binding agents, for example starch, gelatin or acacia, and lubricating agents, for example magnesium stearate, stearic acid or talc and other conventional ingredients such as dicalcium phosphate, magnesium aluminum silicate, calcium sulfate, starch, lactose, methylcellulose, and functionally similar materials. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Soft gelatin capsules are prepared by machine encapsulation of a slurry of the compound with an acceptable vegetable oil, light liquid petrolatum or other inert oil.

Aqueous suspensions contain active materials in admixture with excipients suitable for the manufacture of aqueous suspensions. Such excipients are suspending agents, for example sodium carboxylmethylcellulose, methyl cellulose, hydropropylmethylcellulose, sodium alginate, polyvinylpyrrolidone, gum tragacanth and gum acacia: dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example hepta-decaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl-p-hydroxy benzoate, one or more colouring agents, one or more flavouring agents or one or more sweetening agents, such as sucrose or saccharin.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oil phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

The pharmaceutical compositions may be in the form of a sterile injectable aqueous or oleaginous suspension. This suspension may be formulated according to known art using those suitable dispersing or wetting agents and suspending agents that have been mentioned above. The sterile injectable preparation may also be a sterile injectable solution or a suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. Adjuvants such as local anaesthetics, preservatives and buffering agents can also be included in the injectable solution or suspension.

The compound(s) of the general Formula I may be administered, together or separately, in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

Other pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philidelphia, Pa. (2000).

VI. Administration of Compounds of Formula I

Compounds of Formula I may be administered to a subject by a variety of routes depending on the cancer to be treated, for example, the compounds may be administered orally, topically, parenterally, by inhalation or spray, or rectally in dosage unit formulations. In one embodiment, the compounds are administered systemically to a subject, for example, by bolus injection or infusion into a subject's bloodstream or by oral administration. When used in conjunction with one or more known chemotherapeutic agents, the compounds can be administered prior to, or after, administration of the chemotherapeutic agents, or they can be administered concomitantly. The one or more chemotherapeutic may also be administered systemically, for example, by bolus injection, infusion, or oral administration.

The compounds of Formula I may be used as part of a neo-adjuvant therapy (to primary therapy), or as part of an adjuvant therapy regimen. The present invention contemplates the use of the compounds of Formula I at various stages in tumour development and progression, including in the treatment of advanced and/or aggressive neoplasias (i.e. overt disease in a subject that is not amenable to cure by local modalities of treatment, such as surgery or radiotherapy), metastatic disease, locally advanced disease and/or refractory tumours (i.e. a cancer or tumour that has not responded to treatment).

"Primary therapy" refers to a first line of treatment upon the initial diagnosis of cancer in a subject. Exemplary primary therapies may involve surgery, a wide range of chemotherapies and radiotherapy. "Adjuvant therapy" refers to a therapy that follows a primary therapy and that is administered to subjects at risk of relapsing. Adjuvant systemic therapy is usually begun soon after primary therapy to delay recurrence, prolong survival or cure a subject.

It is contemplated that the compounds of the invention can be used alone or in combination with one or more other chemotherapeutic agents as part of a primary therapy or an adjuvant therapy. Combinations of the compounds of Formula I and standard chemotherapeutics may act to improve the efficacy of the chemotherapeutic and, therefore, can be used to improve standard cancer therapies. This application can be important in the treatment of drug-resistant cancers which are not responsive to standard treatment. Drug-resistant cancers can arise, for example, from heterogeneity of tumour cell populations, alterations in response to chemotherapy and increased malignant potential. Such changes are often more pronounced at advanced stages of disease.

The dosage to be administered is not subject to defined limits, but it will usually be an effective amount. It will usually be the equivalent, on a molar basis of the pharmacologically active free form produced from a dosage formulation upon the metabolic release of the active free drug to achieve its desired pharmacological and physiological effects. The compositions may be formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. Examples of ranges for the compound(s) in each dosage unit are from about 0.05 to about 100 mg, or more usually, from about 1.0 to about 50 mg.

Daily dosages of the compounds of the present invention will typically fall within the range of about 0.01 to about 100 mg/kg of body weight, in single or divided dose. However, it will be understood that the actual amount of the compound(s) to be administered will be determined by a physician, in the light of the relevant circumstances, including the condition to be treated, the chosen route of administration, the actual compound administered, the age, weight, and response of the individual patient, and the severity of the patient's symptoms. The above dosage range is given by way of example only and is not intended to limit the scope of the invention in any way. In some instances dosage levels below the lower limit of the aforesaid range may be more than adequate, while in other cases still larger doses may be employed without causing harmful side effects, for example, by first dividing the larger dose into several smaller doses for administration throughout the day.

VII. Clinical Trials in Cancer Patients

One skilled in the art will appreciate that, following the demonstrated effectiveness of a compound of Formula I in vitro and in animal models, it can be submitted to standard GLP animal toxicology and pharmacokinetic studies and then be entered into Clinical Trials in order to further evaluate its efficacy in the treatment of cancer and to obtain regulatory approval for therapeutic use. As is known in the art, clinical trials progress through phases of testing, which are identified as Phases I, II, III, and IV.

Initially, the selected compound of Formula I will be evaluated in a Phase I trial, which is usually an open-label trial. Typically Phase I trials are used to determine the best mode of administration (for example, by pill or by injection), the frequency of administration, and the toxicity for the compound. Phase I studies frequently include laboratory tests, such as blood tests and biopsies, to evaluate the effects of the compound of Formula I in the body of the patient. For a Phase I trial, a small group of cancer patients are treated with a specific dose of the compound of Formula I. During the trial, the dose is typically increased group by group in order to determine the maximum tolerated dose (MTD) and the dose-limiting toxicities (DLT) associated with the compound. This process determines an appropriate dose to use in a subsequent Phase II trial.

A Phase II trial can be conducted to further evaluate the effectiveness and safety of the compounds according to the present invention. In Phase II trials, these compounds are administered to groups of patients with either one specific type of cancer or with related cancers, using the dosage found to be effective in Phase I trials.

Phase III trials focus on determining how a compound compares to the standard, or most widely accepted, treatment. In Phase III trials, patients are randomly assigned to one of two or more "arms". In a trial with two arms, for example, one arm will receive the standard treatment (control group) and the other arm will receive treatment with a compound according to the present invention (investigational group).

Phase IV trials are used to further evaluate the long-term safety and effectiveness of a compound. Phase IV trials are less common than Phase I, II and III trials and will take place after the compound has been approved for standard use.

A. Eligibility of Patients for Clinical Trials

Participant eligibility criteria can range from general (for example, age, sex, type of cancer) to specific (for example, type and number of prior treatments, tumour characteristics, blood cell counts, organ function). Eligibility criteria may also vary with trial phase. For example, in Phase I and II trials, the criteria often exclude patients who may be at risk from the investigational treatment because of abnormal organ function or other factors. In Phase II and III trials additional criteria are often included regarding disease type and stage, and number and type of prior treatments.

Phase I cancer trials usually comprise 15 to 30 participants for whom other treatment options have not been effective. Phase II trials typically comprise up to 100 participants who have already received chemotherapy, surgery, or radiation treatment, but for whom the treatment has not been effective. Participation in Phase II trials is often restricted based on the previous treatment received. Phase III trials usually comprise hundreds to thousands of participants. This large number of participants is necessary in order to determine whether there are true differences between the effectiveness of the compounds according to the present invention and the standard treatment. Phase III may comprise patients ranging from those newly diagnosed with cancer to those with extensive disease in order to cover the disease continuum.

One skilled in the art will appreciate that clinical trials should be designed to be as inclusive as possible without making the study population too diverse to determine whether the treatment might be as effective on a more narrowly defined population. The more diverse the population included in the trial, the more applicable the results could be to the general population, particularly in Phase III trials. Selection of appropriate participants in each phase of clinical trial is considered to be within the ordinary skills of a worker in the art.

B. Assessment of Patients Prior to Treatment

Prior to commencement of the study, several measures known in the art can be used to first classify the patients. Patients can first be assessed, for example, using the Eastern Cooperative Oncology Group (ECOG) Performance Status (PS) scale. ECOG PS is a widely accepted standard for the assessment of the progression of a patient's disease as measured by functional impairment in the patient, with ECOG PS 0 indicating no functional impairment, ECOG PS 1 and 2 indicating that the patients have progressively greater functional impairment but are still ambulatory and ECOG PS 3 and 4 indicating progressive disablement and lack of mobility.

Patients' overall quality of life can be assessed, for example, using the McGill Quality of Life Questionnaire (MQOL) (Cohen et al (1995) *Palliative Medicine* 9: 207-219). The MQOL measures physical symptoms; physical, psychological and existential well-being; support; and overall quality of life. To assess symptoms such as nausea, mood, appetite, insomnia, mobility and fatigue the Symptom Distress Scale (SDS) developed by McCorkle and Young ((1978) *Cancer Nursing* 1: 373-378) can be used.

Patients can also be classified according to the type and/or stage of their disease and/or by tumour size.

C. Pharmacokinetic Monitoring

To fulfill Phase I criteria, distribution of the compound is monitored, for example, by chemical analysis of samples, such as blood or urine, collected at regular intervals. For example, samples can be taken at regular intervals up until about 72 hours after the start of infusion. In one embodiment, samples are taken at 0, 0.33, 0.67, 1, 1.25, 1.5, 2, 4, 6, 8, 12, 24, 48 and 72 hours after the start of each infusion of compound.

If analysis is not conducted immediately, the samples can be placed on dry ice after collection and subsequently transported to a freezer to be stored at $-70°$ C. until analysis can be conducted. Samples can be prepared for analysis using standard techniques known in the art and the amount of compound present can be determined, for example, by high-performance liquid chromatography (HPLC).

Pharmacokinetic data can be generated and analyzed in collaboration with an expert clinical pharmacologist and used to determine, for example, clearance, half-life and maximum plasma concentration.

D. Monitoring of Patient Outcome

The endpoint of a clinical trial is a measurable outcome that indicates the effectiveness of a compound under evaluation. The endpoint is established prior to the commencement of the trial and will vary depending on the type and phase of the clinical trial. Examples of endpoints include, for example, tumour response rate—the proportion of trial participants whose tumour was reduced in size by a specific amount, usually described as a percentage; disease-free survival—the amount of time a participant survives without cancer occurring or recurring, usually measured in months; overall survival—the amount of time a participant lives, typically measured from the beginning of the clinical trial until the time of death. For advanced and/or metastatic cancers, disease stabilization—the proportion of trial participants whose disease has stabilized, for example, whose tumour(s) has ceased to grow and/or metastasize, can be used as an endpoint. Other endpoints include toxicity and quality of life.

Tumour response rate is a typical endpoint in Phase II trials. However, even if a treatment reduces the size of a participant's tumour and lengthens the period of disease-free survival, it may not lengthen overall survival. In such a case, side effects and failure to extend overall survival might outweigh the benefit of longer disease-free survival. Alternatively, the participant's improved quality of life during the tumour-free interval might outweigh other factors. Thus, because tumour response rates are often temporary and may not translate into long-term survival benefits for the participant, response rate is a reasonable measure of a treatment's effectiveness in a Phase II trial, whereas participant survival and quality of life are typically used as endpoints in a Phase III trial.

VIII. Kits

The present invention additionally provides for therapeutic kits containing one or more compounds of Formula I. In one embodiment, the therapeutic kits are for use in the treatment of cancer. The contents of the kit can be lyophilized and the kit can additionally contain a suitable solvent for reconstitution of the lyophilized components. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, for use or sale for human or animal administration.

When the components of the kit are provided in one or more liquid solutions, the liquid solution can be an aqueous solution, for example a sterile aqueous solution. For in vivo use, the compounds may be formulated into a pharmaceutically acceptable syringeable composition. In this case the container means may itself be an inhalant, syringe, pipette, eye dropper, or other such like apparatus, from which the formulation may be applied to an infected area of the subject, such as the lungs, injected into an subject, or even applied to and mixed with the other components of the kit.

Pharmaceutical kits or packs comprising one or more compound of the present invention in combination with one or more standard chemotherapeutic for combination therapy applications are also contemplated by the present invention.

It has also been demonstrated herein that the compounds of Formula I are capable of chelating transition metal ions. The present invention thus additionally provides for kits containing one or more compounds of Formula I for chelation of transition metal ions.

The invention will now be described with reference to specific examples. It will be understood that the following examples are intended to describe embodiments of the invention and are not intended to limit the invention in any way.

EXAMPLES

Preparation of Compounds:

Exemplary compounds of formula (I) have been prepared according to the scheme shown below:

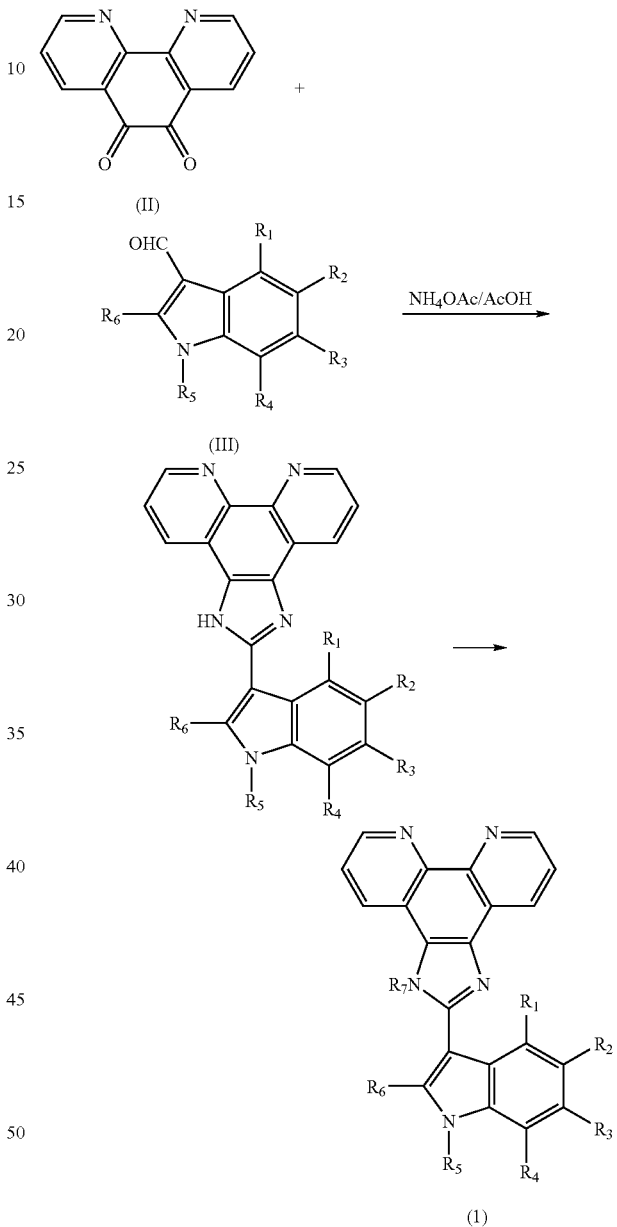

In a typical procedure 1 mmol (1 equiv.) of phenanthrolinequinone was refluxed with the equimolar quantity of the corresponding aldehyde and ammonium acetate 10 mmol (10 equiv.) in glacial acetic acid. The reaction process was monitored by TLC, until complete consumption of the reagents was achieved. After completion of the reaction, the reaction mixture was cooled to room temperature and diluted with water, the impurities were extracted with dichloromethane (DCM) from the obtained solution. The aqueous layer was basified and the separated precipitate of the 2-indolyl imidazo[4,5-d]phenanthroline, was filtered and recrystallized from a suitable solvent. When required, the 2-indolyl imidazo[4,5- d]phenanthroline, wherein R7 is H was treated with R7X to give the compound (I), wherein R7 is other than H.

Indole-3-carboxaldehydes of formula (III) were prepared according to the following scheme:

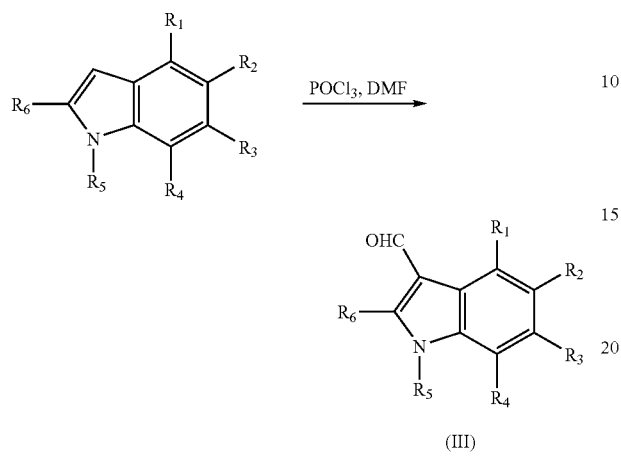

In a typical experimental procedure 11 mmol (1.1 equiv.) of POCl₃ was added drop wise to the magnetically stirred solution of the indole (10 mmol, 1.0 equiv.) in 15-20 ml of dimethylformamide (DMF) at 5-10° C. The mixture was stirred at room temperature for 0.5 hrs and at 60° C. for 0.5 hrs, cooled to room temperature, poured onto 100 g of ice. The obtained solution was basified with NaHCO₃ to pH>7, the mixture was stirred at 60° C. for 1 hr, the separated precipitate was filtered and recrystallized from a suitable solvent.

Melting points were recorded using a MEL-TEMP capillary melting point apparatus, the melting point are uncorrected. ¹H-NMR was performed in a 500 MHz Brucker instrument at room temperature using a suitable deuterated solvent.

Example 1

Preparation of Compound 2

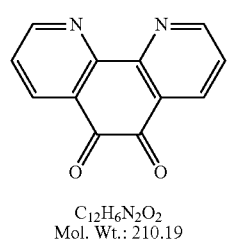

$C_{12}H_6N_2O_2$
Mol. Wt.: 210.19

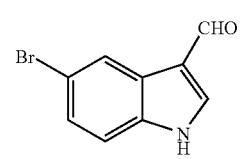

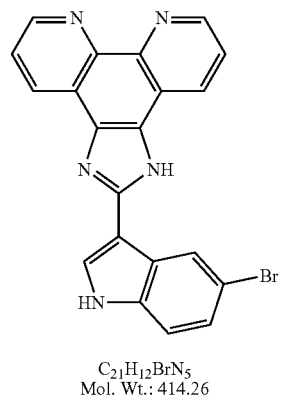

$C_{21}H_{12}BrN_5$
Mol. Wt.: 414.26

2

The suspension of phenanthroquinoline (0.42 g) and 5-bromoindole-3-carboxaldehyde (0.45 g) was refluxed for 1 hr in acetic acid (15 ml) in the presence of ammonium acetate (1.54 g). The formed yellow colored precipitate was filtered, washed with ethanol, crystallized from DMF.

Yield 0.70 g. (85%). M.p.>400° C.

A solution of 0.200 g of compound 2 (0.483 mmol) in DMF was treated with HCL(g) until no more precipitation was observed. The solid was then filtered, washed with dichloromethane and hexanes, dried in vacuum. The resulting desire HCl salt was soluble in water.

Example 2

Preparation of Compound 3

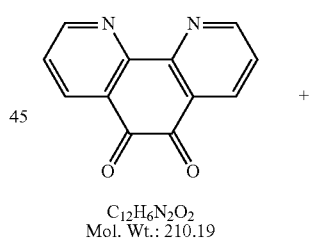

$C_{12}H_6N_2O_2$
Mol. Wt.: 210.19

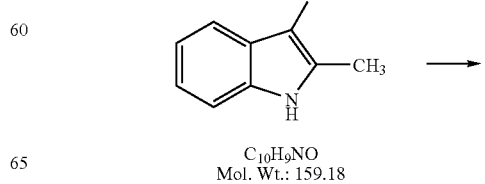

$C_{10}H_9NO$
Mol. Wt.: 159.18

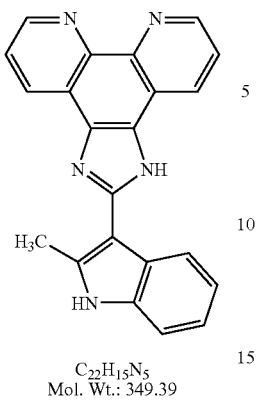

C$_{22}$H$_{15}$N$_5$
Mol. Wt.: 349.39

3

The mixture of phenanthroquinoline (1.05 g) and 2-methylindole-3-carboxaldehyde (0.80 g) was refluxed for 2 hrs in acetic acid (20 ml) in the presence of ammonium acetate (3.85 g). The cooled red colored solution was poured in water (150 ml). The impurities were extracted with DCM (3×50 ml) and discarded. The aqueous layer was neutralized with NaOH (100 ml of 10% solution) and an excess of Na$_2$CO$_3$ to basic solution. The separated precipitate was filtered, washed with water, refluxed in EtOH (30 ml) for 10 min. The crystalline product (compound 3) was filtered, washed with EtOH, DCM and hexane. Yield 0.92 g (57%).

Example 3

Preparation of Compound 4

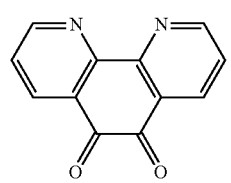

C$_{12}$H$_6$N$_2$O$_2$
Mol. Wt.: 210.19

+

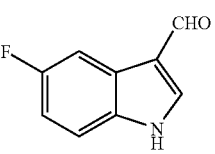

C$_9$H$_6$FNO
Mol. Wt.: 163.15

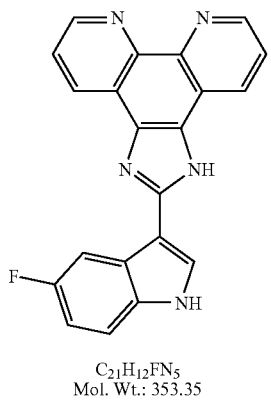

C$_{21}$H$_{12}$FN$_5$
Mol. Wt.: 353.35

4

The mixture of phenanthroquinoline (0.105 g) and 5-fluoroindole-3-carboxaldehyde (0.082 g) was refluxed for 0.5 hrs in acetic acid (3 ml) in the presence of ammonium acetate (0.39 g). The separated precipitate was filtered, washed with aqueous 50% ethanol and EtOH, drained under vacuum. Yield 0.15 g (85%).

Example 4

Preparation of Compound 5

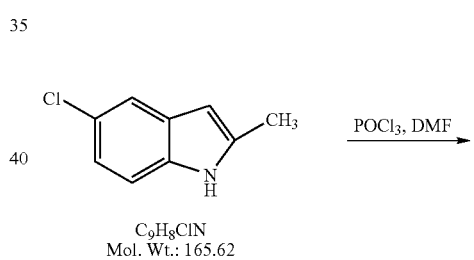

C$_9$H$_8$ClN
Mol. Wt.: 165.62

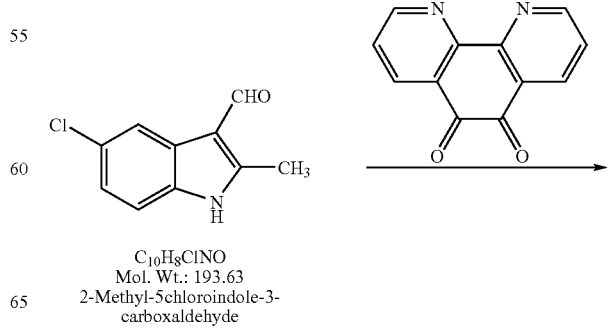

C$_{10}$H$_8$ClNO
Mol. Wt.: 193.63
2-Methyl-5chloroindole-3-carboxaldehyde

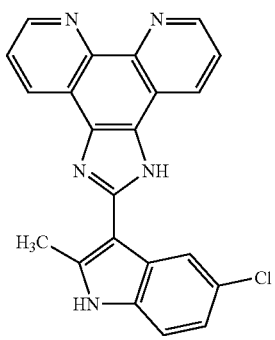

C₂₂H₁₄ClN₅
Mol. Wt.: 383.83

5

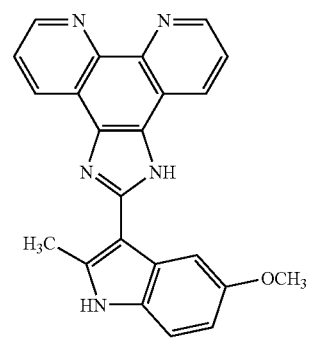

C₂₃H₁₇N₅O
Mol. Wt.: 379.41

6

0.96 g of POCl₃ was added drop wise to a solution of 2-methyl-5-chloroindole (1.0 g) in 20 mL of DMF), at 10° C. The mixture was stirred at 50° C. for 1 hr, cooled and diluted with saturated NaHCO₃. The suspension was heated at 60° C. for 15 min, cooled, and the precipitates of 2-methyl-5-chloroindole-3-carboxaldehyde were filtered. Yield 1.14 g (99%). An analytical sample was crystallized from EtOH.

The mixture of phenanthroquinoline (0.210 g) and of 2-methyl-5-chloroindole-3-carboxaldehyde (0.203 g) was refluxed for 1.5 hrs in acetic acid (5 mL) in the presence of ammonium acetate (0.77 g). The separated precipitate of compound 5 was filtered, and washed with AcOH, EtOH+ H2O and EtOH+EtOAc. Yield 0.230 g (60%).

The mixture of phenanthroquinoline (0.104 g) and 2-methyl-5-OCH₃-indole-3-carbaoxaldehyde (0.095 g) was refluxed for 2.5 hrs, in acetic acid (5 ml) in the presence of ammonium acetate (0.38 g). The solution was diluted with DCM, extracted with water. The aqueous layer was washed with DCM (2×40 ml), basified and extracted with EtOAc. The extract was concentrated and treated with EtOH to give a crystalline product (compound 6), which was filtered and washed with hexane.

Example 6

Preparation of Compound 7

Example 5

Preparation of Compound 6

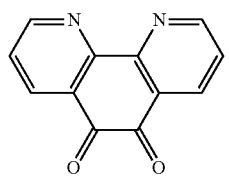

-continued

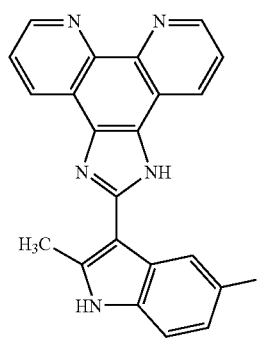

C$_{22}$H$_{14}$FN$_5$
Mol. Wt.: 367.38

7

1.69 g of POCl$_3$ was added to the solution of 2-methyl-5-fluoroindole (1.49 g) in 20 mL of DMF, drop wise at 10° C. The mixture was stirred at 50° C. for 1 hr, cooled and diluted with saturated NaHCO$_3$. The suspension was heated at 60° C. for 15 min, cooled and the precipitates of 2-methyl-5-fluoroindole-3-carboxaldehde were filtered. Yield 1.14 g (99%).

The mixture of phenanthroquinoline (0.210 g) and 2-methyl-5-fluoroindole-3-carboxaldehyde (0.177 g) was refluxed for 1.5 hrs, in acetic acid (5 ml) in the presence of ammonium acetate (0.77 g), poured in 1% HCl, extracted with DCM. The aqueous layer was basified with Na$_2$CO$_3$, the precipitate of compound 7 was filtered and crystallized from EtOH. Yield 0.19 g (52%) of pure product.

Example 7

Preparation of Compound 8

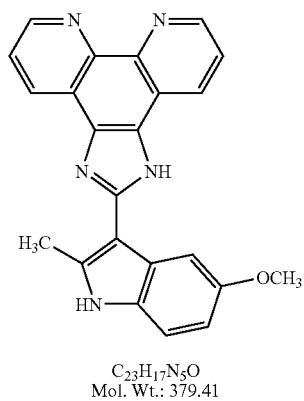

C$_{23}$H$_{17}$N$_5$O
Mol. Wt.: 379.41

6

HBr, H$_2$O →

-continued

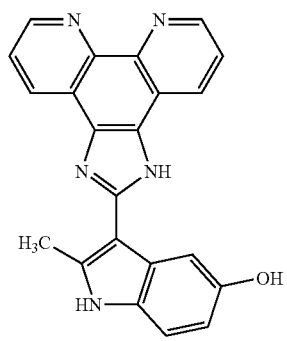

C$_{22}$H$_{15}$N$_5$O
Mol. Wt.: 365.39

8

The mixture of compound 6 (0.150 g) and HBr (4 mL) in 2 mL of AcOH was refluxed for 3.5 hrs. The suspension was diluted with water, alkalinized with saturated aqueous solution of Na$_2$CO$_3$, extracted with EtOAc, and the solvent removed under vacuum. The residue was crystallized from toluene-EtOH and from DMF. Yield 0.03 g (21%).

Example 8

Preparation of Compound 9

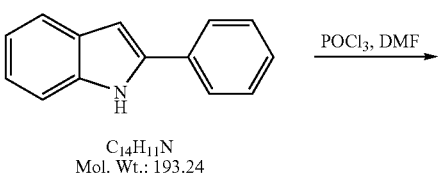

C$_{14}$H$_{11}$N
Mol. Wt.: 193.24

POCl$_3$, DMF →

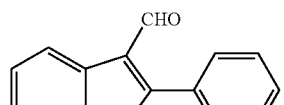

2-phenylindole-3-carboxaldehyde
C$_{15}$H$_{11}$NO
Mol. Wt.: 221.25

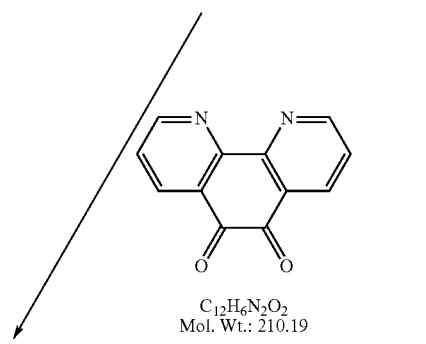

C$_{12}$H$_6$N$_2$O$_2$
Mol. Wt.: 210.19

-continued

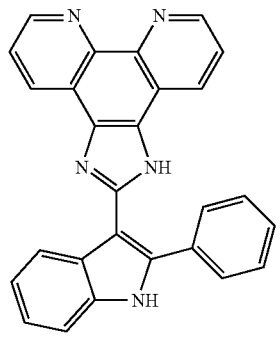

C$_{27}$H$_{17}$N$_5$
Mol. Wt.: 411.46

9

1.7 g of POCl$_3$ was added drop wise to a solution of 2-phenyindole (1.93 g) in 20 mL of DMF, at 10° C. The mixture was stirred at 50° C. for 1 hr, cooled and diluted with saturated NaHCO$_3$. The suspension was heated at 60° C. for 15 min, cooled, the precipitates of 2-phenylindol-3-carboxaldehyde were filtered. Yield 2.05 g (93%).

The mixture of phenanthroquinoline (0.105 g) and 2-phenylindol-3-carboxaldehyde (0.111 g) was refluxed in 3 mL of acetic acid in the presence of 0.39 g of ammonium acetate for 1.5 hrs. The red colored solution was poured in water (100 ml) and washed with DCM (3×40 ml). The aqueous layer was then neutralized with saturated aqueous solution of NA2CO3, the solid obtained was filtered, washed with EtOH and crystallized from DMF: EtOH:H$_2$O=1:1:1. A purified solid 0.12 g was achieved, with a yield of 58%.

Example 9

Preparation of Compound 10

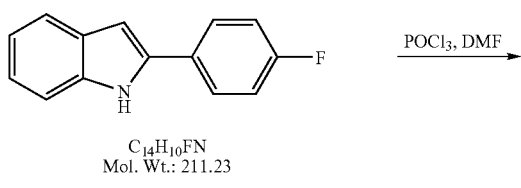

-continued

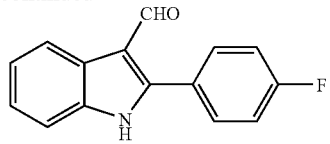

(4-fluorophenyl)-indole-3-carboxaldehyde
C$_{15}$H$_{10}$FNO
Mol. Wt.: 239.24

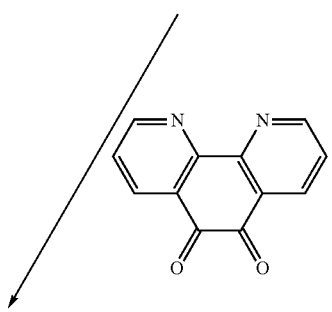

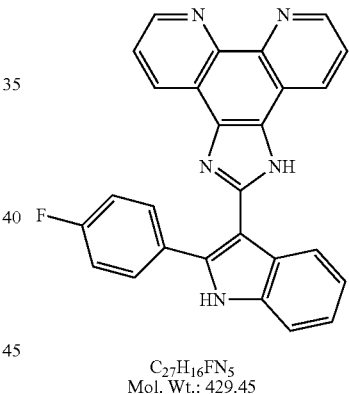

C$_{27}$H$_{16}$FN$_5$
Mol. Wt.: 429.45

10

1.7 mL of POCl$_3$ was added drop wise to a solution of the 2(4-fluorophenyl)-indole (2.11 g) in 20 mL of DMF, at 10° C. The mixture was stirred at 50° C. for 1 hr, cooled and diluted with saturated NaHCO$_3$. The suspension was heated at 60° C. for 15 min, cooled, and the precipitates of 2-(4-fluorophenyl)-indole-3-carboxaldehyde were filtered and crystallized from EtOH. Yield 2.10 g (88%).

The mixture of phenanthroquinoline (0.105 g) and 2-(4-fluorophenyl)-indole-3-carboxaldehyde (0.120 g) was refluxed for 1.5 hrs in acetic acetate (3 mL) in the presence of ammonium acetate (0.38 g), diluted with DCM (50 ml), treated with 50 ml of 5% HCl. The separated yellow precipitate was filtered, treated with aqueous Na$_2$CO$_3$, extracted with EtOAc, and the solvent was removed. The residue was treated with DCM. The separated solid of compound 10 was filtered, and washed with hexane.

Yield 0.08 g (37%).

Example 10

Preparation of Compound 11

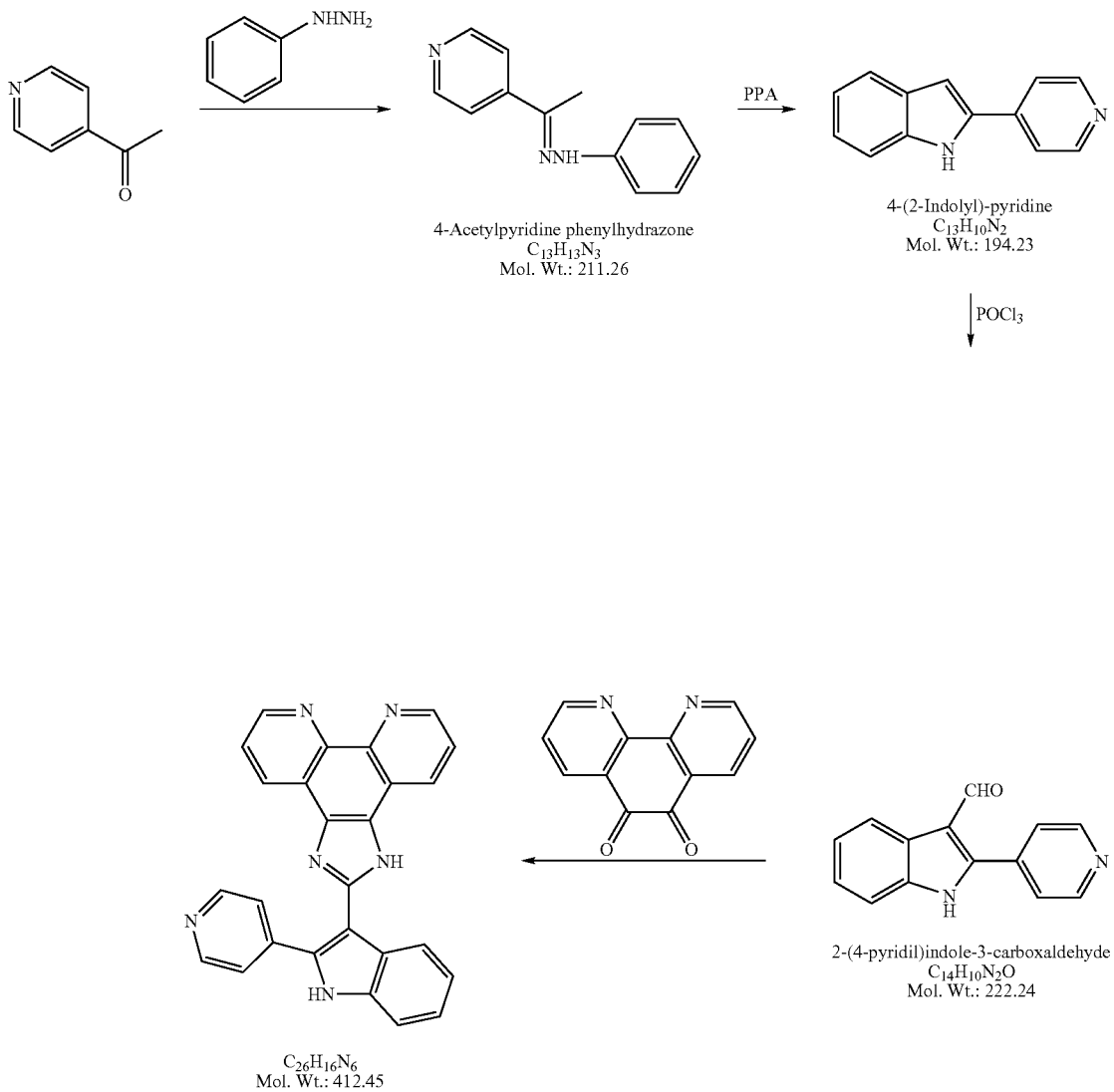

Phenylhydrazine (4.32 g) was added to a solution of 4-acetylpyridine (4.76 g) in 30 ml of abs. EtOH. 3 Drops of AcOH were added and the solution was stirred at room temp. An exothermical reaction occurred and a white precipitate started appearing. The mixture was refluxed for 1 hr. After cooling, the separated precipitates of 4-acetylpyridine phenylhydrazone were filtered, dried. Yield 6.04 g.

The mixture of hydrazone (3.10 g) and polyphosphoric acid (PPA) (18 g) was heated in a bicker, slowly raising the temperature and stirring with a thermometer. The mixture was kept at 180-190° C. for 10 min, cooled, diluted with aqueous $Na_2CO_3$, extracted with EtOAc. The organic layer was concentrated and filtered through silica gel, washed with EtOAc. The filtrate was evaporated, and the residue of 4-(2-indolyl)pyridine was crystallized from toluene.

1.32 g of $POCl_3$ was added drop wise to the solution of the indole 4-(2-indolyl)-pyridine (1.46 g) in 20 mL of DMF, at 10° C. The mixture was stirred at 50° C. for 1 hr, cooled. TLC showed about 50% of transformation, then 0.7 g of $POCl_3$ was added and the mixture was stirred for 0.5 hr at 55-60° C. The mixture was cooled and treated with excess of $NaHCO_3$. The suspension was heated at 60° C. for 1 hr, cooled, and the precipitates of 2-(4-pyridil)indole-3-carboxaldehyde were filtered. Yield 0.98 (59%)g.

The mixture of phenanthroquinoline (0.210 g) and 2-(4-pyridil)indole-3-carboxaldehyde (0.212 g) was refluxed for 1.5 hrs in acetic acid (5 ml) in the presence of ammonium acetate (0.77 g). The precipitate was filtered, dissolved in EtOH, treated with 0.1 ml of $NH_4OH$, the solvent removed almost to dryness. The residue was treated with EtOAc. The precipitates of compound 11 were filtered. Yield 0.25 g (61%).

Example 11

Preparation of Compound 12

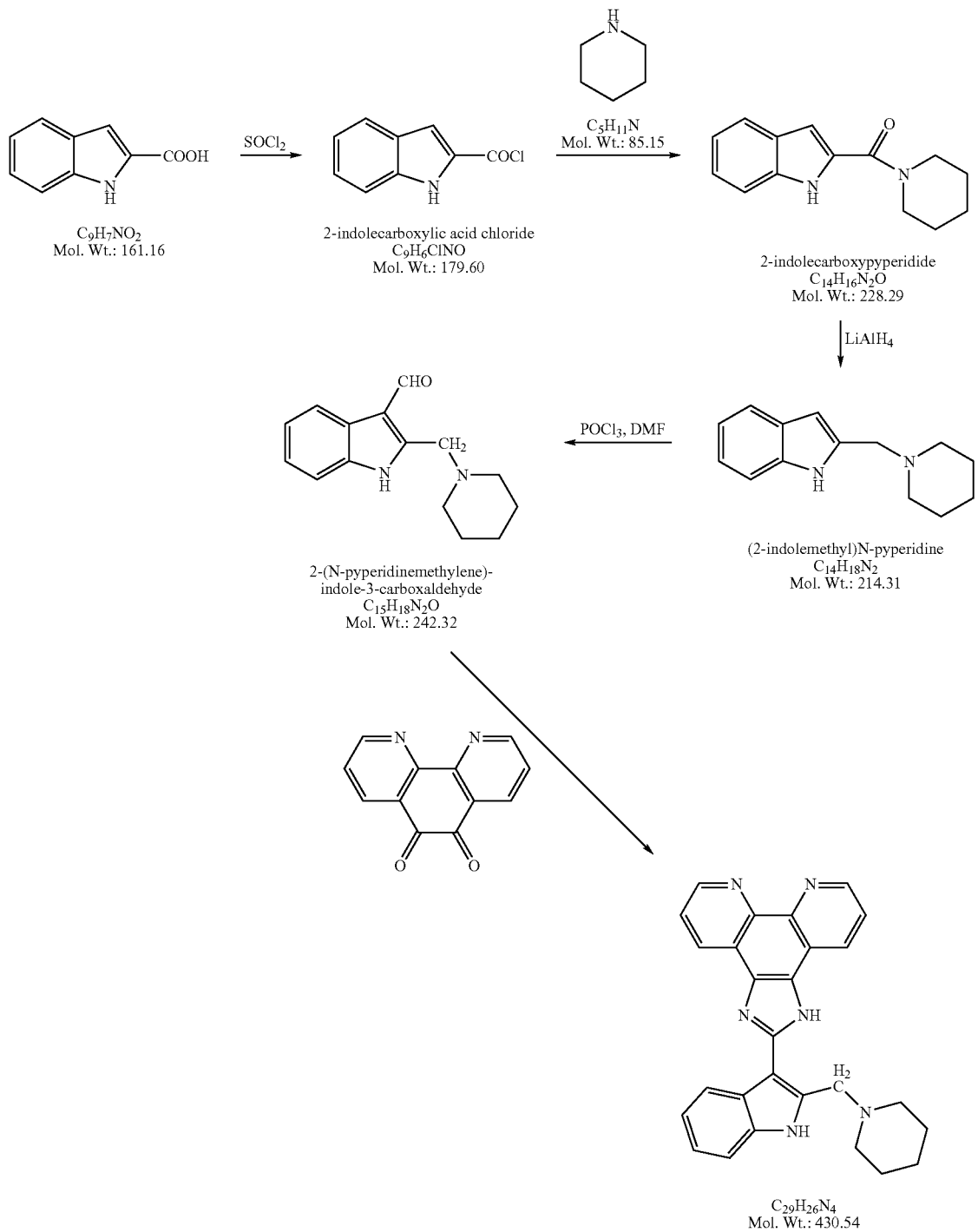

12 mL of SOCl$_2$ was added drop wise to a stirred suspension of 2-indolecarboxylic acid (5.44 g) in toluene externally cooling the flask. After 1 hr the mixture was allowed to warm to room temperature and the mixture was stirred over weekend. Toluene (100 ml) was added to the brown suspension and the obtained mixture was rotevaporated to dryness. The acid chloride was used without purification for the next transformation.

The solution of the acid chloride (7.174 g) in 50 ml of DCM was added drop wise to the solution of pyperidine (10.2 g) in DCM while externally cooling the flesk. The mixture was stirred for 1 hr at room temperature, treated with aqueous saturated NaHCO$_3$. The organic layer was evaporated to the volume of 15 ml and filtered through silica gel, washed with DCM+EtOAc, the solvents evaporated to 15-20 ml, the separated crystals of 2-indolecarboxypyperidide were filtered, washed with hexane after 1 hr of staying at room t-re. Yield 5.37 g.

9.05 g of the crystalline amide (i.e., 2-indolecarboxypyperidide) was added to the stirred suspension of LiAlH$_4$ (3.2 g) in 40 ml of THF, keeping the temperature 45-55° C. After all the amide was added the suspension was stirred with reflux for 2 hrs. The reaction was quenched with EtOAc and 6% NaOH, extracted with EtOAc, the solvent removed to obtain (2-indolemethyl)N-pyperidine as an Oil.

0.85 g of POCl$_3$ was added drop wise to the solution of the indole [i.e., (2-indolemethyl)N-pyperidine] (1.07 g) in 10 mL of DMF at 0° C. The mixture was stirred for 2 hrs at room temperature, poured in water, basified and extracted with EtOAc. The organic layer was extracted with diluted HCl. The aqueous layer was separated, basified and extracted with EtOAc. The solvent was evaporated. The residue of 2-(N-pyperidinemethylene)-indole-3-carboxaldehyde was crystallized from EtOH. Yield 0.30 g (25%).

The mixture of phenanthroquinoline (0.105 g) and 2-(N-pyperidinemethylene)-indole-3-carboxaldehyde (0.121 g) was refluxed for 1.5 hrs in acetic acid (3 ml) in the presence of ammonium acetate (0.38 g), poured in diluted HCl, the impurities extracted with DCM. The aqueous layer was basified and extracted with EtOAc. The organic layer was dried over anhydrous Na$_2$SO$_4$, filtered and evaporated. The oily residue was treated with DCM, The separated crystalline compound 12 was filtered, washed with DCM:hexane-1:1. Yield 0.060 g (28%).

Other exemplary compounds were also prepared by using the procedures as described in the application or the procedures known to a worker skilled in the art.

Example 12

Figure 1:
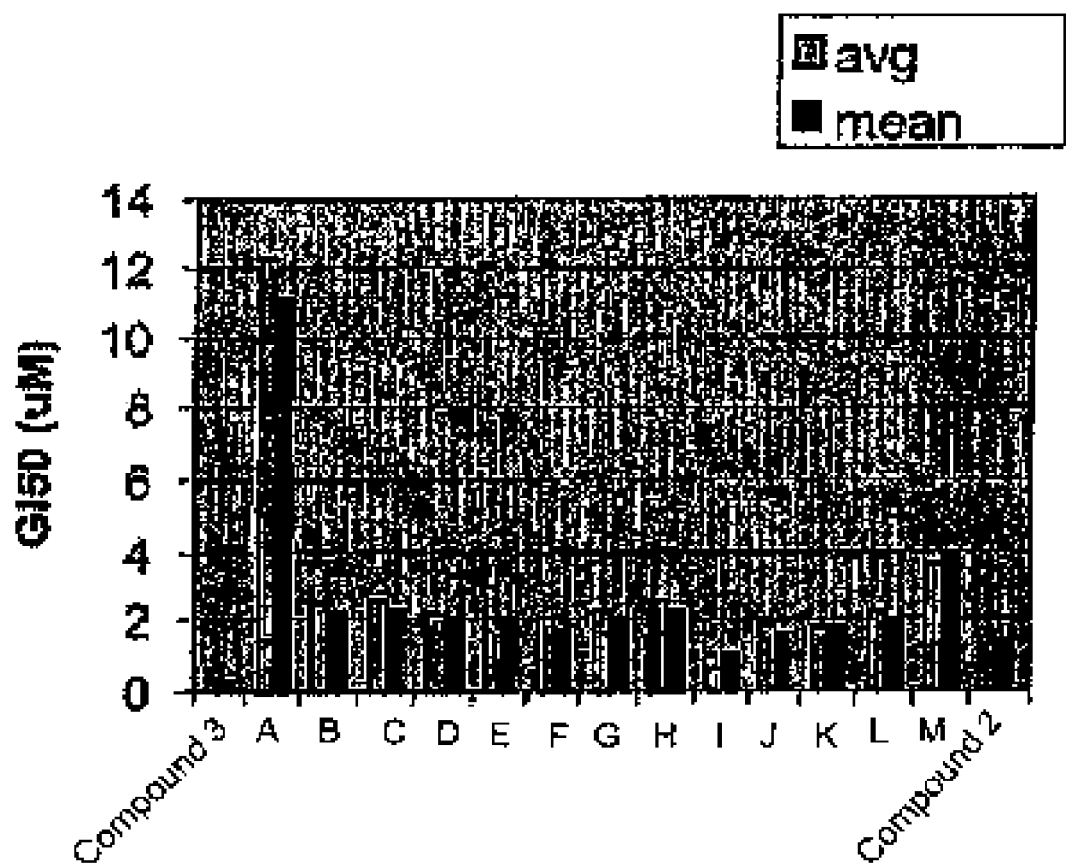
FIG. 1 presents the average and mean $GI_{50}$ values for proliferation of compound 2 and compound 3 in a number of cancer cell lines in vitro.

In Vitro Antiproliferative Activity of Compound 3 in Human Cancer Cell Lines Compounds 2 and 3 were evaluated for their antiproliferative effects in a panel of 60 human cancer cell lines as part of the in vitro anticancer screening services provided by the DTP (Developmental Therapeutics Program) of the US National Cancer Institute (NCI). These compounds exhibited antiproliferative activity against most human tumour cell lines including NSCLC, leukemia, colon cancer, prostate cancer, melanoma, ovarian cancer, renal cancer, CNS cancer, and breast cancer, with an average GI$_{50}$ (growth inhibition by 50%) value of less than 2 μM (FIG. 1).

Figure 2:
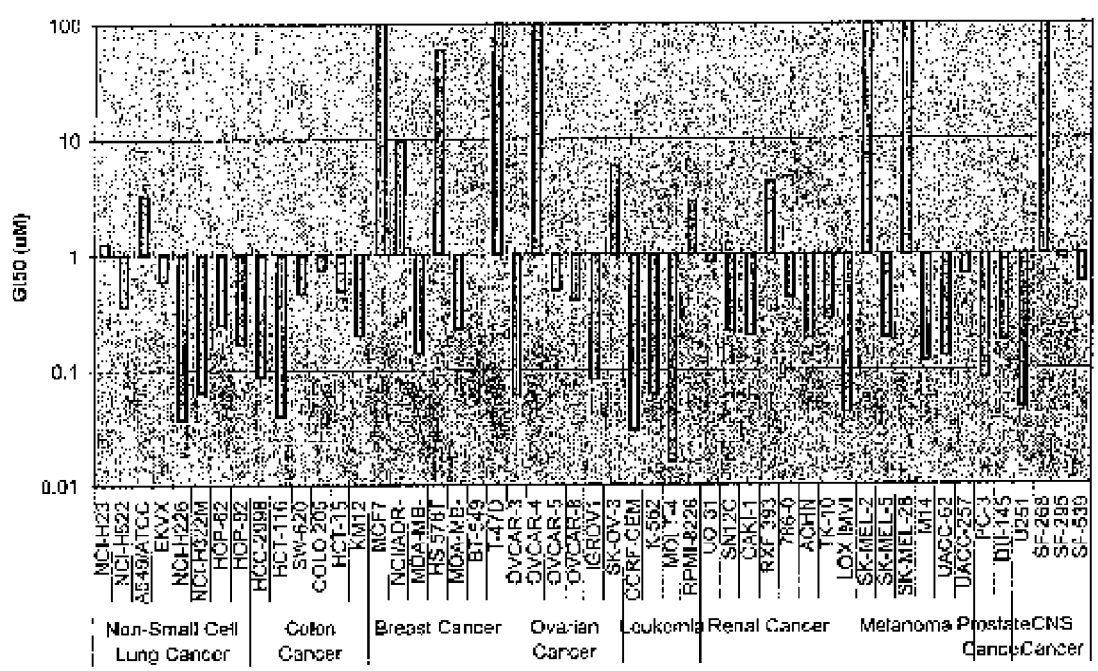
FIG. 2 presents the effect of compound 3 on proliferation of a number of cancer cell lines in vitro.

One of the compounds of Formula I, compound 3, showed inhibitory activities with GI$_{50}$ average values from 0.61 μM to 12.3 μM. Compound 3 was an extremely potent, but selective inhibitor of colon, leukemia, non-small cell lung cancer, and prostate cell lines (FIG. 2). The leukemia cell lines MOLT-4 and CCRF-CEM were the most inhibited, with GI$_{50}$ values of 16 nM and 30 nM respectively. Three leukemia cell lines (MOLT-4, K-562, and CCRF-CEM) had GI$_{50}$ values in the nanomolar range. The fourth leukemia cell line, which had a GI$_{50}$ value of 2.88 μM is, in fact, a myeloma cell line, and may be expected to function differently than the other leukemia cell lines.

Example 13

In Vitro Antiproliferative Activity of Compounds of Formula I in HT-29 Colon Carcinoma Cells The ability of compounds of Formula I to inhibit the proliferation of human colon carcinoma HT-29 cells was tested as follows. HT-29 colon carcinoma cells used in this example and subsequent examples were maintained as a monolayer in a growth medium; McCoy's 5A modified medium (Sigma, St. Louis, Mo.), supplemented with 2 mM L-glutamine (Gibco, Grand Island, N.Y.), 10% fetal bovine serum (FBS) (Multicell, WISENT Inc. St-Bruno, QC), antibiotic-antimycotic (Multicell), at 37° C. in a 5% CO$_2$-humidified incubator. Cells were transferred onto 150 mm tissue culture plates and grown until sub-confluency (70-80%) prior to their use. The in vitro antiproliferative activity of compounds was evaluated by incubating the cells with varying concentrations of the compounds as shown in Table 1 for 6-7 days. The efficacy of these compounds in this cell proliferation assay was measured based in the ability of live cells to reduce the tetrazolium salt XTT to orange colored compounds of formazan (XTT cell proliferation kit II, Roche Applied Science, Montreal, QC). Results of this experiment are shown in Table 3.

TABLE 3

Antiproliferative Activity of Compounds of Formula I

| Compound | R | IC$_{50}$ (μM) |
|---|---|---|
| 2 | Br-substituted 3-methylindole | 0.7 |
| 3 | 2,3-dimethylindole | 0.6 |
| 5 | Cl-substituted 2,3-dimethylindole | 0.35 |
| 6 | H$_3$CO-substituted 2-methylindole | 1.4 |
| 7 | F-substituted 2,3-dimethylindole | 0.7 |

TABLE 3-continued

Antiproliferative Activity of Compounds of Formula I

| Compound | R | IC$_{50}$ (μM) |
|---|---|---|
| 9 | (3-methyl-2-phenyl-1H-indol-2-yl) | 0.3 |
| 10 | (3-methyl-2-(4-fluorophenyl)-1H-indol-2-yl) | 0.18 |
| 11 | (3-methyl-2-(pyridin-4-yl)-1H-indol-2-yl) | >2.5 |
| 12 | (3-methyl-2-(piperidin-1-ylmethyl)-1H-indol-2-yl) | 0.280 |

Example 14

Determination of the Role of Metal Chelation In the Ability of Compound 3 to Inhibit the Growth of HT-29 Colon Carcinoma Cells To determine whether metal chelation is involved in the growth inhibitory activity of compounds of Formula I, exogenous metals ($ZnCl_2$, $FeCl_2 \cdot 4H_2O$, $FeCl_3 \cdot 4H_2O$, $MgCl_2$, at 100 μM) were incubated with HT-29 cells, simultaneously with control vehicle DMSO, compound 3 (5 μM), or compound 13 (25 μM), for 5 days. Compound 13 (see structure below) is a less potent compound than compound 3 and is closely related structurally to compound 3, but lacks the essential chelating-nitrogens in the phenanthroline ring. Growth inhibition by compound 13 is predicted to occur through a different mechanism than compound 3.

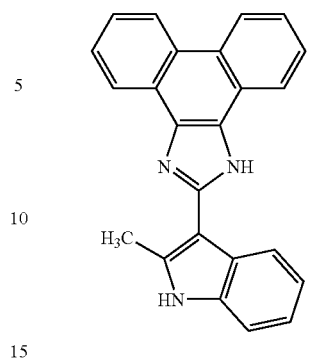

13

Figure 3:
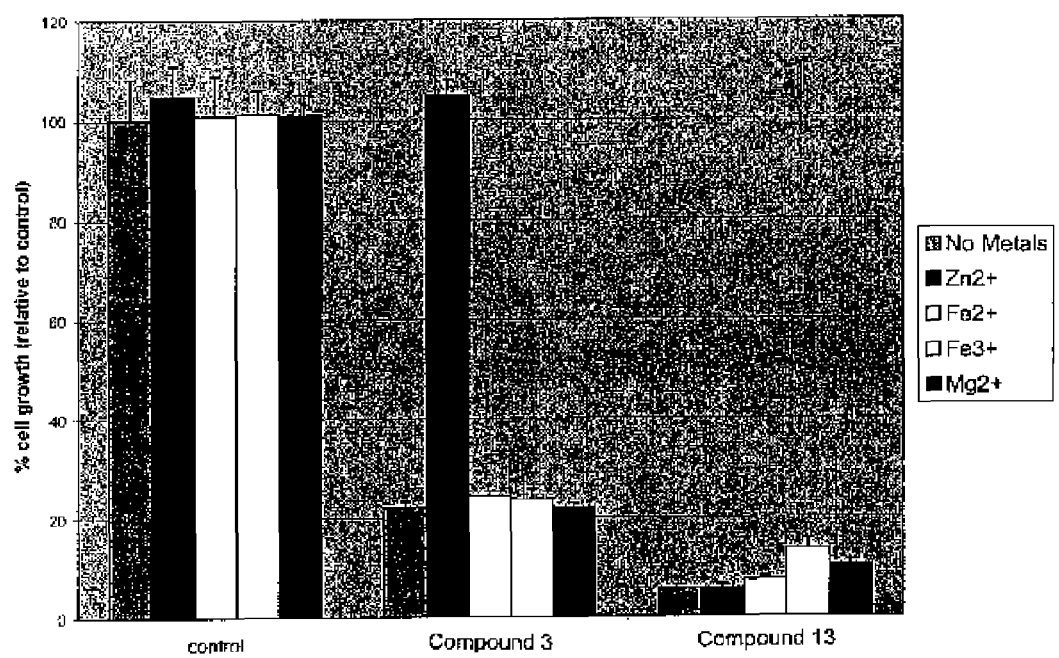
FIG. 3 depicts the effect of metal ions on the ability of compound 3 and compound 13 to inhibit growth of HT-29 cells in vitro.

The results of this experiment are depicted in FIG. 3. Addition of zinc (100 μM) completely impaired the ability of compound 3 to inhibit the growth of HT-29 cells, indicating that compound 3 can function as a chelator of zinc, and that excess zinc may block the ability of this compound to chelate endogenous metals away from essential enzymes. Excess iron and magnesium had no effect on the activity of compound 3. None of the metals had any effects on the activity of the negative control, compound 13, nor did these metals have an effect on the growth of cells on their own. The effect of zinc on the activity of compound 3 was observed to be most evident at low concentrations of compound 3 (1-2 μM), and at 100 μM of zinc.

Example 15

Figure 4:
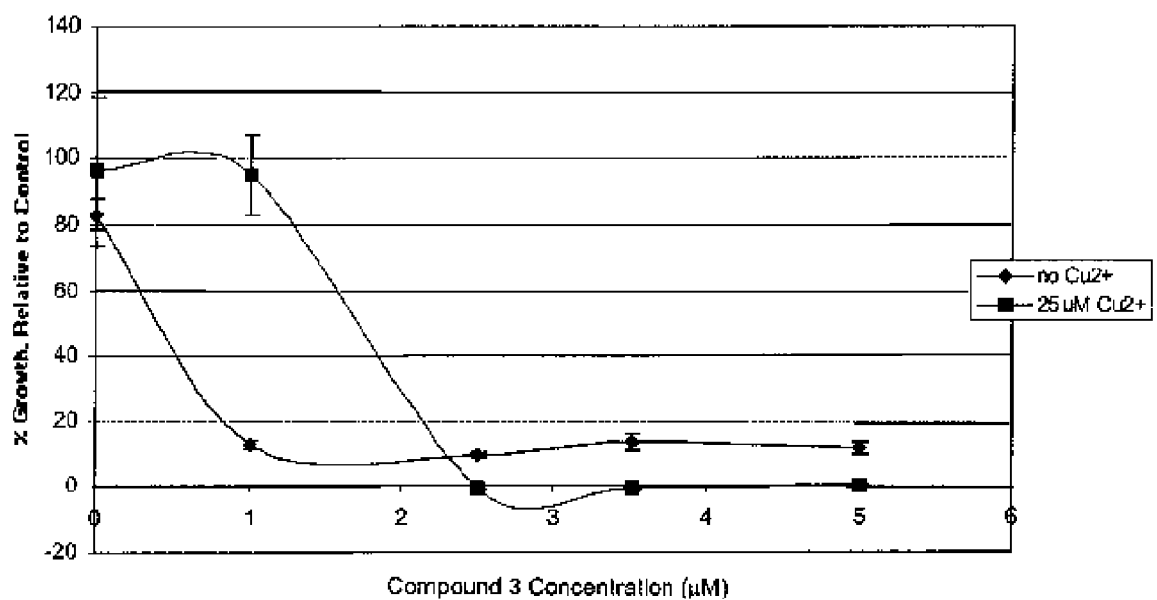
FIG. 4 depicts the effect of copper ions on the ability of compound 3 to inhibit the growth of HT-29 cells in vitro.

Effect of Copper on the Ability of Various Concentrations of Compound 3 to Inhibit Growth of HT-29 Colon Carcinoma Cells To determine whether chelation of copper is involved in the growth inhibitory activity of compounds of Formula I, HT-29 cells were incubated with up to 5 μM of compound 3, in the presence or absence of 25 μM $CuSO_4 \cdot 5H_2O$ for 5 days. As shown in FIG. 4, addition of 25 μM exogenous copper to HT-29 cells impaired the growth inhibitory activities of compound 3 on HT-29 cells, but only at low concentrations of compound 3 (less than 2 μM). In contrast, at high concentrations of compound 3 (>2.5 μM), addition of exogenous copper significantly enhanced the activity of compound 3. Copper had no effect on growth inhibition by compound 13, or on the growth of cells on their own. Similar results were obtained with concentrations of copper up to 100 μM. These results indicate that this compound can function as both a chelator of copper, as well as being able to form cytotoxic chelate-complexes with copper.

Example 16

Figure 5:
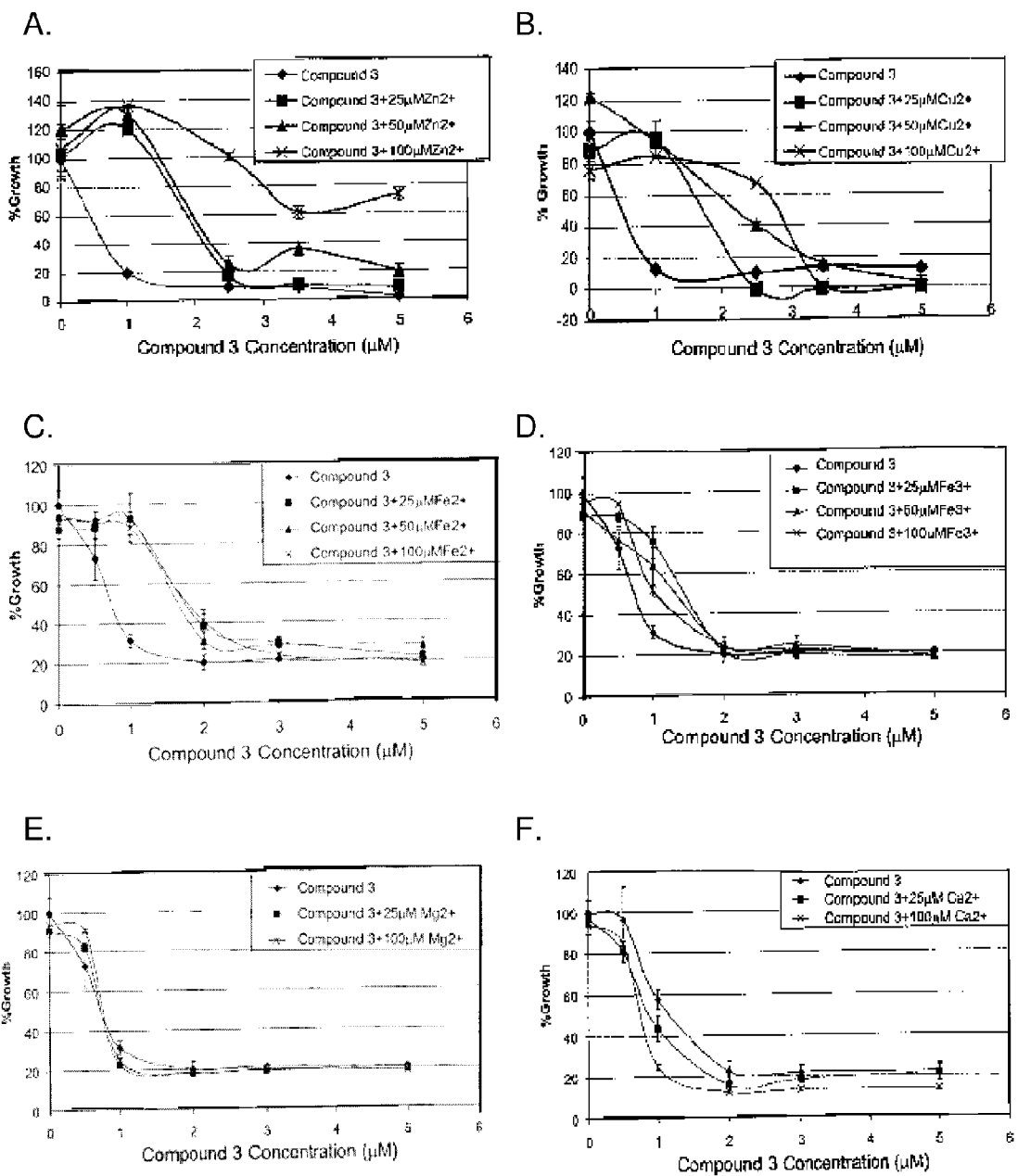
FIG. 5 depicts the effect of metal ions on the ability of compound 3 to inhibit the growth of HT-29 cells in vitro. (A) Effect of zinc ions; (B) Effect of copper ions; (C) Effect of iron (II) ions; (D) Effect of iron (III) ions; (E) Effect of magnesium ions; and (F) Effect of calcium ions.

Effect of Exogenous Metals on the Ability of Compound 3 to Inhibit Growth of HT-29 Colon Cancer Cells In Vitro To determine whether metal chelation is involved in the growth inhibitory activity of compound 3, various concentrations of exogenous metals were incubated with HT-29 cells, simultaneously with various concentrations of compound 3, for 5 days. The exogenous metals tested were: $ZnCl_2$ (zinc), $CuSO_4 \cdot 5H_2O$ (copper), $FeCl_2$ (iron II), $FeCl_3 \cdot 4H_2O$ (iron III), $MgCl_2$ (magnesium), and $CaCl_2 \cdot 2H_2O$ (calcium). HT-29 cells ($4 \times 10^3$/well) in 100 μL volume of the growth medium were seeded in 96-well cell culture plates and incubated overnight at 37° C. The medium was removed and replaced with a total volume of 100 µl growth medium containing concentrations of metal ions as shown in FIG. 5 with compound 3 or 0.1% DMSO vehicle control. After incubation of the cells at 37° C. for 5 days, cell viability was quantitated using the XTT (sodium 3'-[1-(phenylamino-carbonyl)-3,4-tetrazolium}-bis (4-methoxy-6-nitro) benzene sulfonic acid hydrate) calorimetric assay (Roche Applied Science, Penzberg, Germany). XTT labeling reagent (1 mg/mL) was mixed with electron-coupling reagent, following the manufacturer's instructions, and 50 µl of the mixture was added directly to the cells cultured in 100 µl growth medium. The plates were further incubated at 37° C. for 4 hours and the absorbance of each well was measured by a multi-well spectrophotometer (Bio-Tek Instruments Inc.) at 460 nm. The data were adjusted relative to the blank, and were expressed as % of cell growth compared to the DMSO control.

The results indicated that zinc (FIG. 5A), copper, (FIG. 5B), and to a lesser extent, iron(II) (FIG. 5C) impaired the growth inhibitory activities of compound 3, while iron(III) (FIG. 5D), magnesium (FIG. 5E) and calcium (FIG. 5F) had essentially no effect on the activity of compound 3. Copper impaired the growth inhibitory activities of compound 3 at low concentrations of compound 3 (less than 2 µM), and enhanced the activity of compound 3 at high concentrations of compound 3 (>2.5 µM). None of the metals had any effect on the activity of a negative control, compound 13, which is closely related structurally to compound 3 but lacks the essential chelating-nitrogens in the phenanthroline ring (data not shown). These results indicate that compound 3 can function as a chelator of zinc, iron(II) and copper, and that the presence of these metals in excess may block the ability of compound 3 to chelate endogenous metals away from essential enzymes. Compound 3 also appears to form cytotoxic chelate-complexes with copper.

Example 17

Figure 6:
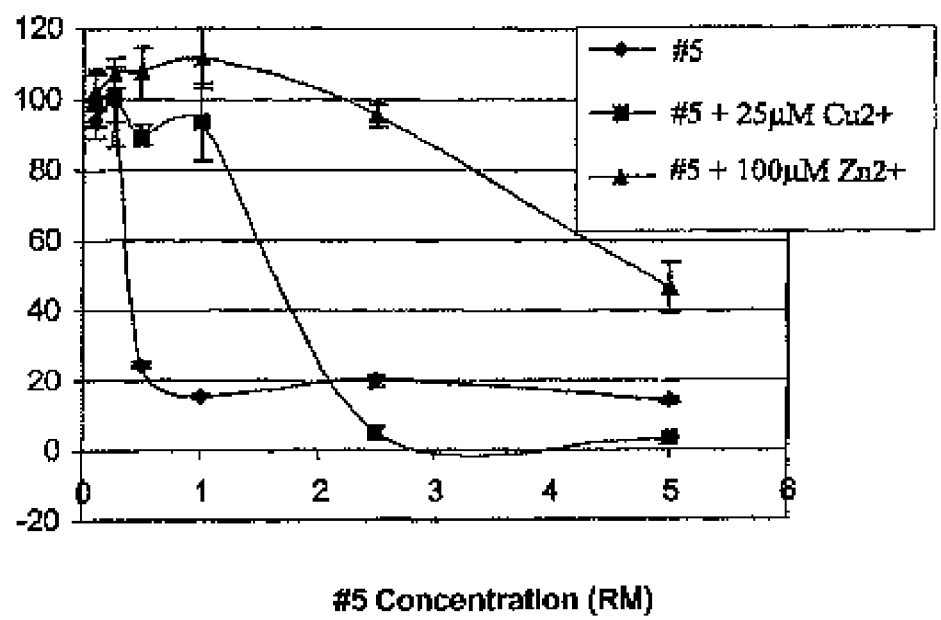
FIG. 6 depicts the effect of copper or zinc ions on the ability of compound 5 (A) and compound 7 (B) to inhibit growth of HT-29 cells in vitro.
Figure 6:
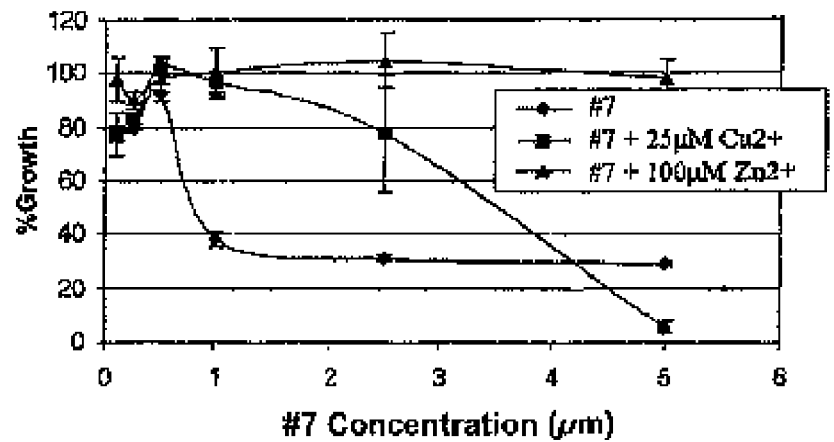

Effect of Exogenous Metals on the Ability of Compounds 5 and 7 to Inhibit Growth of HT-29 Colon Cancer Cells In Vitro To determine the ability of compounds 5 and 7 to chelate metals in cells, exogenous metals were added to HT-29 cells, simultaneously with various concentrations of compounds 5 and 7. Briefly, HT-29 cells were treated with various concentrations compounds 5 and 7, plus or minus copper (25 µM CuSO$_4$.5H$_2$0) or zinc (100 µM of ZnCl$_2$), for 5 days. Cell viability was determined by XTT assay. The effects of copper and zinc on growth inhibition of HT-29 cells are shown in FIG. 6A for compound 5 and in FIG. 6B for compound 7. Similarly to compound 3, zinc impaired the growth inhibitory activities of compounds 5 and 7, while copper impaired the activity only at low concentrations of compounds 5 and 7. The results indicate that compounds 5 and 7 function as chelators of zinc and copper, and the presence of these metals in excess blocks the growth inhibitory effects of compounds 5 and 7.

Example 18

Selectivity of Compounds 3 and 9 for Cancer Cells

To determine if the compounds of Formula I selectively inhibited proliferation of cancer cells compared to proliferation of normal cells, the IC$_{90}$ values for proliferation for compounds 3 and 9 were measured in normal cell lines and cancer cell lines. The normal cells lines used were PrEC (prostate), HMEC (breast), and WI38 (lung fibroblast) cell lines and the cancer cells lines were DU145 (prostate), MDA-MB-435 (breast), HT-29 (colon). IC$_{90}$ values were also determined for the controls doxorubicin and etoposide. The cells were cultured as generally described in Example 13. Various concentrations of the compounds were incubated with the cells for 6 to 7 days, and the number of proliferating cells was measured using the XTT assay. Cancer cell selectivity was calculated as a ratio between the average IC$_{90}$ for all normal and the average IC$_{90}$ for all cancer cell lines. Both compounds 3 and 9 had an IC$_{90}$ ratio (normal/cancer) of >4, indicating that these compounds were selective for cancer cells.

TABLE 4

Cancer cell selectivity

| Compound | Normal/cancer IC$_{90}$ ratio |
|---|---|
| Doxorubicin | 5.6 |
| Etoposide | >5.0 |
| Compound 3 | >4.3 |
| Compound 9 | >5.6 |

Example 19

Ability of Compound 3 to Inhibit Expression of the Metallothionin 1A Gene in Cancer Cells To determine whether compounds of Formula I can chelate zinc in cells, the effect of compound 3 on the expression level of a zinc-regulated gene, metallothionein 1A (MT1A), in human colon carcinoma HT-29 cells, was determined. HT-29 cells, 1×10$^6$ cells in 10 mL volume of the growth medium were seeded in 100 mm dishes and incubated overnight at 37° C. The medium was removed and replaced with the growth medium containing 35 µM ZnCl$_2$, 1 µM or 4 µM TPEN (NNNN-tetrakis(2-pyridyl-methyl)ethylenediamine), or 1 µM or 4 µM compound 3, or 0.1% DMSO vehicle control. After incubation for 16 hours, the cells were detached by trypsinization, collected by centrifugation and washed once with PBS. Total RNA was extracted by using TRIZOL (Invitrogen, Life Technologies, Carlsbad, Calif.), following manufacturer's instruction, and the level of MT1A mRNA was measured by real time PCR using the comparative CT method as follows. First strand cDNA was synthesized from 200 ng total RNA in Biometra Tpersonal Thermal Cycler (Abgene, UK), using pd(N)6 random hexamer (Amersham Biosciences, Piscataway, N.J.) and SuperScript™ II Reverse Transcriptase kit (Invitrogen) by following manufacturer's protocol. Real-time PCR was performed in ABI Prism 7000 Sequence Detection System (Applied Biosystems Inc., ABI, Foster City, Calif.), using 5 µL of cDNA synthesized by above-mentioned procedure and respective TaqMan® Gene Expression Assays (ABI) by following ABI TaqMan® Universal PCR master mix protocol.

Figure 7:
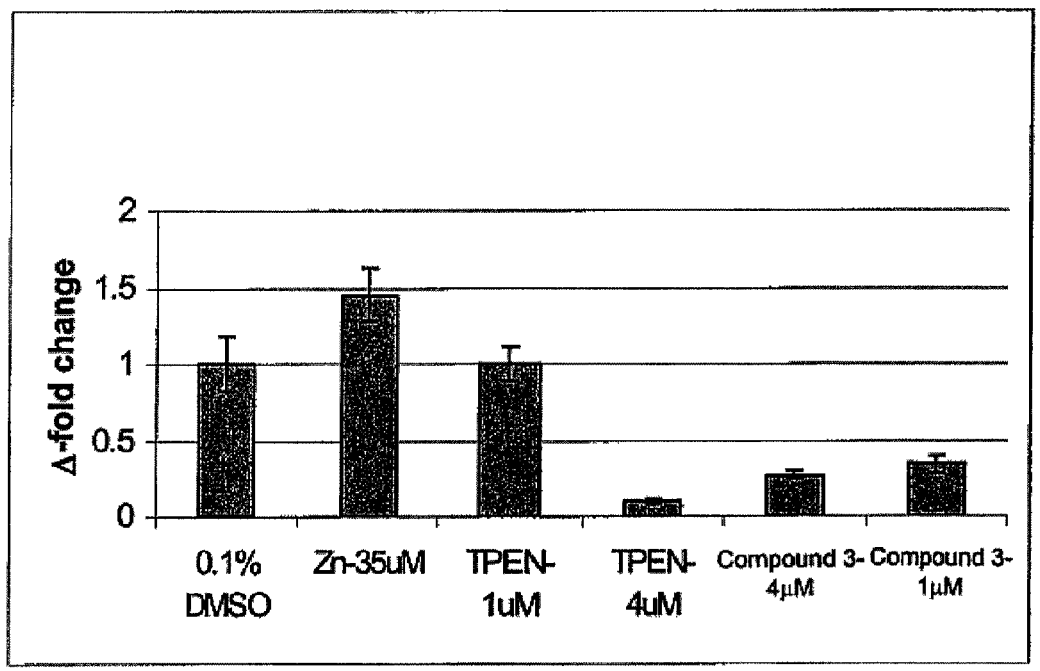
FIG. 7 depicts the effect of compound 3 on expression of a metallothionein gene mRNA in HT-29 cells in vitro.

FIG. 7 shows that the addition of zinc (35 µM) to HT-29 cells increased the expression of the MT1A gene, while addition of the specific zinc chelator TPEN, decreased the expression of MT1A. Compound 3 decreased the expression of MT1A by more than 50%, indicating that compound 3 was able to decrease the amount of labile intracellular zinc. Therefore, compound 3 functions as a chelator of zinc in cells.

Example 20

Figure 8:
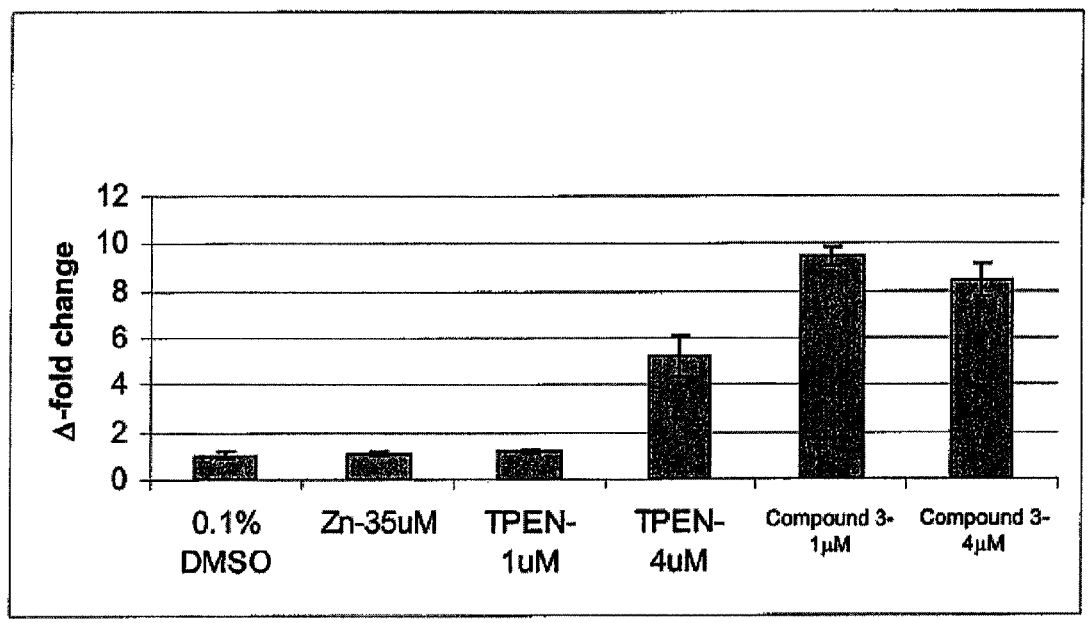
FIG. 8 depicts the effect of compound 3 on expression of KLF4 mRNA in HT-29 cells in vitro.

In Vitro Ability of Compound 3 to Modulate Expression of KLF4 mRNA in HT-29 Cells The ability of compounds of Formula I to modulate the mRNA level of a transition metal-regulated tumour suppressor gene was determined in vitro as follows. Compound 3 was tested to determine its ability to increase the expression of zinc-regulated tumour suppressor KLF4 mRNA in colon carcinoma HT-29 cells. The expression of KLF4 has previously been shown to be induced by changes in intracellular zinc concentration. HT-29 cells were incubated for 16 hours with DMSO as a vehicle control, 35 µM $ZnCl_2$, 1 µM or 4 µM of compound 3, or 1 µM or 4 µM TPEN for 16 hours and mRNA was extracted from the cells as described in Example 19. The expression of KLF4 mRNA was analyzed by real-time polymerase chain reaction using the comparative CT method also as described in Example 19. Compound 3 induced the expression of KLF4 mRNA (approximately 8-fold) in HT-29 cells compared with HT-29 cells treated with vehicle alone (See FIG. 8).

Example 21

Figure 9:
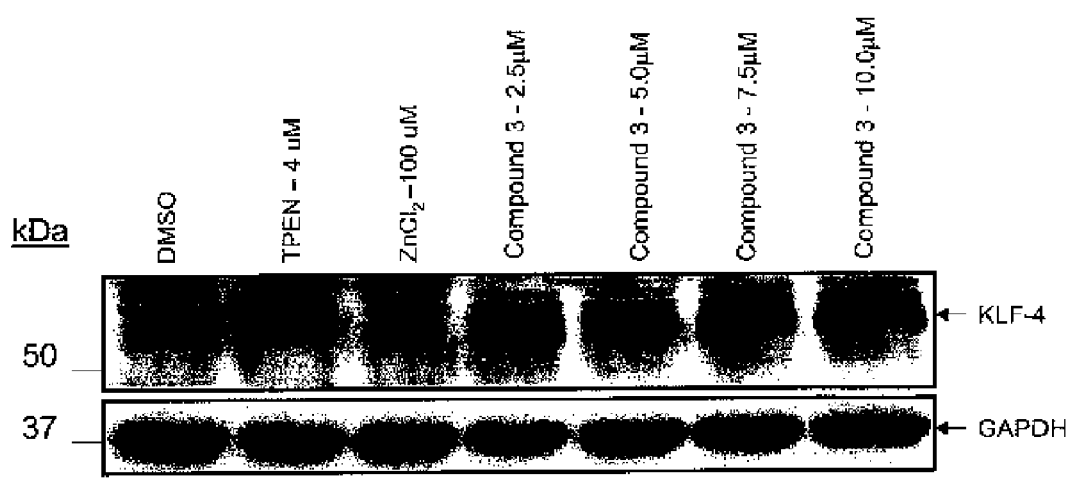
FIG. 9 depicts the effect of compound 3 on expression of KLF4 protein in HT-29 cells in vitro.

In Vitro Ability of Compound 3 to Modulate Expression of KLF4 Protein in HT-29 Cells The ability of compound of Formula I to increase expression of KLF4 protein was determined as follows. HT-29 cells were treated with vehicle control (DMSO), TPEN (4 µM), $ZnCl_2$ (100 µM), or compound 3 (2.5, 5, 7.5 and 10 µM) for 16 hours. Cells were lysed and subjected to Western blot with anti-KLF4 antibodies, or GAPDH antibodies to ensure equal protein loading. As shown in FIG. 9, compound 3 was able to increase the level of KLF4 protein in HT-29 cells after 16 hours of treatment.

Example 22

Effect of Compound 3 on Expression of the Cyclin Dependent Kinase Inhibitor P21

Figure 10:
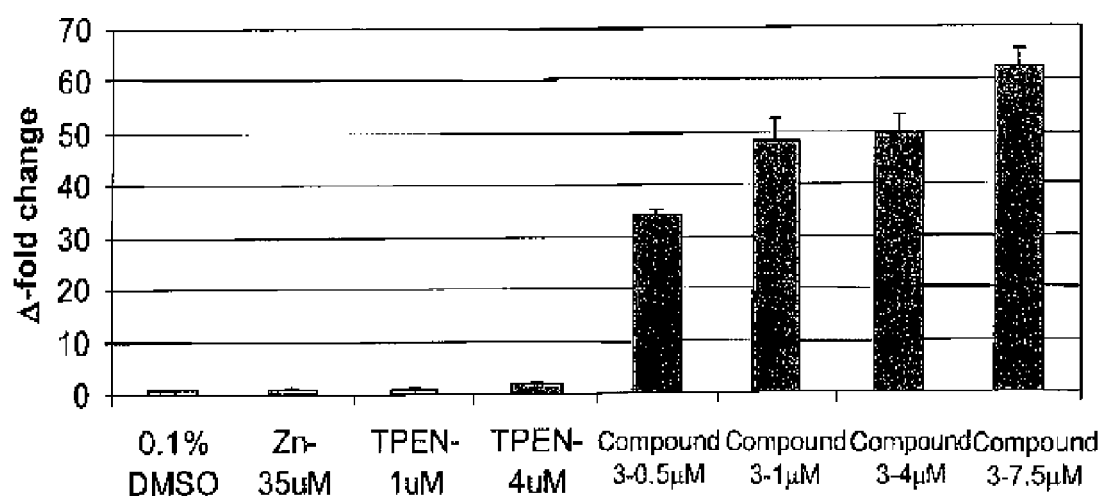
FIG. 10 depicts the effect of compound 3 on expression of p21 mRNA in HT-29 cells in vitro.

The effect of compounds of Formula I on the expression of genes regulated by KLF4 was determined as follows. Compound 3 was tested to determine its ability to increase the expression of the cell cycle regulator p21 (cyclin-dependent kinase inhibitor) in HT-29 colon carcinoma cells. The tumour suppressor KLF4 has been shown to mediate cell cycle arrest through suppression of p21. HT-29 cells were incubated with DMSO (vehicle control), 35 µM $ZnCl_2$, 1 µM or 4 µM TPEN, or 0.5 µM, 1 µM, 4 µM, or 7.5 µM compound 3 for 16 hours, and mRNA was extracted from the cells. The expression of p21 mRNA was analyzed by real-time polymerase chain reaction using the comparative CT method. This assay was carried out using methods described in Example 19. Compound 3 induced the expression of p21 in HT-29 cells by 30- to 60-fold compared with HT-29 cells treated with vehicle alone (See FIG. 10).

Example 23

In Vitro Ability of Compound 3 to Block Cell Cycle Progression in HT-29 and CCRF-CEM Cells To test the ability of compounds of Formula I to block cell cycle progression, compound 3 was incubated with human colon carcinoma HT-29 or human leukemia CCRF-CEM cells to determine alterations in populations of cells at different stages of the cell cycle using flow cytometric analysis. HT-29 cells were maintained as described in Example 13. CCRF-CEM cells used in this example and subsequent examples were maintained as suspension cells in a growth medium; RPMI-1640 medium (Sigma, St. Louis, Mo.), supplemented with 2 mM L-glutamine (Gibco, Grand Island, N.Y.), 10% fetal bovine serum (FBS) (Multicell, WISENT Inc. St-Bruno, QC), antibiotic-antimycotic (Multicell), at 37° C. in a 5% $CO_2$-humidified incubator.

Figure 11:
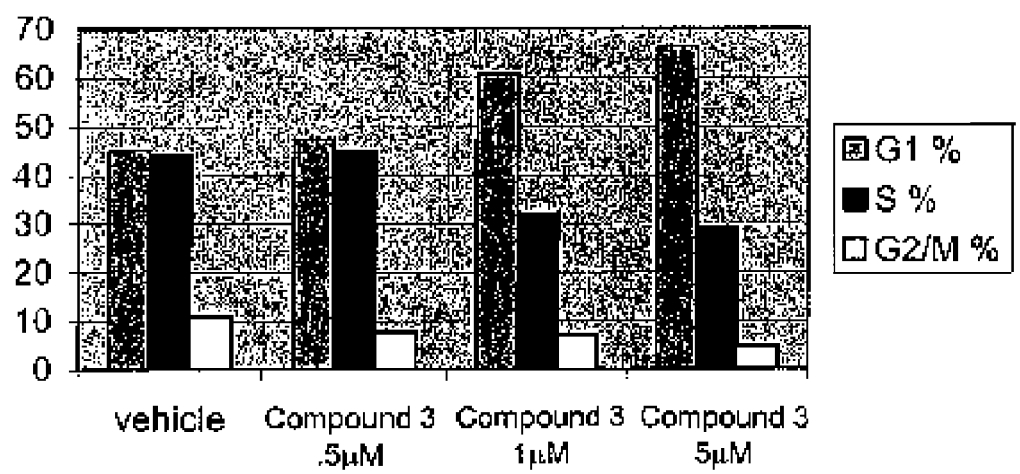
FIG. 11 depicts the ability of compound 3 to block cell cycle progression in HT-29 cells (A) and CCRF-CEM cells (B) in vitro.
Figure 11:
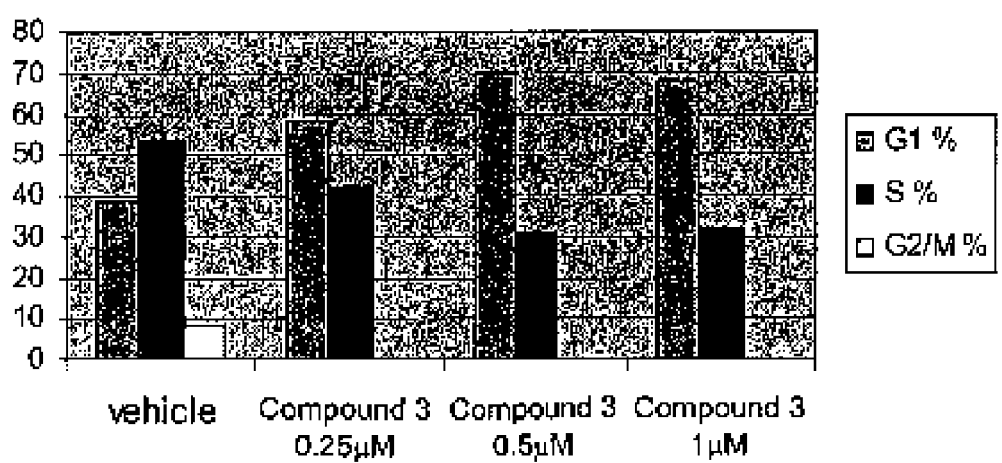

The assay was carried out as follows. For HT-29 cells, $1 \times 10^6$ cells in 10 mL volume of the growth medium were seeded in 100 mm dishes. For CCRF-CEM cells, $3 \times 10^6$ cells in 10 mL volume of the growth medium were seeded in 25 $cm^2$ flask. After 16 hours, the growth medium containing concentrations of compound 3 as shown in FIG. 11 (0.5 µM, 1 µM, or 5 µM, for HT-29 cells, and 0.25 µM, 0.5 µM, or 1 µM for CCRF-CEM cells) or 0.1% DMSO vehicle control was added. After 24 hours, HT-29 cells were detached by trypsination. Both cell types were respectively collected by centrifugation at 2000 rpm for 4 min, washed once with PBS and fixed in 70% ethanol at −20° C. for at least 4 hrs. The fixed cells were centrifuged at 1500 rpm for 3 min, washed once with cold PBS containing 2% FBS, treated with 3 mg/ml ribonuclease (Sigma) and 50 µg/ml propidium iodide (Sigma) for 30 min at 37° C. The fluorescence of stained cells was analyzed using FACScan flow cytometer and the Cell Quest program (BD Biosciences, San Jose, Calif.). Data were evaluated using Modfit software (Verity software House, Topsham, Me.). Values were determined by gate analysis of flow cytometric plots. FIGS. 11A and 11B are presented as a percentage of the total cell population, after eliminating doublets.

The results indicated that treatment of both cell lines (FIGS. 11A and 11B) with compound 3 led to a dose-dependent increase in the percentage of cells in the $G_1$ phase and a decrease in the percentage of cells in the S and $G_2/M$ phases, indicating that compound 3 induced a block in cell cycle progression at the $G_1$ phase.

Example 24

In Vitro Ability of Compound 3 to Induce Apoptosis in CCRF-CEM and MOLT4 Leukemia Cells The ability of compound 3 to alter the population of cells at different stages of apoptosis was measured by determining the effect of compound 3 on populations of CCRF-CEM leukemia cells treated with vehicle (DMSO), 0.1 µM, 0.25 µM, 0.5 µM, or 1 µM of compound 3 for 24 hours. CCRF-CEM cells were seeded and treated with the above concentrations of compound 3 or 0.1% DMSO vehicle control as described in Example 23. After 24 hours, the cells were collected by centrifugation and re-suspended in growth media to approximately $1 \times 10^6$ cells/ml. Then the cells were stained for annexin V binding and PI staining using the annexin V-FITC apoptosis detection kit (Oncogene™ research products, Mass.) and following the manufacturer's RAPID Annexin V Binding protocol. The fluorescence of stained cells was analyzed using FACScan flow cytometer and the Cell Quest program (BD Biosciences, San Jose, Calif.). Data were evaluated using Modfit software (Verity software House, Topsham, Me.) to generate quadrant statistics. Cells stained with Annexin V only are considered to be in early apoptosis, whereas cells stained with both Annexin V and propidium iodide are considered to be in late apoptosis. Cells stained with propidium iodide only are non-viable, whereas no staining indicates viable cells. MOLT-4 leukemia cells were treated similarly.

Figure 12:
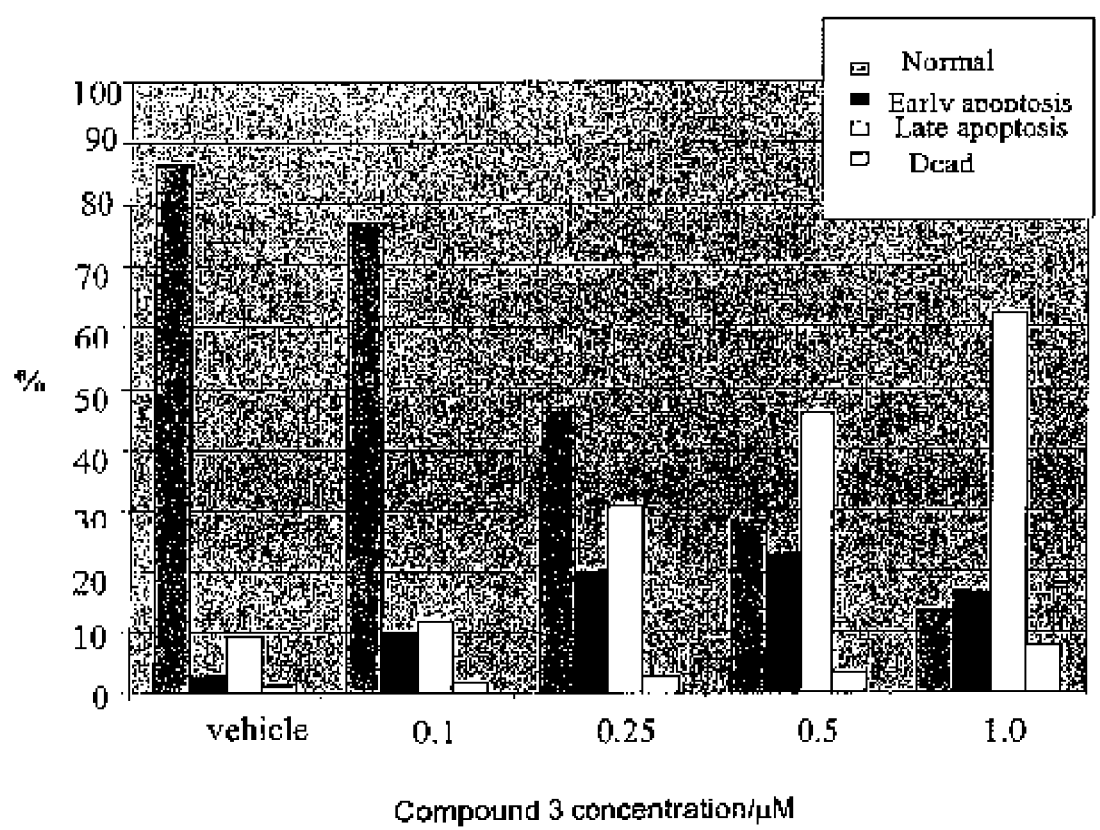
FIG. 12 presents the ability of compound 3 to induce apoptosis in CCRF-CEM cells in vitro.

Increasing concentrations of compound 3 resulted in an increase in the number of early and late apoptotic cells, with a decrease in viable cells (FIG. 12). Only at a high concentration of compound 3 (1.0 µM) was an increase in non-viable cells observed. Similar results were obtained with MOLT4 leukemia cells (data not shown). Therefore, compound 3 was able to induce cells to undergo apoptosis.

Example 25

In Vivo Efficacy of Compound 3 in the Hollow Fiber Assay

The in vivo efficacy of compounds according to Formula I was tested by determining the efficacy of compound 3 in the hollow fiber assay. This assay is described in Decker et al., Eur. J. of Cancer 40: 821-826 (2004), and was carried out by implanting 12 human tumour cell lines (Breast; MDA-MB-231, MDA-MB-435. Glioma; U251, SF-295. Ovarian; OVCAR-3, OVCAR-5. Colon; COLO-205, SW-620. Melanoma; LOX-IMVI, UACC-62 and Lung; NCI-H23, NCI-H522) into athymic mice as follows. Cell cultures were cultivated in RPMI-1640 containing 10% FBS and 2 mM glutamine. The cells were harvested by standard trypsinization, resuspended (2–10×$10^6$ cells/ml), and flushed into 1 mm I.D. polyvinylidene hollow fibers (MW exclusion of 500, 000 Da.). Cultures adhered to the PVDF fibers were cultured at 37° C. in 5% CO2 for 24-48 hours prior to implantation. Each mouse received a total of six implants, 3 fibers placed in the peritoneum and 3 in the subcutaneous compartment, total of 3 cell lines per mouse; 3 mice per group and 6 in control treated with vehicle only. The drug was tested at 2 different dosages and 2 routes (I.P. and S.C), 4 days treatment. The fibers were collected 6-8 days post-implantation and the viability of the cells is evaluated by the MTT method; the agent was considered to have an effect if there is a 50% or greater reduction in growth compared with controls. Cell killing was evaluated by reduction of cell viability compared with initial viability in the implant. The results were scored based on the number of cell lines inhibited (i.e. 12)×2 sites×2 compound dosages×factor 2=maximum of 96. Compounds with a combined score of 20, a SC score of 8 or a net cell kill of one or more cell lines were considered positive.

The results obtained showed that compound 3 had an IP score of 22, SC score of 10=total 32 with positive cell kill as shown in Table 5. These studies demonstrated that compound 3 was effective in killing several types of tumour cells in vivo.

TABLE 5

In Vivo Cancer Cell Growth Inhibition By Compound 3

|  | ip score | sc score | total score | net cell kill |
|---|---|---|---|---|
| Target score | 12 | 8 | 20 | one or more |
| Compound 3 | 22 | 10 | 32 | one or more |

Example 26

In Vivo Efficacy of Compound 3 in a Colon Carcinoma Xenograft Model

Figure 13:
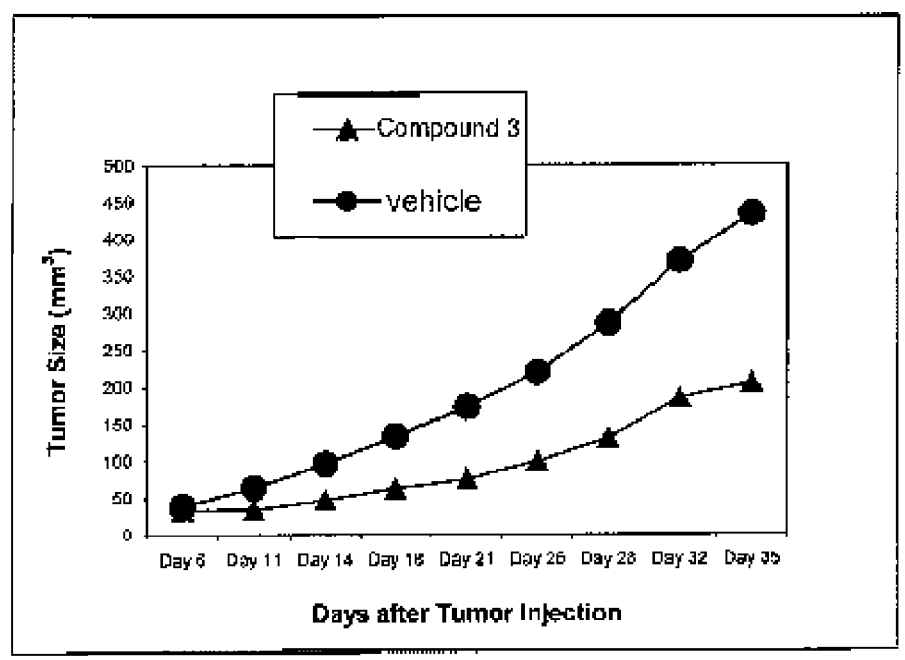
FIG. 13 depicts the ability of compound 3 to decrease tumour size (A) and tumour weight (B) in a colon adenocarcinoma xenograft model.
Figure 13:
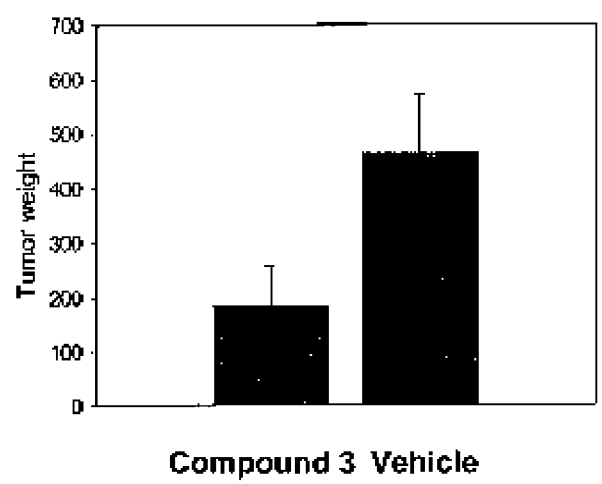

The ability of compound 3 to inhibit colon tumour growth in vivo was tested as follows. CD-1 female nude mice (7 mice per treatment group, 6-7 weeks) were injected intraperitoneally with human colon adenocarcinoma cells HT-29 cells (3×$10^6$ cells in 0.1 ml PBS). Treatment of the mice with vehicle or 50 mg/kg/d of compound 3 was initiated 5 days post-inoculation (size of tumours=20-40 mm$^3$) for 7-day cycles of five days followed by a 2 day break for 5 weeks. The size of the tumours was measured over the course of the experiment using calipers, and the weight of the tumours was measured after the animals were sacrificed. Compound 3 was able to inhibit tumour growth, as measured by tumour size and weight, compared to vehicle-treated control animals (See FIGS. 13A and 13B).

Example 27

In Vivo Efficacy of Compound 3 in a Large-Cell Lung Carcinoma Xenograft Model

The ability of compounds of Formula I to inhibit large-cell lung tumour growth in vivo was tested by determining the efficacy of compound 3 in a xenograft model as described below. Compound 3 was tested as a lipid-based formulation having the following composition: distearoylphosphatidylethanolamine-polyethylene glycol 2000 (DSPE-PEG/5% mole) and egg phosphatidylcoline (ePC/95% mole). The formulation was prepared as follows: Stock solutions of compound 3 and lipid (ePC and DSPE-PEG) were prepared in DMF. Specific volumes of the stock solutions of compound 3 and lipid were then mixed in order to achieve a final lipid concentration of 25 mg/mL (ePC:DSPE-PEG=95:5 (mol %) and a compound 3 to total lipid ratio of 1:10 (w/w). The mixture was stirred for four hours, thoroughly dried under nitrogen and left overnight under vacuum. HEPES buffer saline (HBS 0.01 M, pH=7.4) warmed to 60° C. was then added in order to rehydrate the dried film. The solutions were vortexed, stirred for 48 hours at room temperature and sonicated for two and half hours. The formulation was then centrifuged at 1000 rpm for 5 minutes to remove any free compound 3.

Figure 14:
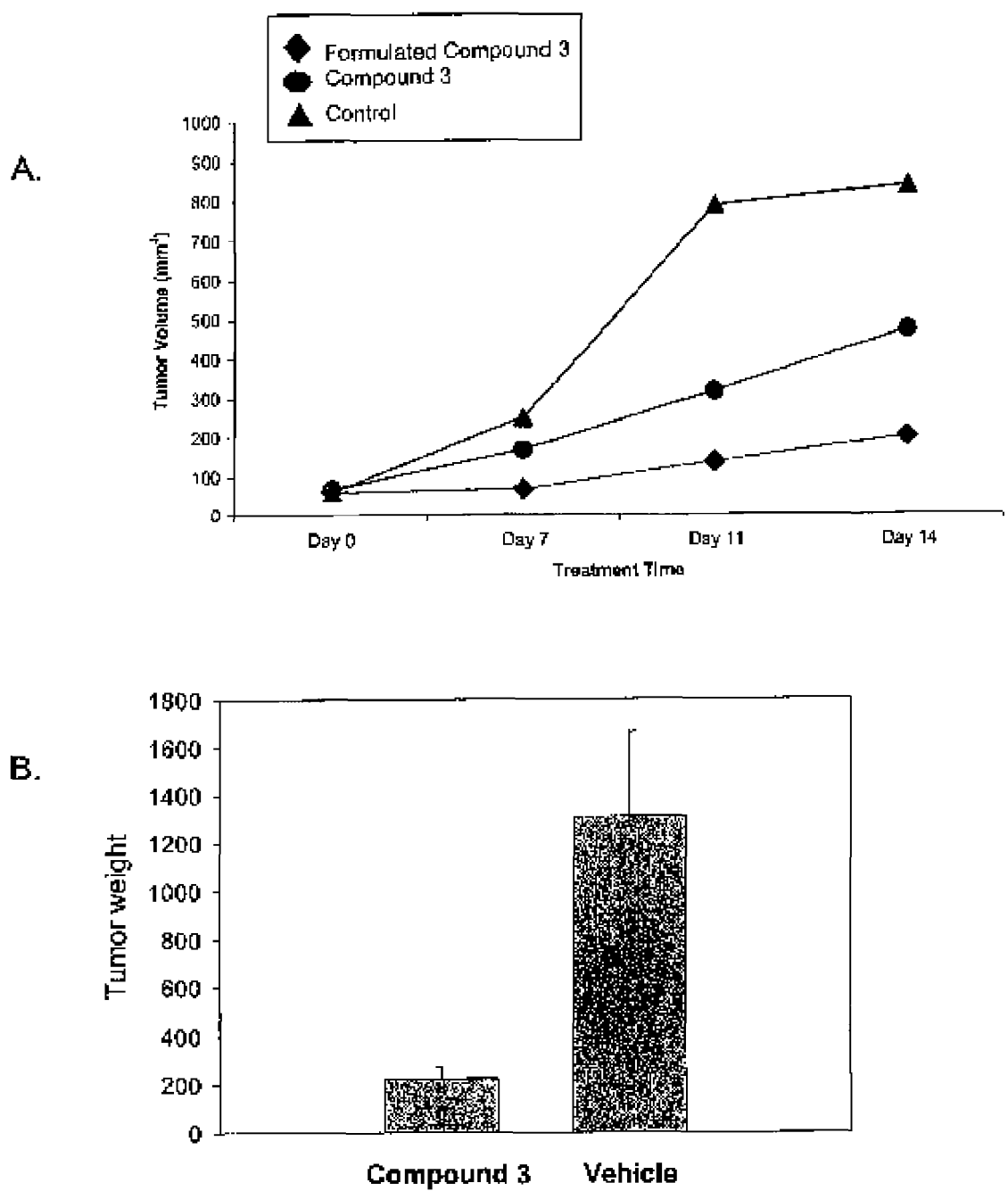
FIG. 14 depicts the ability of compound 3 to decrease tumour size (A) and tumour weight (B) in a large-cell lung carcinoma xenograft model.

CD-1 female nude mice (6-7 weeks, 7 mice per treatment group) were injected intrperitoneally with human lung NCI-H460 cells (3×$10^6$ cells in 0.1 ml PBS) subcutaneously. Treatment of the mice with vehicle or compound 3 was initiated 5 days post-inoculation (size of tumours=20-40 mm$^3$) for 7-day cycles of five days followed by a 2 day break for the duration of the experiment (35 days). Mice were treated with 80 mg/kg/d for the first week followed by 40 mg/kg/d until the end of the experiment. The size of the tumours was measured over the course of the experiment using calipers, and the weight of the tumours was measured after the animals were sacrificed. Compound 3 was able to inhibit large-cell lung tumour growth, as measured by tumour size and weight, compared to vehicle-treated control animals (See FIGS. 14A and 14B).

Example 28

In Vivo Efficacy of Compounds 3, 5, and 7 in a Colon Carcinoma Xenograft Model

The ability of compounds 3, 5, and 7 to inhibit colon carcinoma cell growth in vivo was tested in the mouse xenograft model as described in Example 26. The compounds were tested as Lutrol formulations (administered i.p.), lipid-based formulations micelles (administered i.v.), or water-based formulations (administered i.p.). The vehicle controls included Lutrol control (administered i.p.), lipid micelle control (administered i.v.), and water control (administered i.p.). Lutrol formulations contained 15% Lutrol and 10% DMSO. The composition of the lipid-based formulations and preparation of same was as described in Example 27 above.

Figure 15:
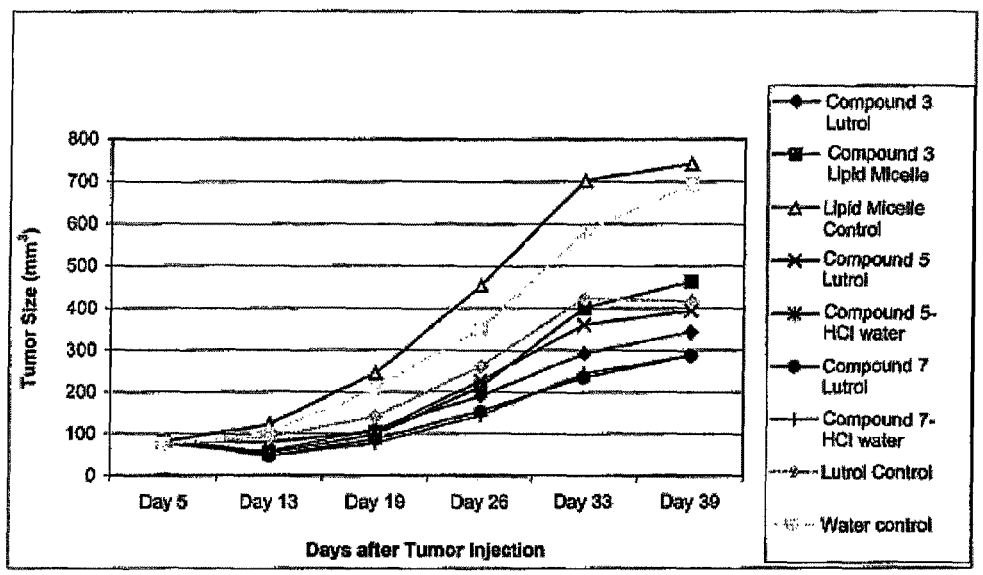
FIG. 15 depicts the ability of compounds 3, 5, and 7 to decrease tumour size (A) and tumour weight (B), in a colon adenocarcinoma xenograft model.
Figure 15:
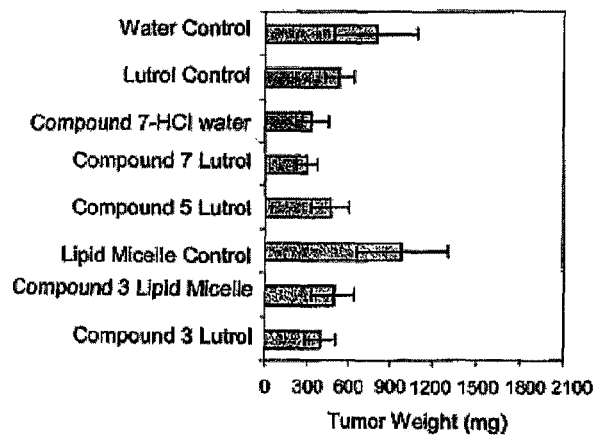

The results (FIG. 15) indicated that these compounds were able to decrease the size (FIG. 15A) and weight (FIG. 15B) of tumours derived from HT-29 cells.

Example 29

In Vivo Efficacy of Compounds 3, 5 and 7 in a Large-Cell Lung Carcinoma Xenograft Model The ability of compounds 3, 5, and 7 to inhibit large-cell lung carcinoma cell growth in vivo was tested in the mouse xenograft model as described in Example 27. The compounds were tested as Lutrol formulations (administered i.p.), lipid-based formulations micelles (administered i.v.), or water-based formulations (administered i.p.). The vehicle controls included Lutrol control (administered i.p.), lipid micelle control (administered i.v.), and water control (administered i.p.). Lutrol formulations contained 15% Lutrol and 10% DMSO. The composition of the lipid-based formulations and preparation of same was as described in Example 27 above.

Figure 16:
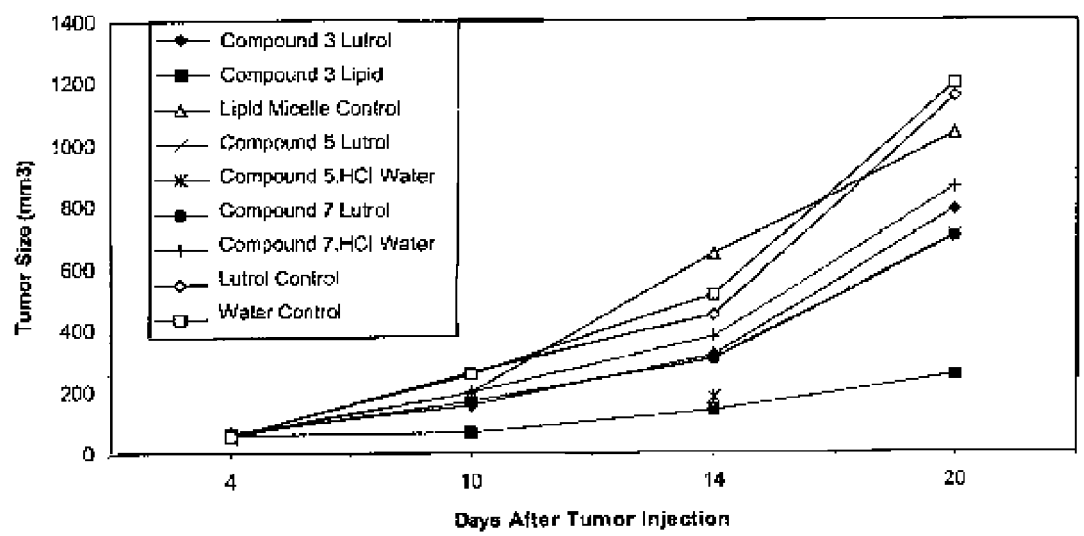
FIG. 16 depicts the ability of compounds 3, 5, and 7 to decrease tumour size (A) and tumour weight (B) in a lung carcinoma xenograft model.
Figure 16:
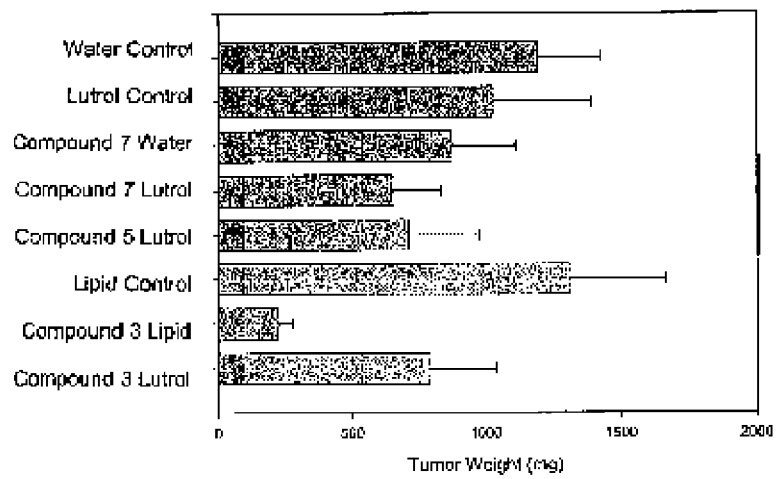

The results (FIG. 16) indicated that compounds 3, 5, and 7 were able to decrease the size (FIG. 16A) and weight (FIG. 16B) of tumours derived from NCI-H460 cells.

Example 30

Ability of Compound 3 to Modulate Expression of KLF4 In Vivo

Figure 17:
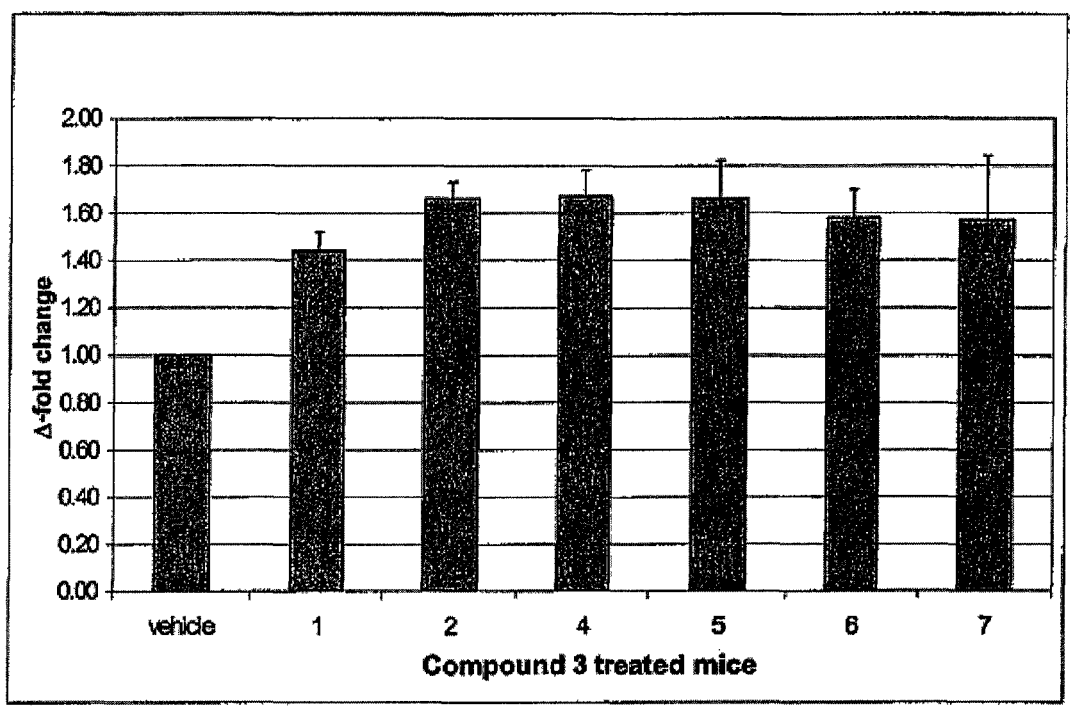
FIG. 17 depicts the effect of compound 3 on KLF4 mRNA levels in vivo in tumours from a colon adenocarcinoma xenograft model.

The ability of compound 3 to modulate expression of KLF4 in HT-29 colon tumour xenograft was determined as follows. Groups of 10 CD-1 female nude mice (6-7 weeks) were injected in the lower mid back with human colon adenocarcinoma cells HT-29 cells ($3 \times 10^6$ cells in 0.1 ml PBS) subcutaneously. Treatment of the mice with vehicle or 50 mg/kg/d of compound 3 was initiated 5 days post-inoculation (size of tumours=20-40 mm$^3$) for cycles of five days and 2 for the duration of the experiment (35 days). After the treatment period, the animals were sacrificed, the tumours excised, and total RNA was extracted from 30 mg of tumour tissue using Rneasy Mini kit (QIAGEN, Valencia, Calif.). The expression of KLF4 mRNA was analyzed by real-time polymerase chain reaction using the comparative CT method as described in Example 19. Compound 3 induced the expression of KLF4 in tumour xenografts from all mice treated with compound 3 by approximately 1.5-fold compared to tumour xenografts treated with vehicle alone (FIG. 17).

Example 31

Ability of Compound 3 to Modulate Expression P21 In Vivo

Figure 18:
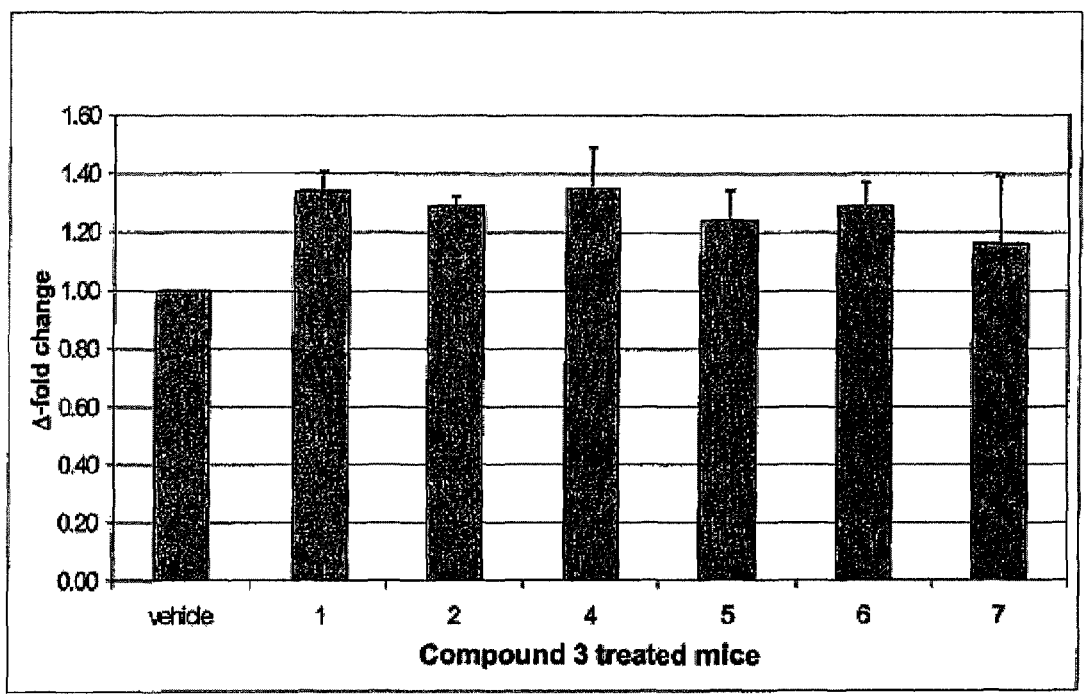
FIG. 18 depicts the effect of compound 3 on p21 mRNA levels in vivo in tumours from a colon adenocarcinoma xenograft model.

The ability of compound 3 to modulate expression of p21 in vivo was determined using the HT-29 colon tumour xenograft model as described in Example 26. The expression of p21 mRNA was analyzed by real-time polymerase chain reaction analysis using the comparative CT method as described in Example 30. Compound 3 induced the expression of p21 in tumour xenografts from all mice treated with compound 3 compared to tumour xenografts treated with vehicle alone (FIG. 18).

Example 32

Ability of Compound 3 to Modulate Expression of Cyclin D1 In Vivo

Figure 19:
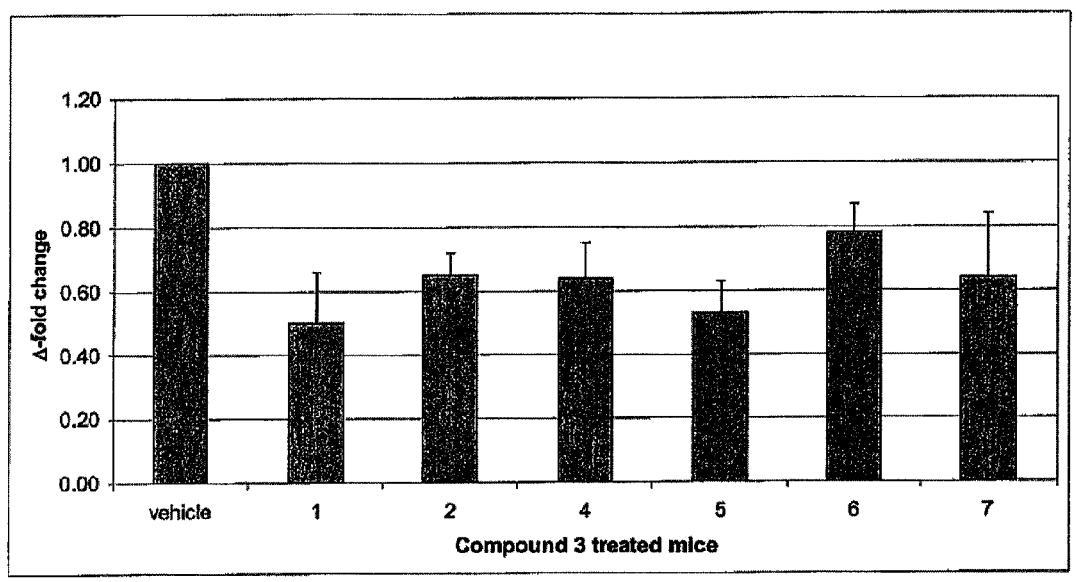
FIG. 19 depicts the effect of compound 3 on Cyclin D1 mRNA levels in vivo, in tumours from a colon adenocarcinoma xenograft model (A).
Figure 20:
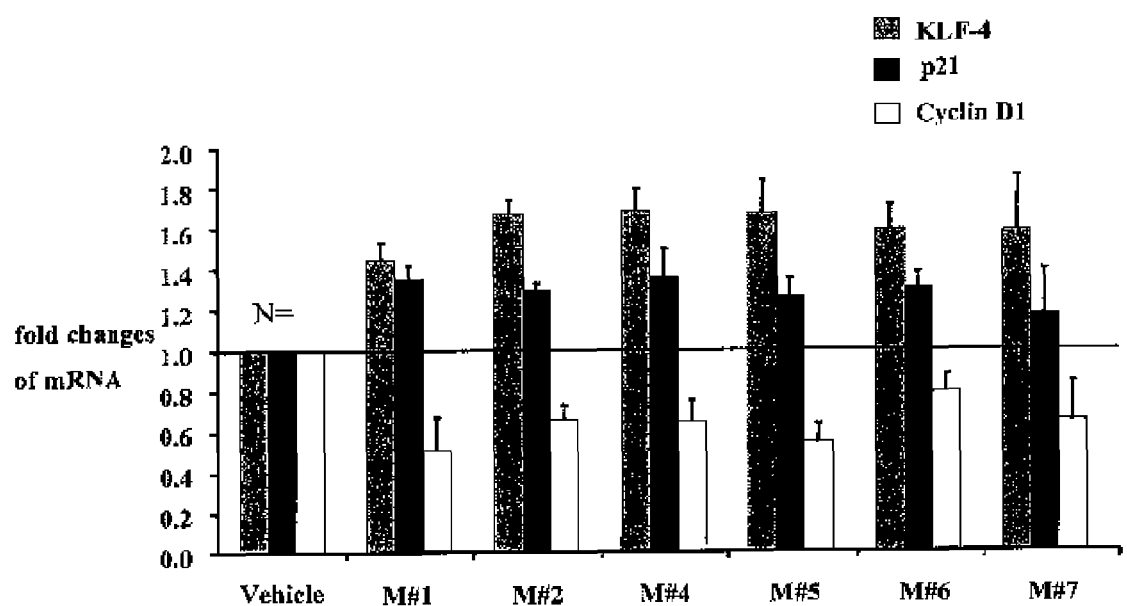
FIG. 20 depicts a comparison of the effect of compound 3 on KLF4, p21, and Cyclin D1 mRNA levels in a colon adenocarcinoma xenograft model.

The ability of compound 3 to modulate expression of Cyclin D1 was determined using the HT-29 colon tumour xenograft model as described in Example 26. The expression of Cyclin D1 mRNA was analyzed by real-time polymerase chain reaction as described in Example 30. Compound 3 consistently reduced the expression of Cyclin D1 in tumour xenografts from mice treated with compound 3 compared to tumour xenografts treated with vehicle alone (FIG. 19). The results of this experiment combined with the results described for the effect of compound 3 in vivo on KLF4 and P21 expression as described in Examples 30 and 31 are shown in FIG. 20.

Example 33

Sub-Acute Toxicity Testing of Compounds

To test the sub-acute toxicity of the compounds of Formula I, female mice were injected with the compounds and toxicity was evaluated based on mortality, changes in behaviour, appearance and weight. Briefly, ICR normal female mice (5-6 weeks old; n=33) weighing about 0.020 kg in body weight, were injected with various compounds at 100 mg/kg and 50 mg/kg or with the vehicle alone (Lutrol (M68, micronized)). Groups of 3 ICR female mice were injected with one intra-peritoneal (i.p.) injection of 250 μl of each compound at 4.0 mg/ml twice per day (100 mg/kg) for 1 week (Group I); or with one intra-peritoneal (i.p.) injection of 250 μl of each compound at 2.0 mg/ml twice per day (50 mg/kg) for 1 week (Group II), or with one intra-peritoneal (i.p.) injection of 250 μl of lutrol vehicle control twice per day for 1 week (Control Group).

The compounds to be tested were prepared to provide enough for one week at concentrations of 4.0 mg/ml and 2.0 mg/ml. Briefly, 50 mg of each compound was dissolved in 1.25 ml of 100% DMSO and diluted with 6.25 ml of Lutrol (30% in water) and 5 ml water, to prepare a solution of 4 mg/ml compound in 15% Lutrol in water. Next, 4 ml of each prepared solution was further diluted with 4 ml of 15% Lutrol in water to provide the 2.0 mg/ml solution of each compound. For the vehicle control solution, 8 ml of 15% Lutrol in water was prepared. Compounds at concentrations of 4.0 mg/ml and 2.0 mg/ml and the vehicle control were administered as described above. Toxicity was evaluated based on mortality, changes in behaviour, appearance and weight and is shown in Table 6.

TABLE 6

Sub-Acute Toxicity Testing

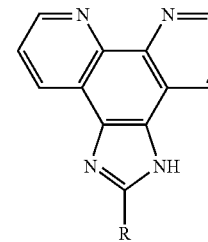

| Compound | R | Sub-acute toxicity +Toxicity-lethality −non-toxic 100 mg/Kg | 50 mg/Kg |
|---|---|---|---|
| 2 | 5-Br-3-methylindole | + | + |
| 3 | 2,3-dimethylindole | + | − |
| 5 | 5-Cl-2,3-dimethylindole | − | − |
| 6 | 5-MeO-2,3-dimethylindole | + | − |
| 7 | 5-F-2,3-dimethylindole | − | − |
| 8 | 5-HO-2,3-dimethylindole | − | − |
| 9 | 3-methyl-2-phenylindole | + | − |
| 10 | 3-methyl-2-(4-fluorophenyl)indole | + | + |

TABLE 6-continued

Sub-Acute Toxicity Testing

| Compound | R | Sub-acute toxicity +Toxicity-lethality −non-toxic 100 mg/Kg | 50 mg/Kg |
|---|---|---|---|
| 11 | 3-methyl-2-(4-pyridyl)indole | + | − |
| 12 | 3-methyl-2-(piperidinylmethyl)indole | + | − |

Example 34

In Vitro Sub-Cellular Localization of Compound 3 in HT-29 Cells

Figure 21:
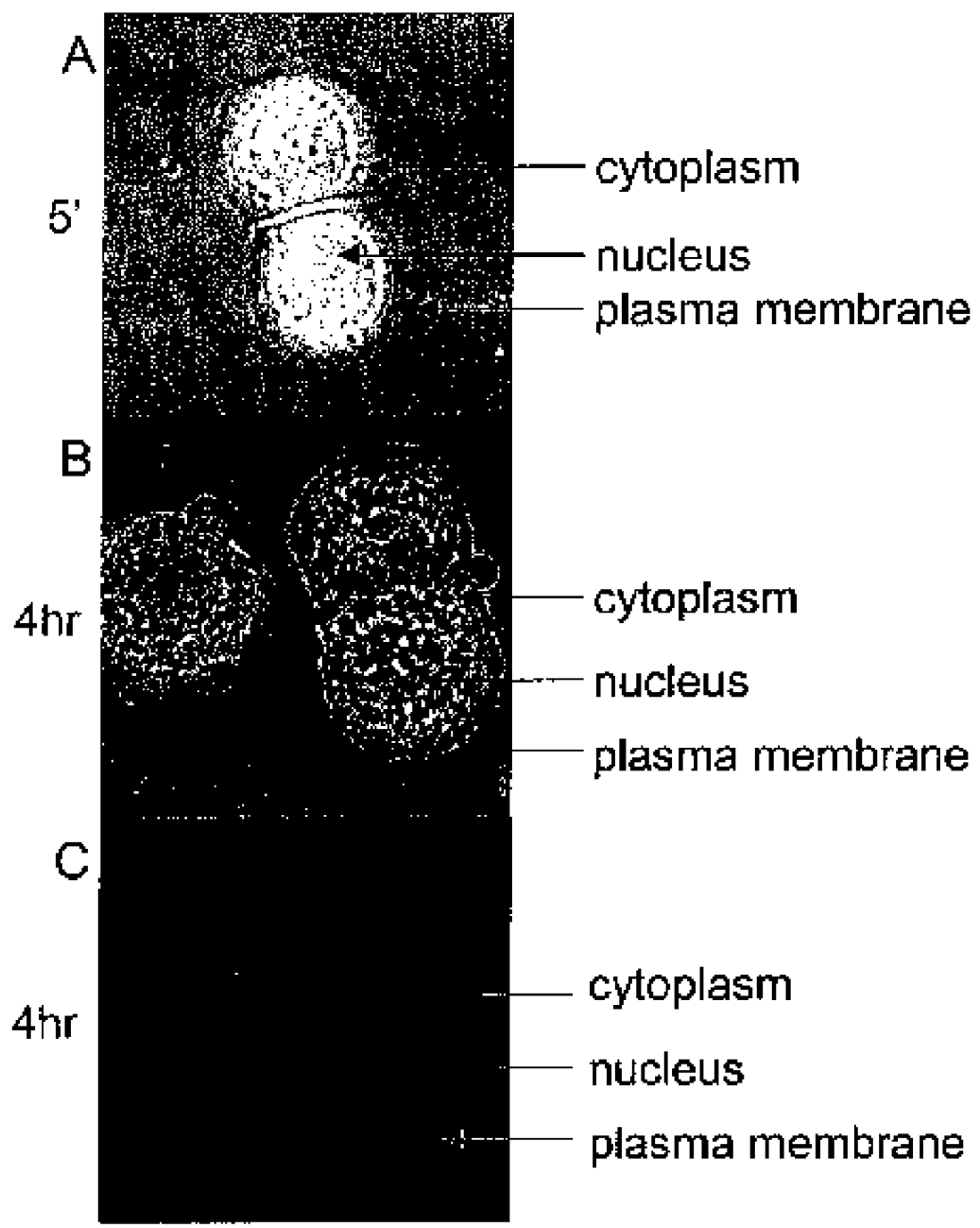
FIG. 21 depicts the sub-cellular localization of compound 3 in HT-29 cells in vitro. (A) Cells treated with compound 3 for 5 minutes; (B) and (C) cells treated for 4 hours. For (A) and (B), differential interference contrast images were overlaid with fluorescent images. (B) and (C) are the same images.

The subcellular localization of compounds of Formula I in cancer cells was determined as follows. Since compound 3 is intrinsically fluorescent, it was possible to examine its subcellular localization in cancer cells by fluorescent microscopy in HT-29 colon carcinoma cells. Cells were treated with 10 or 25 μM compound 3 for 5 minutes (FIG. 21A) or 4 hours (FIGS. 21B and 21C), washed once in PBS, fixed in 3.7% formaldehyde/PBS for 10 minutes, washed again three times, and mounted with Cytoseal. Images were obtained with a Zeiss laser scanning fluorescent microscope with an excitation filter range of 360-370 nm. The results are shown in FIGS. 21A-C. For FIGS. 21A and 21B, differential interference contrast images were overlaid with fluorescent images. FIGS. 21B and 21C are the same images. Compound 3 entered the cell within 5 minutes of treatment, and was evenly distributed throughout the nucleus and cytoplasm, but was excluded from the plasma membrane of HT-29 cells (FIG. 21A). By 4 hours of treatment, compound 3 was localized predominantly around the outside of the nucleus (perinuclear region), but a portion was still located within the nucleus (FIGS. 21B and 21C).

Example 35

Ability of Compounds of Formula I to Cleave DNA In Vitro

Figure 22:
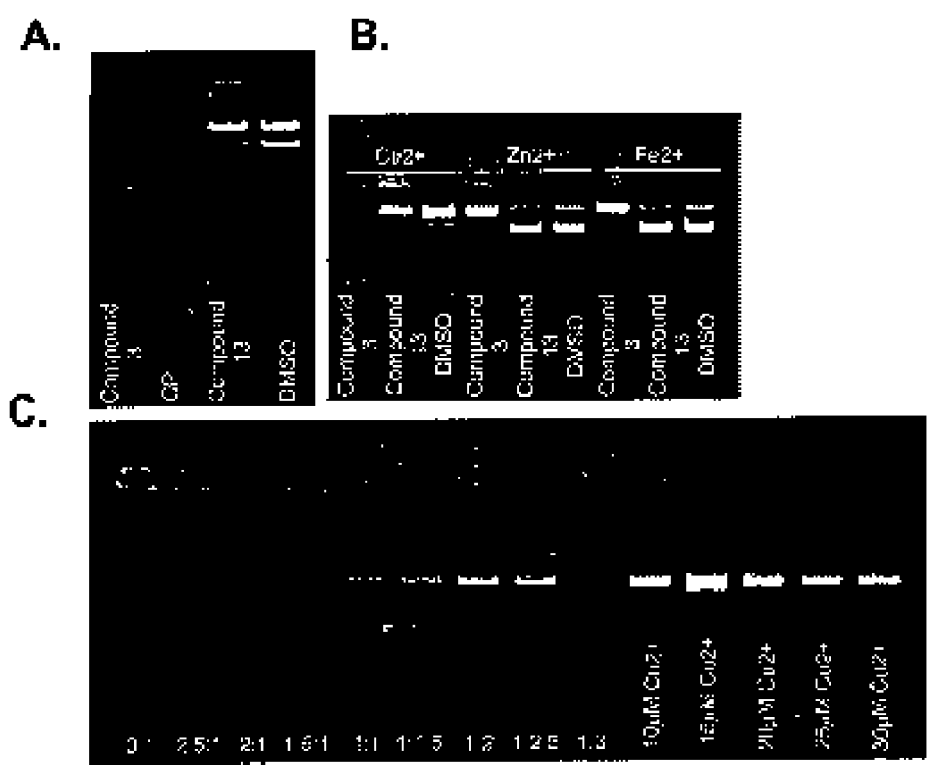
FIG. 22 depicts the ability of compounds 3 and 13 to cleave DNA (A) in the absence of metal ions; (B) in the presence of copper, zinc or iron (II) ions; and (C) in the presence of varying amounts of copper.

Compound 3 was tested for its ability to cleave plasmid DNA in vitro in the presence of copper and the reducing agent ascorbic acid. Experiments were performed in a total of 20 μl, containing 10 mM $NaH_2PO_4/Na_2HPO_4$ buffer (pH 6.7), 1 μg of supercoiled plasmid DNA, 100 μM ascorbic acid, 25 μM drug compound (or vehicle), and 10 μM of $CuSO_4.5H_2O$. The reaction mixture was incubated at 37° C. for 30 minutes, and 1 μl of 0.1 M EDTA was added to terminate the reaction. DNA loading buffer was added, and reactions were run at 80V for 80 minutes on a 1% agarose gel containing ethidium bromide. Both compound 3 and the positive control 1,10-phenanthroline (OP) were able to cleave plasmid DNA, converting the supercoiled and open circular forms into low molecular weight fragments of DNA. The non-chelating compound 13, and the vehicle control, DMSO, were unable to cleave DNA (FIG. 22A). Neither compound 3 nor OP was able to cleave DNA in the absence of copper or reducing agent.

To determine whether ions other than copper could suffice, DNA cleavage reactions were also carried out in the presence of zinc or iron. Reactions were performed as above, in the presence of 25 μM of $CuSO_4.5H_2O$, $ZnCl_2$, or $FeCl_2.4H_2O$. Neither zinc nor iron was able to replace copper in the cleavage reactions with compound 3 (FIG. 22B). Note that copper alone in the presence of ascorbic acid can shift the ratio of supercoiled DNA to open circular DNA.

Figure 23:
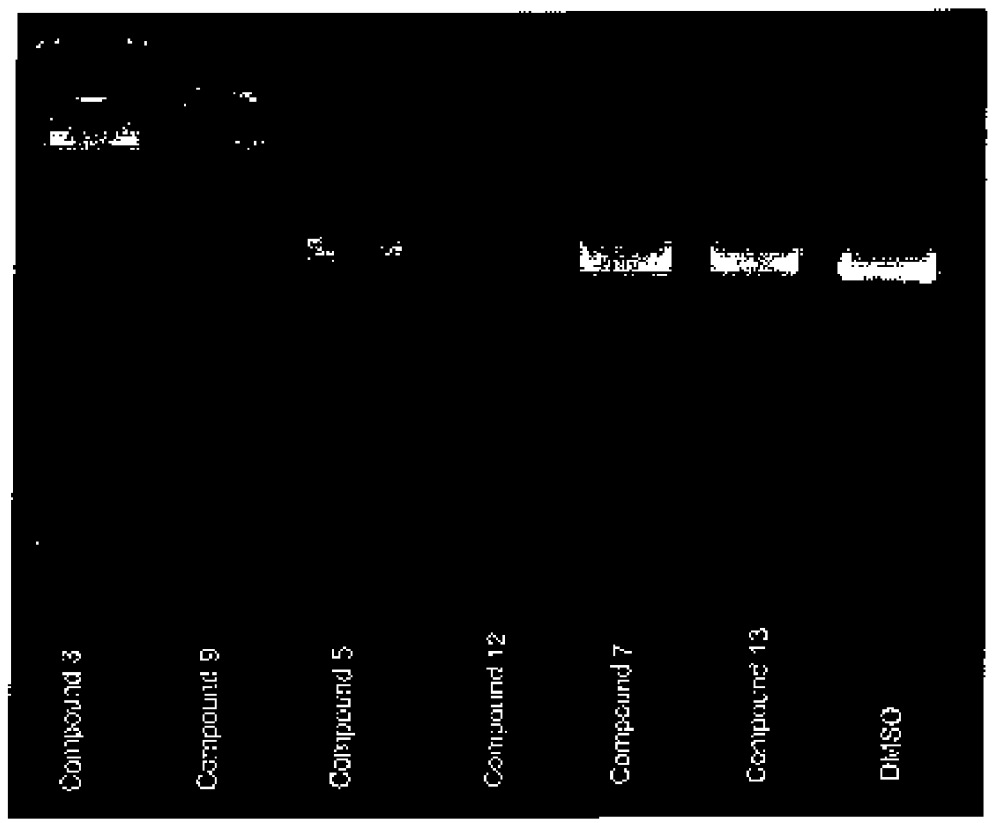
FIG. 23 depicts the ability of compounds 3, 5, 7, 9, 12 and 13 to cleave DNA.

To determine the ratios of compound to copper at which compound 3 was effective, reactions were performed as in FIG. 22A. The ratios of compound 3 to copper of 3:1, 2.5:1, 2:1, 1.5:1, and 1:1, as shown in FIG. 23 were achieved by maintaining the concentration of Cu constant at 10 μM, and varying the concentration of compound 3. The ratios of compound 3 to Cu of 1:1.5, 1:2, 1:2.5, and 1:3, were achieved by maintaining the concentration of compound 3 constant at 10 μM, and varying the concentration of copper. Compound 3 efficiently cleaved DNA when it is present at a ratio greater than 1.5:1 to copper, and was unable to cleave at ratios of 1:1, 1:2, 1:2.5. However, compound 3 was able to cleave at a ratio of 1:3 (FIG. 22C). These results help to provide an indication as to what types of copper-compound 3 complexes are being formed, and which are most cytotoxic.

Other compounds of Formula I, compounds 5, 7, 9 and 13 were also tested for their ability to cleave DNA at a ratio of 2.5:1 to copper (FIG. 23). Ratios of compound 3:copper as indicated, plus concentrations of copper in the absence of compound 3 were used in the DNA cleavage assay as described above. Compounds 9 and 12 were shown to also be capable of cleaving DNA.

Example 36

In vitro Antiproliferative Activity of Compounds of Formula I in HT-29 Colon Carcinoma Cells The ability of compounds of Formula I to inhibit the proliferation of human colon carcinoma HT-29 cells was tested as described above in Example 13. Results of this experiment are shown in Table 7.

TABLE 7

Antiproliferative Activity of Compounds of Formula I

| R = Substituent Group | Name | IC50 μg/ml | MW |
|---|---|---|---|
| 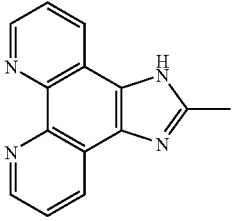 | | | |
| 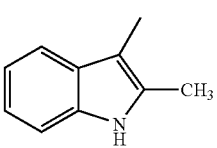 3 | 3 | 0.6 | 349.4 |
| 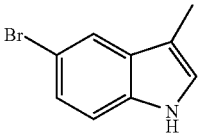 2 | 2 | 1.5 | 414.3 |
| 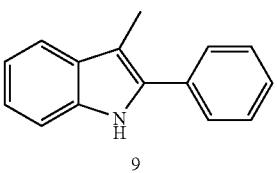 9 | 9 | 0.3 | 411.5 |

TABLE 7-continued
Antiproliferative Activity of Compounds of Formula I
| R = Substituent Group | Name | IC50 µg/ml | MW |
|---|---|---|---|
| 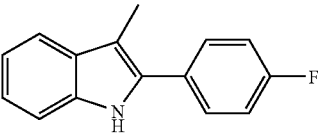 10 | 10 | 0.18 | 429.5 |
| 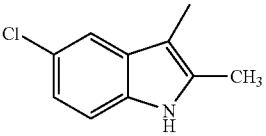 5 | 5 | 0.35 | 383.8 |
| 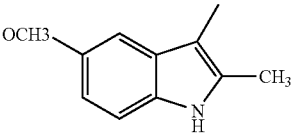 6 | 6 | 1.4 | 379.4 |
| 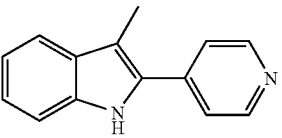 11 | 11 | >2.5 | 412.5 |
| 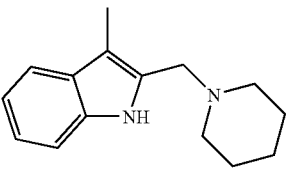 12 | 12 | 0.28 | 432.5 |
| 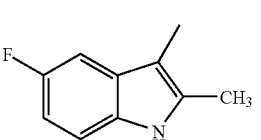 7 | 7 | 0.7 | 367.4 |
| 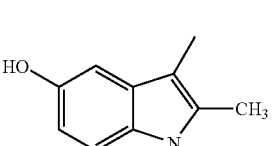 8 | 8 | >25 | 365.4 |
| 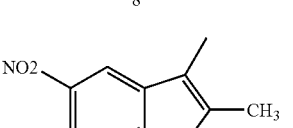 38 | 38 | 3.5 | 394.39 |

TABLE 7-continued
Antiproliferative Activity of Compounds of Formula I
| R = Substituent Group | Name | IC50 µg/ml | MW |
|---|---|---|---|
| 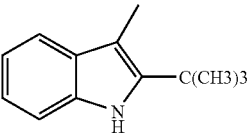 39 | 39 | 0.45 | 391.47 |
| 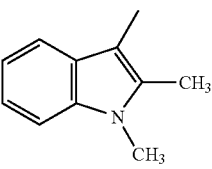 41 | 41 | 0.49 | 363.41 |
| 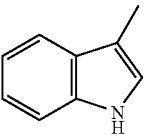 1 | 1 | 2 | 335.36 |
| 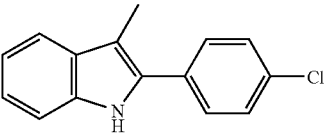 42 | 42 | 0.31 | 445.9 |
| 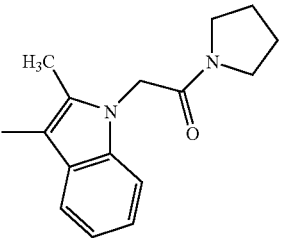 43 | 43 | >5-25< | 460.53 |
| 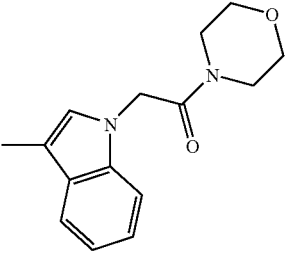 44 | 44 | >5-25<, | 462.18 |

TABLE 7-continued
Antiproliferative Activity of Compounds of Formula I
| R = Substituent Group | Name | IC50 µg/ml | MW |
|---|---|---|---|
| 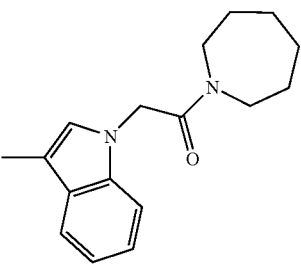 45 | 45 | 7 | 474.56 |
| 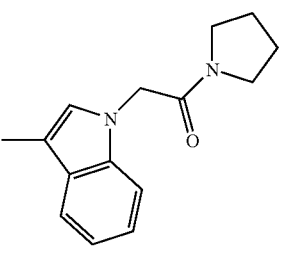 46 | 46 | >5-25< | 446.5 |
| 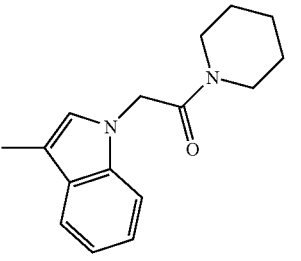 47 | 47 | 5 | 460.53 |
| 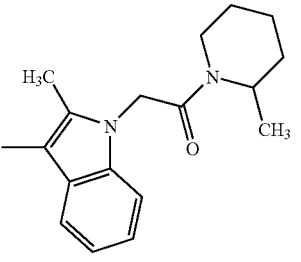 48 | 48 | 3.1 | 488.58 |
| 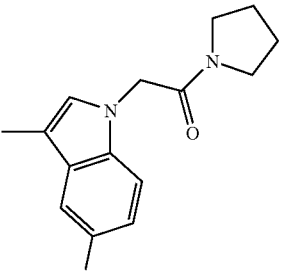 49 | 49 | >5-25< | 525.4 |

TABLE 7-continued
Antiproliferative Activity of Compounds of Formula I
| R = Substituent Group | Name | IC50 μg/ml | MW |
|---|---|---|---|
| 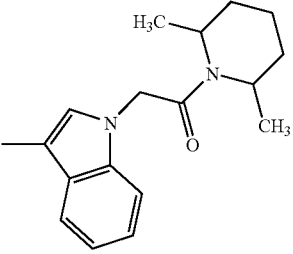 50 | 50 | 2.3 | 488.58 |
| 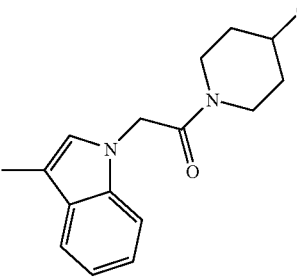 51 | 51 | 5 | 474.56 |
| 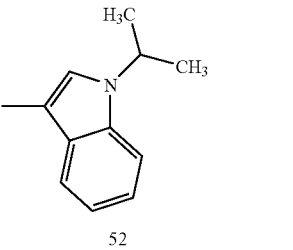 52 | 52 | 0.19 | 377.44 |
| 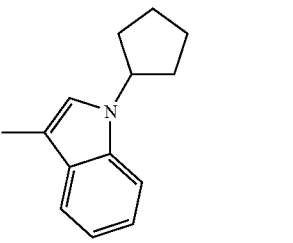 53 | 53 | 0.19 | 403.48 |
| 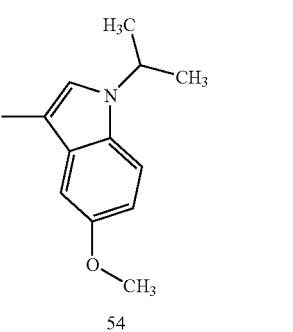 54 | 54 | 0.28 | 407.47 |

TABLE 7-continued
Antiproliferative Activity of Compounds of Formula I
| R = Substituent Group | Name | IC50 μg/ml | MW |
|---|---|---|---|
| 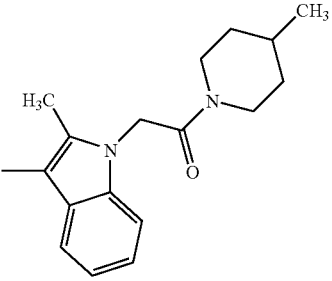 55 | 55 | 2.4 | 488.58 |
| 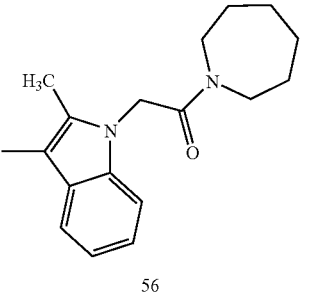 56 | 56 | 5 | 488.58 |
| 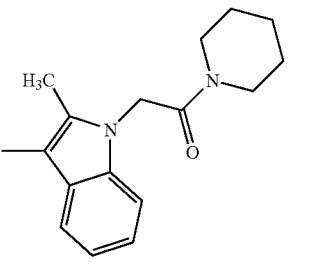 57 | 57 | 5 | 474.56 |
| 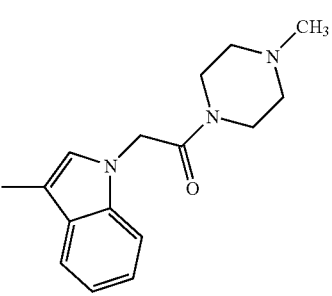 58 | 58 | > | 475.54 |

TABLE 7-continued
Antiproliferative Activity of Compounds of Formula I
| R = Substituent Group | Name | IC50 µg/ml | MW |
|---|---|---|---|
| 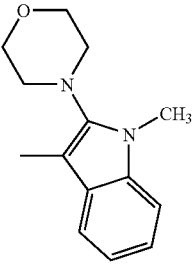 59 | 59 | 0.6 | 434.49 |
| 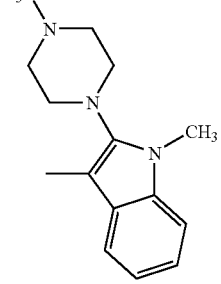 60 | 60 | 0.4 | 447.53 |
| 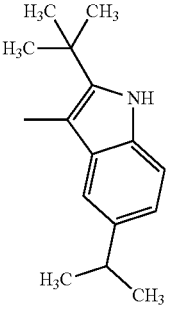 61 | 61 | 0.4 | 433.55 |
| 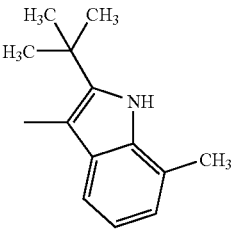 62 | 62 | <0.1 | 405.49 |

TABLE 7-continued

Antiproliferative Activity of Compounds of Formula I

| R = Substituent Group | Name | IC50 µg/ml | MW |
|---|---|---|---|
| 63 | 63 | 0.2 | 447.57 |
| 64 | 64 | 0.15 | 419.52 |
| 65 | 65 | 0.35 | 409.46 |
| 4 | 4 | 3.5 | 353.35 |
| 66 | 66 | 0.4 | 427.45 |

TABLE 7-continued
Antiproliferative Activity of Compounds of Formula I
| R = Substituent Group | Name | IC50 µg/ml | MW |
|---|---|---|---|
| 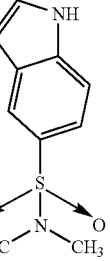<br>67 | 67 | >5, 25< | 498.6 |
| 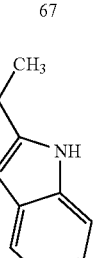<br>68 | 68 | 0.34 | 467.56 |
| 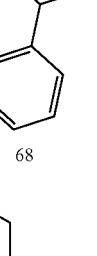<br>69 | 69 | 0.2 | 483.61 |
| 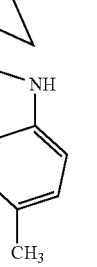<br>70 | 70 | 0.35 | 497.63 |

TABLE 7-continued
Antiproliferative Activity of Compounds of Formula I
| R = Substituent Group | Name | IC50 μg/ml | MW |
|---|---|---|---|
| 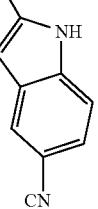 71 | 71 | 3 | 416.48 |
| 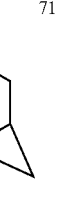 72 | 72 | 0.18 | 487.57 |
| 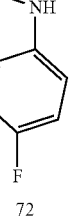 73 | 73 | 0.22 | 459.58 |
| 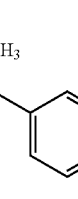 74 | 74 | 0.18 | 481.59 |
| 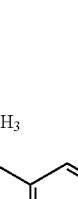 75 | 75 | >25 | 518.97 |

TABLE 7-continued

Antiproliferative Activity of Compounds of Formula I

| R = Substituent Group | Name | IC50 µg/ml | MW |
|---|---|---|---|
| *structure 76: 5-(N,N-dimethylsulfamoyl)-3-methyl-2-chloro-1H-indole* | 76 | >25 | 476.94 |
| *structure 18: 1,3-dimethyl-2-phenyl-1H-indole* | 18 | 0.37 | 425.48 |
| *structure 77: 1-benzyl-5-fluoro-2,3-dimethyl-1H-indole* | 77 | 0.24 | 457.5 |
| *structure 78: 2-(1-adamantyl)-3-methyl-1H-indole* | 78 | 0.38 | 469.58 |
| *structure 79: 2-isopropyl-3-methyl-1H-indole* | 79 | 0.65 | 377.44 |

TABLE 7-continued
Antiproliferative Activity of Compounds of Formula I
| R = Substituent Group | Name | IC50 µg/ml | MW |
|---|---|---|---|
| 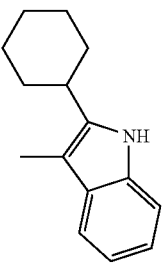 80 | 80 | 0.42 | 417.51 |
| 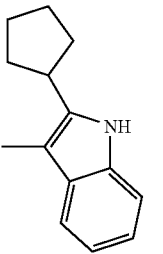 81 | 81 | 0.4 | 403.48 |
| 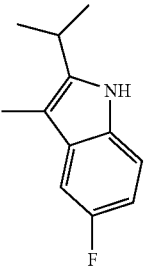 82 | 82 | 0.61 | 395.43 |
| 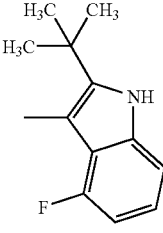 83 | 83 | 0.1 | 423.48 |
| 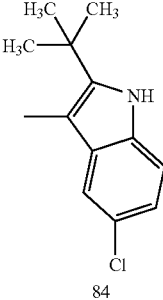 84 | 84 | 0.39 | 439.94 |

TABLE 7-continued

Antiproliferative Activity of Compounds of Formula I

| R = Substituent Group | Name | IC50 μg/ml | MW |
|---|---|---|---|
| (structure 85: 2-tert-butyl-3-methyl-4-chloro-7-methyl-indole) | 85 | 0.24 | 439.94 |
| (structure 86: 2-tert-butyl-3-methyl-5-ethyl-indole) | 86 | 0.47 | 419.52 |
| (structure 87: 2-tert-butyl-3-methyl-6-bromo-indole) | 87 | 0.42 | 470.36 |
| (structure 88: 2-tert-butyl-3-methyl-7-fluoro-indole) | 88 | 0.38 | 409.46 |

Example 37

In Vitro and In Vivo Effects of Compounds of Formula I

Figure 24:
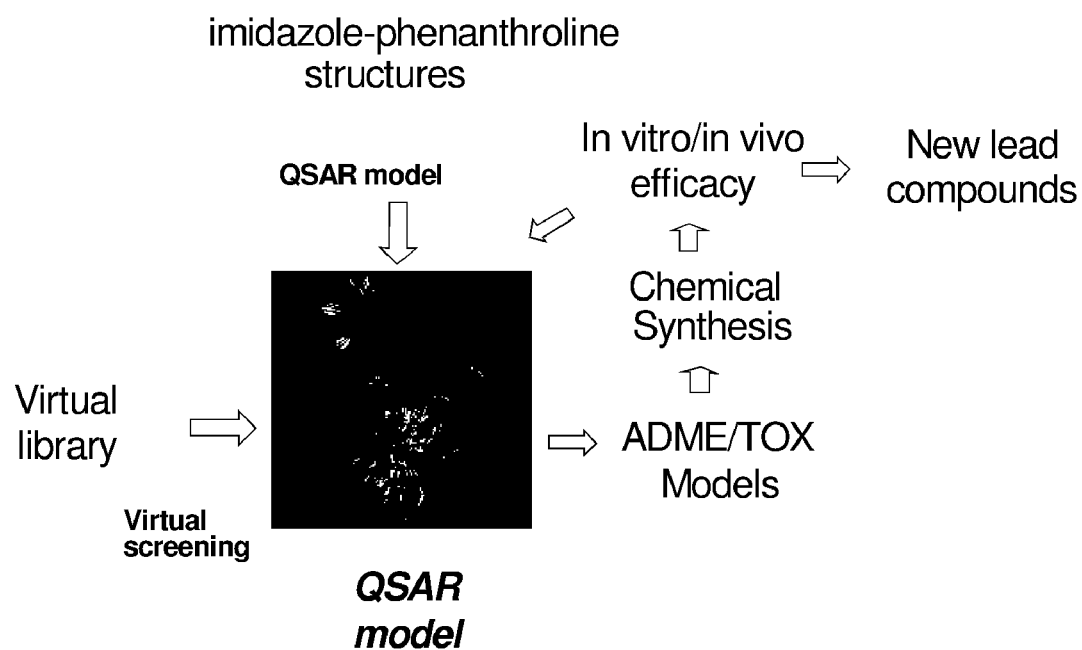
FIG. 24 presents the development of compounds of Formula I.

Metal transcription factor-1 (MTF-1) is a constitutively expressed transcription factor, which regulates target genes by binding to metal-responsive elements, upon activation by zinc. Activation of MTF-1 in hypoxic microenvironment of rapidly proliferating tumor cells, following hypoxia-induced oxidative stress and release of zinc from intracellular stores, is associated with tumor development and progression. Krüppel-like factor 4 (KLF4) is a member of Sp/KLF family transcription factors, which regulates target genes by binding to GC-box and CACCC box DNA sequences. KLF4 is a negative regulator of cell growth by mechanisms such as activation of $p21^{waf1/cip1}$ and suppression of Cyclin D1 expression by counteracting a positive regulator Sp1 binding to Cyclin D1 promoter. Tumor suppressor role of KLF4 has been recognized in T-cell leukemia, gastrointestinal, bladder and prostate cancers. MTF-1, Sp1 and auto-regulation by KLF4 are upstream positive regulators of KLF4. A series of novel small molecules which down-regulate MTF-1 have been developed and their anti-tumor activities in vitro and in vivo have been screened. Compounds of Formula I were selected from more than 3000 imidazole-phenanthroline structures by ligand-based structural design, as shown in FIG. 24.

Analysis of the effects of compounds of Formula I on in vitro and in vivo cell growth inhibition were performed utilizing the methods as described in the preceding Examples. As shown in Example 12, cell growth inhibition by the parental compound 3 was screened by National Cancer Institute 60-cell line assay and leukemia, non-small cell cancer, colon cancer, renal cancer and prostate cancer panels were especially sensitive to compound 3. The average $GI_{50}$ of all cell lines tested was 0.62 µM as shown in FIG. 2.

trol-treated cells of respective cell type as "1". Increased KLF4 expression was observed in different types of cancer, also shown in Table 8. Gene expression studies have revealed that the pattern of gene expression for the breast cancer cell line MDA-MB-435 more closely resembles that of melanoma cell lines than of other breast tumor lines (Ross et al. (2000) *Nat Genet* 24(3): 227-233). Additionally, xenografts of MDA-MB-435 implanted into mammary fat pads of female SCID mice have shown immunohistochemical staining consistent with melanocytic origin (Ellison G, Klinowska T, Westwood R F, Docter E, French T, Fox J C. (2002) *Mol Pathol.* 55(5): 294-299). The breast cancer cell line MDA-MB-435 may be expected to function differently than the other breast cancer cell lines.

TABLE 8

Cell Growth Inhibition $IC_{50}$ (µM) and Modulation of KLF4 Gene Expression by Compounds of Formula I in Different Cancer Cell Types

| Cell line | Cancer | IC50 (cell growth inhibition) | | | | | KLF4 (gene fold increase) | | | | |
|---|---|---|---|---|---|---|---|---|---|---|---|
| | | CMP 3 | CMP 7 | CMP 63 | CMP 64 | CMP 69 | CMP 3 | CMP 7 | CMP 63 | CMP 64 | CMP 69 |
| HT-29 | colon | 0.71 | 0.8 | 0.2 | 0.15 | 0.2 | 6.5 | 8.66 | 5.98 | 5.96 | 6.54 |
| HCT-116 | colon | 0.2 | 0.15 | 0.3 | 0.2 | 0.16 | 5.88 | 6.15 | 2.82 | 3.05 | 3.11 |
| H-460 | lung | 2.9 | 2.6 | 0.4 | 0.3 | 0.4 | 3.4 | 2.1 | 1.55 | 1.64 | 1.95 |
| DU-145 | prostate | 0.35 | 0.22 | 0.4 | 0.3 | 0.4 | 9.16 | 11.24 | 12.95 | 6.75 | 7.46 |
| PC-3 | prostate | 0.3 | 0.21 | 0.32 | 0.46 | 0.34 | 16.28 | 12.17 | 1.34 | 1.36 | 0.95 |
| MDA-MB-231 | breast | 5 | 5 | 3.7 | 5 | 3.3 | 1.52 | 1.6 | 1.77 | 2.06 | 1.61 |
| MDA-MB-435 | breast | 0.35 | 0.2 | 0.5 | 0.5 | 0.6 | 9.09 | 11.71 | 7.67 | 7.59 | 8.91 |
| CCRF-CEM | leukemia | 0.42 | 0.4 | 0.3 | 0.25 | 0.2 | 28.05 | 48.5 | 76.37 | 73.77 | 74.29 |
| MOLT-4 | leukemia | 0.15 | 0.07 | 0.2 | 0.175 | 0.2 | 44.79 | 173.6 | 223.63 | 265.03 | 276.28 |
| SK-MEL-2 | melanoma | 0.25 | 0.2 | 0.17 | 0.2 | 0.18 | 2.38 | 3.32 | 5.46 | 5.35 | 4 |

As shown in Example 25, cell growth inhibition by compound 3 was screened in vivo by National Cancer Institute Hollow Fiber assay. A total score of 20 or greater with at least subcutaneous score of 8 or cell killing of any cell line is considered as a significantly active anti-cancer compound. Compound 3 exhibited a total score of 32 with subcutaneous score of 10 and positive cell killing as shown in Table 5 supra.

Tumor cell growth inhibition is observed in vitro in cancer cell proliferation assays and in vivo in Hollow Fiber assays and mouse tumor xenograft models, by compounds of Formula I in different cancer cell types.

Example 38

In Vitro Ability of Compounds of Formula I to Modulate Cell Growth Inhibition and KLF4 Gene Expression in Human Cancer Cells Lines Cell growth inhibition $IC_{50}$ (µM) by compounds of Formula I was tested on various cancer cell types by XTT cell proliferation assay. Low or sub-micromolar $IC_{50}$ was observed in different types of cancer as shown in Table 8. The growth inhibitory effects of the compounds of Formula I as shown below for the melanoma cell line SK-MEL-2 were reproducible by Lorus Therapeutics Inc.

The $IC_{50}$ values for compounds of Formula I in the breast cancer cell line MDA-MB-435 were between 0.2 µM and 0.6 µM as shown below in Table 8.

Gene expression levels of KLF4, induced by compounds of Formula I, were also examined on various cancer cell types by RT-PCR. Fold changes in KLF4 in compound-treated cells were expressed relative to KLF4 expression in vehicle con- Example 39

Figure 25:
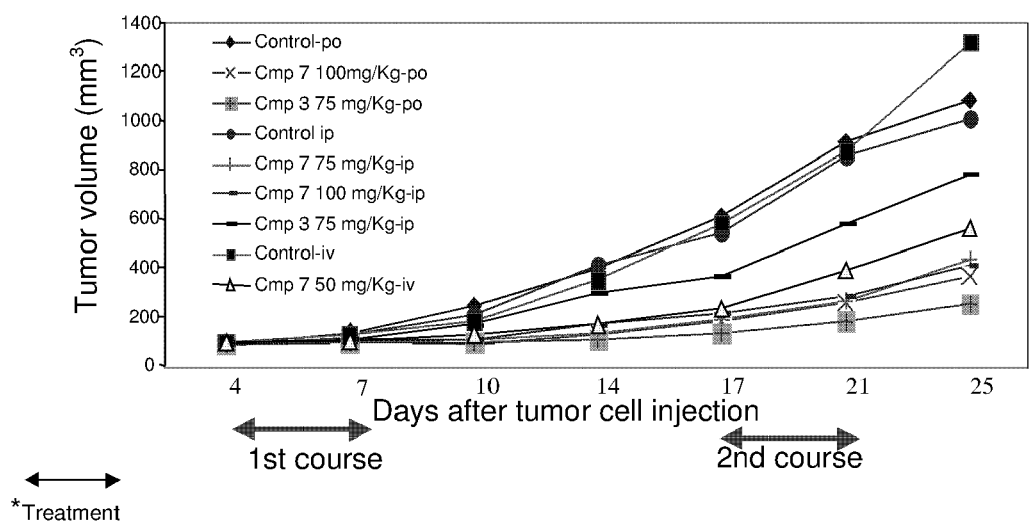
FIG. 25 depicts the ability of compounds 3 and 7 to inhibit tumour growth in a non-small cell lung carcinoma xenograft model (A) and in a colon adenocarcinoma xenograft model (B), the ability of compound 7 to inhibit tumour growth in a non-small cell lung carcinoma xenograft model (C) and the ability of compounds 7, 63, 64, 69, 72, 73, 74, 18 and 78 to inhibit tumour cell growth in a non-small cell lung carcinoma xenograft model (D).
Figure 25:
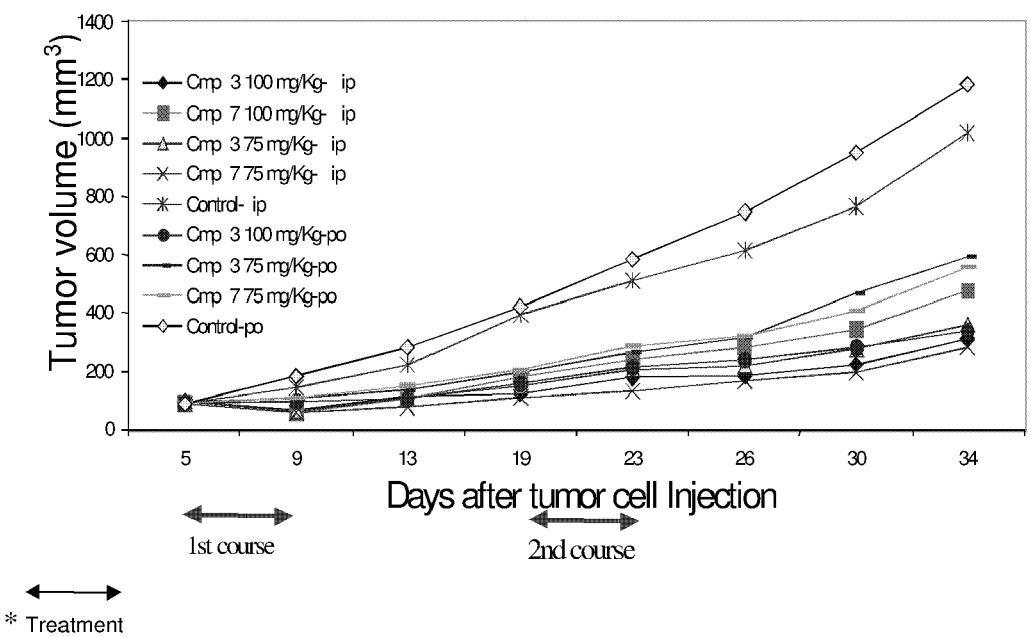
Figure 25:
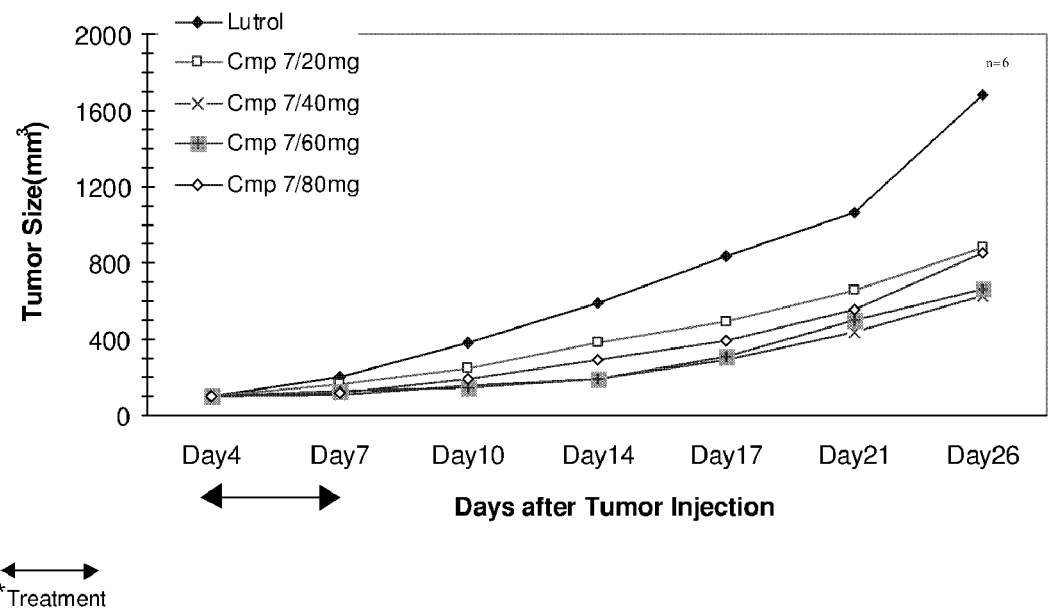
Figure 25:
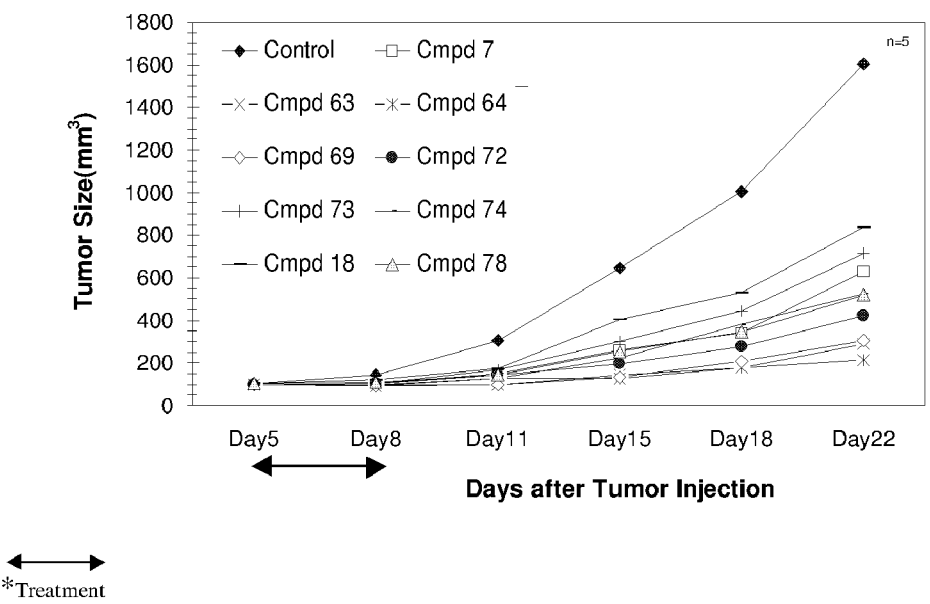

In Vivo Efficacy of Compounds of Formula I in Large-Cell Lung Carcinoma and Colon Carcinoma Xenograft Models Tumor growth inhibition by compounds of Formula I in mouse xenograft models is shown in FIG. 25. Route of administration and schedule studies for non-small cell lung carcinoma (H460) (FIG. 25A) and colon adenocarcinoma (HT-29) (FIG. 25B), minimal effective dose for non-small cell lung carcinoma (H460) (FIG. 25C), and efficacy of optimized compounds of Formula I in non-small cell lung carcinoma (H460) (FIG. 25D).

Example 40

Figure 26:
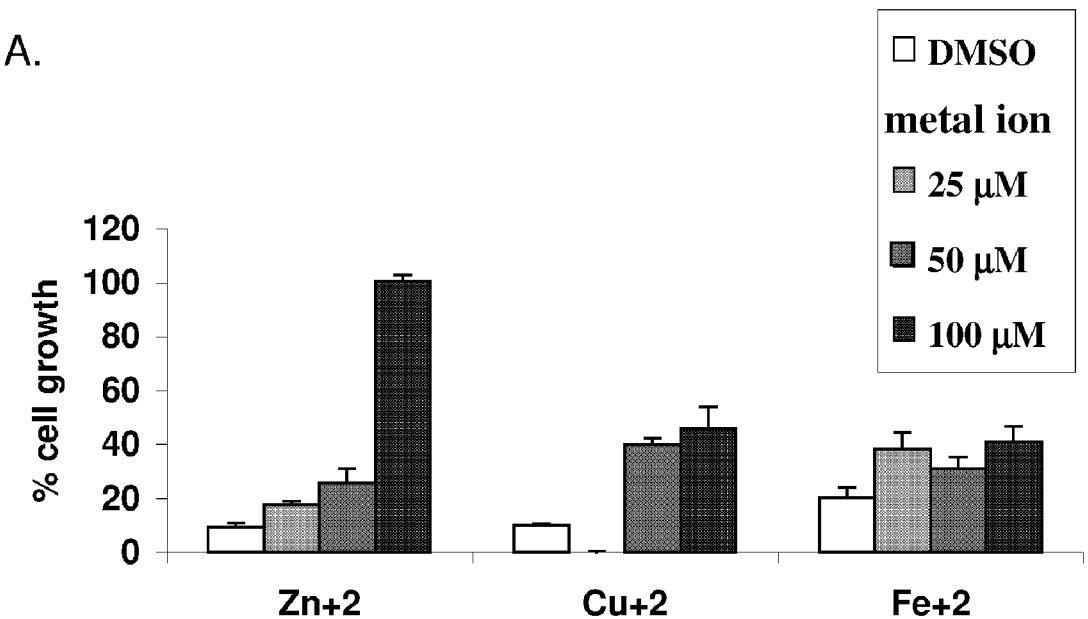
FIG. 26 depicts the effect of metal ion supplements on compound 3-mediated cell growth inhibition, $Zn^{+2}$, $Cu^{+2}$ and $Fe^{+2}$ (A) and $Fe^{+3}$, $Ca^{+2}$ and $Mg^{+2}$ (B).
Figure 26:
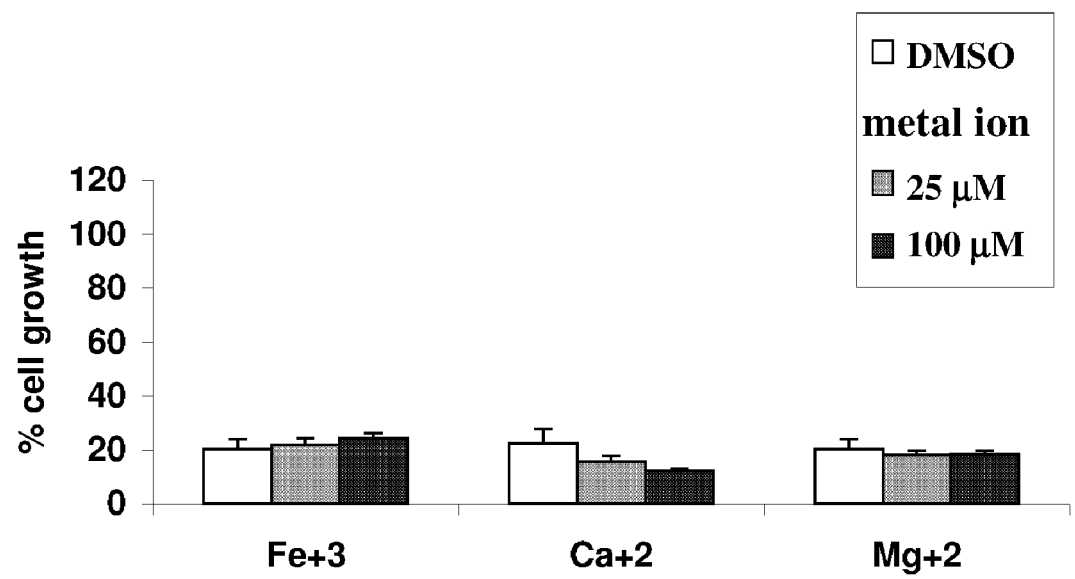

Effect of Exogenous Metals on the Ability of Compound 3 to Inhibit Growth of HT-29 Cells In Vitro Zinc-depletion-induced cell growth inhibition is shown in FIG. 26. Effect of metal ion supplements on compound 3-mediated cell growth inhibition of HT-29 cells was examined by XTT cell proliferation assay. Cell growth inhibition was completely reversed by zinc only as shown in FIGS. 26A and 26B.

Example 41

Figure 27:
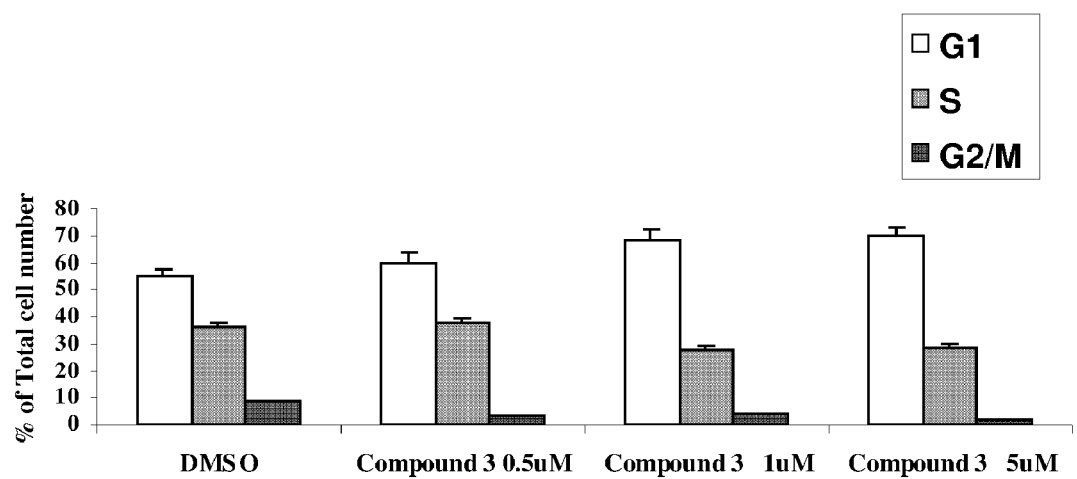
FIG. 27 depicts cell cycle analysis in HT-29 cells treated with compound 3 (A) and compound 7 (B).
Figure 27:
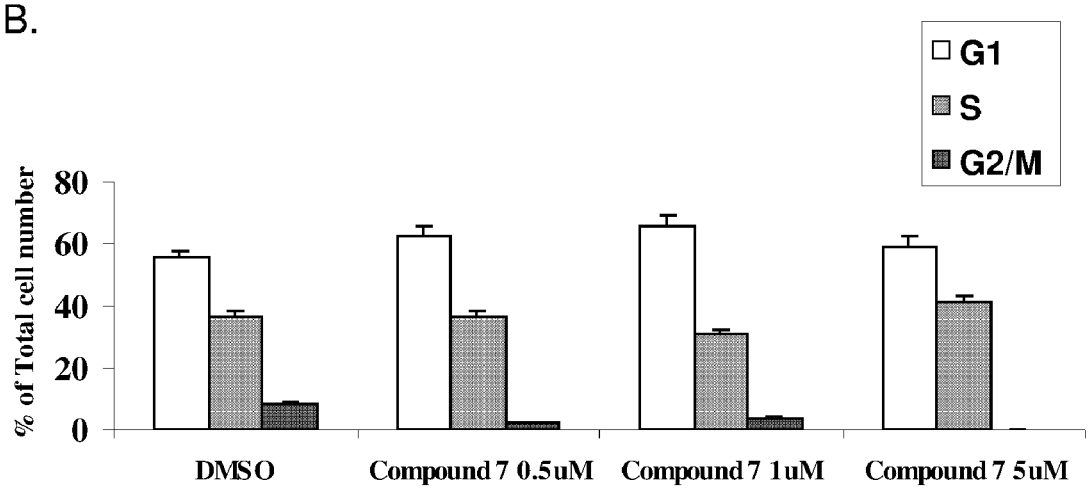

In Vitro Ability of Compound 3 and Compound 7 to Block Cell Cycle Progression in HT-29 Cells Cell cycle analysis was assessed by flow cytometry in HT-29 cells treated with compound 3 as shown in FIG. 27A and compound 7 as shown in FIG. 27B. Cell cycle arrest at G1/S phase was observed after the treatment.

Example 42

In Vitro Ability of Compounds of Formula I to Chelate Metals

Figure 28:
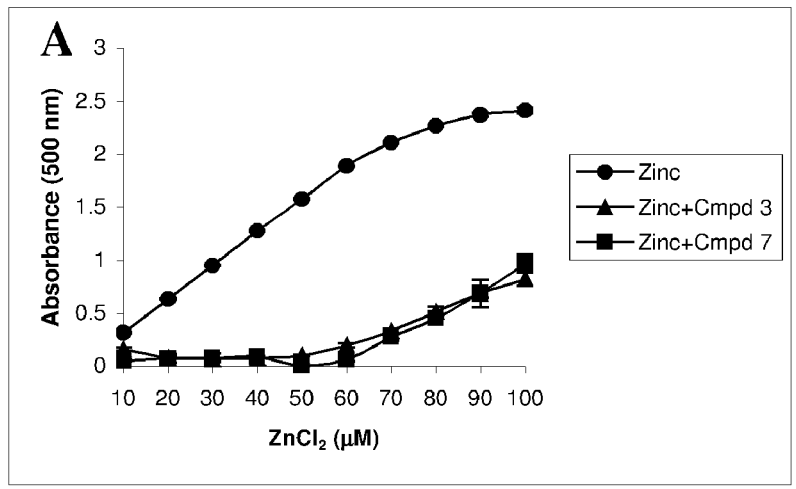
FIG. 28 depicts the metal chelation property of compound 3 and compound 7 in vitro in the presence of $ZnCl_2$ (A), $CuCl_2$ (B) and $FeCl_2$ (C).
Figure 28:
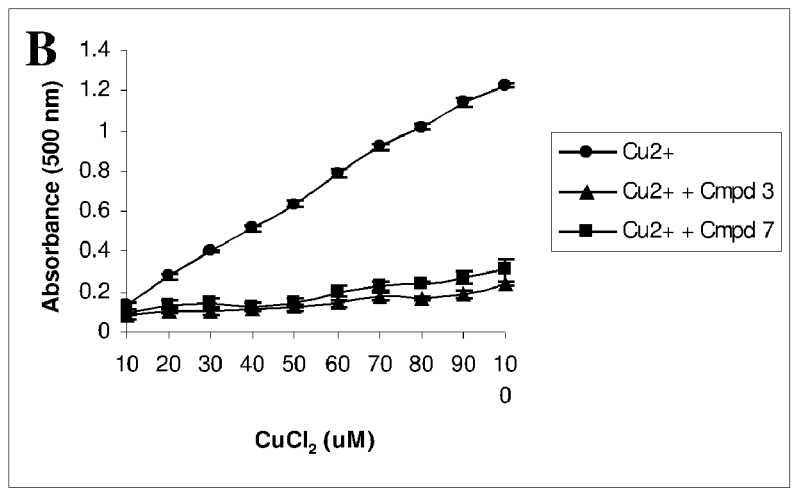
Figure 28:
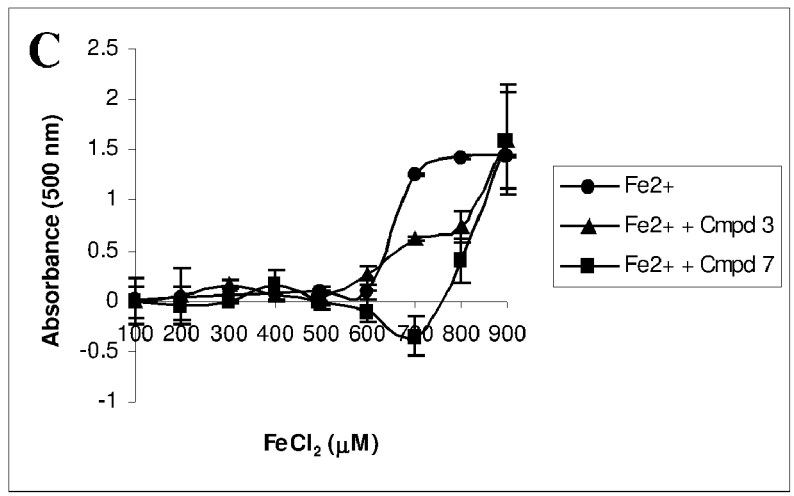

The metal-chelation property of compound 3 and compound 7 is shown in FIG. 28. In vitro 4-(2-pyridylazo) resorcinol (PAR) metal binding assay showed that Zn and $Cu^{+2}$ binding to PAR was attenuated by compound 3, indicating in vitro Zn and $Cu^{+2}$ chelating property of compound 3. Results are shown in FIGS. 28A ($ZnCl_2$), 28B ($CuCl_2$) and 28C ($FeCl_2$). In vitro 4-(2-pyridylazo) resorcinol (PAR) zinc binding assay was performed as follows. In triplicate wells of 96-well plate (Sarstedt, Newton, N.C.), 10 µL volume of indicated final concentrations of $ZnCl_2$ in 0.2M Tris-HCl, pH 7.5 was incubated with 10 µL of 80% acetonitrile-20% DMSO vehicle control or indicated final concentrations of the compounds of Formula I, dissolved in 80% acetonitrile-20% DMSO, for 15 min at room temperature. Then, 80 µL of PAR at final concentration of 200 µM in 0.2M Tris-HCl, pH 7.5 was added and the color development of PAR-$Zn^{2+}$ complex was measured by a multi-well spectrophotometer (Bio-Tek Instruments Inc.) at 500 nm.

Example 43

Figure 29:
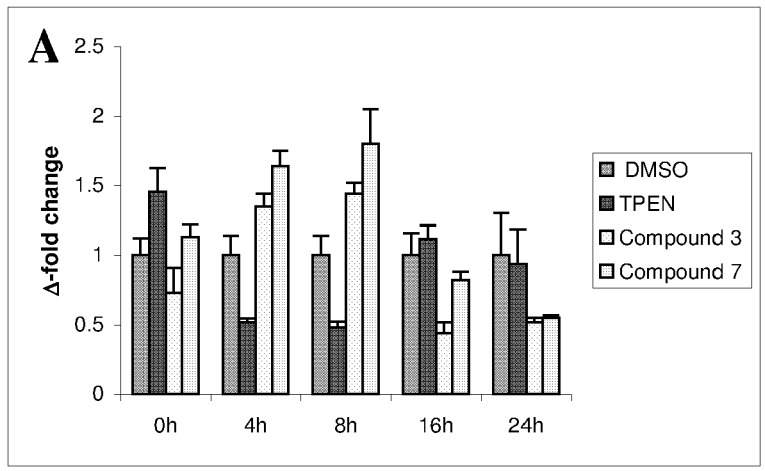
FIG. 29 depicts the changes in expression of metal-sensitive genes zinc-sensitive gene metallothionein 1A (A), copper-sensitive copper transporter 1 (B) and iron-sensitive transferrin receptor-1(C) in HT-29 cells treated with compound 3, compound 7 or respective metal-specific chelators.
Figure 29:
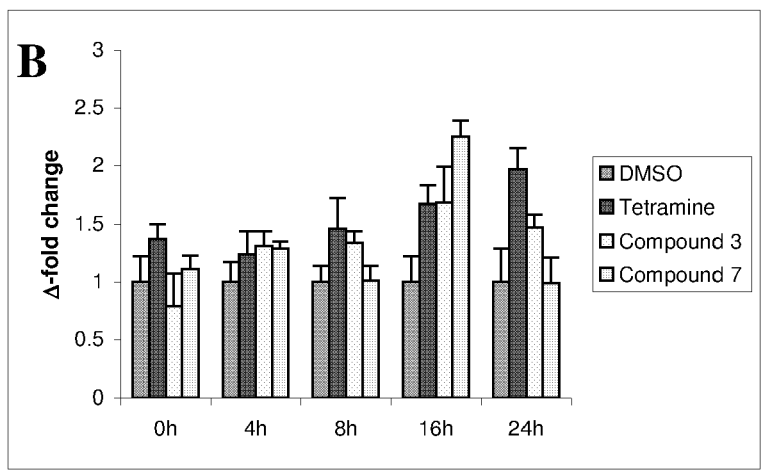
Figure 29:
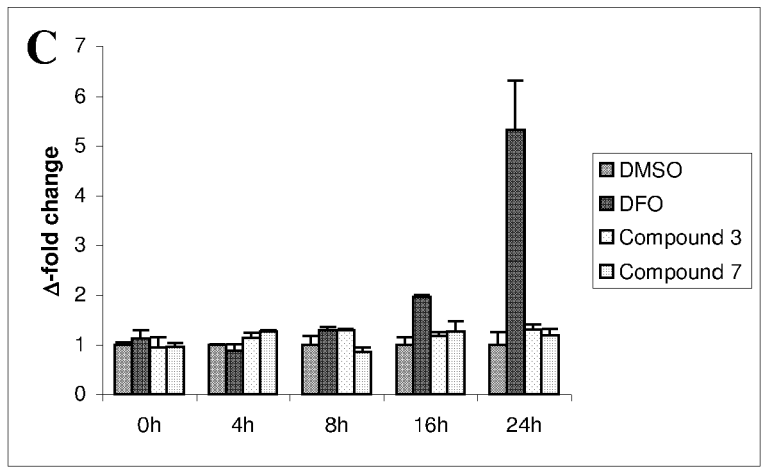

In Vitro Ability of Compound 3 to Modulate Expression of Metal-Sensitive Genes in HT-29 Cells Changes in expression of metal-sensitive genes in HT-29 cells, in comparison with respective metal-specific chelators, was examined by RT-PCR as shown in FIGS. 29A, 29B and 29C. The effect of compound 3 and compound 7 treatment on the expressions of a zinc-storage protein meallothionein 1A (MT1A) (FIG. 29A), a copper transporter, Ctrl also known as SLC31A1 (FIG. 29B) and an iron transporter; transferrin receptor 1 (TfR1) (FIG. 29C) were measured and compared with a known zinc chelator TPEN, a copper chelator tetramine and an iron chelator DFO, respectively. Despite in vitro chelation of $Cu^{+2}$, increase in copper-sensitive gene after compound 3 treatment was transient. In contrast, sustained decrease in zinc-sensitive gene indicated intracellular zinc depletion as a significant consequence following compound 3 treatment.

Example 44

Figure 30:
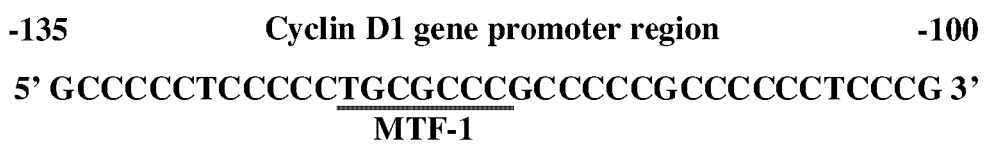
FIG. 30 depicts MTF-1 binding DNA sequences in Cyclin D1 gene promoter (A) and expression levels of MTF-1 and Cyclin D1 in HT-29 colon cancer xennograft tissue treated with compound 3 (B) and compound 7 (C).
Figure 30:
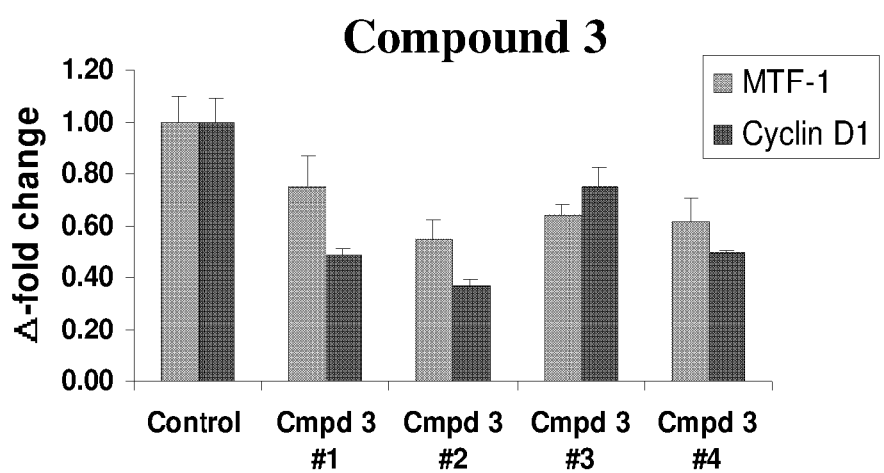
Figure 30:
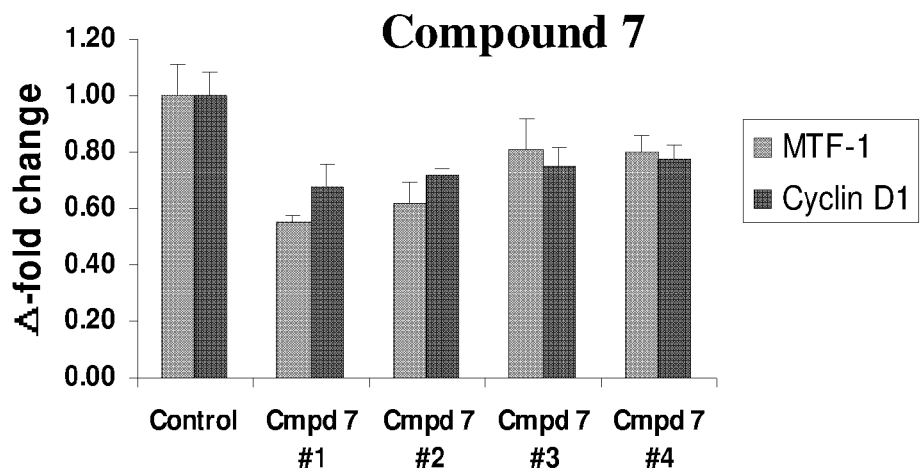

Ability of Compounds of Formula I to Modulate Expression of MTF-1 and Cyclin D1 In Vivo Correlation between zinc-sensitive transcription factor MTF-1 and a cell cycle regulator Cyclin D1 expression in HT-29 colon cancer xenograft tissues is shown in FIG. 30. Based on the presence of putative MTF-1-binding DNA sequences in Cyclin D1 gene promoter region (shown in FIG. 30A), expression levels of MTF-1 and Cyclin D1 in xenograft tissues were examined by RT-PCR, using tissue RNA extract. Decreased MTF-1 expression was correlated with decreased Cyclin D1 expression with compound 3 as shown in FIG. 30B and compound 7 as shown in FIG. 30C.

Example 45

Figure 31:
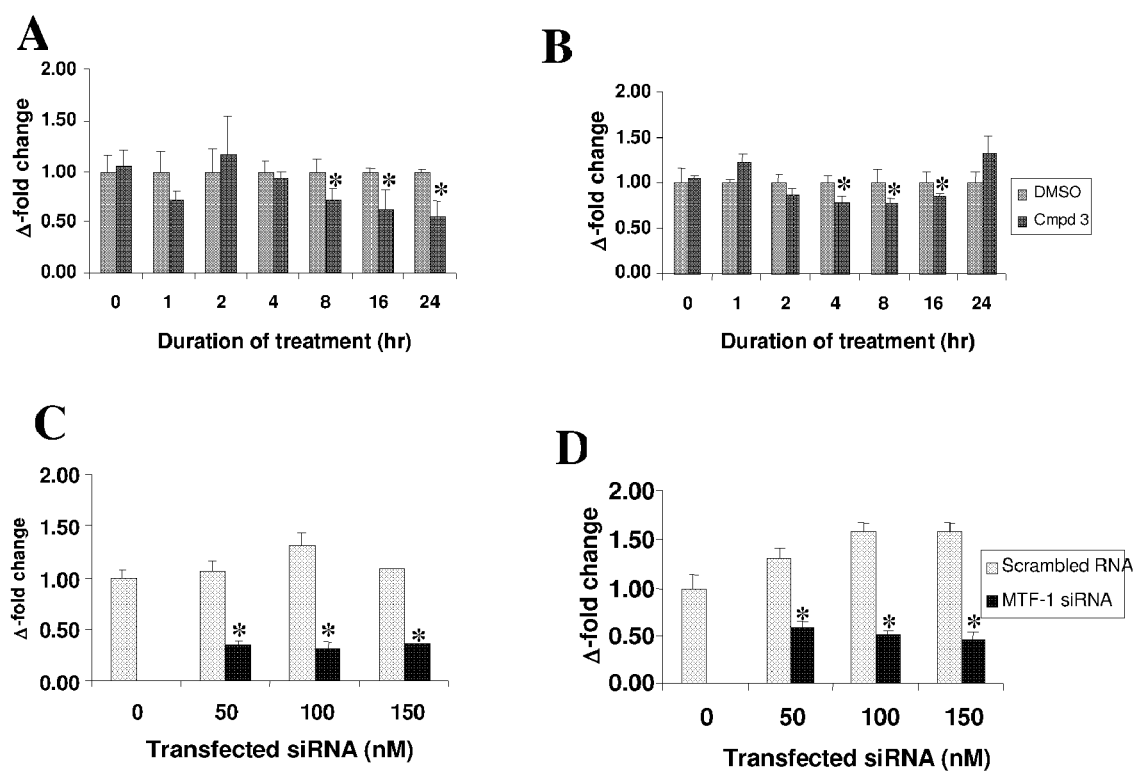
FIG. 31 depicts MTF-1 (A) and Cyclin D1 (B) expression, measured by RT-PCR, after compound 3 treatment in HT-29 cells, and MTF-1 expression (C) and Cyclin D1 expression (D) after MTF-1 gene knock-down by siRNA.

Ability of Compound 3 to Modulate Expression of MTF-1 and Cyclin D1 In Vitro Correlation between MTF-1 and Cyclin D1 gene expression in HT-29 cells is shown in FIG. 31. Time-dependent decreases in MTF-1 (FIG. 31A) and Cyclin D1 (FIG. 31B) expressions, measured by RT-PCR, were observed after compound 3 treatment. Decreased Cyclin D1 (FIG. 31D) expression was observed after MTF-1 gene knock-down by siRNA. MTF-1 levels after MTF-1 gene knock-down by siRNA are shown in FIG. 31C.

Expression and activity of MTF-1 is decreased by the compounds of Formula I. Down-regulation of MTF-1 is correlated with decreased Cyclin D1 expression.

Example 46

Ability of Compound 3 to Modulate KLF4 Binding Activity In Vitro

Decreased MTF-1 expression, leading to induction of tumor suppressor KLF4 is shown in FIG. 32. Based on overlapping transcription factor binding sites on KLF4 gene promoter region (as shown in FIG. 32A), MTF-1 binding may favor increased binding of other KLF4 inducers; Sp1 and KLF4. Increased DNA binding activities of Sp1 (FIG. 32B) and KLF4 (FIG. 32C), from HT-29 cell nuclear extracts, were shown by electrophoretic mobility shift assay (EMSA).

Electrophoretic mobility shift assay (EMSA) was performed as follows. Nuclear extracts from HT-29 cells ($10^7$ cells in 100 mm culture dish in each experimental group) were prepared using nuclear extraction kit (Panomics, Redwood City, Calif.). EMSA assays were performed using KLF4 and Sp1 EMSA "Gel-Shift" kits (Panomics), by following the manufacturer's instruction. Briefly, 5 µg of nuclear extract was used for each binding reaction. After 30 min of binding reaction, the samples were separated on 6% polyacrylamide gel at 4° C. at 120 V, and transferred to Bright-Star™-Plus positively charged nylon membrane. The biotin-labeled probes on the membrane were visualized by using ECL detection system (Panomics).

Decreased MTF-1 activity favors induction of KLF4 by the positive regulators; Sp1 and KLF4 auto-regulation.

Example 47

Ability of Compound 3 to Modulate KLF4 Binding to Cyclin D1 Promoter In Vitro Increased KLF4 expression, leading to repression of Cyclin D1 in HT-29 cells is shown in FIG. 33. Based on overlapping transcription factor binding sites on Cyclin D1 gene promoter region (FIG. 33A), increased binding of a negative regulator KLF4 may replace the binding of a positive regulator Sp1. In vivo KLF4 and Sp1 binding to Cyclin D1 promoter was shown by chromatin immuno-precipitation assay (ChIP) (FIG. 33B). Increased KLF4 and decreased Sp1 binding was observed, after compound 3 treatment.

Chromatin immunoprecipitation (ChIP) was performed as follows. Cell lysates from HT-29 cells ($5.5 \times 10^5$ cells in three 15 cm-culture plates in each experimental group) were prepared at the end of the indicated experiments, and ChIP assays were performed using anti-KLF4 and anti-Sp1 antibodies (Santa Cruz Biotechnology Inc.) and ChIP-IT™ kit (Active Motif, Carlsbad, Calif.) by following the manufacturer's instruction. The primers encompassing-231 to -92 region of Cyclin D1 promoter; 5' primer (5'-CGGACTA-CAGGGGCAA-3') [SEQ ID NO:1] and 3' primer (5'-GCTC-CAGGACTTTGCA-3') [SEQ ID NO:2] were synthesized at Invitrogen.

Increased KLF4 (a negative regulator) binding to Cyclin D1 promoter inhibits Sp1 (a positive regulator) binding and represses Cyclin D1 expression.

Example 48

In Vitro Ability of Compound 3 to Inhibit Cell Growth and Modulate Expression of KLF4 in HT-29 Cells Significance of KLF4 expression in HT-29 cell growth is shown in FIG. 34. KLF4 gene expression, measured by RT-PCR, showed effective knock-down of KLF4 gene by siRNA (FIG. 34A). Cell proliferation, measured by XTT assay showed the loss of compound 3-mediated cell growth inhibition after knock-down of KLF4 gene by siRNA (FIG. 34B).

Small interfering RNA (siRNA) transfection was performed as follows. Pre-designed MTF-1 siRNA (ID #115734) (Ambion, Austin, Tex.) was used to knockdown endogenous MTF-1 mRNA. Similarly, pre-designed KLF4 siRNA (ID #115492) (Ambion, Austin, Tex.) was used to knockdown endogenous KLF4 mRNA. A nonspecific, double-stranded RNA (5'r(CUAGGGUAGACGAUGAGAG)d(TT)3') [SEQ ID NO:3] and (3'd(TT)r(GAUCCCAUCUGCUACUCUC)5') [SEQ ID NO:4]

was synthesized at Qiagen (Cambridge, Mass.) based on the sequence of an unrelated gene. HT-29 cells ($3 \times 10^5$ cells in 35 mm-culture dishes) were transfected with indicated concentrations of siRNA or scrambled RNA control using Lipofectamine™ 2000 transfection reagent (Invitrogen) by following the manufacturer's instruction, for 6 hr. At the end of the incubation period, the transfection medium was supplemented with a complete growth medium and the cells were incubated at 37° C. for 24 hr before indicated experiments.

Example 49

Effect of Compounds of Formula I on the Growth of Human Large Cell Lung Carcinoma (H460) IN CD-1 Nude Mice Tumor growth inhibition by compounds of Formula I in mouse xenograft models of human large cell lung carcinoma (H460) was carried out as described in the Examples above. The results are shown in FIG. 35.

Example 50

In Vitro Chelation of Zinc Ions by Compounds of Formula I

To determine the chelation property of compound 3 with zinc ions in vitro, free available zinc ions were measured by spectrofluorometry using zinc-sensitive fluorescent dye Zinquin, following pre-incubation of $ZnCl_2$ with different concentrations of compound 3 (FIG. 36). $ZnCl_2$ 2 µM was incubated with indicated concentrations of compound 3, in phosphate buffer saline (PBS), followed by addition of Zinquin, 10 µM final concentration for 30 min. Zinquin fluorescence upon zinc binding was measured in a Fluoroskan Ascent luminescence spectrofluorometer, at 364 nm excitation and 485 nm emission wavelengths.

Dose-dependent decrease in Zinquin fluorescence was observed, indicating less zinc ion binding to Zinquin as a result of compound 3 chelation with zinc ions. Similar experiment with $FeCl_2$ and $CuSO_4$ did not show Zinquin fluorescence, indicating the specificity of Zinquin fluorescence for zinc ions only.

Example 51

Chelation of Intracellular Zinc Ion in HT-29 Cells In Vitro after Treatment with Compounds of Formula I To determine the chelation property of compound 3 with intracellular zinc ions, HT-29 cells, with or without pre-loaded with 35 µM $ZnCl_2$ were treated with compound 3, a known zinc chelator TPEN or vehicle control (DMSO), and intracellular free zinc was determined by measuring Zinquin fluorescence as described in the preceding Example (FIG. 37). HT-29 cells ($4 \times 10^5$ cells/group) were pre-treated with 35 µM $ZnCl_2$ for 20 min, followed by addition of indicated concentrations of compound 3 or TPEN and 10 µM Zinquin for 30 min at 37° C., and the fluorescence count was measured (FIG. 37A). For measurement of chelation of endogenous zinc ions in HT-29 cells, HT-29 cells ($1.5 \times 10^6$ cells/group) were treated with indicated concentrations of compound 3 and 10 µM Zinquin for 30 min at 37° C., and the fluorescence count was measured (FIG. 37B).

Dose-dependent decrease in both pre-loaded zinc and endogenous zinc levels were observed after compound 3 or TPEN treatment.

Example 52

Effect of Compounds of Formula I on Zinc Chelation and Expression of Metallothionein 1a Gene in HT-29 Cells In Vitro To confirm the decrease in intracellular zinc level following compound 3 treatment, alteration in gene expression of zinc-storage protein metallothionein 1A (MT1A) was measured as a marker of intracellular zinc status.

HT-29 cells were treated with 1 µM compound 3 for the indicated time and MT1A gene expression was measured as follows. Total RNA was extracted using TRIZOL method and gene expression level was determined by quantitative reverse-transcription polymerase chain reaction (RT-PCR). MT1A gene expression was normalized with β-actin gene expression in the same sample. Fold change in MT1A was expressed relative to MT1A level of DMSO control at respective time points. The decrease in MT1A gene expression was obvious after 8 hr treatment as shown in FIG. 38A.

To verify that the MT1A gene expression reflected the intracellular zinc level, HT-29 cells were treated with 1 µM compound 3, 35 µM $ZnCl_2$ or compound 3 and $ZnCl_2$ together for 16 hr (FIG. 38B). MT1A gene expression was determined by RT-PCR as described above. MT1A gene expression was elevated in response to increased intracellular zinc ions in $ZnCl_2$-treated cells. The decrease in MT1A expression in response to intracellular zinc depletion, following compound 3 treatment, was reversed by addition of zinc supplement (FIG. 38B).

Example 53

Effect of Compounds of Formula I on Zinc Chelation and Expression of Krüppel-Like Factor 4 (KLF4) Gene IN HT-29 Cells In Vitro The change in gene expression of KLF4 upon zinc depletion following compound 3 treatment was determined by RT-PCR as follows. HT-29 cells were treated with 1 µM compound 3 for the indicated time (FIG. 39A) or HT-29 cells were treated with 1 µM compound 3, 35 µM ZnCl$_2$ or compund 3 and ZnCl$_2$ together for 16 hr (FIG. 39B). Total RNA was extracted and gene expression level was determined by RT-PCR.

Time-dependent increase in KLF4 was observed after 4 hr treatment of HT-29 cells with 1 µM compound 3 and the maximum increase was at 16 hr (FIG. 39A). The increase in KLF4 gene expression was reversed by addition of zinc supplement (FIG. 39B), indicating the significance of change in KLF4 gene expression in response to intracellular zinc status.

Example 54

Effect of Compounds of Formula I on Gene Expression and DNA Binding Activity of Zinc-Sensitive Metal-Responsive Element (MRE)-Binding Transcription Factor 1 (MTF-1) in HT-29 Cells In Vitro The gene expression of MTF-1 was examined by RT-PCR following treatment of HT-29 cells with 1 µM compound 3 for indicated time. The decrease in MTF-1 expression was observed after 8 hr treatment with compound 3 (FIG. 40A).

To verify the change in MTF-1 activity at earlier time of incubation, prior to the significant decrease in MTF-1 gene expression, MTF-1 nuclear translocation and DNA-binding activity was determined in nuclear extract of HT-29 cells treated with compound 3 for 4 hr, by electrophoretic mobility shift assay (EMSA) (FIG. 40B) as follows. HT-29 cells were treated with DMSO, 35 µM ZnCl$_2$ (positive control) and 1 µM compound 3 for 4 hr. Nuclear protein was extracted and incubated with biotin-labeled MTF-1 binding oligonucleotide probes. The retarded mobility of labeled probe upon MTF-1 binding was observed as a band shift (FIG. 40B). Three shift bands (block arrows) were observed in lane 1 (DMSO), showing the constitutive DNA binding pattern of MTF-1. In zinc-treated groups, 2 additional shift bands (open arrows) were observed (lane 3), indicating the increase in zinc-dependent MTF-1 activity. Zinc-activated shift bands were not observed in compound 3-treated group (lane 5), indicating that zinc-dependent MTF-1 activity was not increased by compound 3. Excess unlabeled probes were added in lane 2, 4 and 6 to compete the labeled probes binding with MTF-1 in the nuclear extract, showing the specificity of MTF-1-binding shift bands in lane 1, 3 and 5, respectively.

Compared to the mobility shift bands observed in positive control ZnCl$_2$-treated group, significant change in mobility shift was not observed in compound 3-treated cells, confirming that zinc-dependent MTF-1 activity was not increased following compound 3 treatment.

Example 55

In Vitro Ability of Compound 3 to Modulate Gene Expression of KLF4-Opponent; Krüppel-Like Factor 5 (KLF5) in HT-29 Cells KLF 4 and 5 are two closely related members of KLF family transcription factors but KLF5 stimulates cell proliferation while KLF4 inhibits cell growth (Ghaleb et al., (2005) Cell Res. 15(2): 92-96). KLF 4 and 5 bind to similar GC-rich DNA consensus sequence but exhibit opposing transcriptional activities. KLF4 can auto-activate its own gene by binding to GC-rich region in KLF4 promoter while KLF5 inhibits KLF4 transcription by binding to the same DNA element (Dang et al., (2002) Nucleic Acids Res. 30(13):2736-2741).

To identify the consequence of decreased MTF-1 expression/activity, relative to induction of KLF4, MTF-1 mRNA was knocked-down using MTF-1-targeted siRNA and gene expressions of MTF-1, KLF4 and KLF5 were measured by RT-PCR as follows. HT-29 cells were transfected with 100 nM MTF-1 siRNA for 6 hr, using Lipofectamine 2000 reagent. After replacement of the transfection medium with normal growth medium and incubation for 18 hr, total RNA was extracted and gene expression level was determined by RT-PCR. Following inhibition of MTF-1 translation by using MTF-1 gene-specific siRNA, decreased expression of KLF5 gene was observed while KLF4 expression was increased (FIG. 41A).

Decrease in KLF5 gene expression after time-course treatment with compound 3 was also determined as follows. HT-29 cells were treated with 1 µM compound 3 for indicated time (FIG. 41B). Total RNA was extracted and gene expression level was determined by RT-PCR. Consistent with the above result, the decrease in KLF5 gene expression was also detected in HT-29 cells after 4 hr treatment with 1 µM compound 3 (FIG. 41B).

Example 56

In Vitro Ability of Compound 3 to Modulate Cell-Cycle Regulatory Protein P21 Gene and Protein Expression in HT-29 Cells The expressions of p21 gene and proteins were examined following treatment with compound 3. Gene expression of p21 in HT-29 cells treated with 1 µM compound 3 was determined at the indicated times as follows. Total RNA was extracted and gene expression level was determined by RT-PCR (FIG. 42A). The level of p21 protein in total cell lysate was measured by ELISA (FIG. 42B) as follows. HT-29 cells were treated with 1 µM compound 3 with and without 20 µM MG-132 (proteasome inhibitor) for indicated time.

Increased gene expression of p21 was observed after 4 hr compound 3 treatment by RT-PCR (FIG. 42A) but comparable increase in p21 protein expression was not detected by either Western blot analysis (data not shown) or enzyme-linked immunosorbent assay (ELISA) (FIG. 42B). However, increased p21 protein level was detected when HT-29 cells were incubated with compound 3 in the presence of a proteasome inhibitor, MG-132, indicating that p21 protein was rapidly degraded despite a significant increase in p21 gene expression.

Example 57

In Vitro Ability of Compound 3 to Modulate Expression of Cell-Cycle Regulatory Protein Cyclin D1

Gene and protein expression of Cyclin D1 after treatment with compound 3 was determined by RT-PCR and Western blotting as shown in FIGS. 43A and 43B, respectively, as follows. HT-29 cells were treated with 1 µM compound 3 for indicated time. Total RNA was extracted and gene expression level was determined by RT-PCR. Cyclin D1 protein expression in HT-29 cell lysate was determined by SDS-PAGE followed by Western blotting.

The decrease in both gene (FIG. 43A) and protein (FIG. 43B) levels of Cyclin D1 were observed after 8 hr treatment with compound 3.

Example 58

In Vitro Ability of Compound 3 to Modulate Expression of the Tumor-Suppressor Gene, early Growth Response Protein-1 (EGR-1)

Like Sp1, Egr-1 also is a transcription factor with zinc finger DNA-binding domains, which recognizes GC-rich sequences in the regulatory promoter region of the targeted gene (Al-Sarraj et al., (2005) *J. Cell Biochem.* 94(1): 153-167). Changes in Egr-1 gene expression were detected in compound 3-treated HT-29 cells by RT-PCR (FIG. 44A) as follows. HT-29 cells were treated with 1 µM compound 3 for the indicated times. Total RNA was extracted and gene expression level was determined by RT-PCR. To determine the effects of zinc supplement, HT-29 cells were treated with 1 µM compound 3, 35 µM $ZnCl_2$ or compound 3 and $ZnCl_2$ together for 8 hr. Egr-1 gene expression was determined by RT-PCR (FIG. 44B).

A significant increase in Egr-1 gene expression was observed as early as 2 hr after compound 3 treatment as shown in FIG. 44A and which was reversible upon addition of zinc supplement as shown in FIG. 44B.

Example 59

In Vitro Ability of Compound 3 and Compound 7 to Modulate Gene Expression in HT-29 Cells Gene expression patterns in response to the compound 3 and compound 7 were verified by RT-PCR (FIG. 45) as follows. HT-29 cells were treated with 1 µM compound 3 or compound 7 for 8 hr. Total RNA was extracted and gene expression levels were determined by RT-PCR. Similar expression pattern of the genes of interest was observed.

Example 60

Ability of Compound 3 to Modulate Gene Expression of KLF4 and Cyclin D1 IN HT-29 Colon Cancer Xenograft Model To examine the effect of compound 3-mediated changes in KLF4 and Cyclin D1 expressions in vivo, the expressions of respective genes in xenograft tissues of vehicle control (Lutrol) and compound 3-treated HT-29 colon cancer cell-transplanted mice were analyzed by RT-PCR (FIG. 46). Briefly, KLF4 and Cyclin D1 gene expression in HT-29 xenograft tissues after 14 days treatment with compound 3 was measured as follows. The mice subcutaneously transplanted with HT-29 cells were treated with vehicle control (administerd i.p.) or 100 mg/kg compound 3 (administered i.p.) for 14 days (n=6 in each group). Total RNA was extracted and gene expression level was determined by RT-PCR. KLF4 and Cyclin D1 gene expressions were normalized with β-actin gene expression in the same sample. Fold changes in KLF4 and Cyclin D1 were expressed relative to the average of respective gene expression from 6 control mice treated with Lutrol.

Consistent with the expression pattern in HT-29 cell lines in vitro, the increase in KLF4 gene and the decrease in Cyclin D1 gene expressions were observed in vivo (FIG. 46).

Example 61

In Vitro Ability of Compound 3 to Chelate Zinc from Zinc-Storage Protein Metallothionein Intracellular zinc exists as a labile pool, loosely bound to storage proteins metallothioneins (MT), which store up to 7 or 8 zinc per molecule. The labile zinc pool donates zinc to enzymes or transcription factors, which require reversible binding with zinc for their full activity (Tapiero and Tew (2003) *Biomed Pharmacother* 57(9): 399-411). The efficiency of compound 3 to remove zinc from MT was investigated. MT-1 isolated from rabbit liver, containing mainly MT-1a and MT-2e with ~7 zinc per molecule in ≧95% of MT was purchased from Alexis Biochemicals (Lausen, Switzerland). The content of zinc in MT was measured in vitro using 4-(2-pyridylazo) resorcinol (PAR) colorimetric zinc assay as described in the preceding Examples. The change in absorbance of PAR after PAR-zinc ion complex formation was measured at 500 nm (Dinkova-Kostova et al., (2005) *Biochemistry* 44(18): 6889-6899). To determine chelation of zinc from MT-1 by compound 3 in vitro, MT-125 µM in 100 ml volume of 0.2M Tris-HCl, pH 7.5 was added to 96-well plate. Compound 3 (0.15 to 60 µM) in 80% acetonitrile/20% DMSO was added to MT-1 for 15 min at room temperature. PAR (200 µM in 0.2M Tris-HCl, pH 7.5) was added and the color development of PAR-zinc complex was measured by a multi-well spectrophotometer at 500 nm as shown in FIG. 47.

Dose-dependent decreases in PAR absorbance of 25 µM MT was observed after in vitro treatment with increasing dose of compound 3 (FIG. 47) demonstrating removal of zinc by compound 3 from intracellular labile zinc pools.

Example 62

In Vitro Ability of Compound 3 to Effect MTF-1 DNA Binding Activity

The efficiency of compound 3 to inactivate DNA-binding activity of zinc-finger-containing transcription factor metal-responsive element (MRE) binding transcription factor (MTF-1) was investigated. Reversible binding of zinc to the activating zinc-fingers of MTF-1 is required for nuclear translocation of MTF-1 and maximal binding of MTF-1 to MRE (Lichtlen and Schaffner (2001) *Bioessays* 23(11): 1010-1017).

HT-29 cells were treated with 35 µM $ZnCl_2$ for 4 hr and the nuclear extract from zinc-treated cells (zinc-activated MTF-1) was treated with compound 3 in vitro and DNA-binding activity of MTF-1 to MRE sequence was assessed by electrophoretic mobility shift assay (EMSA) (Panomics, Redwood City, Calif.). Inactivation of MTF-1 DNA-binding by compound 3 in vitro is shown in FIG. 48A.

To examine inactivation of MTF-1 by compound 3 in the cells, HT-29 cells were treated with compound 3 for 1 to 4 hr and DNA-binding activity of MTF-1 in the nuclear extract was assessed by EMSA. Significant decrease in MTF-1 activity was observed at 4 hr after treatment of HT-29 cells with compound 3 (FIG. 48B).

Example 63

Ability of Compound 3 to Modulate MTF-1 DNA-Binding Activity in HT-29 Cells

To examine decreased MTF-1 binding to the promoter region of the MTF-1-targeted gene, cell-cycle regulatory gene Cyclin D1, HT-29 cells were treated with compound 3 for 16 hr and MTF-1 binding to Cyclin D1 promoter was assessed by chromatin immuno-precipitation assay (ChIP) (Active Motif, Carlsbad, Calif.). At the end of 16 hr treatment with compound 3, the cells were fixed with 1% formaldehyde to cross-link transcriptions factors and their target chromatin. Chromatin complexes were sheared and MTF-1-bound chromatin was pulled down by using antibody to MTF-1 (Santacruz Biotechnology Inc.). Cross-linking was reversed and the MTF-1-associated DNA was amplified by polymerase chain reaction using the primers encompassing −231 to −92 region of Cyclin D1 promoter. The 5' primer (5'-CGGACTA-CAGGGGCAA-3') [SEQ ID NO:1] and the 3' primer (5'-GCTCCAGGACTTTGCA-3') [SEQ ID NO:2] were synthesized at Invitrogen. Increased MTF-1 binding to Cyclin D1 promoter was observed after treatment with 35 µM $ZnCl_2$ as shown in FIG. 49, indicating that Cyclin D1 is MTF-1 targeted gene. Decreased MTF-1 binding to Cyclin D1 promoter after compound 3, compared to basal level MTF-1 binding, was observed indicating that compound 3 inhibited constitutive Cyclin D1 gene transcriptional activation by MTF-1 (FIG. 49).

Example 64

Effect of Compounds of Formula I on Zinc Chelation and Expression of Cyclin D1 Gene IN HT-29 Cells In Vitro To identify the cell cycle regulatory pathway involved in compound 3-mediated cell cycle arrest as shown in Example 23 and 41, particularly associated with G1/S phase, expression of the key cell cycle regulator of G1/S phase progression, Cyclin D1, was examined. Cyclin D1 gene expression as measured by RT-PCR was significantly decreased after treatment of HT-29 cells with 1 µM compound 3 for 16 hr and which was reversed in the presence of 25 µM $ZnCl_2$, confirming that decreased Cyclin D1 expression was a consequence of zinc depletion (FIG. 50A). Decreased protein expression of Cyclin D1 was also confirmed by SDS-PAGE followed by Western blotting (FIG. 50B). In addition, measurement of the expression of other types of cyclin identified decreased expression of Cyclin E (FIG. 50B).

Example 65

Effect of Compounds of Formula I on Gene Expression of MTF-1 in HT-29 Cells In Vitro To assess the cellular response to zinc depletion, the gene expression of zinc-sensitive transcription factor MTF-1 was examined. A significant decrease in gene expression of MTF-1 (FIG. 51) as measured by RT-PCR was observed after 8 hr treatment of HT-29 cells with 1 µM compound 3 and which was recovered by addition of zinc supplement, confirming that decreased expression of MTF-1 by compound 3 treatment was a consequence of zinc depletion.

HT-29 cells were treated with $ZnCl_2$ and expression of Cyclin D1 gene was measured by RT-PCR. Fold change in gene expression was presented relative to the expression of Cyclin D1 gene in control cells. Increased expression of Cyclin D1 gene was observed after treatment of the cells with zinc, as an activator of MTF-1 (FIG. 51B).

Control or MTF-1 siRNA-treated HT-29 cells were treated with or without $ZnCl_2$ and expression of Cyclin D1 gene was measured by RT-PCR. Fold change in gene expression was presented relative to the expression of Cyclin D1 gene in control cells without transfection in control group, and relative to the expression of Cyclin D1 gene in non-specific siRNA-transfected cells for transfection group. The zinc-dependent increase in Cyclin D1 expression was eliminated when MTF-1 gene was knocked down by siRNA prior to compound 3 addition (FIG. 51C).

Example 66

In Vitro Ability of Compound 3 to Modulate Expression of KLF4 in HT-29 Cells with SIRNA-Mediated MTF-1 Knock-Down To evaluate the significance of decreased MTF-1 expression on KLF4 induction, KLF4 gene expression in response to compound 3 treatment was measured by RT-PCR in HT-29 cells transfected with MTF-1 siRNA. Fold change in KLF4 gene expression was presented relative to KLF4 expression in non-specific siRNA-transfected cells treated with vehicle control. Basal expression of KLF4 gene was significantly reduced after MTF-1 gene knock-down, indicating constitutive MTF-1-dependent KLF4 gene transcription (FIG. 52). However, KLF4 gene expression was still increased following compound 3 treatment, despite the knock-down of MTF-1 gene by siRNA (FIG. 52), suggesting MTF-1 independent activation of KLF4 gene upon compound 3 treatment.

Example 67

In Vitro Effect of Compounds of Formula I on Expression of KLF4, KLF2 and KLF6 Genes in H-460 Non-Small Cell Lung Cancer Cells Expression levels of other potential tumor suppressors; KLF2 (lung-KLF) (Wang et al., (2005) *Oncogene* 22(24): 3878-3885) and KLF6 (Ito et al., (2004) *Cancer Res* 64(11): 3838-3843), were assessed in non-small cell carcinoma cell line, H-460. Expressions of KLF2, 4 and 6 genes in control H-460 cells, were measured by RT-PCR. Gene expression was presented relative to KLF4 expression as "1" (FIG. 53A). KLF4 expression was the highest and only 0.05 and 0.3 folds expression of KLF2 and 6 were detected relative to KLF4 expression as "1" (FIG. 53A).

Expressions of KLF2, 4 and 6 genes in H-460 cells, treated with vehicle control or 2.5 µM compound 3 or compound 7, were measured by RT-PCR. Gene expression was presented relative to respective gene expression in vehicle control-treated group as "1". Treatment with compound 3 or compound 7 also showed increased KLF4 as most significantly changed gene (FIG. 53B).

Example 68

In Vivo Efficacy of Compound 3 and Modulation of Expression of MTF-1, Cyclin D1 and KLF4 in a Colon Cancer Xenograft Model The tumor regression efficacy of compound 3 was assessed in compound 3-treated HT-29-transplanted athymic mice (FIG. 54A), and correlated with gene expressions of MTF-1, KLF4 and Cyclin D1 in HT-29 xenograft tissues (FIG. 54B). CD-1 athymic nude mice (4 per group) were injected subcutaneously with HT-29 cells ($3 \times 10^6$ cells in 0.1 mL PBS). At 5 days after tumor cell inoculation, the mice were intra-peritoneally injected with 200 µL vehicle control or 100 mg/kg compound 3, for 5 days followed by 10 days interval, for 2 cycles (day 5 to 9 as a first cycle injection and day 20 to 24 as a second cycle injection). The tumor size was measured during the course of treatment using calipers (FIG. 54A). The mice were sacrificed at 34 days after tumor cell inoculation. The tumor tissues were excised, frozen immediately and stored at −80° C. until RNA extraction and gene expression was analyzed by RT-PCR (FIG. 54B). Fold change in gene expression was presented relative to the average of 4 control mice injected with lutrol vehicle control.

Significant reduction in tumor size was observed in compound 3-treated mice, compared to vehicle control-injected mice (FIG. 54A). Analysis of gene expression in xenograft tissue also showed a significant increase in KLF4 and a decrease in MTF-1 and Cyclin D1 gene expressions in compound 3-treated mice compared to vehicle control-injected group (FIG. 54B).

Example 69

In Vitro Ability of Compound 3 and Compound 7 to Modulate Expression of MT1A, MTF-1, Cyclin D1 and KLF4 in HT-29 Cells The ability of compounds of Formula I to modulate gene expression of MT1A (FIG. 55A), MTF-1 (FIG. 55B), Cyclin D1 (FIG. 55C) and KLF4 (FIG. 55D) was determined by RT-PCR. HT-29 cells were treated with 1 µM compound 3 or compound 7, 35 µM $ZnCl_2$, compound 3 and $ZnCl_2$ together, or compound 7 and $ZnCl_2$ together for 8 to 16 hr. The respective gene expression was normalized with β-actin gene expression in the same sample. Fold change in gene expression was expressed relative to the respective gene level of DMSO control. As observed with 1 µM compound 3, decreased expressions of MT1A, MTF-1 and Cyclin D1, and increased expression of KLF4 were also detected with compound 7. To emphasize that gene expression changes were the consequence of intracellular zinc depletion, decrease in MT1A (8 hr) (FIG. 55A), MTF-1 (8 hr) (FIG. 55B) and Cyclin D1 (8 hr) (FIG. 55C) and increase in KLF4 (16 hr) (FIG. 55D) after treatment with compound 3 or compound 7 was reversed by addition of zinc supplement.

Example 70

Chelation of Transition Metal Ions by Compound 3 and Compound 64 In Vitro

Metal chelation property of compound 64 and the relative affinity on different metal ions were evaluated and compared with the effect of compound 3 in vitro using 4-(2-pyridylazo) resorcinol (PAR) colorimetric zinc assay utilizing methodology as described above in the preceding Examples. Indicated final concentrations of $ZnCl_2$ (FIG. 56A), $CuCl_2$ (FIG. 56B) or $FeCl_2$ (FIG. 56C) were incubated with 80% acetonitrile-20% DMSO vehicle control or 200 µM of the compounds of Formula I. The color development of PAR-metal ion complex was measured by a multi-well spectrophotometer at 500 nm.

The dose-dependent increase in PAR-$Zn^{2+}$ (FIG. 56A) and PAR-$Cu^{2+}$ (FIG. 56B) absorbance following addition of an increasing dose of zinc or copper respectively was eliminated in the presence of compound 3 and compound 64, indicating the chelation property of the compounds, competing against PAR for binding with $Zn^{2+}$ and $Cu^{2+}$. The dose-dependent color development of PAR-$Fe^{2+}$ was minimally affected by addition of the compounds (FIG. 56C), indicating the preference of both compound 3 and compound 64 for $Zn^{2+}$ and $Cu^{2+}$ over $Fe^{2+}$.

Example 71

In Vitro Ability of Compound 64 to Modulate Gene Expression of MT1A, MTF-1, Cyclin D1 and KLF4 in HT-29 Cells The effect of compound 3 and compound 64 on gene expression changes in MT1A (FIG. 57A), MTF-1 (FIG. 57B), Cyclin D1 (FIG. 57C) and KLF4 (FIG. 57D) in HT-29 cells was determined by RT-PCR. HT-29 cells were treated with 1 µM compound 3 or compound 64, 35 µM $ZnCl_2$, compound 3 and $ZnCl_2$ together, or compound 64 and $ZnCl_2$ together for 8 to 16 hr. The respective gene expression was normalized with β-actin gene expression in the same sample. Fold change in gene expression was expressed relative to the respective gene level of DMSO control.

As observed with 1 µM compound 3, decreased expressions of MT1A, MTF-1 and Cyclin D1, and increased expression of KLF4 were also detected with compound 64. Decrease in MT1A (8 hr) (FIG. 57A), MTF-1 (8 hr) (FIG. 57B) and Cyclin D1 (8 hr) (FIG. 57C) and increase in KLF4 (16 hr) (FIG. 57D) after treatment with compound 3 or compound 64 was reversed by addition of zinc supplement.

The disclosure of all patents, publications, including published patent applications, and database entries referenced in this specification are specifically incorporated by reference in their entirety to the same extent as if each such individual patent, publication, and database entry were specifically and individually indicated to be incorporated by reference.

Although the invention has been described with reference to certain specific embodiments, various modifications thereof will be apparent to those skilled in the art without departing from the spirit and scope of the invention as outlined in the claims appended hereto.

The embodiments of the invention in which an exclusive property or privilege is claimed are defined as follows:

1. A compound of Formula (I):

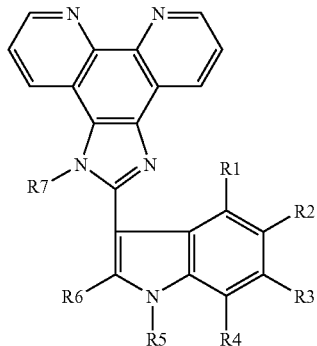

I or a salt thereof, wherein:
R1, R3, R4, R5, and R7 are hydrogen;
R2 is halogen; and
R6 is C1-C4 alkyl.

2. The compound according to claim 1, wherein:
R6 is $CH_3$, isopropyl, or t-butyl.

3. The compound according to claim 1, wherein:
R6 is $CH_3$.

4. The compound according to claim 1, wherein:
R2 is F or Br.

5. The compound according to claim 1, wherein:
R2 is F.

6. The compound according to claim 1, wherein said compound is selected from the group consisting of:

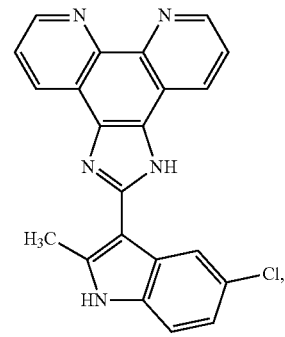

5

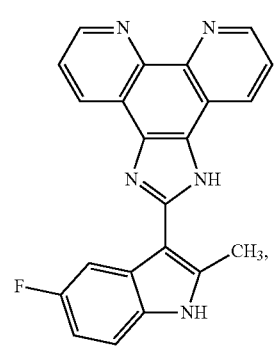

7

-continued

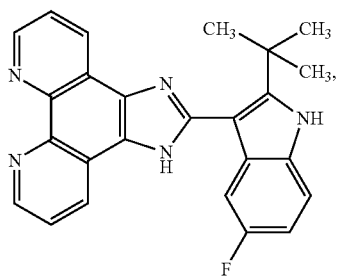

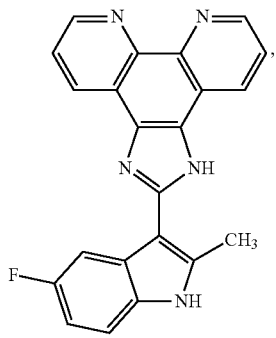

or a salt thereof.

7. The compound according to claim 1, wherein said compound is:

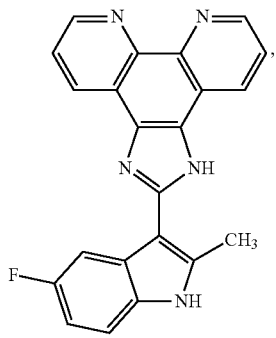

or a salt thereof.

8. A pharmaceutical composition comprising the compound according to claim 1, or a salt thereof, and a pharmaceutically acceptable carrier.

9. The pharmaceutical composition according to claim 8, wherein in the compound of Formula I: R6 is CH$_3$, isopropyl, or t-butyl.

10. The pharmaceutical composition according to claim 8, wherein in the compound of Formula I: R6 is CH$_3$.

11. The pharmaceutical composition according to claim 8, wherein in the compound of Formula I: R2 is F or Br.

12. The pharmaceutical composition according to claim 8, wherein in the compound of Formula I: R2 is F.

13. The pharmaceutical composition according to claim 8, wherein the compound is selected from the group consisting of:

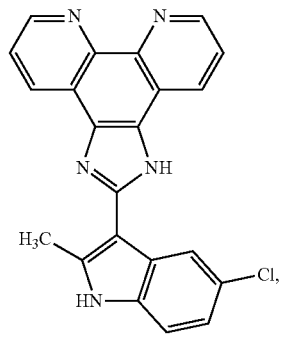

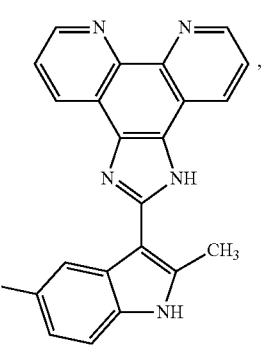

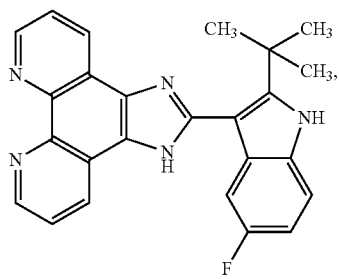

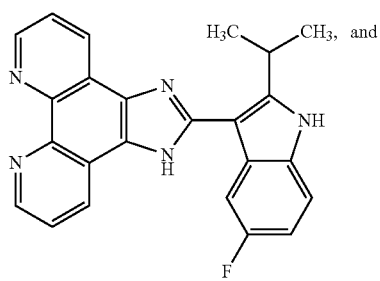

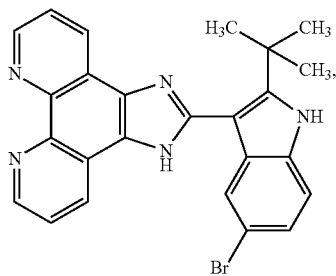

or a salt thereof.

14. The pharmaceutical composition according to claim 8, wherein the compound is:

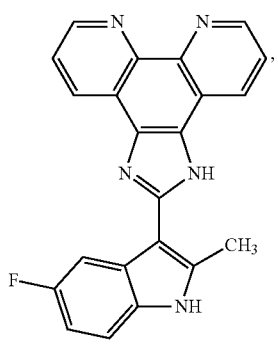

or a salt thereof.

15. A method of treating cancer in a mammal, comprising administering to said mammal an effective amount of a compound according to claim 1, or a salt thereof, wherein said cancer is non-small cell lung cancer, colon cancer, breast cancer, ovarian cancer, leukemia, renal cancer, melanoma, prostate cancer or CNS cancer.

16. The method according to claim 15, wherein in the compound of Formula I: R6 is CH₃, isopropyl, or t-butyl.

17. The method according to claim 15, wherein in the compound of Formula I: R6 is CH₃.

18. The method according to claim 15, wherein in the compound of Formula I: R2 is F or Br.

19. The method according to claim 15, wherein in the compound of Formula I: R2 is F.

20. The method according to claim 15, wherein the compound is selected from the group consisting of:

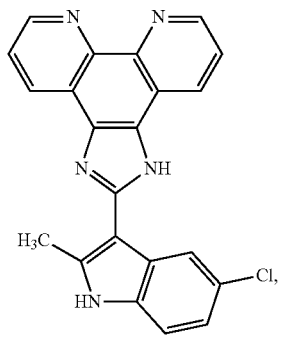

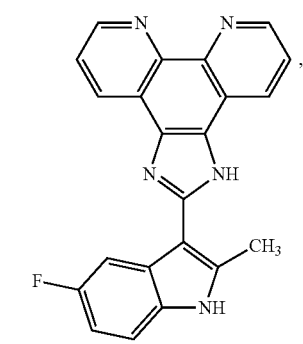

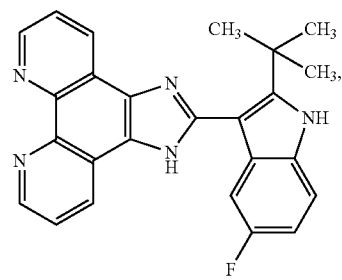

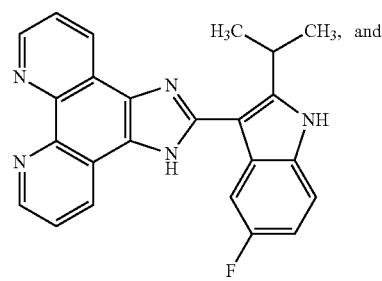

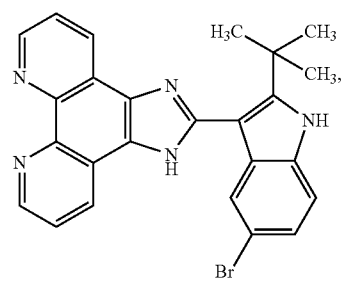

or a salt thereof.

21. The method according to claim 15, wherein the compound is:

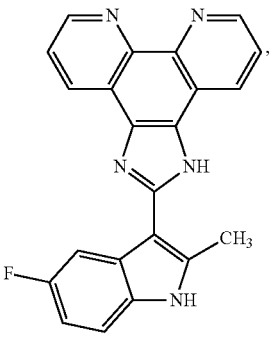

or a salt thereof.

22. The method according to claim 15, wherein said cancer is a solid tumour.

23. The method according to claim 22, wherein said solid tumour is selected from the group of: non-small cell lung tumour, colon tumour, prostate tumour, breast tumour, and melanoma tumour.

24. The method according to claim 15, wherein said cancer is a leukaemia.

25. The compound according to claim 1, wherein said salt is an HCl salt.

26. The pharmaceutical composition according to claim 8, wherein said composition is a liposomal or lipid micelle formulation.

27. The pharmaceutical composition according to claim 8, wherein said salt is an HCl salt.

28. The pharmaceutical composition according to claim 8, wherein said composition is formulated for intravenous administration.

29. The method according to claim 15, wherein said compound is administered as a liposomal or lipid micelle formulation.

30. The method according to claim 15, wherein said salt is an HCl salt.

31. The method according to claim 15, wherein said compound is administered to said mammal intravenously.

32. The method according to claim 15, wherein said CNS cancer is a glioma.

33. The method according to claim 15, wherein said cancer is non-small cell lung cancer.

34. The method according to claim 15, wherein said cancer is colon cancer.

35. The method according to claim 21, wherein said cancer is non-small cell lung cancer.

36. The method according to claim 21, wherein said cancer is colon cancer.

* * * * *

SEQUENCE LISTING

```
<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: DNA Primer

<400> SEQUENCE: 1
cggactacag ggcaa                                                    15
```

```
<210> SEQ ID NO 2
<211> LENGTH: 16
<212> TYPE: DNA
<213> ORGANISM: Artificial Sequence
<220> FEATURE:
<223> OTHER INFORMATION: DNA Primer

<400> SEQUENCE: 2
gctccaggac tttgca                                               16

<210> SEQ ID NO 3
<211> LENGTH: 21
<212> TYPE: DNA
<213> ORGANISM: Artificial Sequence
<220> FEATURE:
<223> OTHER INFORMATION: siRNA

<400> SEQUENCE: 3
cuaggguaga cgaugagagt t                                         21

<210> SEQ ID NO 4
<211> LENGTH: 21
<212> TYPE: DNA
<213> ORGANISM: Artificial Sequence
<220> FEATURE:
<223> OTHER INFORMATION: siRNA

<400> SEQUENCE: 4
cucucaucgu cuacccuagt t                                         21
```